(12) United States Patent
Gerlach et al.

(10) Patent No.: US 8,912,189 B2
(45) Date of Patent: Dec. 16, 2014

(54) PYRIDOPYRAZINE DERIVATIVES AND THEIR USE

(75) Inventors: Matthias Gerlach, Brachttal (DE); Irene Seipelt, Offenbach (DE); Lars Blumenstein, Frankfurt am Main (DE); Gilbert Mueller, Frankfurt am Main (DE); Eckhard Guenther, Maintal (DE); Tilmann Schuster, Grossostheim (DE); Michael Teifel, Weiterstadt (DE)

(73) Assignee: Aeterna Zentaris GmbH, Frankfurt (DE)

( * ) Notice: Subject to any disclaimer, the term of this patent is extended or adjusted under 35 U.S.C. 154(b) by 78 days.

(21) Appl. No.: 13/439,107

(22) Filed: Apr. 4, 2012

(65) Prior Publication Data

US 2012/0259151 A1    Oct. 11, 2012

Related U.S. Application Data

(60) Provisional application No. 61/472,245, filed on Apr. 6, 2011.

(30) Foreign Application Priority Data

Apr. 6, 2011 (EP) ..................... 11161248

(51) Int. Cl.
*A61K 31/4985* (2006.01)
*C07D 471/04* (2006.01)
*A61K 31/501* (2006.01)
*A61K 31/5377* (2006.01)

(52) U.S. Cl.
CPC ........... *A61K 31/4985* (2013.01); *A61K 31/501* (2013.01); *A61K 31/5377* (2013.01); *C07D 471/04* (2013.01)
USPC .......................................... 514/249; 544/350

(58) Field of Classification Search
CPC .................................................... C07D 471/04
USPC ....................................................... 544/350
See application file for complete search history.

(56) References Cited

U.S. PATENT DOCUMENTS

| | | | |
|---|---|---|---|
| 7,276,507 B2 | 10/2007 | Claus et al. | |
| 7,323,468 B2 | 1/2008 | Claus et al. | |
| 2004/0266777 A1 | 12/2004 | Claus et al. | |
| 2007/0123494 A1 | 5/2007 | Seipelt et al. | |
| 2007/0149484 A1 | 6/2007 | Claus et al. | |
| 2007/0275972 A1 | 11/2007 | Claus et al. | |
| 2008/0113991 A1 | 5/2008 | Claus et al. | |
| 2009/0275534 A1 | 11/2009 | Gerlack et al. | |
| 2011/0158944 A1 | 6/2011 | Hosted et al. | |

FOREIGN PATENT DOCUMENTS

| | | |
|---|---|---|
| EP | 1 785 423 A1 | 5/2007 |
| EP | 1 990 342 A1 | 11/2008 |
| WO | WO 2004/104002 A1 | 12/2004 |
| WO | WO 2004/104003 A1 | 12/2004 |
| WO | WO 2007/054556 A1 | 5/2007 |
| WO | WO 2007/079999 A2 | 7/2007 |
| WO | WO 2009/073513 A1 | 6/2009 |

OTHER PUBLICATIONS

U.S. Appl. No. 13/542,101, filed Jul. 5, 2012, Gerlach, et al.
U.S. Appl. No. 13/523,968, filed Jun. 15, 2012, Claus, et al.
U.S. Appl. No. 13/455,187, filed Apr. 25, 2012, Gerlach, et al.
U.S. Appl. No. 13/455,435, filed Apr. 25, 2012, Gerlach, et al.
U.S. Appl. No. 13/439,150, filed Apr. 4, 2012, Gerlach, et al.
European Search Report issued Sep. 7, 2011 in patent application No. EP 11 16 1248.
U.S. Appl. No. 13/770,470, filed Feb. 19, 2013, Claus, et al.

*Primary Examiner* — Brian McDowell
(74) *Attorney, Agent, or Firm* — Oblon, Spivak, McClelland, Maier & Neustadt, L.L.P.

(57) ABSTRACT

The present invention provides new pyridopyrazine compounds of Formula (I) which are suitable for the treatment or prevention of physiological and/or pathophysiological states mediated and/or modulated by signal transduction pathways and/or enzymes in mammals and in particular in humans.

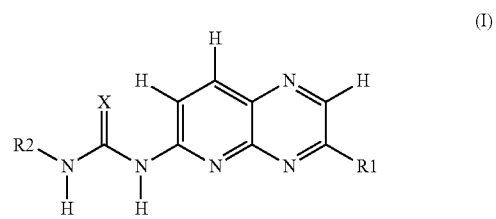

9 Claims, No Drawings

PYRIDOPYRAZINE DERIVATIVES AND THEIR USE

CROSS-REFERENCE TO RELATED APPLICATIONS

This application claims the benefit of U.S. 61/472,245 filed Apr. 6, 2011 and EP 1161248.7 filed Apr. 6, 2011.

FIELD OF THE INVENTION

The present invention relates to pyridopyrazine derivatives with new biological action and their use for the treatment of physiological and/or pathophysiological states mediated and/or modulated by signal transduction pathways in mammals and in particular in humans.

BACKGROUND OF THE INVENTION

The signal transduction cascades ras-Raf-Mek-Erk and PI3K-Akt play a central role in cell growth, cell proliferation, apoptosis, adhesion, migration and glucose metabolism. Consequently, the fundamental involvement in the pathogenesis of diseases such as cancer, neurodegeneration and inflammatory diseases is proven both for the ras-Raf-Mek-Erk and for the PI3K-Akt signal pathway. The individual components of these signal cascades are therefore important therapeutic points of attack for intervention in various disease processes (Weinstein-Oppenheimer C. R. et al. 2000, Chang F. et al. 2003, Katso R. et al 2001 and Lu Y. et al 2003).

The molecular and biochemical properties of both signal pathways are first described separately hereinafter.

A plurality of growth factors, cytokines and oncogenes transduce their growth-promoting signals via the activation of G-protein coupled ras which leads to the activation of serine threonine kinase Raf and to the activation of mitogen-activated protein kinase kinase 1 and 2 (MAPKK1/2 or Mek1/2) and results in the phosphorylation and activation of MAPK 1 and 2—also known as extracellular signal regulated kinase (Erk1 and 2). Compared to other signal pathways, the ras-Raf-Mek-Erk signal pathway combines a large number of proto-oncogenes, including ligands, tyrosine kinase receptors, G-proteins, kinases and nuclear transcription factors. Tyrosine kinases such as, for example, EGFR (Mendelsohn J. et al., 2000) frequently mediate constitutively active signals to the downstream ras-Raf-Mek-Erk signal pathway in tumour events caused by overexpression and mutation. Ras mutations are mutated in 30% of all human tumours (Khleif S. N. et al., 1999, Marshall C., 1999), the highest incidence of 90% being found in pancreatic carcinomas (Friess H. et al., 1996, Sirivatanauksorn V. et al., 1998). For c-Raf a deregulated expression and/or activation has been described in various tumours (Hoshino R. et al., 1999, McPhillips F. et al., 2001). B-Raf point mutants were detected in 66% of all human malignant melanomas, 14% of all ovarian carcinomas and 12% of all carcinomas of the colon (Davies H. et al., 2002). It is therefore not surprising that Erk1/2 is primarily involved in many cellular processes such as cell growth, cell proliferation and cell differentiation (Lewis T. S. et al., 1998, Chang F. et al., 2003).

In addition, the members of the Raf kinases also have Mek-Erk-independent anti-apoptotic functions whose molecular steps have not yet been fully described. Ask1, Bcl-2, Akt and Bag1 have been described as possible interaction partners for the Mek-Erk-independent Raf activity (Chen J et al., 2001, Troppmaier J. et al., 2003, Rapp U. R. et al., 2004, Gotz R. et al., 2005). It is assumed nowadays that both Mek-Erk-dependent and Mek-Erk-independent signal transduction mechanisms control the activation of the upstream ras and Raf stimuli.

The isoenzymes of the phosphatidylinositol 3-kinases (PI3Ks) function predominantly as lipid kinases and catalyse the D3 phosphorylation of the second-messenger lipids Ptdlns (phosphatidylinositol) to Ptdlns(3)P, Ptdlns(3,4)$P_2$, Ptdlns(3,4,5)$P_3$ phosphatidylinositol phosphates. The class I PI3Ks are composed structurally of the catalytic (p110alpha, beta, gamma, delta) and the regulatory (p85alpha, beta or p101gamma) subunits. Furthermore, the class II (PI3K-C2alpha, PI3K-C2beta) and class III (Vps34p) enzymes belong to the family of the P13 kinases (Wymann M. P. et al., 1998, VanHaesebroeck B. et al., 2001). The PIP increase triggered by the PI3Ks activates the proliferative ras-Raf-Mek-Erk signal pathway via the coupling of ras on the one hand (Rodriguez-Viciana P. et al., 1994) and on the other hand stimulates the anti-apoptotic signal pathway by recruiting Akt to the cell membrane and consequent overactivation of this kinase (Alessi D. R. et al., 1996, Chang H. W. et al., 1997, Moore S. M. et al., 1998). Consequently, the activation of PI3Ks fulfils at least two crucial mechanisms for tumour formation, namely the activation of cell growth and cell differentiation and the inhibition of apoptosis. In addition, PI3K also have protein-phosphorylating properties (Dhand et al., 1994, Bondeva T. et al., 1998, Bondev A. et al., 1999, Van-Haesebroeck B. et al., 1999) which can trigger a PI3Ks-intrinsically regulating serine autophosphorylation for example. In addition, it is known that PI3Ks also have kinase-independent regulating effector properties, e.g. during control of cardiac contraction (Crackower M. A. et al., 2002, Patrucco et al., 2004). It is furthermore proven that PI3Kdelta and PI3Kgamma are specifically expressed on hematopoietic cells and therefore constitute potential points of attack for isoenzyme-specific PI3Kdelta and PI3Kgamma inhibitors in the treatment of inflammatory diseases such as rheumatism, asthma and allergies and in the treatment of B and T cell lymphomas (Okkenhaug K. et al., 2003, Ali K. et al., 2004, Sujobert P. et al., 2005). PI3Kalpha, which was recently identified as a proto-oncogene (Shayesteh L. et al., 1999, Ma Y. Y. et al., 2000, Samuels Y. et al., 2004, Campbell I. G. et al., 2004, Levine D. A., 2005) is considered to be an important target in the treatment of tumour diseases. The importance of PI3K species as a target for the development of active substances is therefore extremely diverse (Chang F. & Lee J. T. et al, 2003).

The kinases related to PI3K (PIKK), which include the serine/threonine kinases mTOR, ATM, ATR, h-SMG-1 and DNA-PK (Chiang G. G. et al 2004) are also of great interest. Their catalytic domains have a high sequence homology to the catalytic domains of PI3Ks.

In addition, the loss of the tumour suppressor protein PTEN (Li J. et al., 1997, Steck P. A. et al., 1997)—whose function is the reversion of the phosphorylation initiated by the PI3K—contributes to an overactivation of Akt and its downstream cascade components and thereby emphasise the causal importance of PI3K as a target molecule for tumour therapy.

Various inhibitors of individual components of the ras-Raf-Mek-Erk and PI3K-Akt signal pathways have already been published and patented.

The present state of development in the field of kinase inhibitors, in particular of the ras-Raf-Mek-Erk and PI3K-Akt pathway, is described in the reviews of H. T. Arkenau et al, 2011, M. S. Chapman & J. N. Miner, 2011 and P. Liu et al, 2009. These publications contain comprehensive listings of the published low-molecular ras-Raf-Mek-Erk- and PI3K inhibitors.

The kinase inhibitor Sorafenib (Bay 43-9006; WO 99/32111, WO 03/068223) which was approved in, 2006 shows a relatively non-specific inhibition pattern of serine/threonine and of tyrosine kinases such as Raf, VEGFR2/3, Flt-3, PDGFR, c-Kit and other kinases. Great importance is attached to this inhibitor in angiogenesis-induced advanced tumour diseases (e.g. in renal cell carcinoma) and also in melanomas having a high B-Raf mutation rate. No inhibition of the kinases in the PI3K-Akt signal pathway has been described for Bay 43-9006. Other Raf-specific inhibitors like PLX-4032 and GSK2118436 (Arkenau H. T. et al, 2011) are currently under clinical evaluation.

Several Mek1/2 inhibitors (AZD-6244, XL-518, GSK1120212 and others) currently undergo clinical testing (reviewed by M S Chapman & J N Miner, 2011). However, no interaction with Erk1 or Erk2 nor any PI3K-Akt signal pathway inhibiting function or its simultaneous modulation has yet been disclosed for these Mek inhibitors.

Patent specification WO 2009/077766 describes pyrido[2,3-b]pyrazines as RAF inhibitors.

In addition, the patent specifications WO 2008/040820, WO 2008/009908 and WO 2005/123733 describe pyrido[2,3-b]pyrazines as agrochemical fungicides and herbicides, respectively.

The Korean invention KR 2008004646 relates to 2-alkenyloxy-3-ethynylpyrido[2,3-b]pyrazine derivatives and their pharmaceutically salts which with inhibit the expression of hypoxia-inducible transcriptional factor 1 (HIF-1) gene.

Patent specifications WO 04/104002 and WO 04/104003 describe pyrido[2,3-b]pyrazines, which can be substituted in the 6- or 7-position with urea, thiourea, amidine or guanidine groups. These compounds possess properties as inhibitors or modulators of kinases, in particular of tyrosine and serine/threonine kinases, and a use as a medicament is specified. However, no use of these compounds as modulators of lipid kinases, alone or in combination with tyrosine and serine/threonine kinases has been described.

In addition, patent specification WO 99/17759 describes pyrido[2,3-b]pyrazines which, among other things, carry alkyl-, aryl- and heteroaryl-substituted carbamates in the 6-position. These compounds are to be used to modulate serine threonine protein kinases.

Patent specification WO 05/007099 describes, among other things, urea-substituted pyrido[2,3-b]pyrazines as inhibitors of the serine/threonine kinase PKB. A use in the treatment of cancer diseases is specified for these compounds. However, no specific examples of urea-substituted pyridopyrazines with these biological properties are given.

Further examples of pyrido[2,3-b]pyrazines substituted with urea in the 6- and 7-position are given in patent specification WO 05/056547. The compounds in this patent specification are described as inhibitors of protein kinases, in particular GSK-3, Syk und JAK-3. A use in the treatment of proliferative diseases is given for these compounds among other things. No use of these compounds as modulators of lipid kinases, alone or in combination with serine/threonine kinases is described.

The patent application WO 04/005472 describes, among other things pyrido[2,3-b]pyrazines substituted with carbamate in the 6-position which inhibit the growth of bacteria as antibacterial substances. No antitumour effect is described.

Certain diphenyl quinoxalines and pyrido[2,3-b]pyrazines with special alkylpyrrolidine, alkylpiperidine or alkyl sulfonamides group at a phenyl ring which can additionally also bear urea or carbamate substitutions in the 6- or 7-position are described in patent specifications WO 03/084473, WO 03/086394 and WO 03/086403 as inhibitors of the activity of the serine/threonine kinase Akt. A use in the treatment of cancer diseases is specified for these compounds. No defined indication of a biological effect is given for the pyrido[2,3-b]pyrazine compounds described therein as examples.

Patent specification WO 03/024448 describes amide and acrylamide-substituted pyrido[2,3-b]pyrazines which can also contain carbamates as additional substituents and can be used as histone deacetylase inhibitors for the treatment of cell proliferation diseases.

The publication (S. Laufer, J. Med. Chem. 2010, 53(3), 1128-1137) describes pyridinylpyridopyrazines as lead compounds for novel p38α Mitogen-Activated Protein Kinase Inhibitors.

In another publication (M. R. Dobler, Pest Management Science, 2010, 66(2), 178-185) pyrido[2,3-b]pyrazines are described as tubulin polymerisation promoters.

In the publication (Temple C. et al. 1990) the synthesis of a 6-ethylcarbamate-substituted pyrido[2,3-b]pyrazine derivative is described as one example. No antitumour effect is disclosed or made obvious.

The synthesis of further derivatives of 6-ethylcarbamate-substituted pyrido[2,3-b]pyrazine is described in a publication by R. D. Elliott (J. Org. Chem. 1968). No biological effect of these compounds is described or disclosed.

The publication by C. Temple (1968) describes the synthesis and investigation of 6-ethylcarbamate-substituted pyrido[2,3-b]pyrazines as potential antimalarial drugs. No antitumour effect is disclosed or made obvious.

Several PI3K inhibitors (NVP-Bez-235, GDC-0941, XL-147 and others) undergo clinical trials (reviewed by Maira S. M., et al, 2010).

DESCRIPTION OF THE INVENTION

The object of the present invention is to provide new compounds which can be used for the treatment or prevention of physiological and/or pathophysiological states in mammals, in particular in humans, which are mediated by signal transduction pathways selected from the group consisting of: the PI3K-Akt signal transduction pathway and the ras-Raf-Mek-Erk signal transduction pathway.

The inventive object was surprisingly achieved in one aspect by preparing a compound according to the general formula (I)

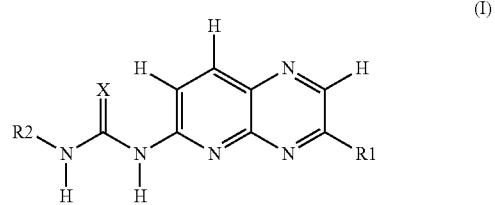

wherein the substituents R1, R2, X have the following meaning:

X O or S

R1

(I) unsubstituted or substituted alkyl, wherein the alkyl group can be substituted with one or more, the same or different F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-NH$_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, NHSO$_2$-alkyl, NHSO$_2$-cycloalkyl, NHSO$_2$-heterocyclyl, NHSO$_2$-aryl, NHSO$_2$-heteroaryl, NHSO$_2$-alkyl-aryl, NHSO$_2$-alkyl-heteroaryl, NO$_2$, SH, S-alkyl, S-aryl, S-heteroaryl, OH, OCF$_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, O—(CH$_2$)$_n$—O, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, OSO$_3$H, OSO$_2$-alkyl, OSO$_2$-cycloalkyl, OSO$_2$-heterocyclyl, OSO$_2$-aryl, OSO$_2$-heteroaryl, OSO$_2$-alkyl-aryl, OSO$_2$-alkyl-heteroaryl, OP(O)(OH)$_2$, C(O)-alkyl, C(O)-aryl, C(O)-heteroaryl, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkyl-heterocyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, SO$_2$-alkyl, SO$_2$-aryl, SO$_2$NH$_2$, SO$_2$NH-alkyl, SO$_2$NH-aryl, SO$_2$NH-heteroaryl, SO$_2$NH-alkyl-aryl, SO$_3$H, SO$_2$O-alkyl, SO$_2$O-aryl, SO$_2$O-alkyl-aryl, alkyl, cycloalkyl, heterocyclyl, aryl or heteroaryl, n can have the value 1, 2 or 3 and the alkyl-, cycloalkyl-, heterocyclyl-, aryl-, heteroaryl-, alkyl-cycloalkyl-, alkyl-heterocyclyl-, alkyl-aryl- and alkyl-heteroaryl substituents for their part can in turn be substituted, (II) unsubstituted or substituted aryl, wherein the aryl group can be substituted with one or more, the same or different F, Cl, Br, I, CF$_3$, CN, NH$_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-NH$_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, NHSO$_2$-alkyl, NHSO$_2$-cycloalkyl, NHSO$_2$-heterocyclyl, NHSO$_2$-aryl, NHSO$_2$-heteroaryl, NHSO$_2$-alkyl-aryl, NHSO$_2$-alkyl-heteroaryl, NO$_2$, SH, S-alkyl, S-aryl, S-heteroaryl, OH, OCF$_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, O—(CH$_2$)$_n$—O, O—CH$_2$—CH$_2$—O—CH$_2$—CH$_2$—O—CH$_2$—CH$_2$—OH; OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, OC(O)—NH-Alkyl, OSO$_3$H, OSO$_2$-alkyl, OSO$_2$-cycloalkyl, OSO$_2$-heterocyclyl, OSO$_2$-aryl, OSO$_2$-heteroaryl, OSO$_2$-alkyl-aryl, OSO$_2$-alkyl-heteroaryl, OP(O)(OH)$_2$, C(O)-alkyl, C(O)-aryl, C(O)-heteroaryl, O—CO$_2$-alkyl, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkyl-heterocyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, SO$_2$-alkyl, SO$_2$-heterocyclyl; SO$_2$-aryl, SO$_2$NH$_2$, SO$_2$NH-alkyl, SO$_2$NH-aryl, SO$_2$NH-heteroaryl, SO$_2$NH-alkyl-aryl, SO$_3$H, SO$_2$O-alkyl, SO$_2$O-aryl, SO$_2$O-alkyl-aryl, alkyl, cycloalkyl, heterocyclyl, aryl or heteroaryl, n can have the value 1, 2 or 3 and the alkyl-, cycloalkyl-, heterocyclyl-, aryl-, heteroaryl-, alkyl-cycloalkyl-, alkyl-heterocyclyl-, alkyl-aryl- and alkyl-heteroaryl substituents for their part can in turn be substituted, (III) unsubstituted or substituted heteroaryl, wherein the heteroaryl group can be substituted with one or more, the same or different F, Cl, Br, I, CF$_3$, CN, NH$_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-NH$_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, NHSO$_2$-alkyl, NHSO$_2$-cycloalkyl, NHSO$_2$-heterocyclyl, NHSO$_2$-aryl, NHSO$_2$-heteroaryl, NHSO$_2$-alkyl-aryl, NHSO$_2$-alkyl-heteroaryl, NO$_2$, SH, S-alkyl, S-aryl, S-heteroaryl, OH, OCF$_3$, O-alkyl, O-cycloalkyl, O-aryl, O-heteroaryl, O-alkyl-cycloalkyl, O-alkyl-heterocyclyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, OSO$_3$H, OSO$_2$-alkyl, OSO$_2$-cycloalkyl, OSO$_2$-heterocyclyl, OSO$_2$-aryl, OSO$_2$-heteroaryl, OSO$_2$-alkyl-aryl, OSO$_2$-alkyl-heteroaryl, OP(O)(OH)$_2$, C(O)-alkyl, C(O)-aryl, C(O)-heteroaryl, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkyl-heterocyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, Si(Alkyl)$_3$, SO$_2$NH$_2$, SO$_2$NH-alkyl, SO$_2$NH-aryl, SO$_2$NH-heteroaryl, SO$_2$NH-alkyl-aryl, SO3H, SO$_2$O-alkyl, SO$_2$O-aryl, SO$_2$O-alkyl-aryl, alkyl, cycloalkyl, heterocyclyl, alkyl-cycloalkyl, alkyl-heterocyclyl, alkyl-aryl, alkyl-heteroaryl, aryl or heteroaryl, and the alkyl-, cycloalkyl-, heterocyclyl-, alkyl-cycloalkyl, alkyl-heterocyclyl, alkyl-aryl, alkyl-heteroaryl, aryl- and heteroaryl substituents for their part can in turn be substituted, and R2:

(I) unsubstituted or substituted alkyl wherein the alkyl group can be substituted with one or more, the same or different F, Cl, Br, I, CF$_3$, CN, NH$_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, NHSO$_2$-alkyl, NHSO$_2$-cycloalkyl, NHSO$_2$-heterocyclyl, NHSO$_2$-aryl, NHSO$_2$-heteroaryl, NHSO$_2$-alkyl-aryl, NHSO$_2$-alkyl-heteroaryl, NO$_2$, SH, S-alkyl, S-cycloalkyl, S-heterocyclyl, S-aryl, S-heteroaryl, OH, OCF$_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, OSO$_3$H, OSO$_2$-alkyl, OSO$_2$-cycloalkyl, OSO$_2$-heterocyclyl, OSO$_2$-aryl, OSO$_2$-heteroaryl, OSO$_2$-alkyl-aryl, OSO$_2$-alkyl-heteroaryl, OP(O)(OH)$_2$, C(O)-alkyl, C(O)-aryl, C(O)-heteroaryl, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkyl-heterocyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, SO$_2$-alkyl, SO$_2$-aryl, SO₂NH₂, SO₂NH-alkyl, SO₂NH-aryl, SO₂NH-heteroaryl, SO₂NH-alkyl-aryl, SO₃H, SO₂O-alkyl, SO₂O-aryl, SO₂O-alkyl-aryl, cycloalkyl or heterocyclyl, (II) unsubstituted or substituted cycloalkyl, wherein the cycloalkyl group can be substituted with one or more, the same or different F, Cl, Br, I, NH₂, NH-alkyl, NH-cycloalkyl, NH-heterocyclyl, NH-aryl, NH-heteroaryl, NH-alkyl-aryl, NH-alkyl-heteroaryl, N(alkyl)₂, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, NHSO₂-alkyl, NHSO₂-cycloalkyl, NHSO₂-heterocyclyl, NHSO₂-aryl, NHSO₂-heteroaryl, NHSO₂-alkyl-aryl, NHSO₂-alkyl-heteroaryl, OH, O-alkyl, O-cycloalkyl, O-heterocyclyl, O-aryl, O-heteroaryl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, OSO₃H, OSO₂-alkyl, OSO₂-cycloalkyl, OSO₂-heterocyclyl, OSO₂-aryl, OSO₂-heteroaryl, OSO₂-alkyl-aryl, OSO₂-alkyl-heteroaryl, OP(O)(OH)₂, CO₂H, CO₂-alkyl, CO₂-cycloalkyl, CO₂-heterocyclyl, CO₂-aryl, CO₂-heteroaryl, CO₂-alkyl-cycloalkyl, CO₂-alkyl-heterocyclyl, CO₂-alkyl-aryl, CO₂-alkyl-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)₂, C(O)N(cycloalkyl)₂, C(O)N(aryl)₂, C(O)N(heteroaryl)₂, alkyl or aryl, its physiologically tolerated salts, in the form of its racemates, in the form of its pure enantiomers and/or diastereomers or in the form of mixtures of these enantiomers and/or diastereomers or in the form of its tautomers;

which can be used for the production of a medicament for the treatment or prevention of physiological and/or pathophysiological states in mammals mediated by signal transduction pathways selected from the group consisting of: the PI3K-Akt signal transduction pathway and the ras-Raf-Mek-Erk signal transduction pathway.

In a preferred embodiment, compounds according to the general formula (I) are prepared, wherein the alkyl group is selected from the group consisting of: "methyl, ethyl, n-propyl, 2-propyl, n-butyl, sec.-butyl, tert.-butyl, n-pentyl, iso-pentyl, neo-pentyl, n-hexyl, 2-hexyl, n-octyl, ethylenyl (vinyl), ethynyl, propenyl (—CH2CH═CH2; —CH═CH—CH3, —C(═CH2)-CH3), propinyl (—CH2-C≡CH, —C≡C—CH3), butenyl, butinyl, pentenyl, pentinyl, hexenyl, hexinyl, heptenyl, heptinyl, octenyl, octinyl" which can be used for the production of a medicament for the treatment or prevention of physiological and/or pathophysiological states in mammals mediated by signal transduction pathways selected from the group consisting of:

the PI3K-Akt signal transduction pathway and the ras-Raf-Mek-Erk signal transduction pathway.

In a further preferred embodiment, compounds according to the general formula (I) are prepared for the aforementioned use, wherein the heterocyclyl group is selected from the group consisting of: "tetrahydrofuryl, tetrahydropyranyl, pyrrolidinyl, piperidinyl, piperazinyl, morpholinyl".

In a further preferred embodiment, compounds according to the general formula (I) are prepared for the aforementioned use, wherein the heteroaryl group is selected from the group consisting of: "pyrrolyl, furyl, thienyl, thiazolyl, oxazolyl, isoxazolyl, pyrazolyl, imidazolyl, pyridinyl, pyrimidinyl, pyridazinyl, pyrazinyl, phthalazinyl, indolyl, indazolyl, indolizinyl, benzimidazolyl, quinolinyl, isoquinolinyl, quinoxalinyl, quinazolinyl, carbazolyl, phenazinyl, phenothiazinyl, acridinyl".

In a further preferred embodiment compounds according to the general formula (I) are prepared for the aforementioned use, wherein the alkyl group is selected from the group consisting of: "methyl, ethyl, n-propyl, 2-propyl, n-butyl, sec.-butyl, tert.-butyl, n-pentyl, iso-pentyl, neo-pentyl, n-hexyl, 2-hexyl, n-octyl, ethylenyl (vinyl), ethynyl, propenyl (—CH2CH═CH2; —CH═CH—CH3, —C(═CH2)-CH3), propinyl (—CH2-C≡CH, —C≡C—CH3), butenyl, butinyl, pentenyl, pentinyl, hexenyl, hexinyl, heptenyl, heptinyl, octenyl, octinyl" and/or wherein the heterocyclyl group is selected from the group consisting of: "tetrahydrofuryl, tetrahydropyranyl, pyrrolidinyl, piperidinyl, piperazinyl, morpholinyl" and/or the heteroaryl group is selected from the group consisting of: "pyrrolyl, furyl, thienyl, thiazolyl, oxazolyl, isoxazolyl, pyrazolyl, imidazolyl, pyridinyl, pyrimidinyl, pyridazinyl, pyrazinyl, phthalazinyl, indolyl, indazolyl, indolizinyl, benzimidazolyl, quinolinyl, isoquinolinyl, quinoxalinyl, quinazolinyl, carbazolyl, phenazinyl, phenothiazinyl, acridinyl".

The inventive object was surprisingly achieved in a further aspect by preparing pyridopyrazine compounds selected from the group consisting of:

Compound 1: 1-Ethyl-3-{3-[1-(3,4,5-trimethoxybenzyl)-1H-pyrazol-4-yl]-pyrido[2,3-b]pyrazin-6-yl}-urea

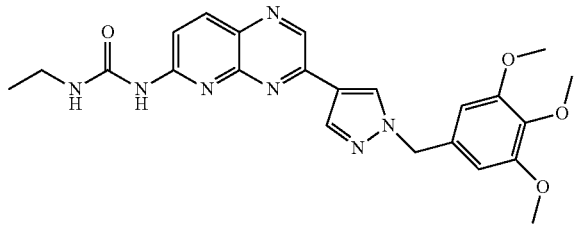

Compound 2: 1-Ethyl-3-[3-(1-pyridin-2-ylmethyl-1H-pyrazol-4-yl)-pyrido[2,3-b]pyrazin-6-yl]-thiourea

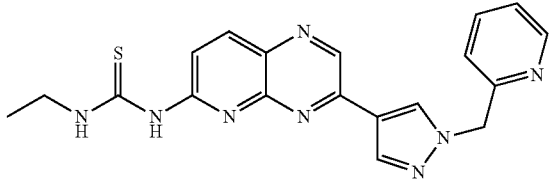 [SMILES: CCNC(=S)Nc1ccc2ncc(-c3cnn(Cc4ccccn4)c3)nc2n1]

Compound 3: 1-{3-[1-(3-Difluoromethoxy-benzyl)-1H-pyrazol-4-yl]-pyrido[2,3-b]pyrazin-6-yl}-3-ethyl-urea

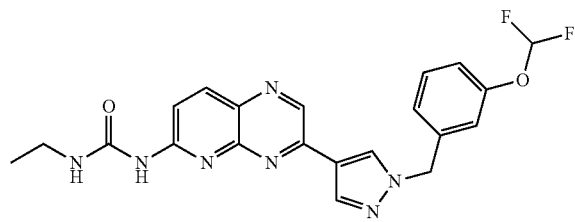 [SMILES: CCNC(=O)Nc1ccc2ncc(-c3cnn(Cc4cccc(OC(F)F)c4)c3)nc2n1]

Compound 4: 1-Ethyl-3-{3-[1-(3-hydroxy-benzyl)-1H-pyrazol-4-yl]-pyrido[2,3-b]pyrazin-6-yl}-urea

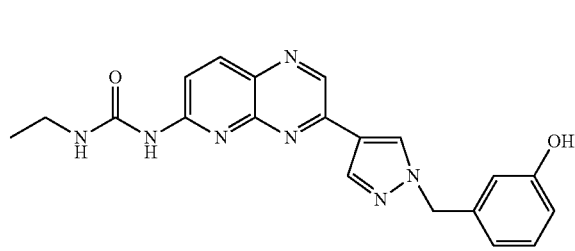 [SMILES: CCNC(=O)Nc1ccc2ncc(-c3cnn(Cc4cccc(O)c4)c3)nc2n1]

Compound 5: 1-[3-(1-Benzo[1,3]dioxol-5-ylmethyl-1H-pyrazol-4-yl)-pyrido[2,3-b]pyrazin-6-yl]-3-ethyl-thiourea

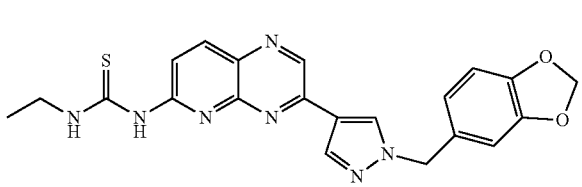 [SMILES: CCNC(=S)Nc1ccc2ncc(-c3cnn(Cc4ccc5c(c4)OCO5)c3)nc2n1]

Compound 6: 1-Ethyl-3-{3-[1-(4-trifluoromethoxy-benzyl)-1H-pyrazol-4-yl]-pyrido[2,3-b]pyrazin-6-yl}-urea

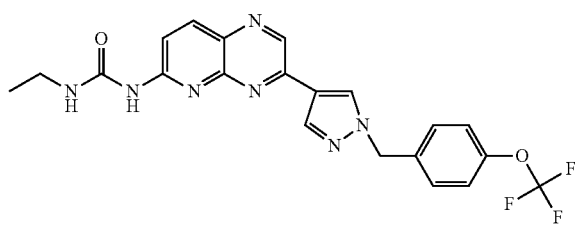 [SMILES: CCNC(=O)Nc1ccc2ncc(-c3cnn(Cc4ccc(OC(F)(F)F)cc4)c3)nc2n1]

Compound 7: 1-{3-[1-(3,4-Dimethoxy-benzyl)-1H-pyrazol-4-yl]-pyrido[2,3-b]pyrazin-6-yl}-3-(2-methoxy-ethyl)-thiourea

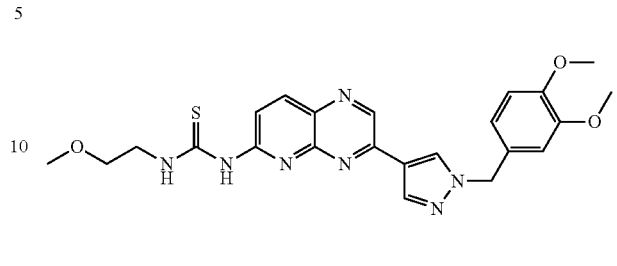

Compound 8: 1-{3-[1-(3-Chloro-4-fluoro-benzyl)-1H-pyrazol-4-yl]-pyrido[2,3-b]pyrazin-6-yl}-3-ethyl-urea

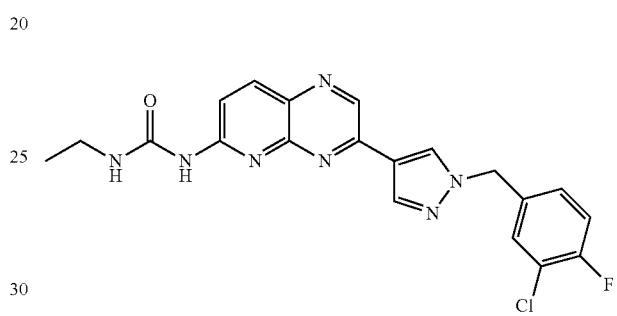

Compound 9: 1-Ethyl-3-{3-[1-(3-phenyl-propyl)-1H-pyrazol-4-yl]-pyrido[2,3-b]pyrazin-6-yl}-urea

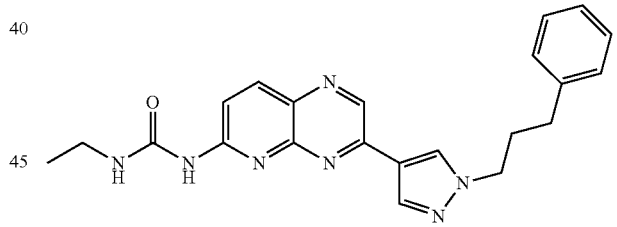

Compound 10: 1-{3-[1-(4-Cyano-benzyl)-1H-pyrazol-4-yl]-pyrido[2,3-b]pyrazin-6-yl}-3-ethyl-urea

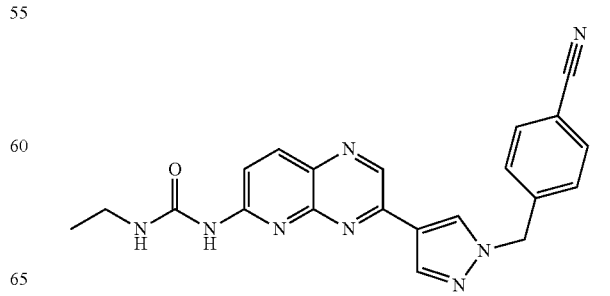

11

Compound 11: 1-{3-[1-(4-Difluoromethoxy-benzyl)-1H-pyrazol-4-yl]-pyrido[2,3-b]pyrazin-6-yl}-3-ethyl-urea

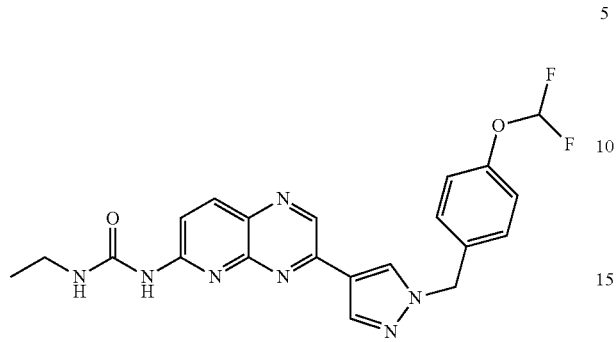

Compound 12: 1-{3-[1-(3,5-Dimethyl-benzyl)-1H-pyrazol-4-yl]-pyrido[2,3-b]pyrazin-6-yl}-3-ethyl-thiourea

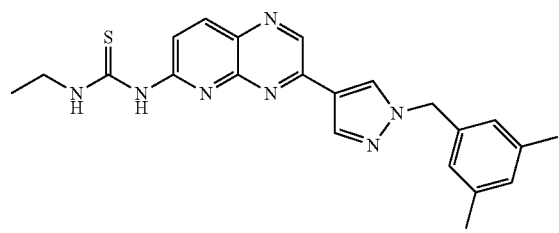 [SMILES: CCNC(=S)Nc1ccc2ncc(-c3cnn(Cc4cc(C)cc(C)c4)c3)nc2n1]

Compound 13: 1-Ethyl-3-{3-[1-(3-methyl-benzyl)-1H-pyrazol-4-yl]-pyrido[2,3-b]pyrazin-6-yl}-urea

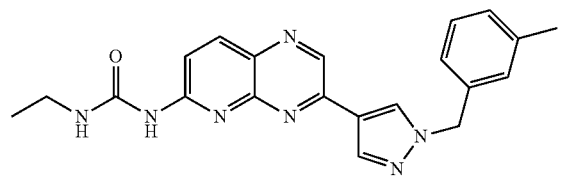 [SMILES: CCNC(=O)Nc1ccc2ncc(-c3cnn(Cc4cccc(C)c4)c3)nc2n1]

Compound 14: 1-Ethyl-3-[3-(1-pyridin-4-ylmethyl-1H-pyrazol-4-yl)-pyrido[2,3-b]pyrazin-6-yl]-urea

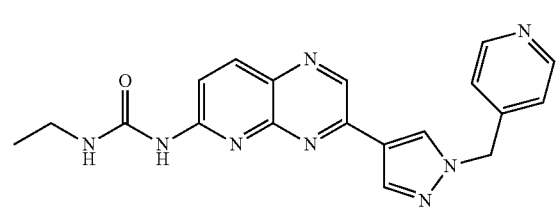 [SMILES: CCNC(=O)Nc1ccc2ncc(-c3cnn(Cc4ccncc4)c3)nc2n1]

12

Compound 15: 1-Ethyl-3-{3-[1-(4-methyl-benzyl)-1H-pyrazol-4-yl]-pyrido[2,3-b]pyrazin-6-yl}-urea

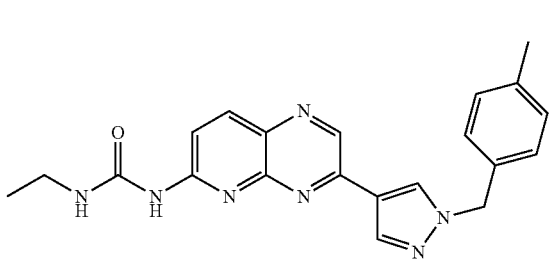 [SMILES: CCNC(=O)Nc1ccc2ncc(-c3cnn(Cc4ccc(C)cc4)c3)nc2n1]

Compound 16: 1-Ethyl-3-{3-[1-(4-phenyl-butyl)-1H-pyrazol-4-yl]-pyrido[2,3-b]pyrazin-6-yl}-urea

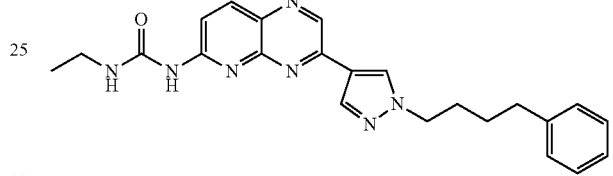

Compound 17: 1-Ethyl-3-{3-[1-(4-hydroxy-benzyl)-1H-pyrazol-4-yl]-pyrido[2,3-b]pyrazin-6-yl}-urea

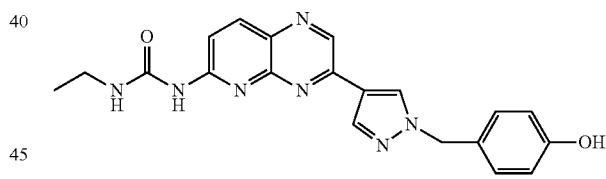

Compound 18: 1-{3-[1-(4-Chloro-benzyl)-1H-pyrazol-4-yl]-pyrido[2,3-b]pyrazin-6-yl}-3-ethyl-urea

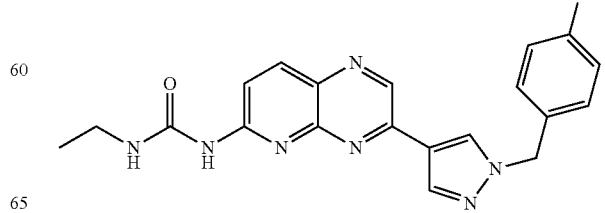

Compound 19: 1-{3-[1-(2,5-Dimethoxy-benzyl)-1H-pyrazol-4-yl]-pyrido[2,3-b]pyrazin-6-yl}-3-ethyl-thiourea

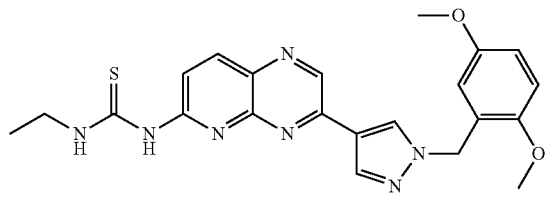 [SMILES: CCNC(=S)Nc1ccc2ncc(-c3cnn(Cc4cc(OC)ccc4OC)c3)nc2n1]

Compound 20: 1-Ethyl-3-{3-[1-(4-methyl-benzyl)-1H-pyrazol-4-yl]-pyrido[2,3-b]pyrazin-6-yl}-thiourea

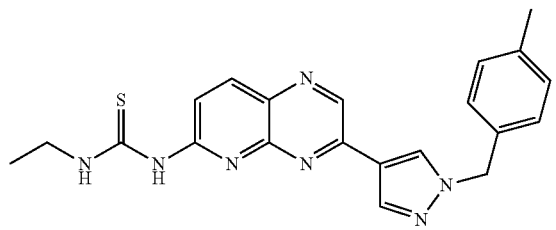

Compound 21: 1-{3-[1-(3-Benzyloxy-benzyl)-1H-pyrazol-4-yl]-pyrido[2,3-b]pyrazin-6-yl}-3-ethyl-thiourea

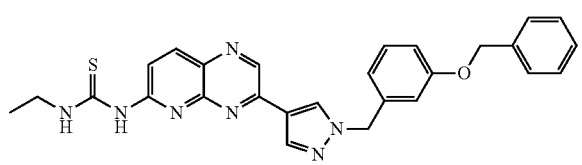 [SMILES: CCNC(=S)Nc1ccc2ncc(-c3cnn(Cc4cccc(OCc5ccccc5)c4)c3)nc2n1]

Compound 22: 1-{3-[1-(4-Bromo-3-methyl-benzyl)-1H-pyrazol-4-yl]-pyrido[2,3-b]pyrazin-6-yl}-3-ethyl-urea

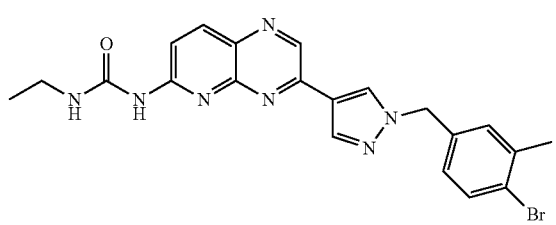 [SMILES: CCNC(=O)Nc1ccc2ncc(-c3cnn(Cc4ccc(Br)c(C)c4)c3)nc2n1]

Compound 23: 1-Ethyl-3-{3-[1-(4-methoxy-benzyl)-1H-pyrazol-4-yl]-pyrido[2,3-b]pyrazin-6-yl}-thiourea

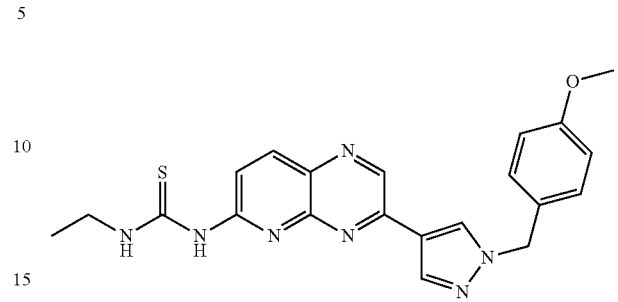

Compound 24: 1-Ethyl-3-[3-(1-pyridin-3-ylmethyl-1H-pyrazol-4-yl)-pyrido[2,3-b]pyrazin-6-yl]-thiourea

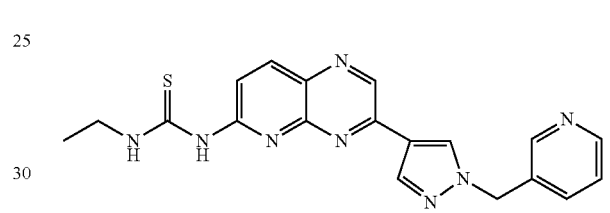

Compound 25: 1-Ethyl-3-{3-[1-(3-fluoro-5-methyl-benzyl)-1H-pyrazol-4-yl]-pyrido[2,3-b]pyrazin-6-yl}-thiourea

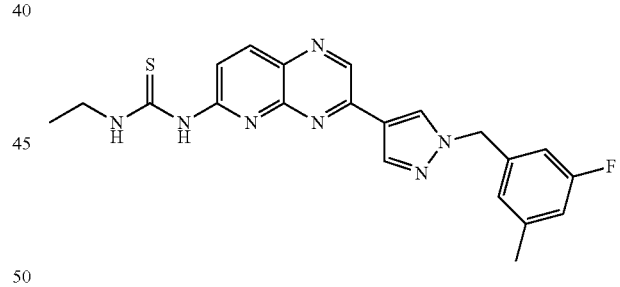

Compound 26: 1-{3-[1-(2,3-Dimethoxy-benzyl)-1H-pyrazol-4-yl]-pyrido[2,3-b]pyrazin-6-yl}-3-ethyl-thiourea

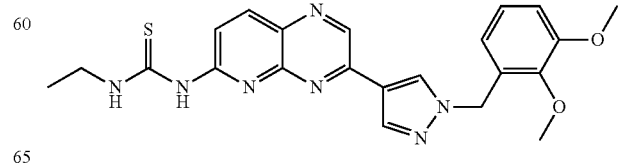

Compound 27: 1-{3-[1-(3-Difluoromethoxy-benzyl)-1H-pyrazol-4-yl]-pyrido[2,3-b]pyrazin-6-yl}-3-ethyl-thiourea

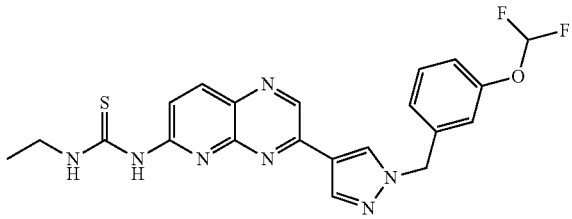 [SMILES: CCNC(=S)Nc1ccc2ncc(-c3cnn(Cc4cccc(OC(F)F)c4)c3)nc2n1]

Compound 28: 1-{3-[1-(3,4-Dimethoxy-benzyl)-1H-pyrazol-4-yl]-pyrido[2,3-b]pyrazin-6-yl}-3-ethyl-thiourea

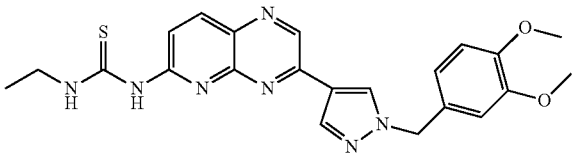

Compound 29: 1-Ethyl-3-{3-[1-(2-fluoro-3-methoxy-benzyl)-1H-pyrazol-4-yl]-pyrido[2,3-b]pyrazin-6-yl}-thiourea

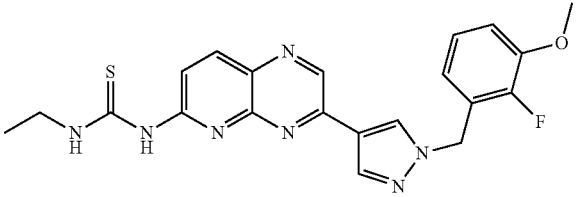

Compound 30: 1-Ethyl-3-[3-(1-phenyl-1H-pyrazol-4-yl)-pyrido[2,3-b]pyrazin-6-yl]-urea

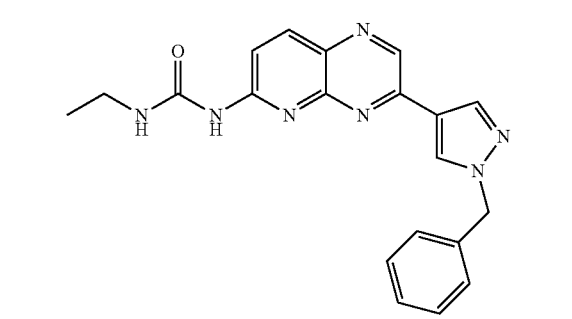 [SMILES: CCNC(=O)Nc1ccc2ncc(-c3cnn(Cc4ccccc4)c3)nc2n1]

Compound 31: 1-[3-(1-Benzyl-1H-pyrazol-4-yl)-pyrido[2,3-b]pyrazin-6-yl]-3-(2-methoxy-ethyl)-thiourea

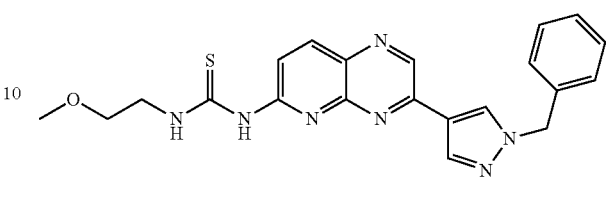

Compound 32: 1-{3-[1-(3-Methoxy-benzyl)-1H-pyrazol-4-yl]-pyrido[2,3-b]pyrazin-6-yl}-3-(2-methoxy-ethyl)-thiourea

Compound 33: 1-{3-[1-(3-Methoxy-benzyl)-1H-pyrazol-4-yl]-pyrido[2,3-b]pyrazin-6-yl}-3-methoxymethyl-thiourea

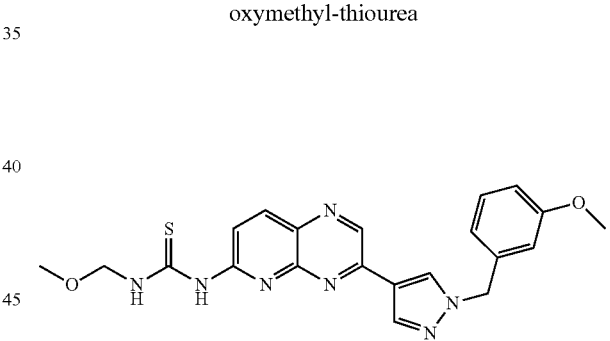

Compound 34: 1-[3-(1-Benzyl-1H-pyrazol-4-yl)-pyrido[2,3-b]pyrazin-6-yl]-3-methoxymethyl-thiourea

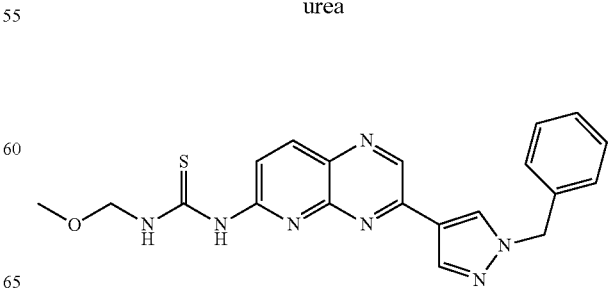

Compound 35: 1-{3-[1-(3,4-Dimethoxy-benzyl)-1H-pyrazol-4-yl]-pyrido[2,3-b]pyrazin-6-yl}-3-methoxymethyl-thiourea

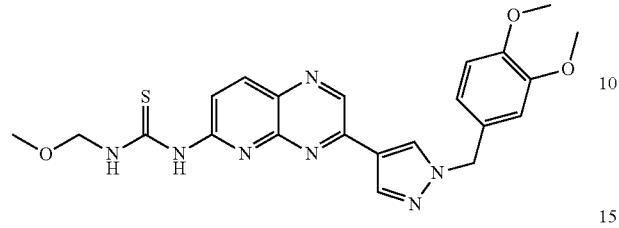

Compound 36: 1-Ethyl-3-{3-[1-(3-hydroxy-benzyl)-1H-pyrazol-4-yl]-pyrido[2,3-b]pyrazin-6-yl}-thiourea

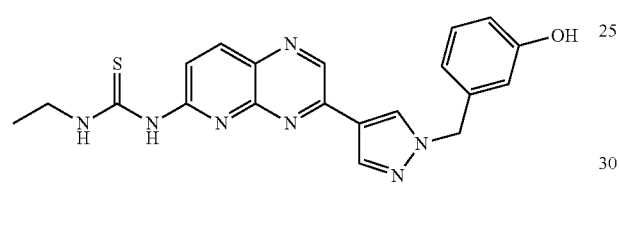

Compound 37: 1-{3-[1-(3-Dimethylamino-benzyl)-1H-pyrazol-4-yl]-pyrido[2,3-b]pyrazin-6-yl}-3-ethyl-thiourea

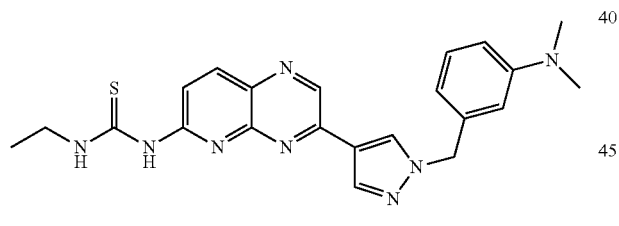

Compound 38: 1-{3-[1-(3-Chloro-4-fluoro-benzyl)-1H-pyrazol-4-yl]-pyrido[2,3-b]pyrazin-6-yl}-3-ethyl-thiourea

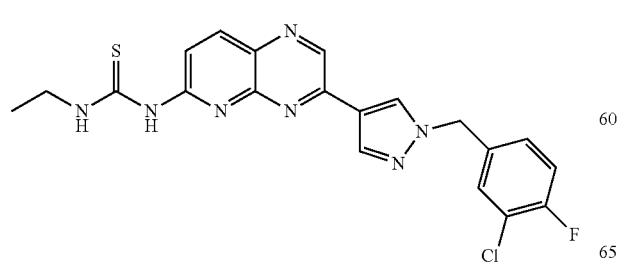

Compound 39: 1-{3-[1-(3,5-Dimethoxy-benzyl)-1H-pyrazol-4-yl]-pyrido[2,3-b]pyrazin-6-yl}-3-ethyl-thiourea

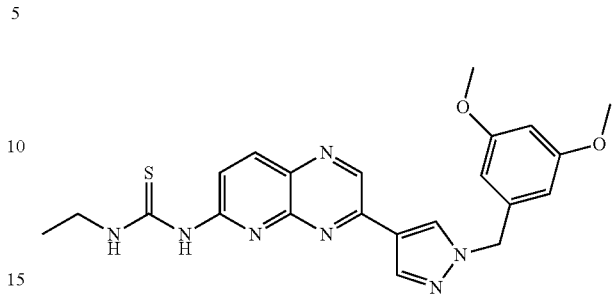

Compound 40: 1-Ethyl-3-{3-[1-(3-methoxy-benzyl)-1H-pyrazol-4-yl]-pyrido[2,3-b]pyrazin-6-yl}-thiourea

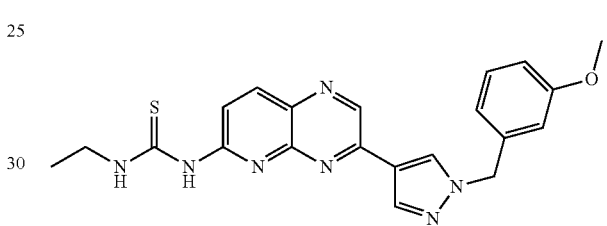

Compound 41: 1-Ethyl-3-{3-[1-(3-methyl-benzyl)-1H-pyrazol-4-yl]-pyrido[2,3-b]pyrazin-6-yl}-thiourea

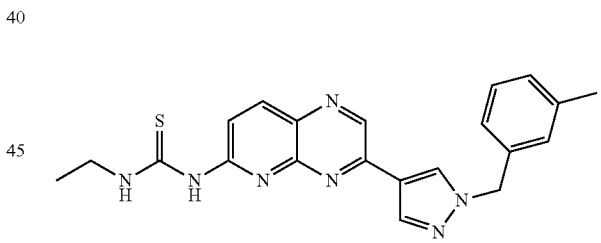

Compound 42: 1-{3-[1-(3,4-Dimethoxy-benzyl)-1H-pyrazol-4-yl]-pyrido[2,3-b]pyrazin-6-yl}-3-ethyl-urea

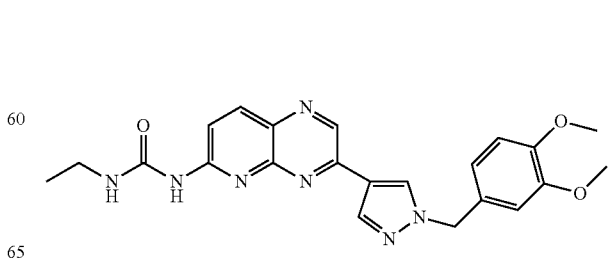

Compound 43: 1-Ethyl-3-{3-[1-(2,3,4-trimethoxy-benzyl)-1H-pyrazol-4-yl]-pyrido[2,3-b]pyrazin-6-yl}-thiourea

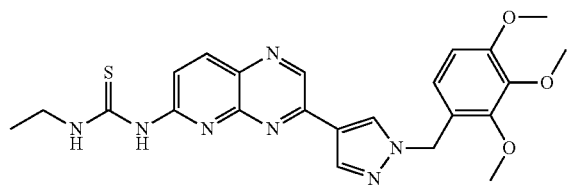 [SMILES: CCNC(=S)Nc1ccc2ncc(-c3cnn(Cc4ccc(OC)c(OC)c4OC)c3)nc2n1]

Compound 44: 1-Ethyl-3-{3-[1-(3-phenyl-propyl)-1H-pyrazol-4-yl]-pyrido[2,3-b]pyrazin-6-yl}-thiourea

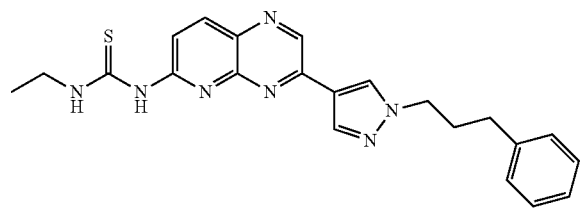 [SMILES: CCNC(=S)Nc1ccc2ncc(-c3cnn(CCCc4ccccc4)c3)nc2n1]

Compound 45: 1-[3-(1-Benzyl-1H-pyrazol-4-yl)-pyrido[2,3-b]pyrazin-6-yl]-3-ethyl-thiourea

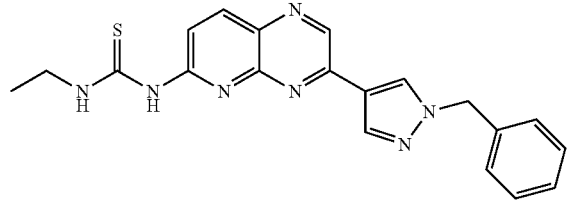 [SMILES: CCNC(=S)Nc1ccc2ncc(-c3cnn(Cc4ccccc4)c3)nc2n1]

Compound 46: 1-Ethyl-3-{3-[1-(3,4,5-trimethoxy-benzyl)-1H-pyrazol-4-yl]-pyrido[2,3-b]pyrazin-6-yl}-thiourea

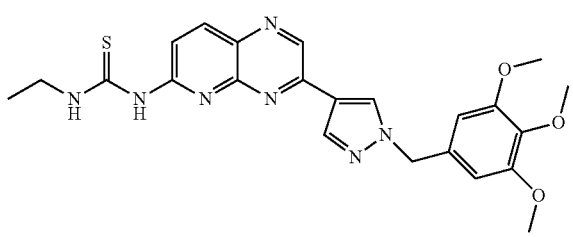 [SMILES: CCNC(=S)Nc1ccc2ncc(-c3cnn(Cc4cc(OC)c(OC)c(OC)c4)c3)nc2n1]

Compound 47: 1-{3-[1-(3-Methoxy-benzyl)-1H-pyrazol-4-yl]-pyrido[2,3-b]pyrazin-6-yl}-3-(2,2,2-trifluoro-ethyl)-thiourea

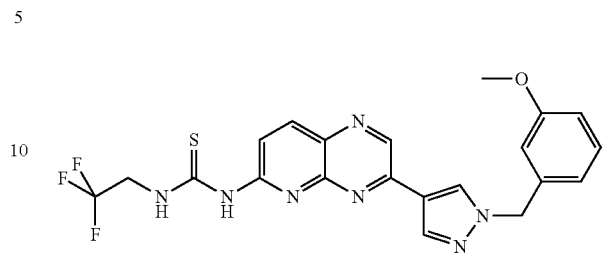

Compound 48: 1-Ethyl-3-{3-[1-(2-fluoro-3-methyl-benzyl)-1H-pyrazol-4-yl]-pyrido[2,3-b]pyrazin-6-yl}-thiourea

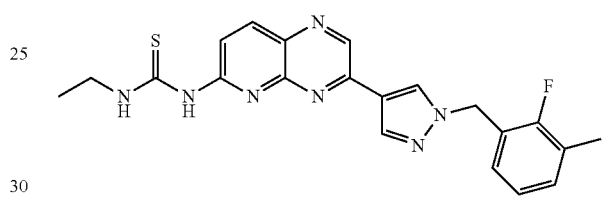

Compound 49: 1-{3-[1-(3-Ethoxy-benzyl)-1H-pyrazol-4-yl]-pyrido[2,3-b]pyrazin-6-yl}-3-ethyl-thiourea

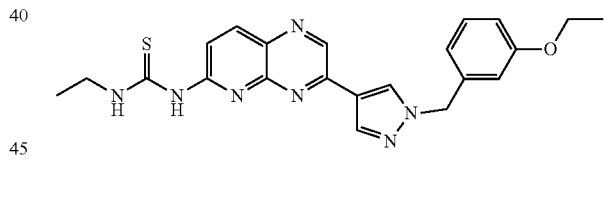

Compound 50: 1-{3-[1-(4-Chloro-benzyl)-1H-pyrazol-4-yl]-pyrido[2,3-b]pyrazin-6-yl}-3-ethyl-thiourea

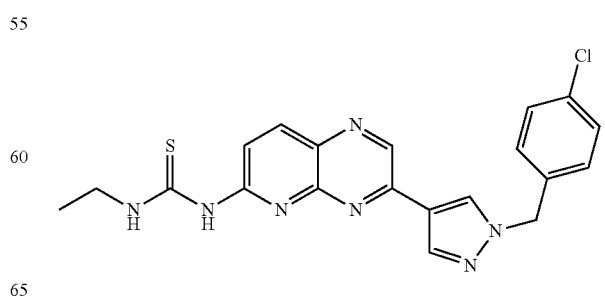

Compound 51: 1-{3-[1-(3-Methyl-benzyl)-1H-pyrazol-4-yl]-pyrido[2,3-b]pyrazin-6-yl}-3-(2,2,2-trifluoro-ethyl)-thiourea Compound 55: 1-Ethyl-3-{3-[1-(4-hydroxy-3-methoxy-benzyl)-1H-pyrazol-4-yl]-pyrido[2,3-b]pyrazin-6-yl}-thiourea

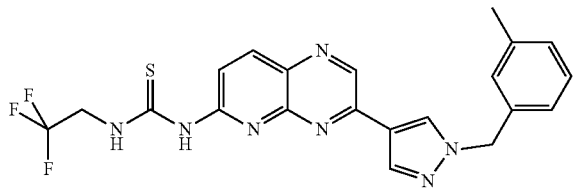 [SMILES: Cc1cccc(Cn2cc(-c3cnc4ccc(NC(=S)NCC(F)(F)F)nc4n3)cn2)c1]

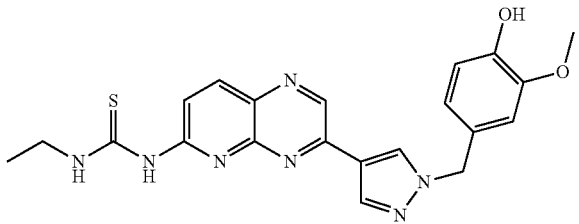

Compound 52: 1-Ethyl-3-{3-[1-(2-methyl-benzyl)-1H-pyrazol-4-yl]-pyrido[2,3-b]pyrazin-6-yl}-thiourea Compound 56: 1-Ethyl-3-{3-[1-(3-hydroxy-4-methoxy-benzyl)-1H-pyrazol-4-yl]-pyrido[2,3-b]pyrazin-6-yl}-urea

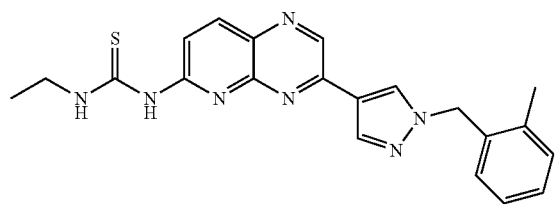 [SMILES: CCNC(=S)Nc1ccc2ncc(-c3cnn(Cc4ccccc4C)c3)nc2n1]

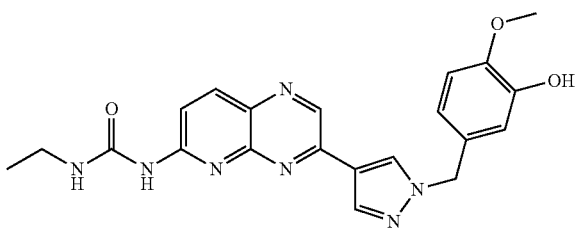

Compound 53: 1-Ethyl-3-[3-(1-phenethyl-1H-pyrazol-4-yl)-pyrido[2,3-b]pyrazin-6-yl]-thiourea Compound 57: 1-Ethyl-3-{3-[1-(3-hydroxy-4-methoxy-benzyl)-1H-pyrazol-4-yl]-pyrido[2,3-b]pyrazin-6-yl}-thiourea

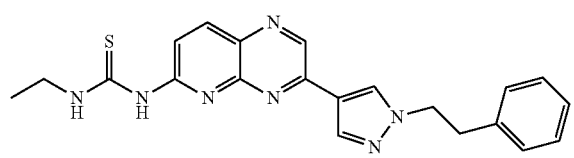 [SMILES: CCNC(=S)Nc1ccc2ncc(-c3cnn(CCc4ccccc4)c3)nc2n1]

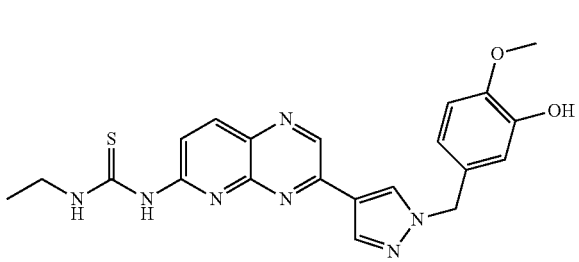

Compound 54: 1-Ethyl-3-{3-[1-(4-hydroxy-3-methoxy-benzyl)-1H-pyrazol-4-yl]-pyrido[2,3-b]pyrazin-6-yl}-urea Compound 58: 1-{3-[1-(3,5-Dichloro-benzyl)-1H-pyrazol-4-yl]-pyrido[2,3-b]pyrazin-6-yl}-3-ethyl-urea

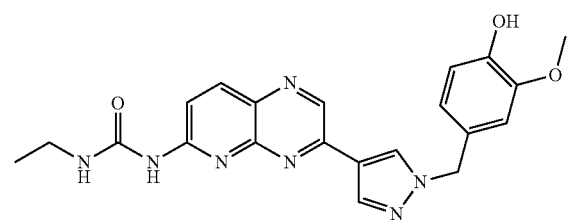 [SMILES: CCNC(=O)Nc1ccc2ncc(-c3cnn(Cc4ccc(O)c(OC)c4)c3)nc2n1]

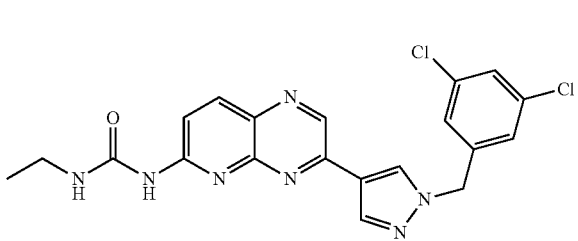 [SMILES: CCNC(=O)Nc1ccc2ncc(-c3cnn(Cc4cc(Cl)cc(Cl)c4)c3)nc2n1]

Compound 59: 1-{3-[1-(3,5-Dichloro-benzyl)-1H-pyrazol-4-yl]-pyrido[2,3-b]pyrazin-6-yl}-3-ethyl-thiourea

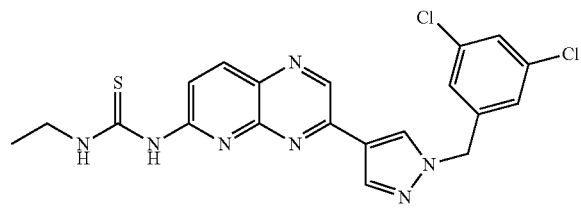 [SMILES: CCNC(=S)Nc1ccc2ncc(-c3cnn(Cc4cc(Cl)cc(Cl)c4)c3)nc2n1]

Compound 60: 1-{3-[1-(3-Amino-benzyl)-1H-pyrazol-4-yl]-pyrido[2,3-b]pyrazin-6-yl}-3-ethyl-urea

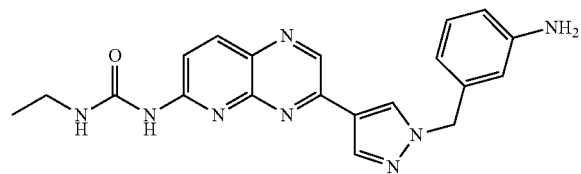 [SMILES: CCNC(=O)Nc1ccc2ncc(-c3cnn(Cc4cccc(N)c4)c3)nc2n1]

Compound 61: 1-{3-[1-(3-Amino-benzyl)-1H-pyrazol-4-yl]-pyrido[2,3-b]pyrazin-6-yl}-3-ethyl-thiourea

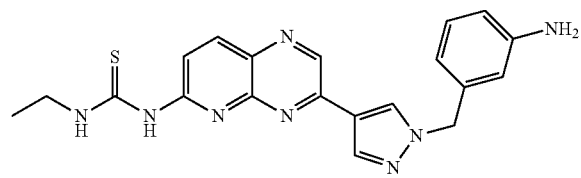

Compound 62: 1-Ethyl-3-[3-(1-pyridazin-3-ylmethyl-1H-pyrazol-4-yl)-pyrido[2,3-b]pyrazin-6-yl]-urea

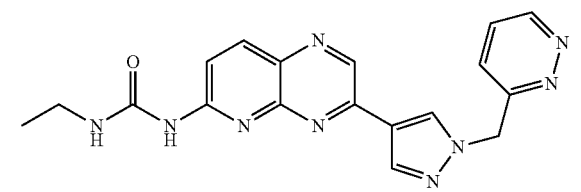 [SMILES: CCNC(=O)Nc1ccc2ncc(-c3cnn(Cc4cccnn4)c3)nc2n1]

Compound 63: 1-Ethyl-3-[3-(1-pyridazin-3-ylmethyl-1H-pyrazol-4-yl)-pyrido[2,3-b]pyrazin-6-yl]-thiourea

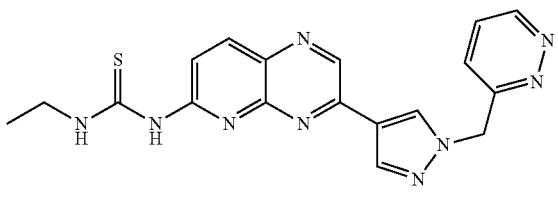 [SMILES: CCNC(=S)Nc1ccc2ncc(-c3cnn(Cc4cccnn4)c3)nc2n1]

Compound 64: 1-Ethyl-3-{3-[1-(3-methanesulfonyl-benzyl)-1H-pyrazol-4-yl]-pyrido[2,3-b]pyrazin-6-yl}-urea

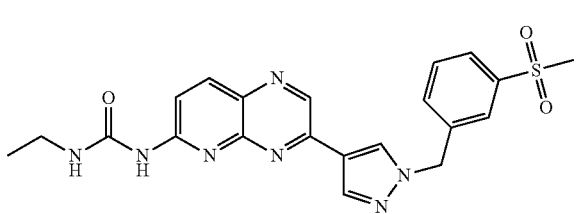 [SMILES: CCNC(=O)Nc1ccc2ncc(-c3cnn(Cc4cccc(S(C)(=O)=O)c4)c3)nc2n1]

Compound 65: 1-Ethyl-3-{3-[1-(3-methanesulfonyl-benzyl)-1H-pyrazol-4-yl]-pyrido[2,3-b]pyrazin-6-yl}-thiourea

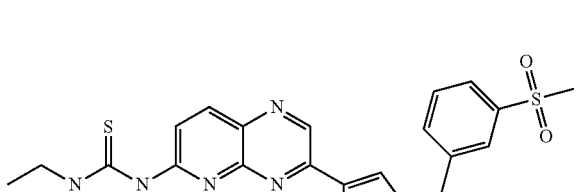

Compound 66: 1-Ethyl-3-(3-{1-[3-(2-methoxy-ethoxy)-benzyl]-1H-pyrazol-4-yl}-pyrido[2,3-b]pyrazin-6-yl)-urea

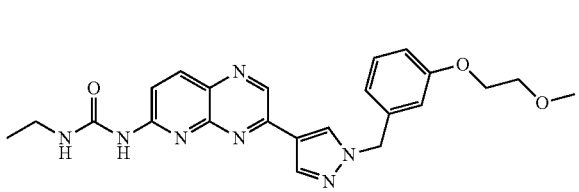 [SMILES: CCNC(=O)Nc1ccc2ncc(-c3cnn(Cc4cccc(OCCOC)c4)c3)nc2n1]

Compound 67: 1-Ethyl-3-(3-{1-[3-(2-methoxy-ethoxy)-benzyl]-1H-pyrazol-4-yl}-pyrido[2,3-b]pyrazin-6-yl)-thiourea

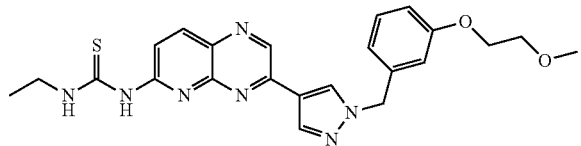

Compound 68: 1-Ethyl-3-(3-{1-[3-(4-methyl-piperazin-1-ylmethyl)-benzyl]-1H-pyrazol-4-yl}-pyrido[2,3-b]pyrazin-6-yl)-urea

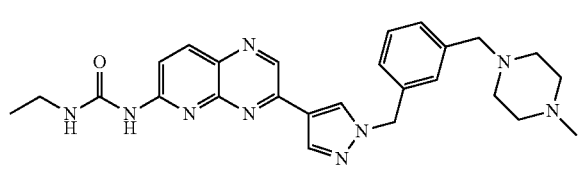 [SMILES: CCNC(=O)Nc1ccc2ncc(-c3cnn(Cc4cccc(CN5CCN(C)CC5)c4)c3)nc2n1]

Compound 69: 1-Ethyl-3-(3-{1-[3-(4-methyl-piperazin-1-ylmethyl)-benzyl]-1H-pyrazol-4-yl}-pyrido[2,3-b]pyrazin-6-yl)-thiourea

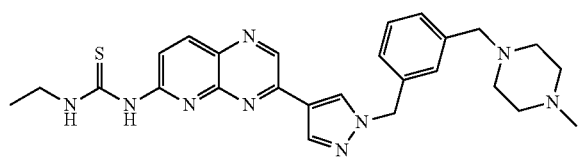 [SMILES: CCNC(=S)Nc1ccc2ncc(-c3cnn(Cc4cccc(CN5CCN(C)CC5)c4)c3)nc2n1]

Compound 70: Phosphoric acid mono-(3-{4-[6-(3-ethyl-ureido)-pyrido[2,3-b]pyrazin-3-yl]-pyrazol-1-ylmethyl}-phenyl)ester

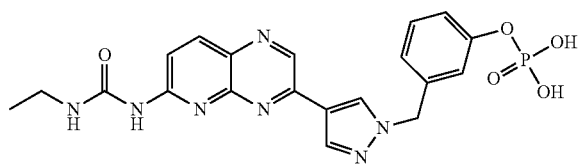 [SMILES: CCNC(=S)Nc1ccc2ncc(-c3cnn(Cc4cccc(OP(=O)(O)O)c4)c3)nc2n1]

Compound 71: Phosphoric acid mono-(3-{4-[6-(3-ethyl-thioureido)-pyrido[2,3-b]-pyrazin-3-yl]-pyrazol-1-ylmethyl}-phenyl)ester

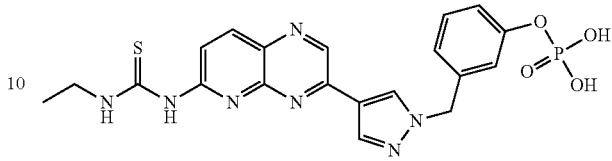

Compound 72: 1-[3-(1-Benzyl-1H-pyrazol-4-yl)-pyrido[2,3-b]pyrazin-6-yl]-3-(2-methoxy-ethyl)-urea Compound 73: 1-{3-[1-(3-Methoxy-benzyl)-1H-pyrazol-4-yl]-pyrido[2,3-b]pyrazin-6-yl}-3-(2-methoxy-ethyl)-urea

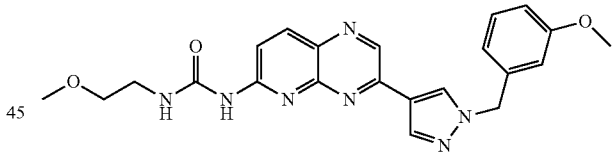

Compound 74: 1-{3-[1-(3,4-Dimethoxy-benzyl)-1H-pyrazol-4-yl]-pyrido[2,3-b]pyrazin-6-yl}-3-(2-methoxy-ethyl)-urea

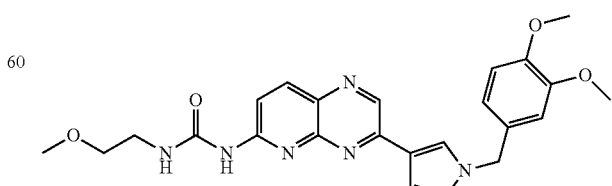

Compound 75: 1-[3-(1-Benzyl-1H-pyrazol-4-yl)-pyrido[2,3-b]pyrazin-6-yl]-3-(2,2-dimethoxy-ethyl)-thiourea

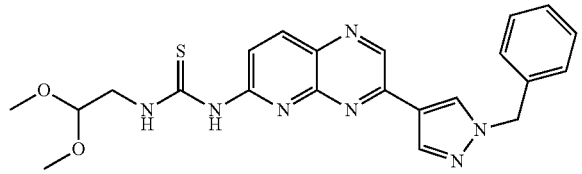 [SMILES: COC(CNC(=S)Nc1ccc2ncc(-c3cnn(Cc4ccccc4)c3)nc2n1)OC]

Compound 76: 1-(2,2-Dimethoxy-ethyl)-3-{3-[1-(3-methoxy-benzyl)-1H-pyrazol-4-yl]-pyrido[2,3-b]pyrazin-6-yl}-thiourea

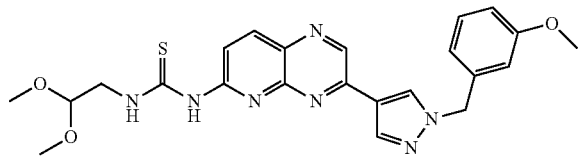

Compound 77: 1-{3-[1-(3,4-Dimethoxy-benzyl)-1H-pyrazol-4-yl]-pyrido[2,3-b]pyrazin-6-yl}-3-(2,2-dimethoxy-ethyl)-thiourea

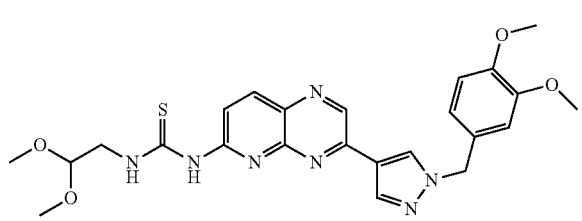

Compound 78: 1-Ethyl-3-(3-{1-[2-(2-methoxy-ethoxy)-ethyl]-1H-pyrazol-4-yl}-pyrido[2,3-b]pyrazin-6-yl)-urea

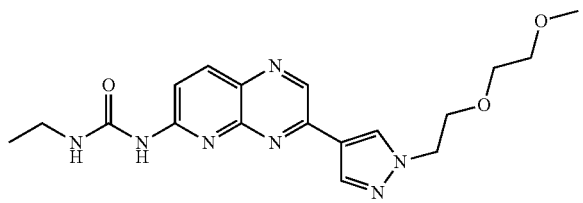 [SMILES: CCNC(=S)Nc1ccc2ncc(-c3cnn(CCOCCOC)c3)nc2n1]

Compound 79: 1-Ethyl-3-(3-{1-[2-(2-methoxy-ethoxy)-ethyl]-1H-pyrazol-4-yl}-pyrido[2,3-b]pyrazin-6-yl)-thiourea

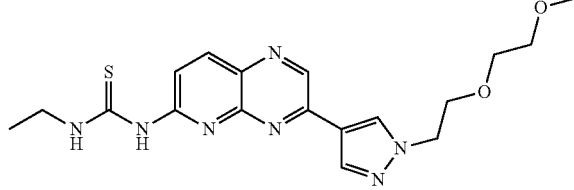

Compound 80: 1-Ethyl-3-[3-(1-{2-[2-(2-methoxy-ethoxy)-ethoxy]-ethyl}-1H-pyrazol-4-yl)-pyrido[2,3-b]pyrazin-6-yl]-urea Compound 81: 1-Ethyl-3-[3-(1-{2-[2-(2-methoxy-ethoxy)-ethoxy]-ethyl}-1H-pyrazol-4-yl)-pyrido[2,3-b]pyrazin-6-yl]-thiourea

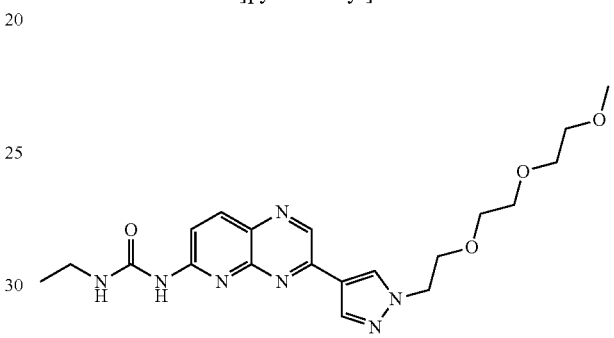

Compound 82: 1-Ethyl-3-(3-{1-[2-(2-hydroxy-ethoxy)-ethyl]-1H-pyrazol-4-yl}-pyrido[2,3-b]pyrazin-6-yl)-urea

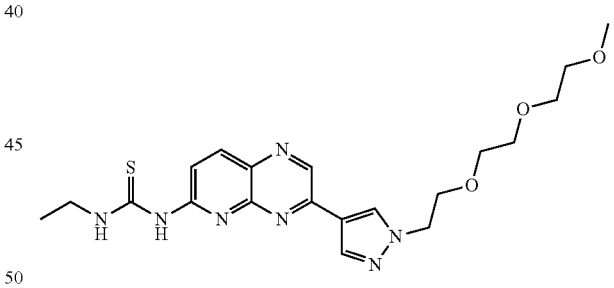

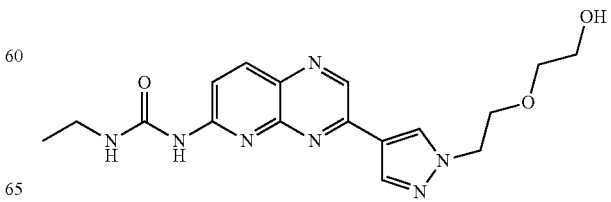

Compound 83: 1-Ethyl-3-(3-{1-[2-(2-hydroxy-ethoxy)-ethyl]-1H-pyrazol-4-yl}-pyrido[2,3-b]pyrazin-6-yl)-urea

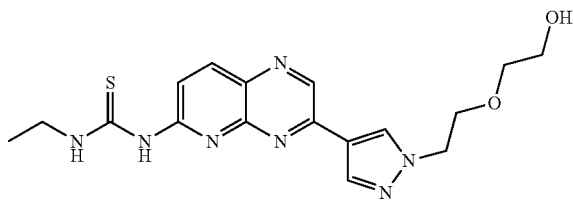 [SMILES: CCNC(=S)Nc1ccc2ncc(-c3cnn(CCOCCO)c3)nc2n1]

Compound 84: 1-[3-(1-Benzyl-1H-[1,2,3]triazol-4-yl)-pyrido[2,3-b]pyrazin-6-yl]-3-ethyl-urea

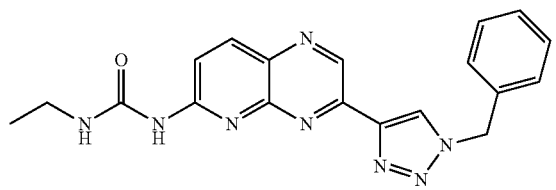

Compound 85: 1-[3-(1-Benzyl-1H-[1,2,3]triazol-4-yl)-pyrido[2,3-b]pyrazin-6-yl]-3-ethyl-urea

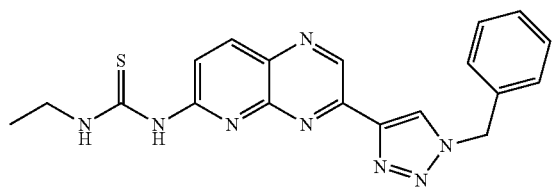 [SMILES: CCNC(=O)Nc1ccc2ncc(-c3cn(Cc4ccccc4)nn3)nc2n1]

Compound 86: 1-Ethyl-3-{3-[1-(3-methoxy-benzyl)-1H-[1,2,3]triazol-4-yl]-pyrido[2,3-b]pyrazin-6-yl}-urea

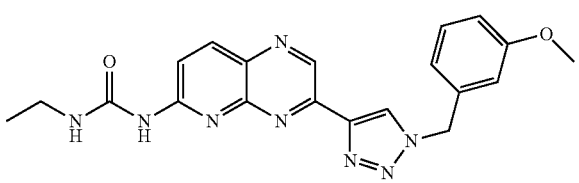 [SMILES: CCNC(=O)Nc1ccc2ncc(-c3cn(Cc4cccc(OC)c4)nn3)nc2n1]

Compound 87: 1-Ethyl-3-{3-[1-(3-methoxy-benzyl)-1H-[1,2,3]triazol-4-yl]-pyrido[2,3-b]pyrazin-6-yl}-thiourea

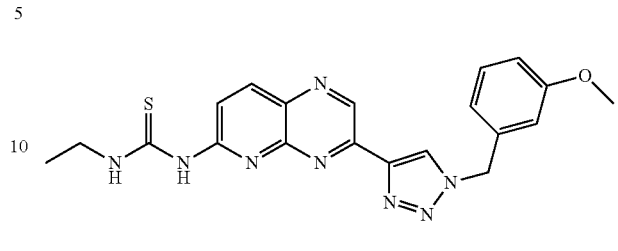

Compound 88: 1-{3-[1-(3,4-Dimethoxy-benzyl)-1H-[1,2,3]triazol-4-yl]-pyrido[2,3-b]pyrazin-6-yl}-3-ethyl-urea

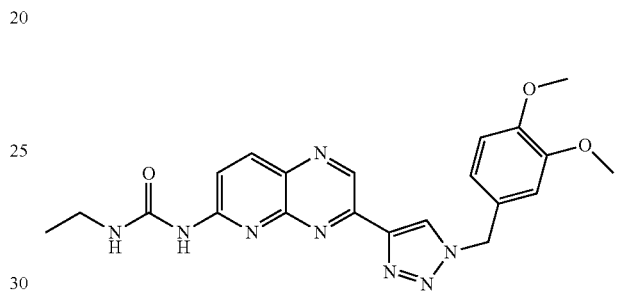

Compound 89: 1-{3-[1-(3,4-Dimethoxy-benzyl)-1H-[1,2,3]triazol-4-yl]-pyrido[2,3-b]pyrazin-6-yl}-3-ethyl-thiourea

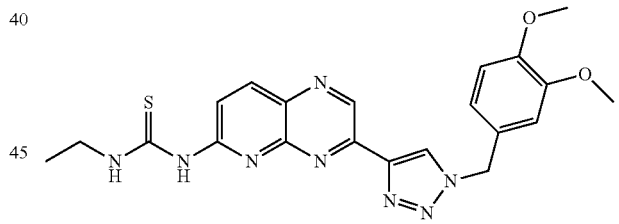

Compound 190: 1-Ethyl-3-{3-[1-(4-methoxy-cyclohexylmethyl)-1H-pyrazol-4-yl]-pyrido[2,3-b]pyrazin-6-yl}-thiourea

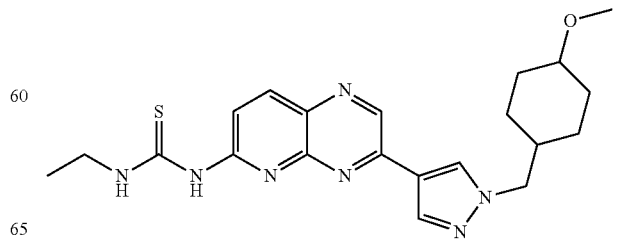

Compound 191: 1-Ethyl-3-{3-[1-(5-methoxy-pentyl)-1H-pyrazol-4-yl]-pyrido[2,3-b]pyrazin-6-yl}-thiourea

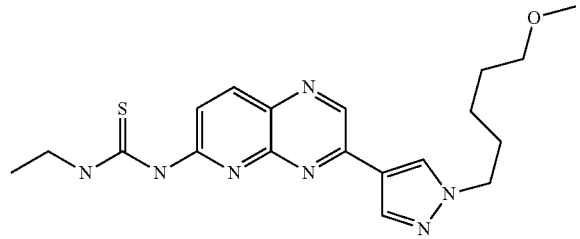 [SMILES: CCNC(=S)Nc1ccc2ncc(-c3cnn(CCCCCOC)c3)nc2n1]

Compound 192: 1-Ethyl-3-[3-(2-methoxy-ethyl)-pyrido[2,3-b]pyrazin-6-yl]-thiourea

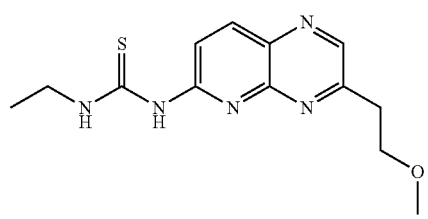 [SMILES: CCNC(=S)Nc1ccc2ncc(CCOC)nc2n1]

Compound 193: 2-[6-(3-Ethyl-thioureido)-pyrido[2,3-b]pyrazin-3-yl]-acetamide

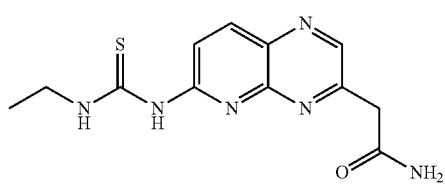 [SMILES: CCNC(=S)Nc1ccc2ncc(CC(N)=O)nc2n1]

Compound 210: 1-Ethyl-3-{3-[1-(4-hydroxy-benzyl)-1H-pyrazol-4-yl]-pyrido[2,3-b]pyrazin-6-yl}-thiourea

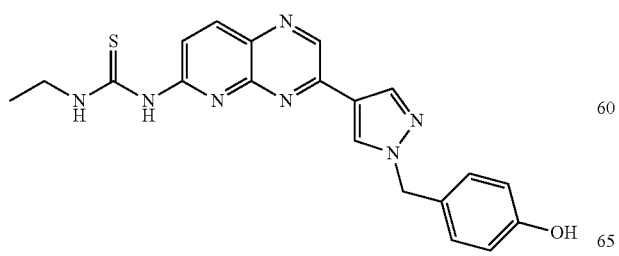

Compound 211: 1-Ethyl-3-(3-{1-[4-methoxy-3-(2-methoxy-ethoxy)-benzyl]-1H-pyrazol-4-yl}-pyrido[2,3-b]pyrazin-6-yl)-urea

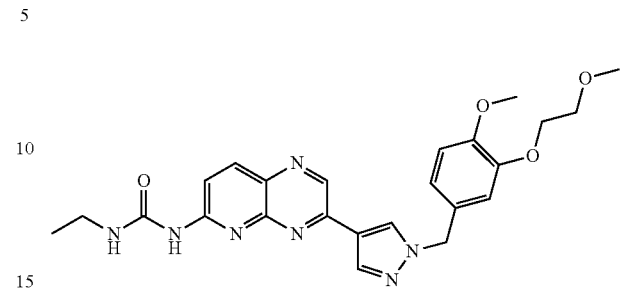

Compound 212: 4-[6-(3-Ethyl-ureido)-pyrido[2,3-b]pyrazin-3-yl]-thiophene-2-carboxylic acid

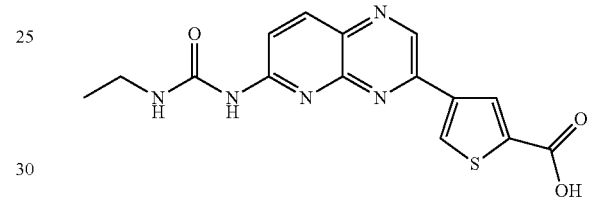

Compound 213: 1-Ethyl-3-[3-(5-methyl-furan-2-yl)-pyrido[2,3-b]pyrazin-6-yl]-urea

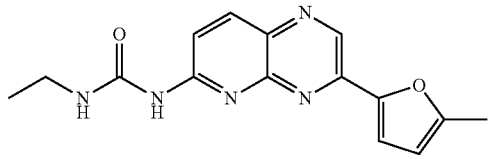 [SMILES: CCNC(=O)Nc1ccc2ncc(-c3ccc(C)o3)nc2n1]

Compound 214: 1-Ethyl-3-[3-(5-methyl-furan-2-yl)-pyrido[2,3-b]pyrazin-6-yl]-thiourea

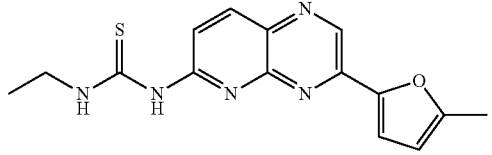 [SMILES: CCNC(=S)Nc1ccc2ncc(-c3ccc(C)o3)nc2n1]

Compound 215: 4-[6-(3-Ethyl-thioureido)-pyrido[2,3-b]pyrazin-3-yl]-thiophene-2-carboxylic acid

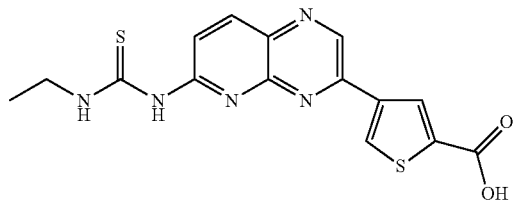

Compound 216: (2-{4-[6-(3-Ethyl-thioureido)-pyrido[2,3-b]pyrazin-3-yl]-pyrazol-1-yl}-ethyl)-carbamic acid tert-butyl ester

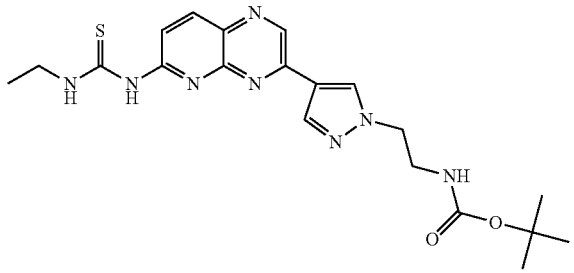 [SMILES: CCNC(=S)Nc1ccc2ncc(-c3cnn(CCNC(=O)OC(C)(C)C)c3)nc2n1]

Compound 217: 3-{4-[6-(3-Ethyl-thioureido)-pyrido[2,3-b]pyrazin-3-yl]-pyrazol-1-yl}-propionamide

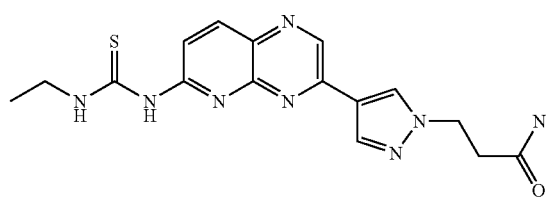

Compound 218: Sodium; 4-{4-[6-(3-ethyl-thioureido)-pyrido[2,3-b]pyrazin-3-yl]-pyrazol-1-ylmethyl}-phenolate

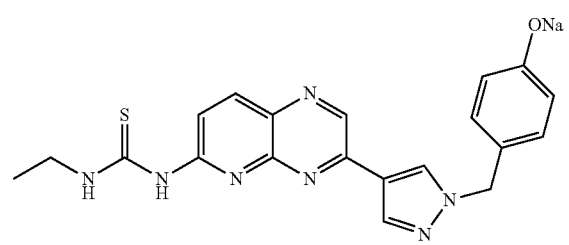

Compound 219: 1-Ethyl-3-{3-[1-(4-methoxymethoxy-benzyl)-1H-pyrazol-4-yl]-pyrido[2,3-b]pyrazin-6-yl}-thiourea

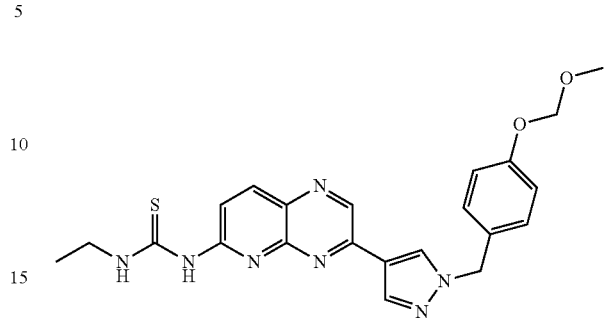

Compound 220: (4-{4-[6-(3-Ethyl-thioureido)-pyrido[2,3-b]pyrazol-3-yl]-pyrazol-1-ylmethyl}-phenoxy)-acetic acid

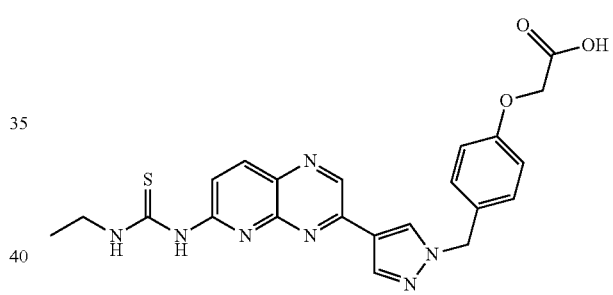

Compound 221: 1-Ethyl-3-(3-{1-[4-(2-hydroxy-ethoxy)-benzyl]-1H-pyrazol-4-yl}-pyrido[2,3-b]pyrazin-6-yl)-thiourea

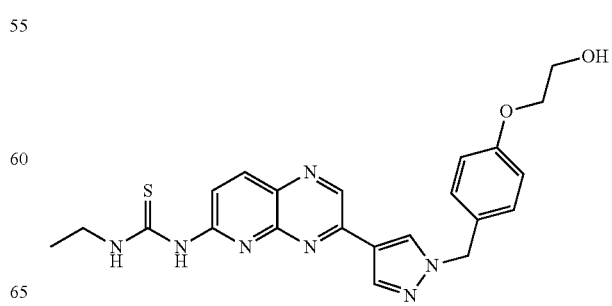

Compound 222: 1-Ethyl-3-(3-{1-[4-(2-methoxy-ethoxy)-benzyl]-1H-pyrazol-4-yl}-pyrido[2,3-b]pyrazin-6-yl)-thiourea

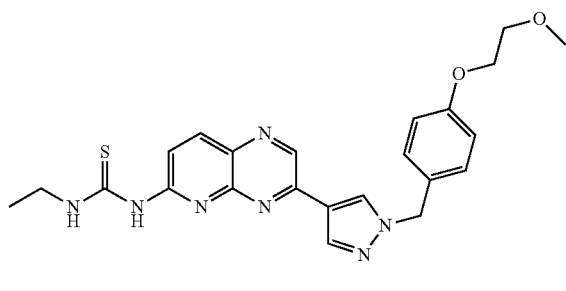 [SMILES: CCNC(=S)Nc1ccc2ncc(-c3cnn(Cc4ccc(OCCOC)cc4)c3)nc2n1]

Compound 223: 1-(3-{1-[4-(2-Dimethylamino-ethoxy)-benzyl]-1H-pyrazol-4-yl}-pyrido[2,3-b]pyrazin-6-yl)-3-ethyl-thiourea

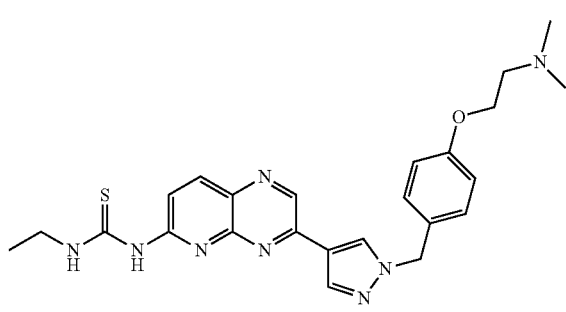 [SMILES: CCNC(=S)Nc1ccc2ncc(-c3cnn(Cc4ccc(OCCN(C)C)cc4)c3)nc2n1]

Compound 224: 1-Ethyl-3-(3-{1-[4-(2-morpholin-4-yl-ethoxy)-benzyl]-1H-pyrazol-4-yl}-pyrido[2,3-b]pyrazin-6-yl)-thiourea

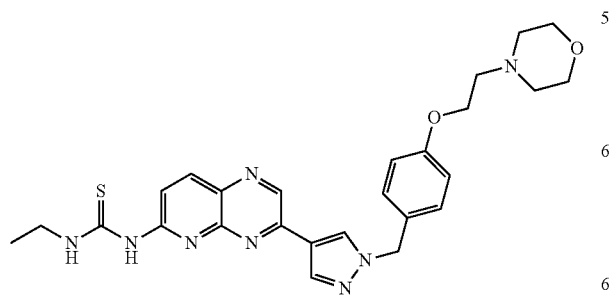

Compound 225: 1-Ethyl-3-[3-(1-{4-[2-(2-hydroxy-ethoxy)-ethoxy]-benzyl}-1H-pyrazol-4-yl)-pyrido[2,3-b]pyrazin-6-yl]-thiourea

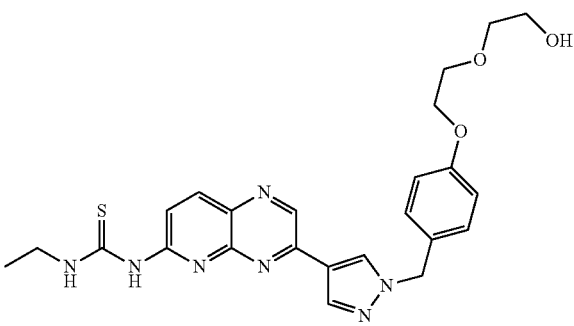 [SMILES: CCNC(=S)Nc1ccc2ncc(-c3cnn(Cc4ccc(OCCOCCO)cc4)c3)nc2n1]

Compound 226: Dimethylamino-acetic acid 4-{4-[6-(3-ethyl-thioureido)-pyrido[2,3-b]pyrazin-3-yl]-pyrazol-1-ylmethyl}-phenyl ester Compound 227: 2-Amino-3-hydroxy-propionic acid 4-{4-[6-(3-ethyl-thioureido)-pyrido[2,3-b]pyrazin-3-yl]-pyrazol-1-ylmethyl}-phenyl ester

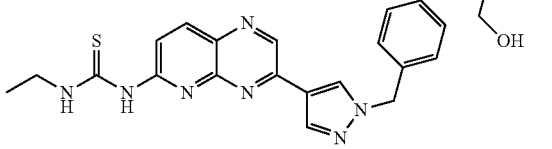

Compound 228: 1-{3-[1-(4-Dimethylamino-benzyl)-1H-pyrazol-4-yl]-pyrido[2,3-b]pyrazin-6-yl}-3-ethyl-thiourea

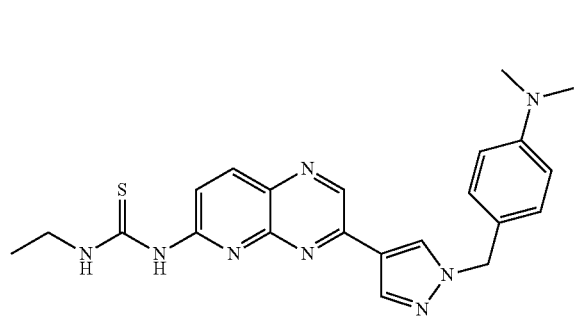 [SMILES: CCNC(=S)Nc1ccc2ncc(-c3cnn(Cc4ccc(N(C)C)cc4)c3)nc2n1]

Compound 229: 1-Ethyl-3-{3-[1-(4-methanesulfonyl-benzyl)-1H-pyrazol-4-yl]-pyrido[2,3-b]pyrazin-6-yl}-thiourea

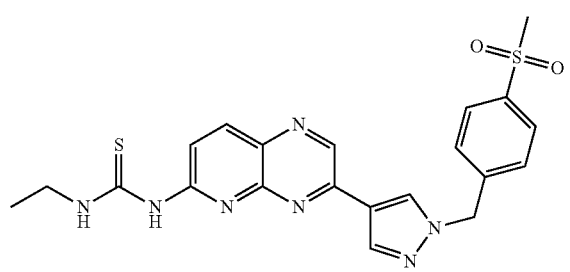 [SMILES: CCNC(=S)Nc1ccc2ncc(-c3cnn(Cc4ccc(S(C)(=O)=O)cc4)c3)nc2n1]

Compound 230: 1-Allyl-3-[3-(5-methyl-thiophen-2-yl)-pyrido[2,3-b]pyrazin-6-yl]-urea

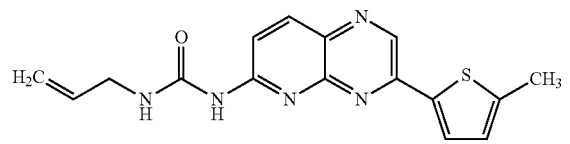

Compound 231: 1-Allyl-3-[3-(5-methyl-thiophen-2-yl)-pyrido[2,3-b]pyrazin-6-yl]-thiourea

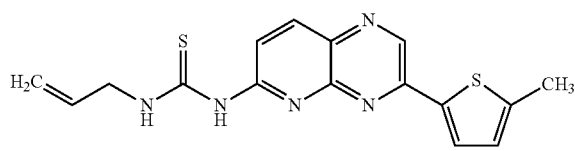 [SMILES: C=CCNC(=O)Nc1ccc2ncc(-c3ccc(C)s3)nc2n1]

Compound 232: 1-Allyl-3-[3-(4-methyl-thiophen-2-yl)-pyrido[2,3-b]pyrazin-6-yl]-urea

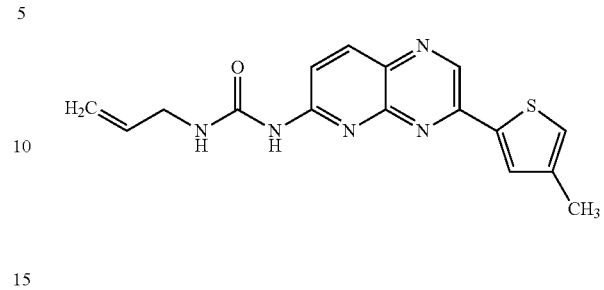

Compound 233: 1-Allyl-3-[3-(4-methyl-thiophen-2-yl)-pyrido[2,3-b]pyrazin-6-yl]-thiourea

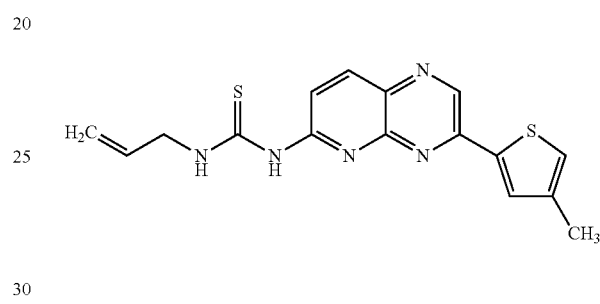

Compound 234: {5-[6-(3-Allyl-ureido)-pyrido[2,3-b]pyrazin-3-yl]-thiophen-2-ylmethyl}-carbamic acid tert-butyl ester

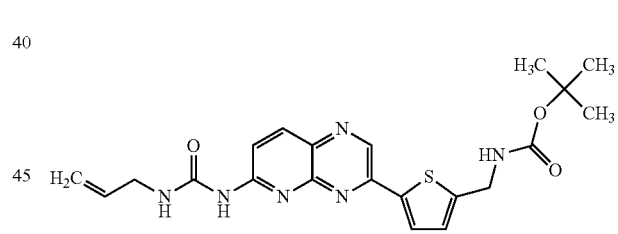

Compound 235: {5-[6-(3-Allyl-thioureido)-pyrido[2,3-b]pyrazin-3-yl]-thiophen-2-ylmethyl}-carbamic acid tert-butyl ester

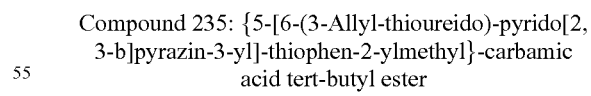
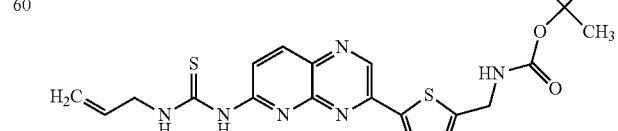

Compound 236: 1-Allyl-3-[3-(5-hydroxymethyl-thiophen-2-yl)-pyrido[2,3-b]pyrazin-6-yl]-urea

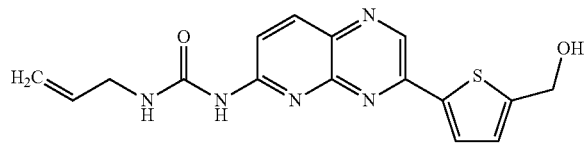 [SMILES: C=CCNC(=O)Nc1ccc2ncc(-c3ccc(CO)s3)nc2n1]

Compound 237: 1-Allyl-3-[3-(5-hydroxymethyl-thiophen-2-yl)-pyrido[2,3-b]pyrazin-6-yl]-thiourea

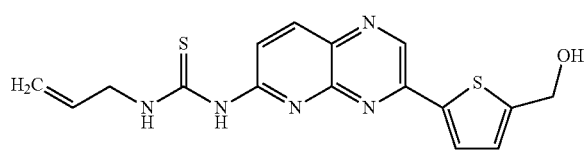 [SMILES: C=CCNC(=S)Nc1ccc2ncc(-c3ccc(CO)s3)nc2n1]

Compound 238: 5-[6-(3-Allyl i-ureido)-pyrido[2,3-b]pyrazin-3-yl]-thiophene-2-carboxylic acid

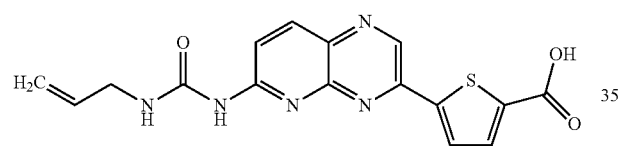

Compound 239: 5-[6-(3-Allyl-thioureido)-pyrido[2,3-b]pyrazin-3-yl]-thiophene-2-carboxylicacid

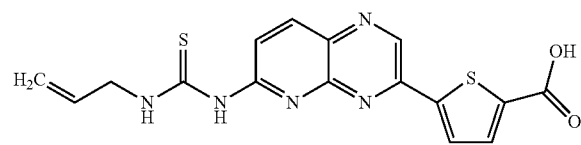 [SMILES: C=CCNC(=S)Nc1ccc2ncc(-c3ccc(C(=O)O)s3)nc2n1]

Compound 240: 4-[6-(3-Allyl-ureido)-pyrido[2,3-b]pyrazin-3-yl]-pyrazole-1-carboxylic acid tert-butyl ester

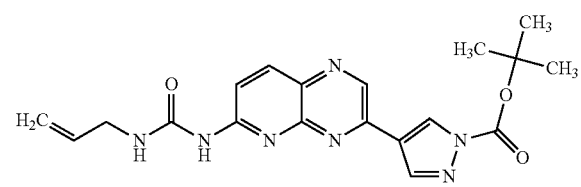 [SMILES: C=CCNC(=O)Nc1ccc2ncc(-c3cnn(C(=O)OC(C)(C)C)c3)nc2n1]

Compound 241: 4-[6-(3-Allyl-thioureido)-pyrido[2,3-b]pyrazin-3-yl]-pyrazole-1-carboxylic acid tert-butylester

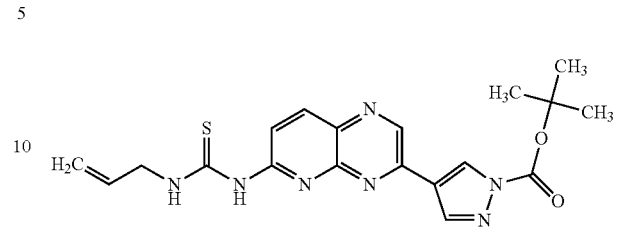

Compound 242: {4-[6-(3-Allyl-ureido)-pyrido[2,3-b]pyrazin-3-yl]-pyrazol-1-yl}-acetic acid ethyl ester

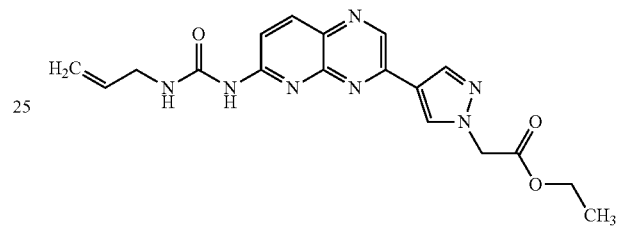

Compound 243: {4-[6-(3-Allyl-thioureido)-pyrido[2,3-b]pyrazin-3-yl]-pyrazol-1-yl}-acetic acid ethyl ester

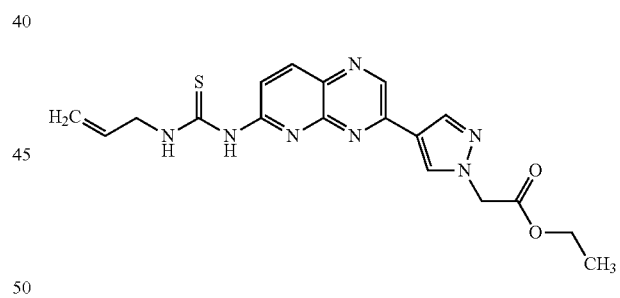

Compound 244: 3-{4-[6-(3-Allyl-ureido)-pyrido[2,3-b]pyrazin-3-yl]-pyrazol-1-yl}-propionamide

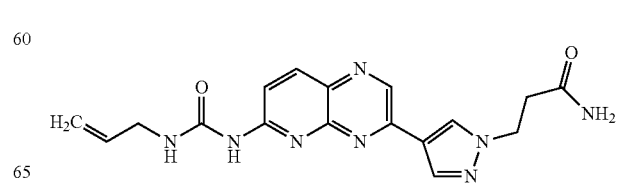

Compound 245: 3-{4-[6-(3-Allyl-thioureido)-pyrido[2,3-b]pyrazin-3-yl]-pyrazol-1-yl}-propionamide

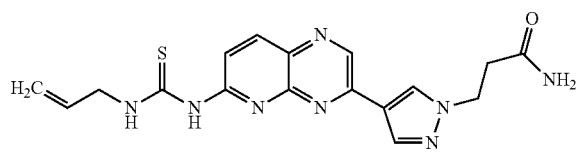 [SMILES: C=CCNC(=S)Nc1ccc2ncc(-c3cnn(CCC(N)=O)c3)nc2n1]

Compound 246: (2-{4-[6-(3-Allyl-ureido)-pyrido[2,3-b]pyrazin-3-yl]-pyrazol-1-yl}-ethyl)-carbamic acid tert-butyl ester

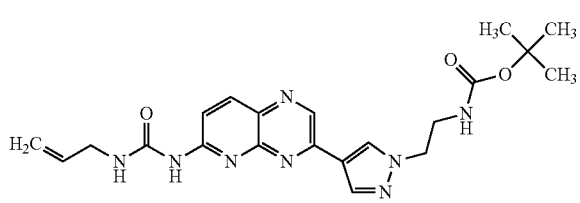 [SMILES: C=CCNC(=O)Nc1ccc2ncc(-c3cnn(CCNC(=O)OC(C)(C)C)c3)nc2n1]

Compound 247: (2-{4-[6-(3-Allyl-thioureido)-pyrido[2,3-b]pyrazin-3-yl]-pyrazol-1-yl}-ethyl)-carbamic acid tert-butyl ester

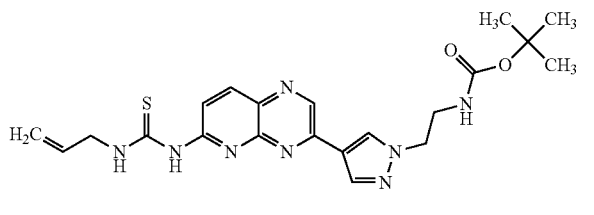 [SMILES: C=CCNC(=S)Nc1ccc2ncc(-c3cnn(CCNC(=O)OC(C)(C)C)c3)nc2n1]

Compound 248: 5-[6-(3-Allyl-ureido)-pyrido[2,3-b]pyrazin-3-yl]-2-methyl-furan-3-carboxylic acid methyl ester

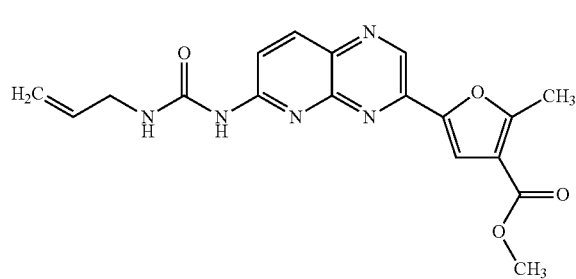 [SMILES: C=CCNC(=O)Nc1ccc2ncc(-c3cc(C(=O)OC)c(C)o3)nc2n1]

Compound 249: 5-[6-(3-Allyl-thioureido)-pyrido[2,3-b]pyrazin-3-yl]-2-methyl-furan-3-carboxylic acid methyl ester

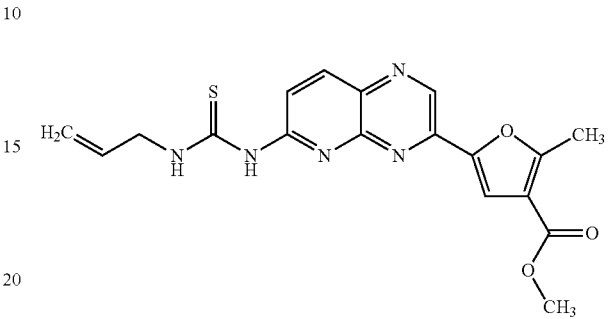

Compound 250: 1-Allyl I-3-[3-(5-isopropyl-furan-2-yl)-pyrido[2,3-b]pyrazin-6-yl]urea

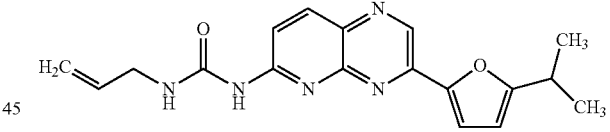

Compound 251: 1-Allyl-3-[3-(5-isopropyl-furan-2-yl)-pyrido[2,3-b]pyrazin-6-yl]-thiourea

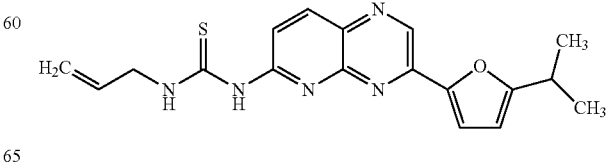

Compound 252: 1-[3-(5-Ethoxymethoxymethyl-furan-2-yl)-pyrido[2,3-b]pyrazin-6-yl]-3-Allyl-urea

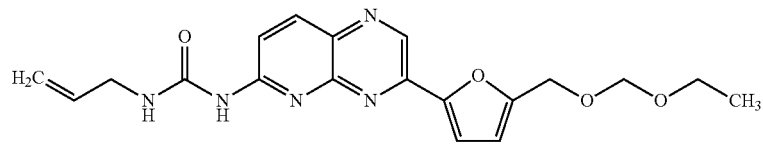 [SMILES: C=CCNC(=O)Nc1ccc2ncc(-c3ccc(COCOCC)o3)nc2n1]

Compound 253: 1-[3-(5-Ethoxymethoxymethyl-furan-2-yl)-pyrido[2,3-b]pyrazin-6-yl]-3-Allyl-thio-urea

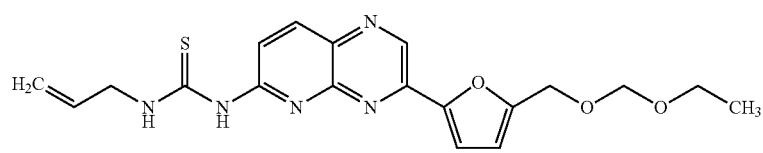 [SMILES: C=CCNC(=S)Nc1ccc2ncc(-c3ccc(COCOCC)o3)nc2n1]

Compound 254: 1-Allyl-3-[3-(5-trimethylsilanyl-furan-2-yl)-pyrido[2,3-b]pyrazin-6-yl]-urea

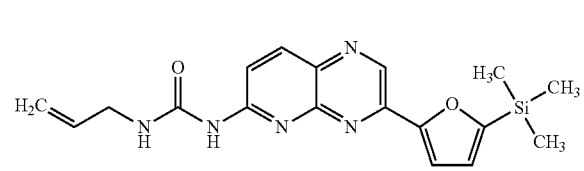 [SMILES: C=CCNC(=O)Nc1ccc2ncc(-c3ccc([Si](C)(C)C)o3)nc2n1]

Compound 255: 1-Allyl-3-[3-(5-trimethylsilanyl-furan-2-yl)-pyrido[2,3-b]pyrazin-6-yl]-thiourea

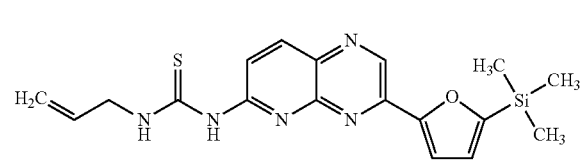 [SMILES: C=CCNC(=S)Nc1ccc2ncc(-c3ccc([Si](C)(C)C)o3)nc2n1]

Compound 256: 1-Allyl-3-[3-(5-methyl-furan-2-yl)-pyrido[2,3-b]pyrazin-6-yl]urea

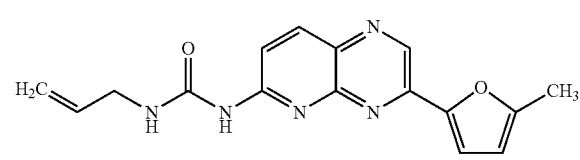 [SMILES: C=CCNC(=O)Nc1ccc2ncc(-c3ccc(C)o3)nc2n1]

Compound 257: 1-Allyl-3-[3-(5-methyl-furan-2-yl)-pyrido[2,3-b]pyrazin-6-yl]-thiourea

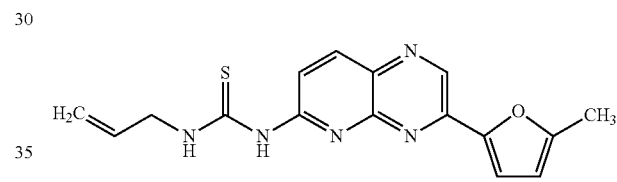

Compound 258: 1-Allyl-3-(3-thiazol-5-yl-pyrido[2,3-b]pyrazin-6-yl)-urea

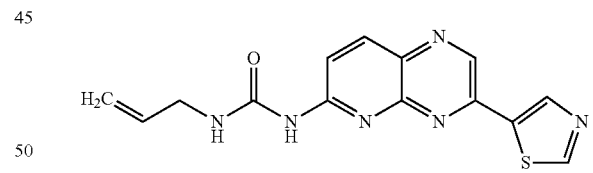

Compound 259: 1-Allyl-3-(3-thiazol-5-yl-pyrido[2,3-b]pyrazin-6-yl)-thiourea

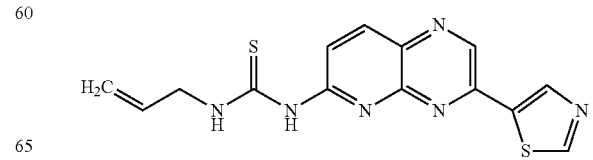

Compound 260: 1-Allyl-3-[3-(2-methyl-thiazol-4-yl)-pyrido[2,3-b]pyrazin-6-yl]-urea

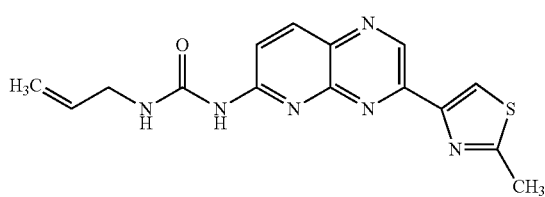

Compound 261: 1-Allyl-3-[3-(2-methyl-thiazol-4-yl)-pyrido[2,3-b]pyrazin-6-yl]-thiourea

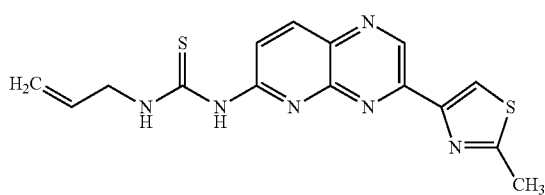 [SMILES: C=CCNC(=O)Nc1ccc2ncc(-c3csc(C)n3)nc2n1]

Compound 262: 1-Allyl-3-[3-(1-isopropyl-1H-pyrazol-3-yl)-pyrido[2,3-b]pyrazin-6-yl]-urea

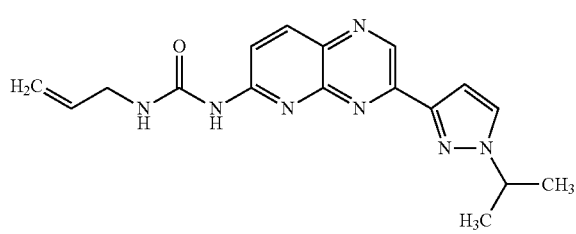 [SMILES: C=CCNC(=O)Nc1ccc2ncc(-c3ccn(C(C)C)n3)nc2n1]

Compound 263: 1-Allyl-3-[3-(1-isopropyl-1H-pyrazol-3-yl)-pyrido[2,3-b]pyrazin-6-yl]-thiourea

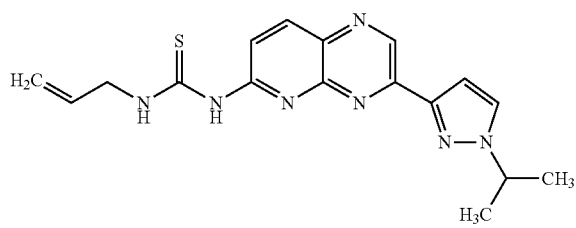 [SMILES: C=CCNC(=S)Nc1ccc2ncc(-c3ccn(C(C)C)n3)nc2n1]

Compound 264: 1-Allyl-3-[3-(5-hydroxymethyl-thiophen-3-yl)-pyrido[2,3-b]pyrazin-6-yl]-urea

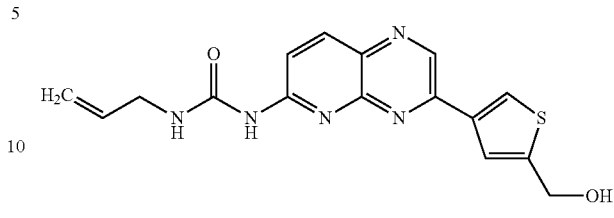

Compound 265: 1-Allyl-3-[3-(5-hydroxymethyl-thiophen-3-yl)-pyrido[2,3-b]pyrazin-6-yl]-thiourea

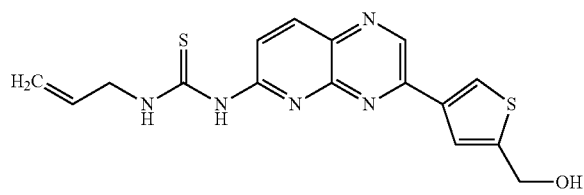 [SMILES: C=CCNC(=O)Nc1ccc2ncc(-c3csc(CO)c3)nc2n1]

Compound 266: 4-[6-(3-Allyl-ureido)-pyrido[2,3-b]pyrazin-3-yl]-thiophene-2-carboxylic acid ethyl ester

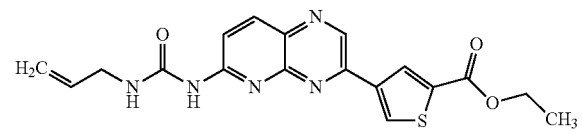 [SMILES: C=CCNC(=O)Nc1ccc2ncc(-c3csc(C(=O)OCC)c3)nc2n1]

Compound 267: 4-[6-(3-Allyl-thioureido)-pyrido[2,3-b]pyrazin-3-yl]-thiophene-2-carboxylic acid ethyl ester Compound 268: 4-[6-(3-Allyl-ureido)-pyrido[2,3-b]pyrazin-3-yl]-thiophene-2-carboxylic acid

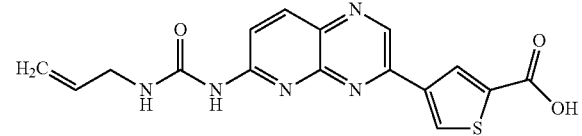

Compound 269: 4-[6-(3-Allyl-thioureido)-pyrido[2,3-b]pyrazin-3-yl]-thiophene-2-carboxylic acid

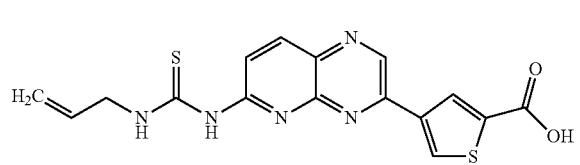 [SMILES: C=CCNC(=O)Nc1ccc2ncc(-c3csc(C(=O)O)c3)nc2n1]

Compound 270: 1-Allyl-3-[3-(4-methyl-thiazol-2-yl)-pyrido[2,3-b]pyrazin-6-yl]-urea

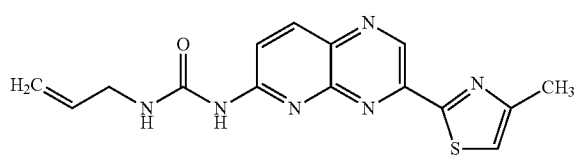 [SMILES: C=CCNC(=O)Nc1ccc2ncc(-c3nc(C)cs3)nc2n1]

Compound 271: 1-Allyl-3-[3-(4-methyl-thiazol-2-yl)-pyrido[2,3-b]pyrazin-6-yl]-thiourea

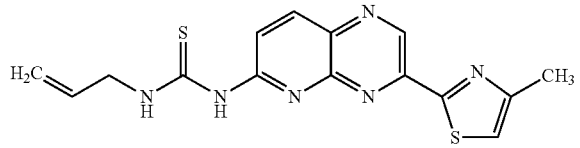 [SMILES: C=CCNC(=S)Nc1ccc2ncc(-c3nc(C)cs3)nc2n1]

Compound 272: 1-Allyl-3-(3-furan-3-yl-pyrido[2,3-b]pyrazin-6-yl)-urea

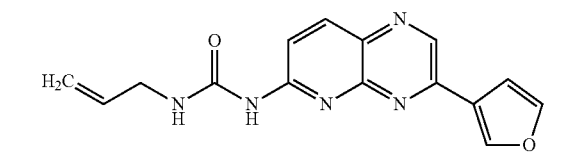 [SMILES: C=CCNC(=O)Nc1ccc2ncc(-c3ccoc3)nc2n1]

Compound 273: 1Allyl-3-(3-furan-3-yl-pyrido[2,3-b]pyrazin-6-yl)-thiourea

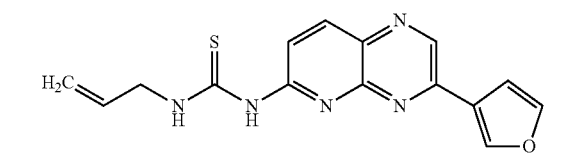

Compound 274: 1-Allyl-3-[3-(1-methyl-1H-imidazol-4-yl)-pyrido[2,3-b]pyrazin-6-yl]-urea

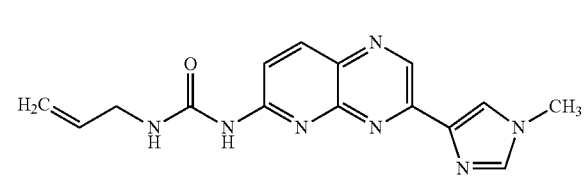 [SMILES: C=CCNC(=O)Nc1ccc2ncc(-c3cn(C)cn3)nc2n1]

Compound 276: 1-Allyl-3-[3-(1-methyl-1H-imidazol-4-yl)-pyrido[2,3-b]pyrazin-6-yl]-thiourea

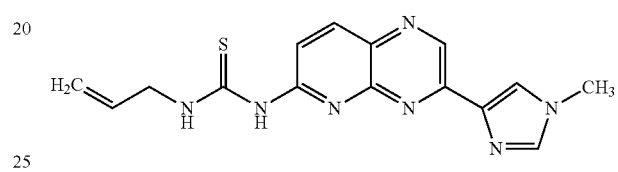

Compound 276: 1-Allyl-3-[3-(1-methyl-1H-[1,2,3]triazol-4-yl)-pyrido[2,3-b]pyrazin-6-yl]-urea

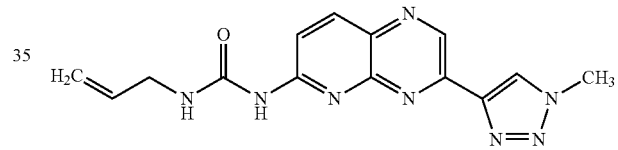

Compound 277: 1-Allyl-3-[3-(1-methyl-1H-[1,2,3]triazol-4-yl)-pyrido[2,3-b]pyrazin-6-yl]-thiourea

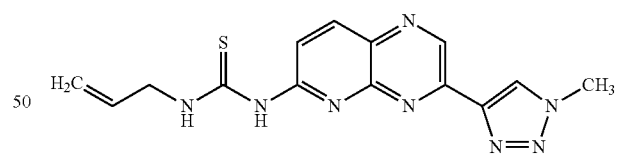

Compound 278: 1-Allyl I-3-(3-isoxazol-4-yl-pyrido[2,3-b]pyrazin-6-yl)-urea

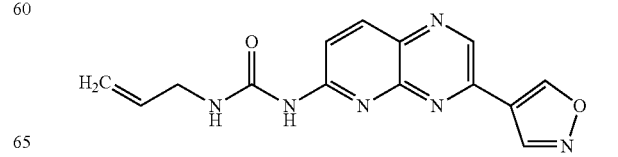

Compound 279: 1-Allyl-3-(3-isoxazol-4-yl-pyrido[2,3-b]pyrazin-6-yl)-thiourea

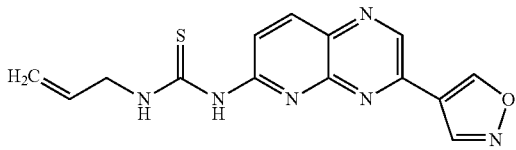 [SMILES: C=CCNC(=S)Nc1ccc2ncc(-c3cnoc3)nc2n1]

Compound 280: 1-Allyl-3-[3-(1H-imidazol-2-yl)-pyrido[2,3-b]pyrazin-6-yl]-urea

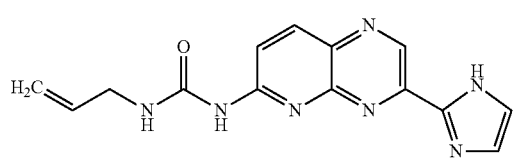 [SMILES: C=CCNC(=O)Nc1ccc2ncc(-c3ncc[nH]3)nc2n1]

Compound 281: 1-Allyl 1-3-[3-(1H-imidazol-2-yl)-pyrido[2,3-b]pyrazin-6-yl]-thiourea

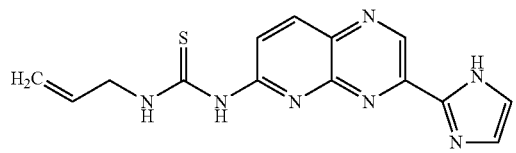

Compound 282: 1-[3-(6-Chloro-pyridin-2-yl)-pyrido[2,3-b]pyrazin-6-yl]-3-allyl-urea

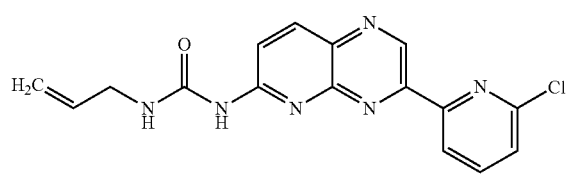 [SMILES: C=CCNC(=O)Nc1ccc2ncc(-c3cccc(Cl)n3)nc2n1]

Compound 283: 1-[3-(6-Chloro-pyridin-2-yl)-pyrido[2,3-b]pyrazin-6-yl]-3-allyl-thiourea

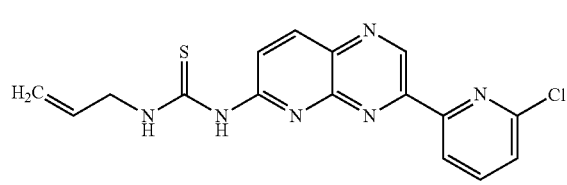

Compound 284: 1-Cyclopentyl-3-[3-(5-methyl-thiophen-2-yl)-pyrido[2,3-b]pyrazin-6-yl]-urea

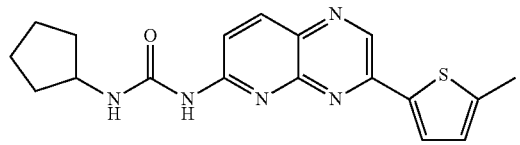 [SMILES: Cc1ccc(-c2cnc3ccc(NC(=O)NC4CCCC4)nc3n2)s1]

Compound 285: 1-Cyclopentyl-3-[3-(5-methyl-thiophen-2-yl)-pyrido[2,3-b]pyrazin-6-yl]-thiourea

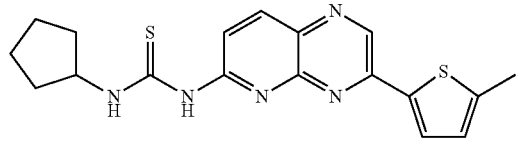 [SMILES: Cc1ccc(-c2cnc3ccc(NC(=S)NC4CCCC4)nc3n2)s1]

Compound 286: 1-Cyclopentyl-3-[3-(4-methyl-thiophen-2-yl)-pyrido[2,3-b]pyrazin-6-yl]-urea

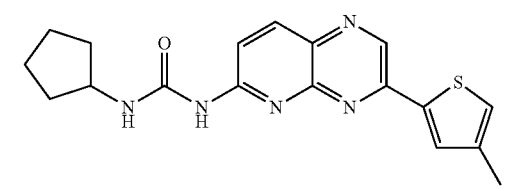 [SMILES: Cc1csc(-c2cnc3ccc(NC(=O)NC4CCCC4)nc3n2)c1]

Compound 287: Compound 220: 1-Cyclopentyl-3-[3-(4-methyl-thiophen-2-yl)-pyrido[2,3-b]pyrazin-6-yl]-thiourea

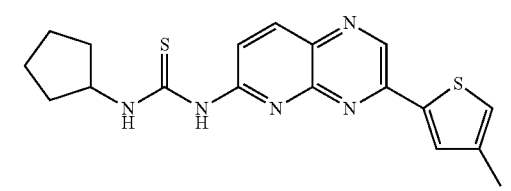

Compound 288: {5-[6-(3-Cyclopentyl-ureido)-pyrido[2,3-b]pyrazin-3-yl]-thiophen-2-ylmethyl}-carbamic acid tert-butyl ester

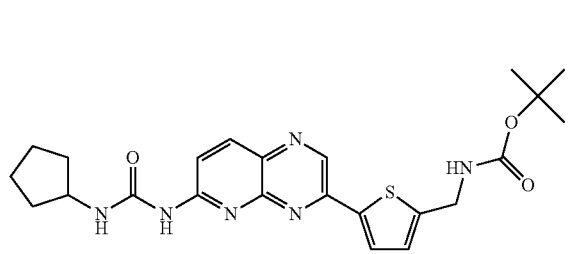 [SMILES: CC(C)(C)OC(=O)NCc1ccc(-c2cnc3ccc(NC(=O)NC4CCCC4)nc3n2)s1]

Compound 289: {5-[6-(3-Cyclopentyl-thioureido)-pyrido[2,3-b]pyrazin-3-yl]-thiophen-2-ylmethyl}-carbamic acid tert-butyl ester

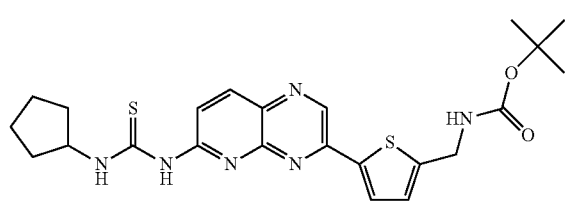 [SMILES: CC(C)(C)OC(=O)NCc1ccc(-c2cnc3ccc(NC(=S)NC4CCCC4)nc3n2)s1]

Compound 290: 1-Cyclopentyl-3-[3-(5-hydroxymethyl-thiophen-2-yl)-pyrido[2,3-b]pyrazin-6-yl]-urea

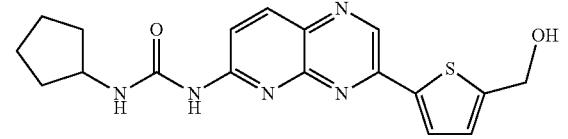 [SMILES: O=C(Nc1ccc2ncc(-c3ccc(CO)s3)nc2n1)NC1CCCC1]

Compound 291: 1-Cyclopentyl-3-[3-(5-hydroxymethyl-thiophen-2-yl)-pyrido[2,3-b]pyrazin-6-yl]-thiourea

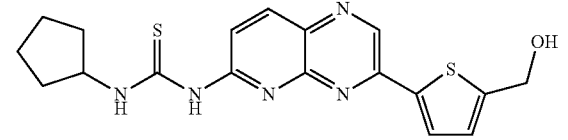 [SMILES: OCc1ccc(-c2cnc3ccc(NC(=S)NC4CCCC4)nc3n2)s1]

Compound 292: 5-[6-(3-Cyclopentyl-ureido)-pyrido[2,3-b]pyrazin-3-yl]-thiophene-2-carboxylic acid

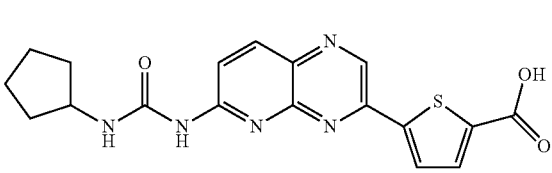 [SMILES: O=C(Nc1ccc2ncc(-c3ccc(C(=O)O)s3)nc2n1)NC1CCCC1]

Compound 293: 5-[6-(3-Cyclopentyl-thioureido)-pyrido[2,3-b]pyrazin-3-yl]-thiophene-2-carboxylic acid

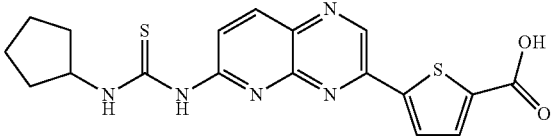 [SMILES: O=C(O)c1ccc(-c2cnc3ccc(NC(=S)NC4CCCC4)nc3n2)s1]

Compound 294: 4-[6-(3-Cyclopentyl-ureido)-pyrido[2,3-b]pyrazin-3-yl]-pyrazole-1-carboxylic acid tert-butyl ester

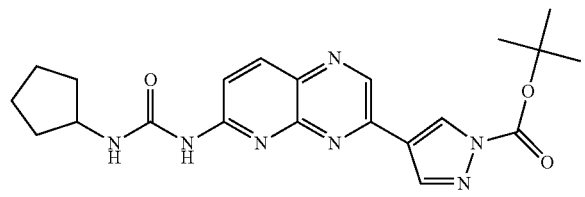

Compound 295: {4-[6-(3-Cyclopentyl-ureido)-pyrido[2,3-b]pyrazin-3-yl]-pyrazol-1-yl}-acetic acid ethyl ester

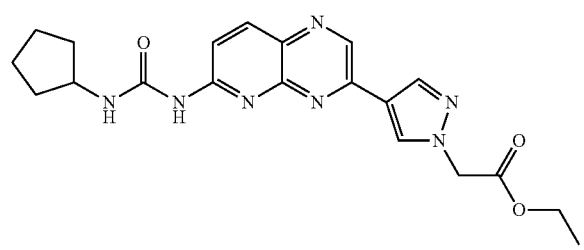 [SMILES: CCOC(=O)Cn1cc(-c2cnc3ccc(NC(=O)NC4CCCC4)nc3n2)cn1]

Compound 296: {4-[6-(3-Cyclopentyl-thioureido)-pyrido[2,3-b]pyrazin-3-yl]-pyrazol-1-yl}-acetic acid ethyl ester

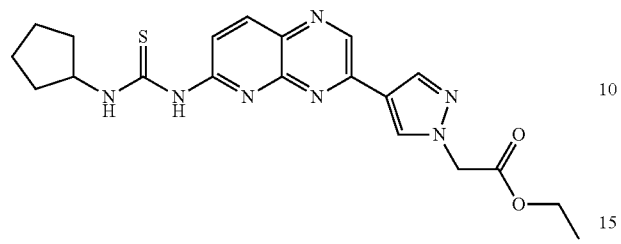

Compound 297: 3-{4-[6-(3-Cyclopentyl-ureido)-pyrido[2,3-b]pyrazin-3-yl]-pyrazol-1-yl}-propionamide

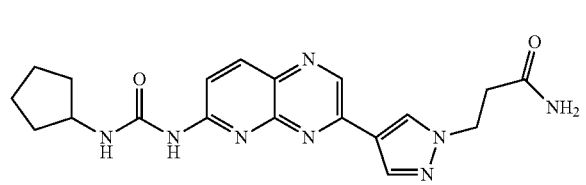 [SMILES: NC(=O)CCn1cc(-c2cnc3ccc(NC(=O)NC4CCCC4)nc3n2)cn1]

Compound 298: 3-{4-[6-(3-Cyclopentyl-thioureido)-pyrido[2,3-b]pyrazin-3-yl]-pyrazol-1-yl}-propionamide

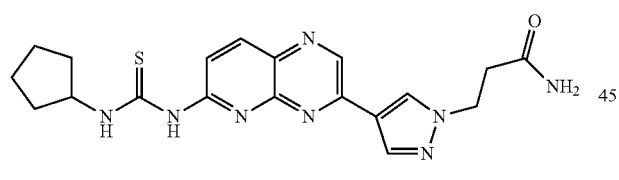

Compound 299: (2-{4-[6-(3-Cyclopentyl-thioureido)-pyrido[2,3-b]pyrazin-3-yl]-pyrazol-1-yl}-ethyl)-carbamic acid tert-butyl ester

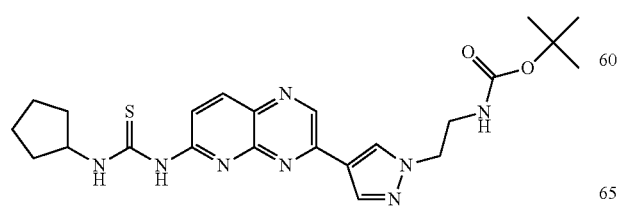

Compound 300: 2-Methyl-5-[6-(3-Cyclopentyl-ureido)-pyrido[2,3-b]pyrazin-3-yl]-furan-3-carboxylic acid methyl ester

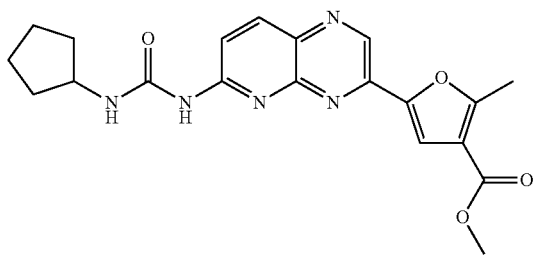 [SMILES: COC(=O)c1cc(-c2cnc3ccc(NC(=O)NC4CCCC4)nc3n2)oc1C]

Compound 301: 2-Methyl-5-[6-(3-Cyclopentyl-thioureido)-pyrido[2,3-b]pyrazin-3-yl]-furan-3-carboxylic acid methyl ester

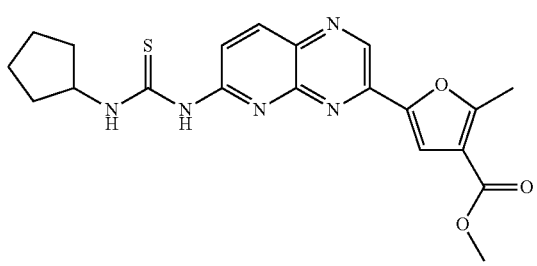 [SMILES: COC(=O)c1cc(-c2cnc3ccc(NC(=S)NC4CCCC4)nc3n2)oc1C]

Compound 302: 1-[3-(5-Isopropyl-furan-2-yl)-pyrido[2,3-b]pyrazin-6-yl]-3-cyclopentyl-urea

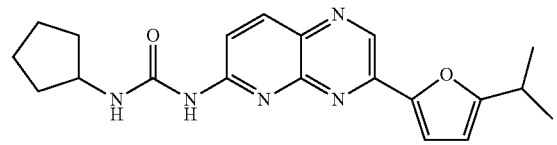 [SMILES: CC(C)c1ccc(-c2cnc3ccc(NC(=S)NC4CCCC4)nc3n2)o1]

Compound 303: 1-[3-(5-Isopropyl-furan-2-yl)-pyrido[2,3-b]pyrazin-6-yl]-3-cyclopentyl-thiourea

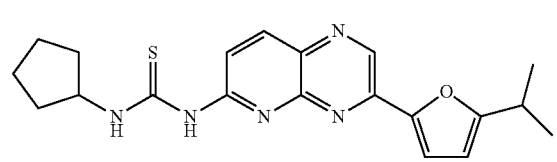

Compound 304: 1-[3-(5-Ethoxymethoxymethyl-furan-2-yl)-pyrido[2,3-b]pyrazin-6-yl]-3-cyclopentyl-urea

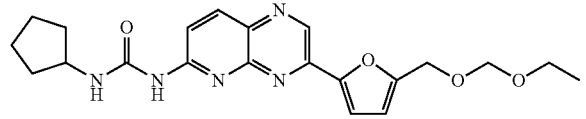 [SMILES: CCOCOCc1ccc(-c2cnc3ccc(NC(=O)NC4CCCC4)nc3n2)o1]

Compound 305: 1-[3-(5-Ethoxymethoxymethyl-furan-2-yl)-pyrido[2,3-b]pyrazin-6-yl]-3-cyclopentyl-thiourea

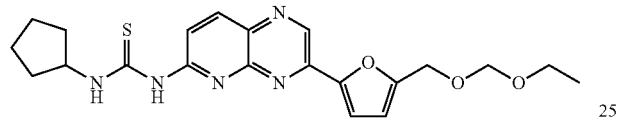

Compound 306: 1-Cyclopentyl-3-[3-(5-trimethylsilanyl-furan-2-yl)-pyrido[2,3-b]pyrazin-6-yl]-urea

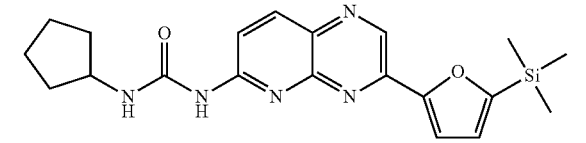 [SMILES: C[Si](C)(C)c1ccc(-c2cnc3ccc(NC(=O)NC4CCCC4)nc3n2)o1]

Compound 307: 1-Cyclopentyl-3-[3-(5-trimethylsilanyl-furan-2-yl)-pyrido[2,3-b]pyrazin-6-yl]-thiourea

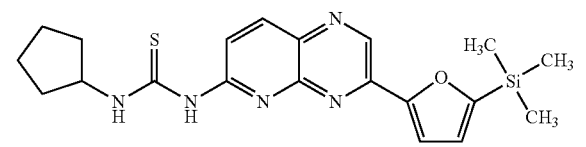 [SMILES: C[Si](C)(C)c1ccc(-c2cnc3ccc(NC(=S)NC4CCCC4)nc3n2)o1]

Compound 308: 1-Cyclopentyl I-3-[3-(5-methyl-furan-2-yl)-pyrido[2,3-b]pyrazin-6-yl]-urea

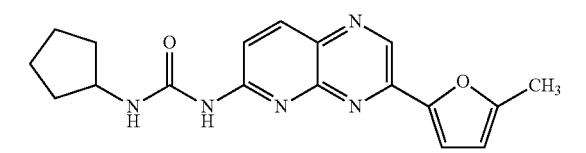 [SMILES: Cc1ccc(-c2cnc3ccc(NC(=O)NC4CCCC4)nc3n2)o1]

Compound 309: 1-Cyclopentyl-3-[3-(5-methyl-furan-2-yl)-pyrido[2,3-b]pyrazin-6-yl]-thiourea

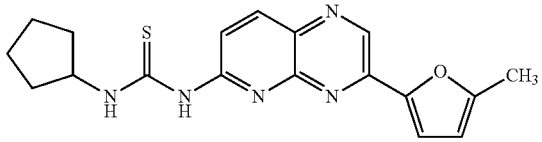 [SMILES: Cc1ccc(-c2cnc3ccc(NC(=S)NC4CCCC4)nc3n2)o1]

Compound 310: 1-Cyclopentyl-3-(3-thiazol-5-yl-pyrido[2,3-b]pyrazin-6-yl)-urea

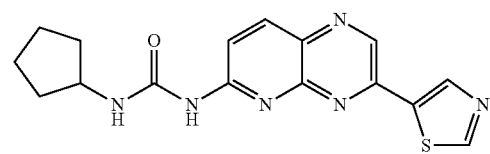 [SMILES: O=C(Nc1ccc2ncc(-c3cncs3)nc2n1)NC1CCCC1]

Compound 311: 1-Cyclopentyl I-3-(3-thiazol-5-yl-pyrido[2,3-b]pyrazin-6-yl)-thiourea

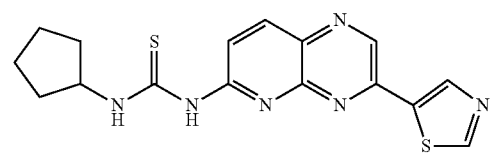 [SMILES: S=C(Nc1ccc2ncc(-c3cncs3)nc2n1)NC1CCCC1]

Compound 312: 1-Cyclopentyl I-3-[3-(2-methyl-thiazol-4-yl)-pyrido[2,3-b]pyrazin-6-yl]-urea

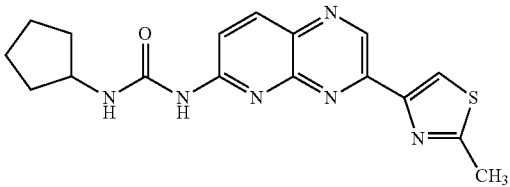 [SMILES: Cc1nc(-c2cnc3ccc(NC(=O)NC4CCCC4)nc3n2)cs1]

Compound 313: 1-Cyclopentyl-3-[3-(2-methyl-thiazol-4-yl)-pyrido[2,3-b]pyrazin-6-yl]-thiourea

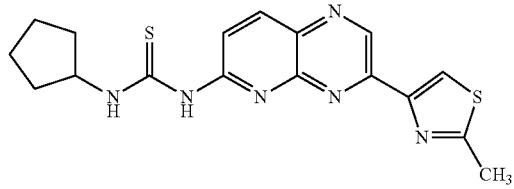 [SMILES: Cc1nc(-c2cnc3ccc(NC(=S)NC4CCCC4)nc3n2)cs1]

Compound 314: 1-Cyclopentyl-3-[3-(1-isopropyl-1H-pyrazol-3-yl)-pyrido[2,3-b]pyrazin-6-yl]-urea

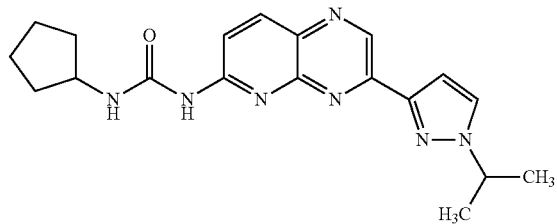 [SMILES: CC(C)n1ccc(-c2cnc3ccc(NC(=O)NC4CCCC4)nc3n2)n1]

Compound 315: 1-Cyclopentyl-3-[3-(1-isopropyl-1H-pyrazol-3-yl)-pyrido[2,3-b]pyrazin-6-yl]-thiourea

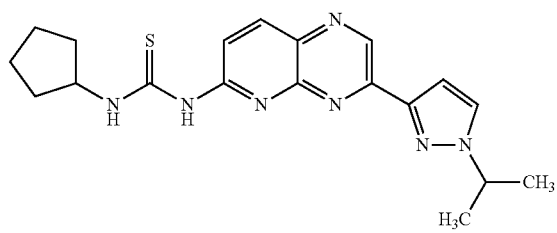 [SMILES: CC(C)n1ccc(-c2cnc3ccc(NC(=S)NC4CCCC4)nc3n2)n1]

Compound 316: 1-Cyclopentyl-3-[3-(5-hydroxymethyl-thiophen-3-yl)-pyrido[2,3-b]pyrazin-6-yl]-urea

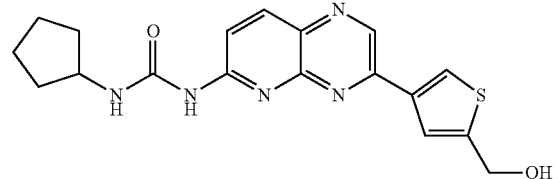 [SMILES: O=C(Nc1ccc2ncc(-c3csc(CO)c3)nc2n1)NC1CCCC1]

Compound 317: 1-Cyclopentyl-3-[3-(5-hydroxymethyl-thiophen-3-yl)-pyrido[2,3-b]pyrazin-6-yl]-thiourea

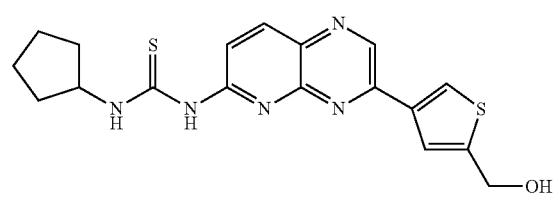

Compound 318: 4-[6-(3-Cyclopentyl-ureido)-pyrido[2,3-b]pyrazin-3-yl]-thiophene-2-carboxylic acid ethyl ester

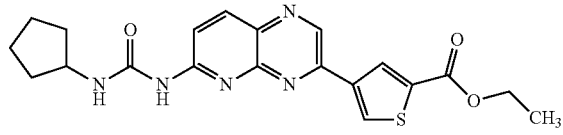

Compound 319: 4-[6-(3-Cyclopentyl-thioureido)-pyrido[2,3-b]pyrazin-3-yl]-thiophene-2-carboxylic acid ethyl ester

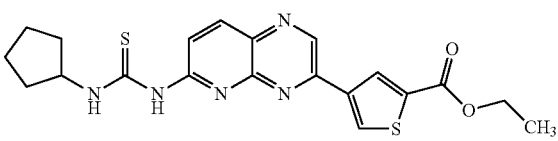 [SMILES: CCOC(=O)c1cc(-c2cnc3ccc(NC(=O)NC4CCCC4)nc3n2)cs1]

Compound 320: 4-[6-(3-Cyclopentyl-ureido)-pyrido[2,3-b]pyrazin-3-yl]-thiophene-2-carboxylic acid

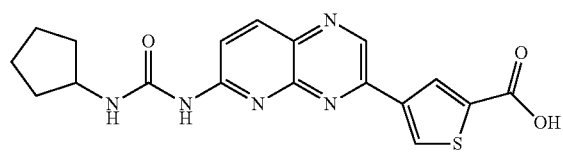 [SMILES: O=C(Nc1ccc2ncc(-c3csc(C(=O)O)c3)nc2n1)NC1CCCC1]

Compound 321: 4-[6-(3-Cyclopentyl l-thioureido)-pyrido[2,3-b]pyrazin-3-yl]-thiophene-2-carboxylic acid

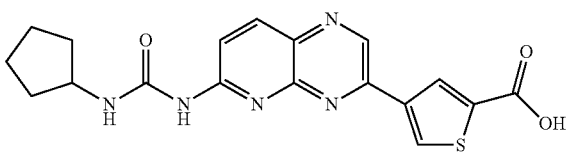 [SMILES: O=C(Nc1ccc2ncc(-c3csc(C(=O)O)c3)nc2n1)NC1CCCC1]

Compound 322: 1-Cyclopentyl-3-[3-(4-methyl-thiazol-2-yl)-pyrido[2,3-b]pyrazin-6-yl]-urea

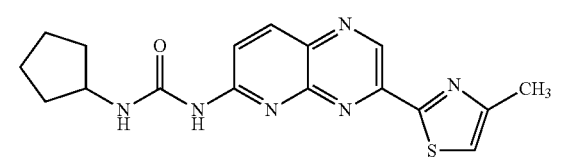

Compound 323: 1-Cyclopentyl-3-[3-(4-methyl-thiazol-2-yl)-pyrido[2,3-b]pyrazin-6-yl]-thiourea

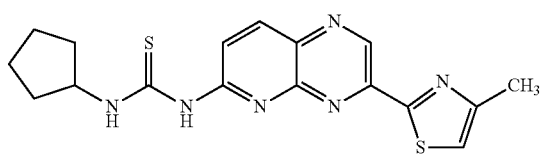 [SMILES: Cc1csc(-c2cnc3ccc(NC(=O)NC4CCCC4)nc3n2)n1]

Compound 324: 1-Cyclopentyl-3-(3-furan-3-yl-pyrido[2,3-b]pyrazin-6-yl)-urea

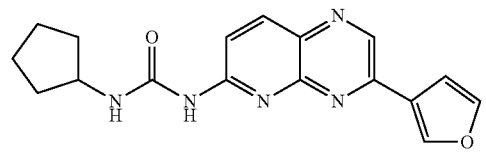 [SMILES: O=C(Nc1ccc2ncc(-c3ccoc3)nc2n1)NC1CCCC1]

Compound 325: 1-Cyclopentyl-3-(3-furan-3-yl-pyrido[2,3-b]pyrazin-6-yl)-thiourea

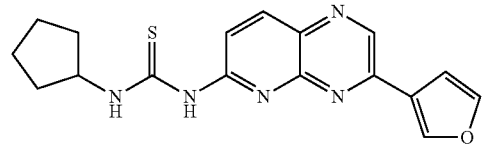 [SMILES: S=C(Nc1ccc2ncc(-c3ccoc3)nc2n1)NC1CCCC1]

Compound 326: 1-Cyclopentyl-3-[3-(1-methyl-1H-imidazol-4-yl)-pyrido[2,3-b]pyrazin-6-yl]-urea

Compound 327: 1-Cyclopentyl-3-[3-(1-methyl-1H-imidazol-4-yl)-pyrido[2,3-b]pyrazin-6-yl]-thiourea

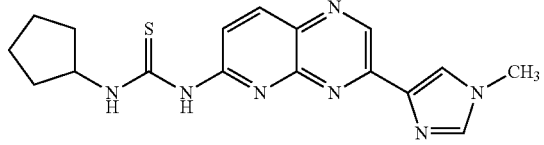 [SMILES: Cn1cnc(-c2cnc3ccc(NC(=S)NC4CCCC4)nc3n2)c1]

Compound 328: 1-Cyclopentyl-3-[3-(1-methyl-1H-[1,2,3]triazol-4-yl)-pyrido[2,3-b]pyrazin-6-yl]-urea

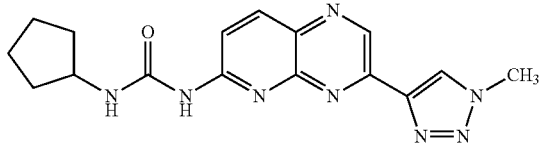 [SMILES: Cn1cc(-c2cnc3ccc(NC(=O)NC4CCCC4)nc3n2)nn1]

Compound 329: 1-Cyclopentyl-3-[3-(1-methyl-1H-[1,2,3]triazol-4-yl)-pyrido[2,3-b]pyrazin-6-yl]-thiourea

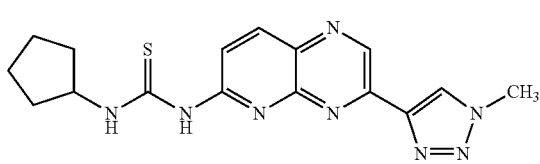 [SMILES: Cn1cc(-c2cnc3ccc(NC(=S)NC4CCCC4)nc3n2)nn1]

Compound 330: 1-Cyclopentyl-3-(3-isoxazol-4-yl-pyrido[2,3-b]pyrazin-6-yl)-urea

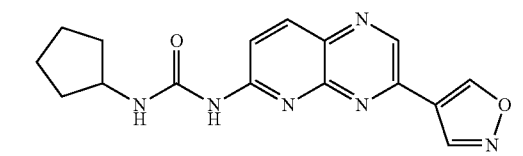

Compound 331: 1-Cyclopentyl I-3-(3-isoxazol-4-yl-pyrido[2,3-b]pyrazin-6-yl)-thiourea

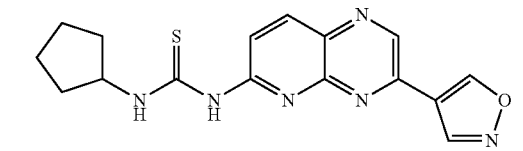 [SMILES: O=C(Nc1ccc2ncc(-c3cnoc3)nc2n1)NC1CCCC1]

Compound 332: 1-Cyclopentyl-3-[3-(1H-imidazol-2-yl)-pyrido[2,3-b]pyrazin-6-yl]-urea

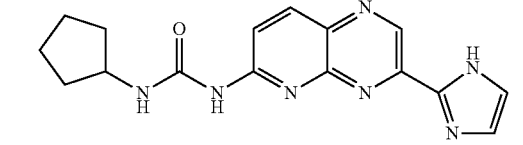 [SMILES: O=C(Nc1ccc2ncc(-c3ncc[nH]3)nc2n1)NC1CCCC1]

Compound 333: 1-Cyclopentyl-3-[3-(1H-imidazol-2-yl)-pyrido[2,3-b]pyrazin-6-yl]-thiourea

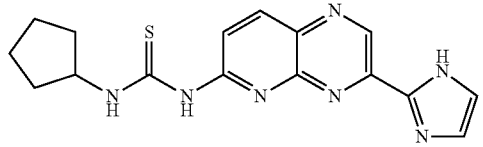 [SMILES: S=C(Nc1ccc2ncc(-c3ncc[nH]3)nc2n1)NC1CCCC1]

Compound 334: 1-[3-(6-Chloro-pyridin-2-yl)-pyrido[2,3-b]pyrazin-6-yl]-3-cyclopentyl-urea

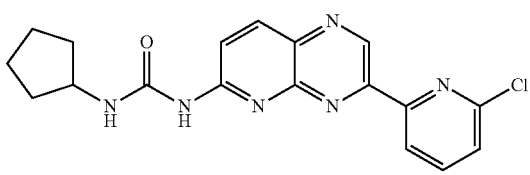 [SMILES: O=C(Nc1ccc2ncc(-c3cccc(Cl)n3)nc2n1)NC1CCCC1]

Compound 335: 1-[3-(6-Chloro-pyridin-2-yl)-pyrido[2,3-b]pyrazin-6-yl]-3-cyclopentyl-thiourea

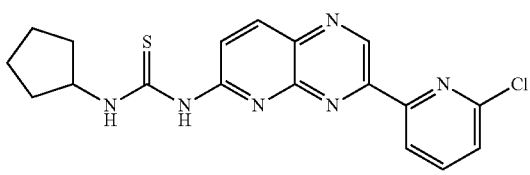

Compound 336: 1-Cyclopropyl-3-[3-(5-methyl-thiophen-2-yl)-pyrido[2,3-b]pyrazin-6-yl]-urea

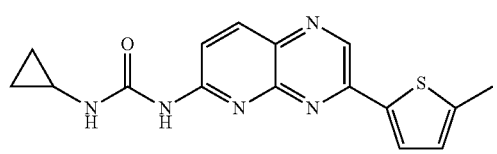 [SMILES: Cc1ccc(-c2cnc3ccc(NC(=O)NC4CC4)nc3n2)s1]

Compound 337: 1-Cyclopropyl-3-[3-(5-methyl-thiophen-2-yl)-pyrido[2,3-b]pyrazin-6-yl]thiourea

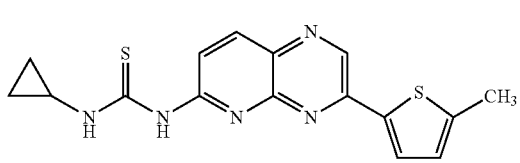 [SMILES: Cc1ccc(-c2cnc3ccc(NC(=S)NC4CC4)nc3n2)s1]

Compound 338: 1-Cyclopropyl-3-[3-(4-methyl-thiophen-2-yl)-pyrido[2,3-b]pyrazin-6-yl]-urea

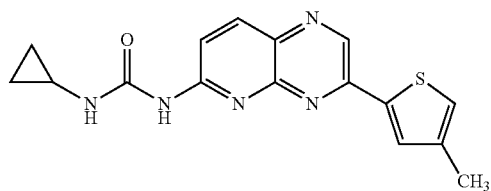

Compound 339: 1-Cyclopropyl-3-[3-(4-methyl-thiophen-2-yl)-pyrido[2,3-b]pyrazin-6-yl]-thiourea

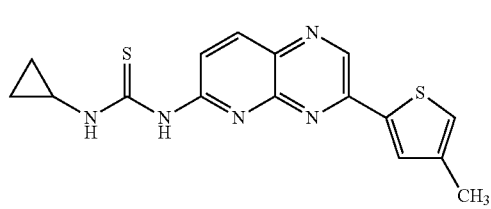 [SMILES: Cc1csc(-c2cnc3ccc(NC(=S)NC4CC4)nc3n2)c1]

Compound 340: {5-[6-(3-Cyclopropyl-ureido)-pyrido[2,3-b]pyrazin-3-yl]-thiophen-2-ylmethyl}-carbamic acid tert-butyl ester

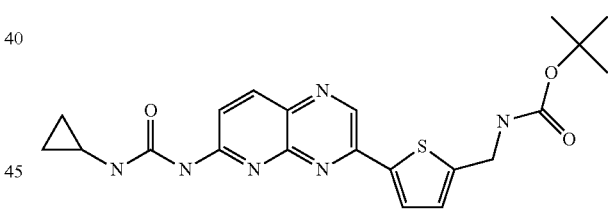

Compound 341: {5-[6-(3-Cyclopropyl-thioureido)-pyrido[2,3-b]pyrazin-3-yl]-thiophen-2-ylmethyl}-carbamic acid tert-butyl ester

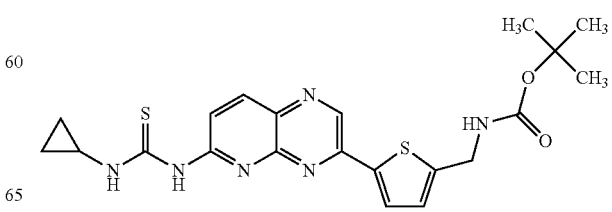

Compound 342: 1-Cyclopropyl-3-[3-(5-hydroxymethyl-thiophen-2-yl)-pyrido[2,3-b]pyrazin-6-yl]-urea

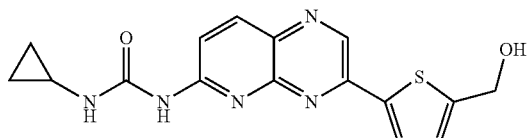

Compound 343: 1-Cyclopropyl-3-[3-(5-hydroxymethyl-thiophen-2-yl)-pyrido[2,3-b]pyrazin-6-yl]-thiourea

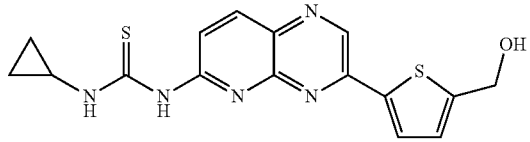 [SMILES: OCc1ccc(-c2cnc3ccc(NC(=S)NC4CC4)nc3n2)s1]

Compound 344: 5-[6-(3-Cyclopropyl-ureido)-pyrido[2,3-b]pyrazin-3-yl]-thiophene-2-carboxylic acid

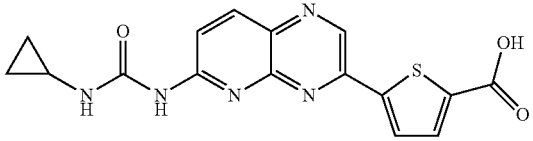 [SMILES: O=C(Nc1ccc2ncc(-c3ccc(C(=O)O)s3)nc2n1)NC1CC1]

Compound 345: 5-[6-(3-Cyclopropyl-thioureido)-pyrido[2,3-b]pyrazin-3-yl]-thiophene-2-carboxylicacid

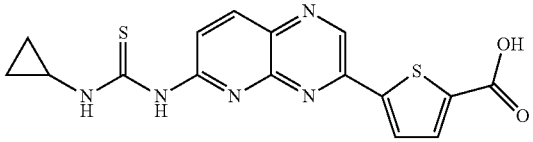 [SMILES: O=C(O)c1ccc(-c2cnc3ccc(NC(=S)NC4CC4)nc3n2)s1]

Compound 346: 4-[6-(3-Cyclopropyl-ureido)-pyrido[2,3-b]pyrazin-3-yl]-pyrazole-1-carboxylic acid tert-butyl ester

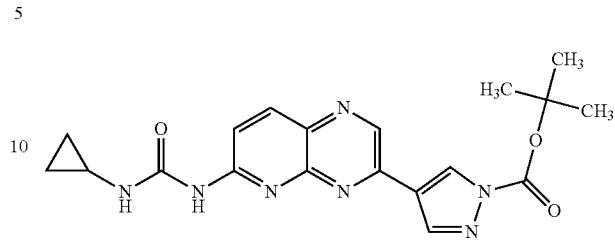

Compound 347: 4-[6-(3-Cyclopropyl-thioureido)-pyrido[2,3-b]pyrazin-3-yl]-pyrazole-1-carboxylic acid tert-butylester

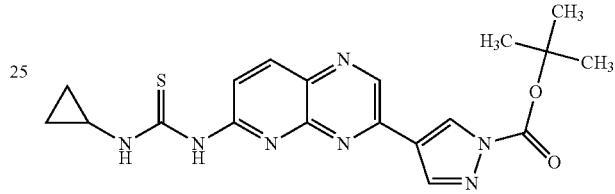

Compound 348: {4-[6-(3-Cyclopropyl-ureido)-pyrido[2,3-b]pyrazin-3-yl]-pyrazol-1-yl}-acetic acid ethyl ester

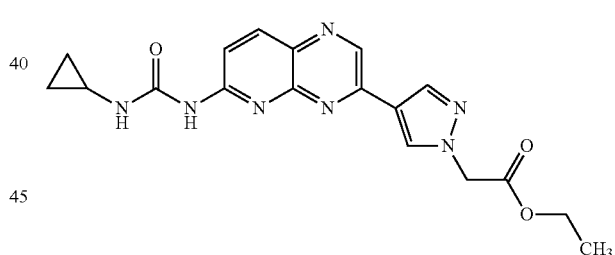

Compound 349: {4-[6-(3-Cyclopropyl-thioureido)-pyrido[2,3-b]pyrazin-3-yl]-pyrazol-1-yl}-acetic acid ethyl ester

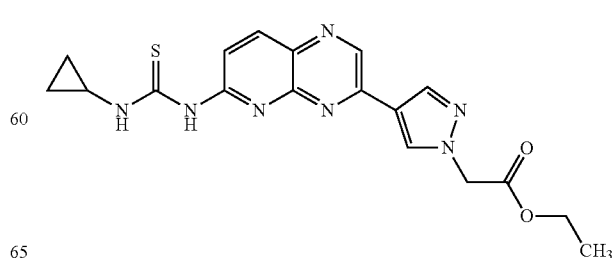

Compound 350: 3-{-4-[6-(3-Cyclopropyl-ureido)-pyrido[2,3-b]pyrazin-3-yl]-pyrazol-1-yl}-propionamide

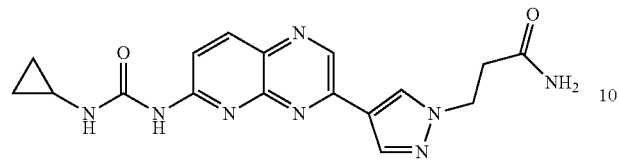

Compound 351: 3-{4-[6-(3-Cyclopropyl-thioureido)-pyrido[2,3-b]pyrazin-3-yl]-pyrazol-1-yl}-propionamide

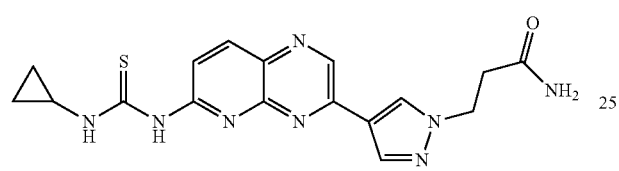

Compound 352: (2-{4-[6-(3-Cyclopropyl-ureido)-pyrido[2,3-b]pyrazin-3-yl]-pyrazol-1-yl}-ethyl)-carbamic acid tert-butyl ester

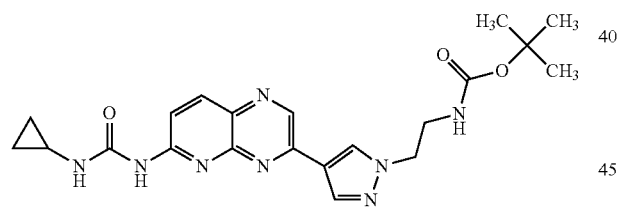

Compound 353: (2-{4-[6-(3-Cyclopropyl-thioureido)-pyrido[2,3-b]pyrazin-3-yl]-pyrazol-1-yl}-ethyl)-carbamic acid tert-butyl ester

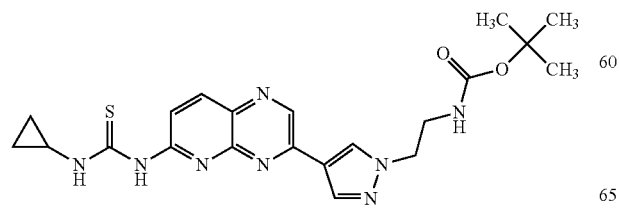

Compound 354: 5-[6-(3-Cyclopropyl 1-ureido)-pyrido[2,3-b]pyrazin-3-yl]-2-methyl-furan-3-carboxylic acid methyl ester

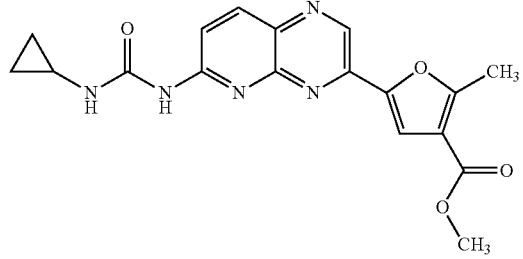

Compound 355: 5-[6-(3-Cyclopropyl-thioureido)-pyrido[2,3-b]pyrazin-3-yl]-2-methyl-furan-3-carboxylic acid methyl ester

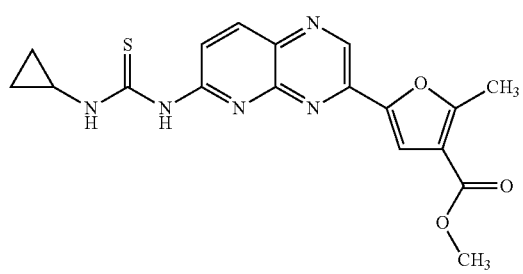 [SMILES: COC(=O)c1cc(-c2cnc3ccc(NC(=O)NC4CC4)nc3n2)oc1C]

Compound 356: 1-Cyclopropyl-3-[3-(5-isopropyl-furan-2-yl)-pyrido[2,3-b]pyrazin-6-yl]-urea

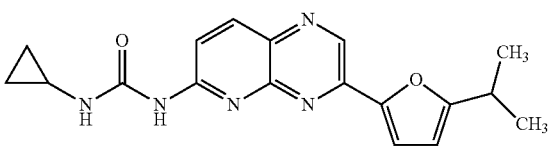 [SMILES: CC(C)c1ccc(-c2cnc3ccc(NC(=O)NC4CC4)nc3n2)o1]

Compound 357: 1-Cyclopropyl-3-[3-(5-isopropyl-furan-2-yl)-pyrido[2,3-b]pyrazin-6-yl]-thiourea

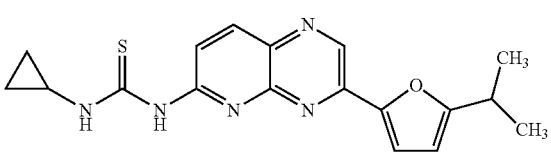 [SMILES: CC(C)c1ccc(-c2cnc3ccc(NC(=S)NC4CC4)nc3n2)o1]

Compound 358: 1-Cyclopropyl-3-[3-(5-ethoxymethoxymethyl-furan-2-yl)-pyrido[2,3-b]pyrazin-6-yl]-urea

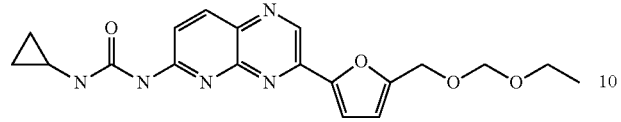

Compound 359: 1-Cyclopropyl-3-[3-(5-ethoxymethoxymethyl-furan-2-yl)-pyrido[2,3-b]pyrazin-6-yl]-thiourea

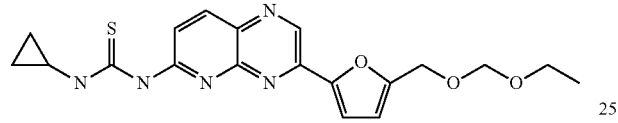

Compound 360: 1-Cyclopropyl-3-[3-(5-trimethylsilanyl-furan-2-yl)-pyrido[2,3-b]pyrazin-6-yl]-urea

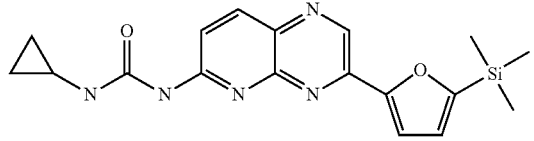 [SMILES: C[Si](C)(C)c1ccc(-c2cnc3ccc(NC(=O)NC4CC4)nc3n2)o1]

Compound 361: 1-Cyclopropyl-3-[3-(5-trimethylsilanyl-furan-2-yl)-pyrido[2,3-b]pyrazin-6-yl]-thiourea

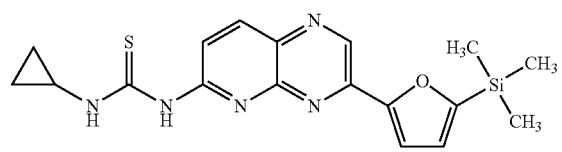 [SMILES: C[Si](C)(C)c1ccc(-c2cnc3ccc(NC(=S)NC4CC4)nc3n2)o1]

Compound 362: 1-Cyclopropyl-3-[3-(5-methyl-furan-2-yl)-pyrido[2,3-b]pyrazin-6-yl]-urea

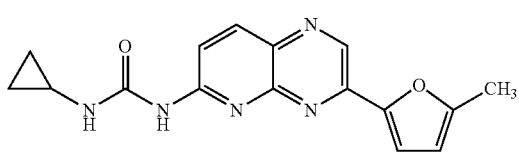 [SMILES: Cc1ccc(-c2cnc3ccc(NC(=O)NC4CC4)nc3n2)o1]

Compound 363: 1-Cyclopropyl-3-[3-(5-methyl-furan-2-yl)-pyrido[2,3-b]pyrazin-6-yl]-thiourea

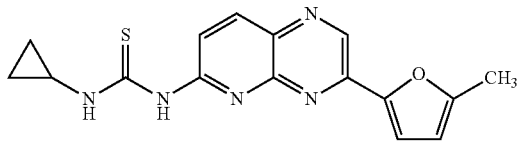

Compound 364: 1-Cyclopropyl-3-(3-thiazol-5-yl-pyrido[2,3-b]pyrazin-6-yl)-urea

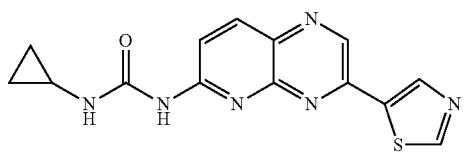 [SMILES: O=C(Nc1ccc2ncc(-c3cncs3)nc2n1)NC1CC1]

Compound 365: 1-Cyclopropyl-3-(3-thiazol-5-yl-pyrido[2,3-b]pyrazin-6-yl)-thiourea

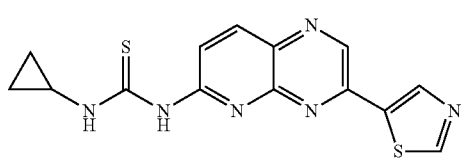 [SMILES: S=C(Nc1ccc2ncc(-c3cncs3)nc2n1)NC1CC1]

Compound 366: 1-Cyclopropyl-3-[3-(2-methyl-thiazol-4-yl)-pyrido[2,3-b]pyrazin-6-yl]-urea

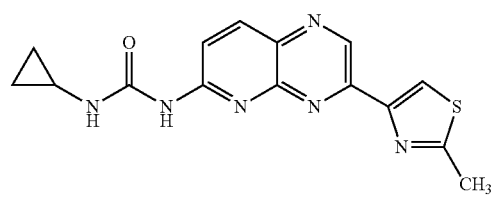 [SMILES: Cc1nc(-c2cnc3ccc(NC(=O)NC4CC4)nc3n2)cs1]

Compound 367: 1-Cyclopropyl-3-[3-(2-methyl-thiazol-4-yl)-pyrido[2,3-b]pyrazin-6-yl]-thiourea

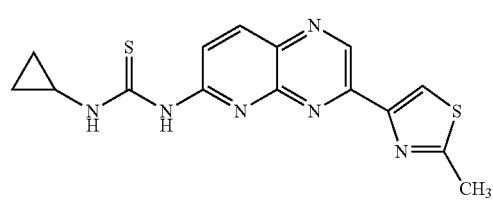 [SMILES: Cc1nc(-c2cnc3ccc(NC(=S)NC4CC4)nc3n2)cs1]

Compound 368: 1-Cyclopropyl-3-[3-(1-isopropyl-1H-pyrazol-3-yl)-pyrido[2,3-b]pyrazin-6-yl]-urea

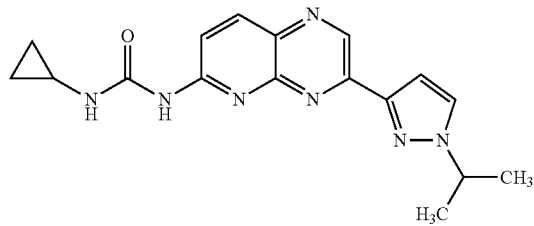 [SMILES: CC(C)n1ccc(-c2cnc3ccc(NC(=O)NC4CC4)nc3n2)n1]

Compound 369: 1-Cyclopropyl-3-[3-(1-isopropyl-1H-pyrazol-3-yl)-pyrido[2,3-b]pyrazin-6-yl]-thiourea

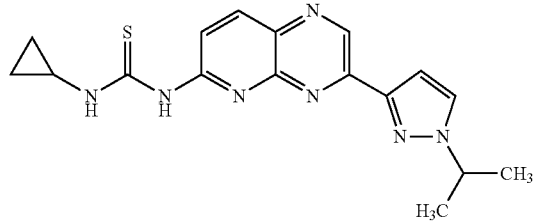 [SMILES: CC(C)n1ccc(-c2cnc3ccc(NC(=S)NC4CC4)nc3n2)n1]

Compound 370: 1-Cyclopropyl-3-[3-(5-hydroxymethyl-thiophen-3-yl)-pyrido[2,3-b]pyrazin-6-yl]-urea

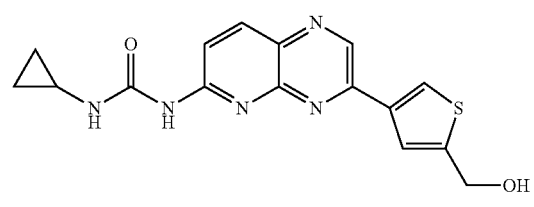 [SMILES: O=C(Nc1ccc2ncc(-c3csc(CO)c3)nc2n1)NC1CC1]

Compound 371: 1-Cyclopropyl-3-[3-(5-hydroxymethyl-thiophen-3-yl)-pyrido[2,3-b]pyrazin-6-yl]-thiourea

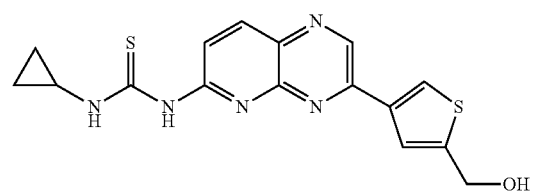

Compound 372: 4-[6-(3-Cyclopropyl-ureido)-pyrido[2,3-b]pyrazin-3-yl]-thiophene-2-carboxylic acid ethyl ester

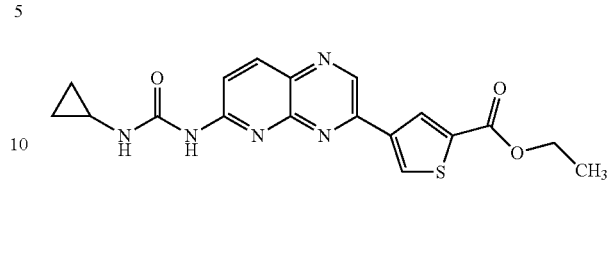

Compound 373: 4-[6-(3-Cyclopropyl-thioureido)-pyrido[2,3-b]pyrazin-3-yl]-thiophene-2-carboxylic acid ethyl ester

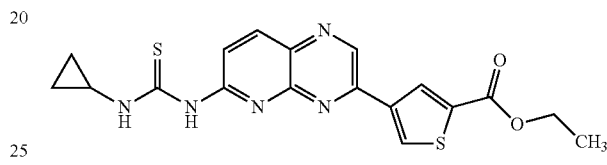

Compound 374: 4-[6-(3-Cyclopropyl-ureido)-pyrido[2,3-b]pyrazin-3-yl]-thiophene-2-carboxylic acid

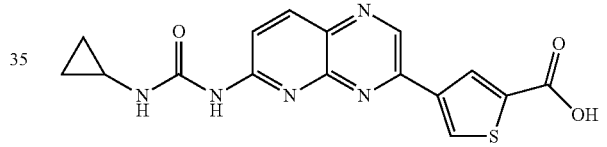

Compound 375: 4-[6-(3-Cyclopropyl-thioureido)-pyrido[2,3-b]pyrazin-3-yl]-thiophene-2-carboxylic acid

Compound 376: 1-Cyclopropyl-3-[3-(4-methyl-thiazol-2-yl)-pyrido[2,3-b]pyrazin-6-yl]-urea

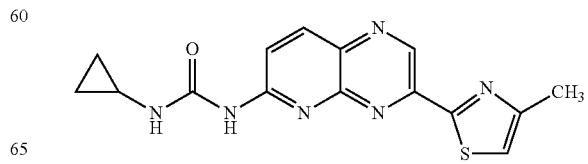

Compound 377: 1-Cyclopropyl-3-[3-(4-methyl-thiazol-2-yl)-pyrido[2,3-b]pyrazin-6-yl]-thiourea

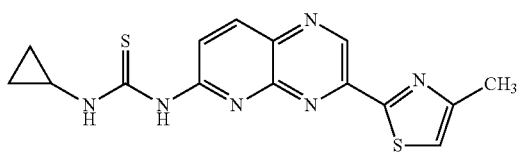 [SMILES: Cc1csc(-c2cnc3ccc(NC(=O)NC4CC4)nc3n2)n1]

Compound 378: 1-Ethyl-3-(3-furan-3-yl-pyrido[2,3-b]pyrazin-6-yl)-urea

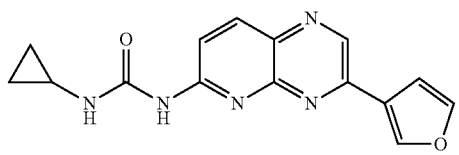 [SMILES: O=C(Nc1ccc2ncc(-c3ccoc3)nc2n1)NC1CC1]

Compound 379: 1-Cyclopropyl-3-(3-furan-3-yl-pyrido[2,3-b]pyrazin-6-yl)-thiourea

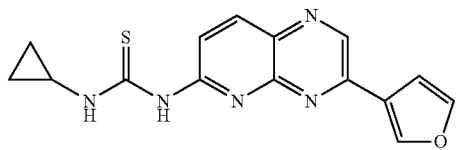 [SMILES: S=C(Nc1ccc2ncc(-c3ccoc3)nc2n1)NC1CC1]

Compound 380: 1-Cyclopropyl-3-[3-(1-methyl-1H-imidazol-4-yl)-pyrido[2,3-b]pyrazin-6-yl]-urea

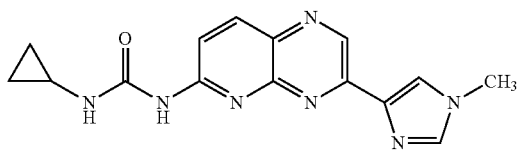 [SMILES: Cn1cnc(-c2cnc3ccc(NC(=O)NC4CC4)nc3n2)c1]

Compound 381: 1-Cyclopropyl-3-[3-(1-methyl-1H-imidazol-4-yl)-pyrido[2,3-b]pyrazin-6-yl]-thiourea

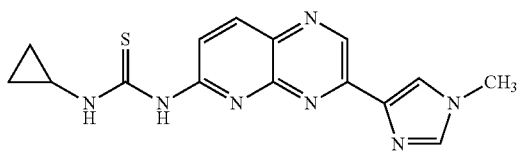

Compound 382: 1-Cyclopropyl-3-[3-(1-methyl-1H-[1,2,3]triazol-4-yl)-pyrido[2,3-b]pyrazin-6-yl]-urea

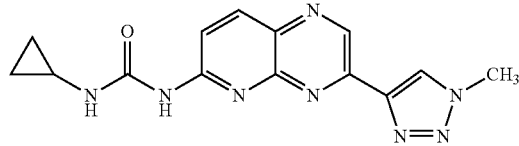 [SMILES: Cn1cc(-c2cnc3ccc(NC(=O)NC4CC4)nc3n2)nn1]

Compound 383: 1-Cyclopropyl-3-[3-(1-methyl-1H-[1,2,3]triazol-4-yl)-pyrido[2,3-b]pyrazin-6-yl]-thiourea

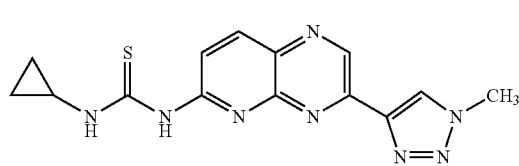 [SMILES: Cn1cc(-c2cnc3ccc(NC(=S)NC4CC4)nc3n2)nn1]

Compound 384: 1-Cyclopropyl-3-(3-isoxazol-4-yl-pyrido[2,3-b]pyrazin-6-yl)-urea

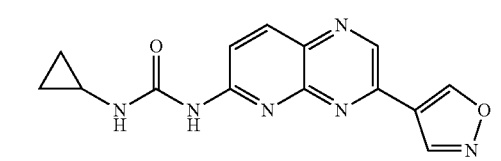 [SMILES: O=C(Nc1ccc2ncc(-c3cnoc3)nc2n1)NC1CC1]

Compound 385: 1-Cyclopropyl-3-(3-isoxazol-4-yl-pyrido[2,3-b]pyrazin-6-yl)-thiourea

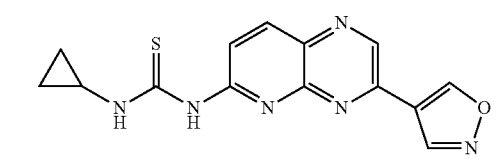 [SMILES: S=C(Nc1ccc2ncc(-c3cnoc3)nc2n1)NC1CC1]

Compound 386: 1-Cyclopropyl-3-[3-(1H-imidazol-2-O-pyrido[2,3-b]pyrazin-6-yl]-urea

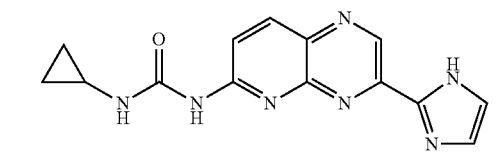 [SMILES: O=C(Nc1ccc2ncc(-c3ncc[nH]3)nc2n1)NC1CC1]

Compound 387: 1-Cyclopropyl-3-[3-(1H-imidazol-2-yl)-pyrido[2,3-b]pyrazin-6-yl]-thiourea

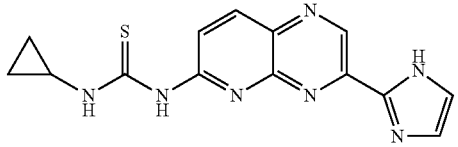 [SMILES: S=C(Nc1ccc2ncc(-c3ncc[nH]3)nc2n1)NC1CC1]

Compound 388: 1-[3-(6-Chloro-pyridin-2-yl)-pyrido[2,3-b]pyrazin-6-yl]-3-cyclopropyl-urea

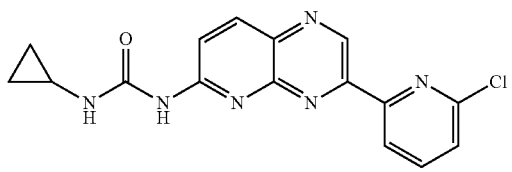 [SMILES: O=C(Nc1ccc2ncc(-c3cccc(Cl)n3)nc2n1)NC1CC1]

Compound 389: 1-[3-(6-Chloro-pyridin-2-yl)-pyrido[2,3-b]pyrazin-6-yl]-3-cyclopropyl-thiourea

Compound 390: 1-Ethyl-3-[3-(5-methyl-thiophen-2-yl)-pyrido[2,3-b]pyrazin-6-yl]-urea

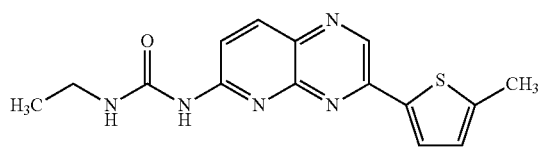

Compound 391: 1-Ethyl-3-[3-(5-methyl-thiophen-2-yl)-pyrido[2,3-b]pyrazin-6-yl]thiourea

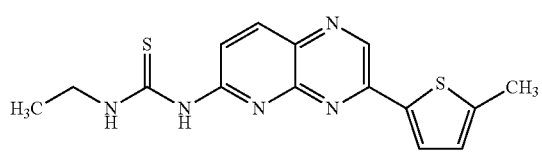

Compound 392: 1-Ethyl-3-[3-(4-methyl-thiophen-2-yl)-pyrido[2,3-b]pyrazin-6-yl]-urea

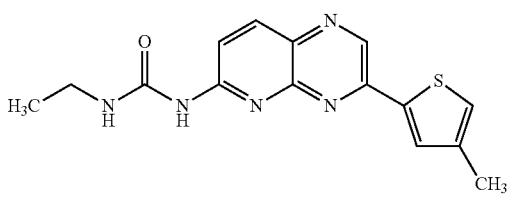 [SMILES: CCNC(=O)Nc1ccc2ncc(-c3cc(C)cs3)nc2n1]

Compound 393: 1-Ethyl-3-[3-(4-methyl-thiophen-2-yl)-pyrido[2,3-b]pyrazin-6-yl]-thiourea

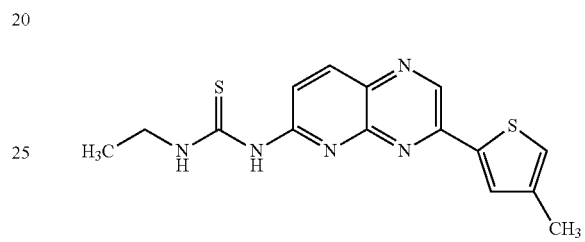

Compound 394: {5-[6-(3-Ethyl-ureido)-pyrido[2,3-b]pyrazin-3-yl]-thiophen-2-ylmethyl}-carbamic acid tert-butyl ester

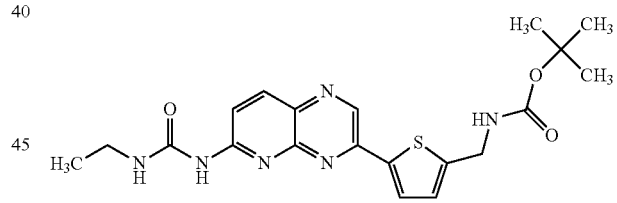

Compound 395: {5-[6-(3-Ethyl-thioureido)-pyrido[2,3-b]pyrazin-3-yl]-thiophen-2-ylmethyl}-carbamic acid tert-butyl ester

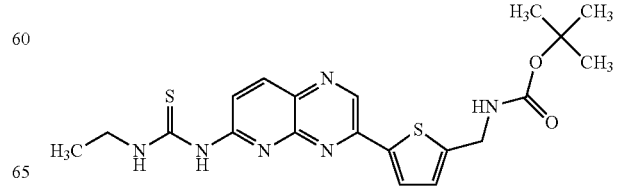

Compound 396: 1-Ethyl-3-[3-(5-hydroxymethyl-thiophen-2-yl)-pyrido[2,3-b]pyrazin-6-yl]-urea

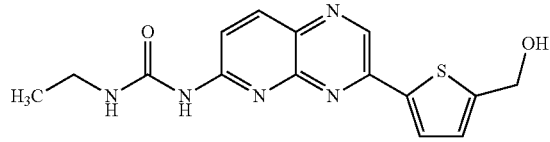 [SMILES: CCNC(=O)Nc1ccc2ncc(-c3ccc(CO)s3)nc2n1]

Compound 397: 1-Ethyl-3-[3-(5-hydroxymethyl-thiophen-2-yl)-pyrido[2,3-b]pyrazin-6-yl]-thiourea

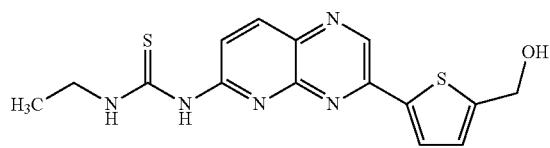 [SMILES: CCNC(=S)Nc1ccc2ncc(-c3ccc(CO)s3)nc2n1]

Compound 398: 5-[6-(3-Ethyl-ureido)-pyrido[2,3-b]pyrazin-3-yl]-thiophene-2-carboxylic acid

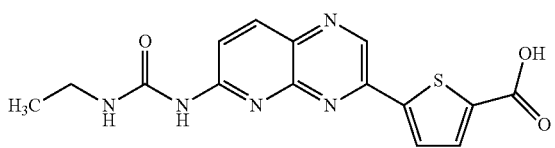 [SMILES: CCNC(=O)Nc1ccc2ncc(-c3ccc(C(=O)O)s3)nc2n1]

Compound 399: 5-[6-(3-Ethyl-thioureido)-pyrido[2,3-b]pyrazin-3-yl]-thiophene-2-carboxylicacid

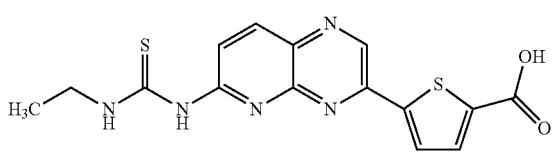 [SMILES: CCNC(=S)Nc1ccc2ncc(-c3ccc(C(=O)O)s3)nc2n1]

Compound 400: 4-[6-(3-Ethyl-ureido)-pyrido[2,3-b]pyrazin-3-yl]-pyrazole-1-carboxylic acid tert-butyl ester

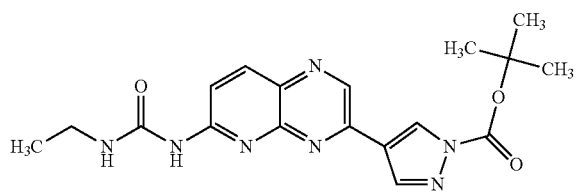 [SMILES: CCNC(=O)Nc1ccc2ncc(-c3cnn(C(=O)OC(C)(C)C)c3)nc2n1]

Compound 401: 4-[6-(3-Ethyl-thioureido)-pyrido[2,3-b]pyrazin-3-yl]-pyrazole-1-carboxylic acid tert-butylester

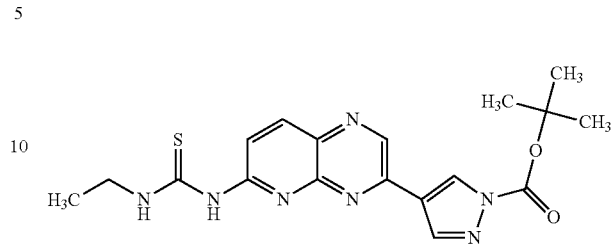

Compound 402: {4-[6-(3-Ethyl-ureido)-pyrido[2,3-b]pyrazin-3-yl]-pyrazol-1-yl}-acetic acid ethyl ester

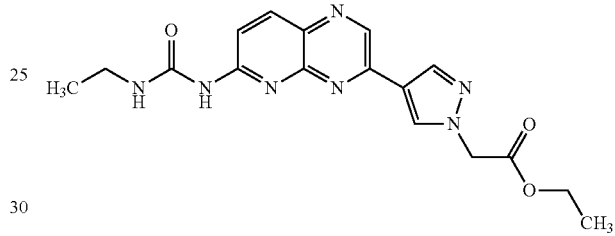

Compound 403: {4-[6-(3-Ethyl-thioureido)-pyrido[2,3-b]pyrazin-3-yl]-pyrazol-1-yl}-acetic acid ethyl ester

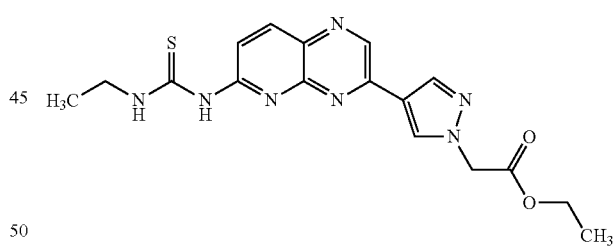

Compound 404: 3-{4-[6-(3-Ethyl-ureido)-pyrido[2,3-b]pyrazin-3-yl]-pyrazol-1-yl}-propionamide

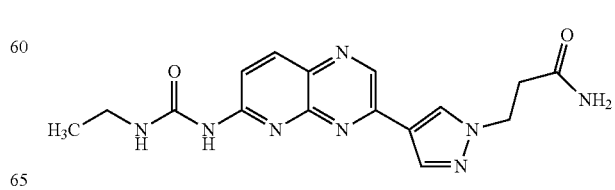

Compound 405: 3-{4-[6-(3-Ethyl-thioureido)-pyrido[2,3-b]pyrazin-3-yl]-pyrazol-1-yl}-propionamide

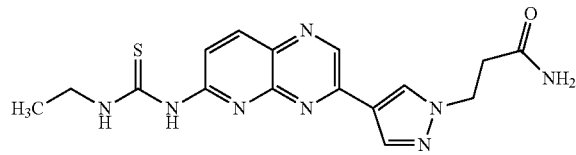

Compound 406: (2-{4-[6-(3-Ethyl-ureido)-pyrido[2,3-b]pyrazin-3-yl]-pyrazol-1-yl}-ethyl)-carbamic acid tert-butyl ester

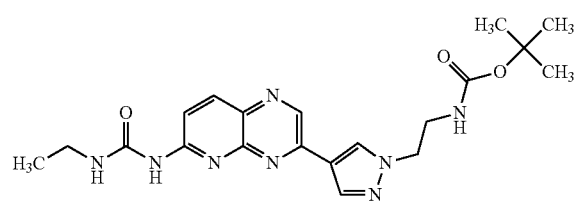 [SMILES: CCNC(=O)Nc1ccc2ncc(-c3cnn(CCNC(=O)OC(C)(C)C)c3)nc2n1]

Compound 407: (2-{4-[6-(3-Ethyl-thioureido)-pyrido[2,3-b]pyrazin-3-yl]-pyrazol-1-yl}-ethyl)-carbamic acid tert-butyl ester

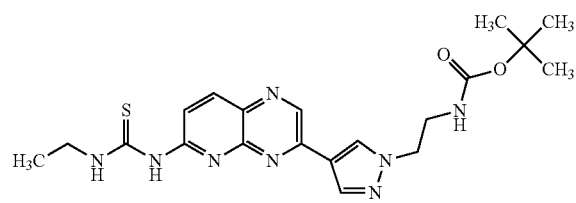 [SMILES: CCNC(=S)Nc1ccc2ncc(-c3cnn(CCNC(=O)OC(C)(C)C)c3)nc2n1]

Compound 408: 5-[6-(3-Ethyl-ureido)-pyrido[2,3-b]pyrazin-3-yl]-2-methyl-furan-3-carboxylic acid methyl ester

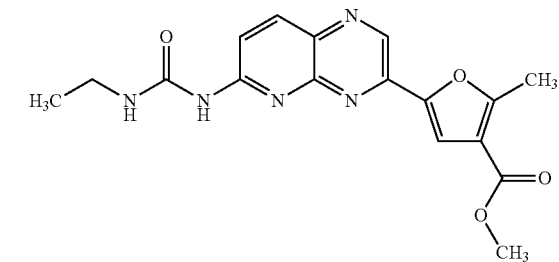 [SMILES: CCNC(=O)Nc1ccc2ncc(-c3cc(C(=O)OC)c(C)o3)nc2n1]

Compound 409: 5-[6-(3-Ethyl-thioureido)-pyrido[2,3-b]pyrazin-3-yl]-2-methyl-furan-3-carboxylic acid methyl ester

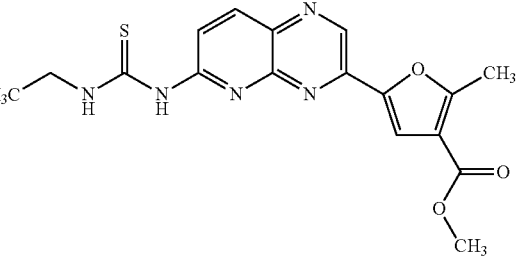

Compound 410: 1-Ethyl-3-[3-(5-isopropyl-furan-2-yl)-pyrido[2,3-b]pyrazin-6-yl]-urea

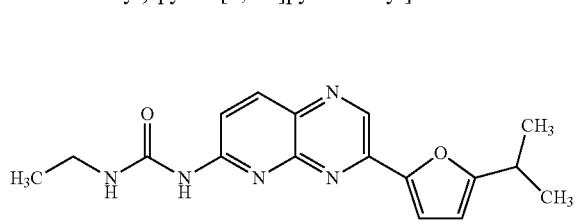

Compound 411: 1-Ethyl-3-[3-(5-isopropyl-furan-2-yl)-pyrido[2,3-b]pyrazin-6-yl]-thiourea

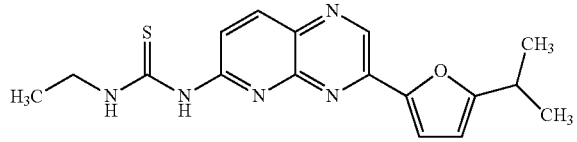 [SMILES: CCNC(=S)Nc1ccc2ncc(-c3ccc(C(C)C)o3)nc2n1]

Compound 412: 1-[3-(5-Ethoxymethoxymethyl-furan-2-yl)-pyrido[2,3-b]pyrazin-6-yl]-3-ethyl-urea

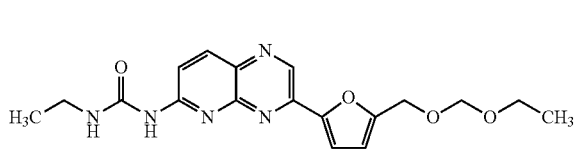 [SMILES: CCNC(=O)Nc1ccc2ncc(-c3ccc(COCOCC)o3)nc2n1]

Compound 413: 1-[3-(5-Ethoxymethoxymethyl-furan-2-yl)-pyrido[2,3-b]pyrazin-6-yl]-3-ethyl-thiourea

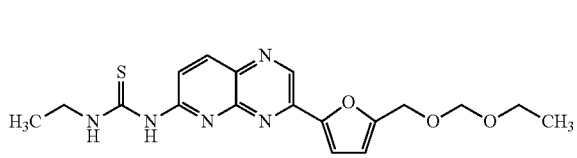 [SMILES: CCNC(=S)Nc1ccc2ncc(-c3ccc(COCOCC)o3)nc2n1]

Compound 414: 1-Ethyl-3-[3-(5-trimethylsilanyl-furan-2-yl)-pyrido[2,3-b]pyrazin-6-yl]-urea

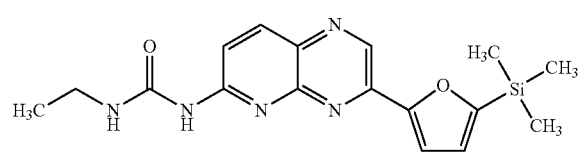 [SMILES: CCNC(=O)Nc1ccc2ncc(-c3ccc([Si](C)(C)C)o3)nc2n1]

Compound 415: 1-Ethyl-3-[3-(5-trimethylsilanyl-furan-2-yl)-pyrido[2,3-b]pyrazin-6-yl]-thiourea

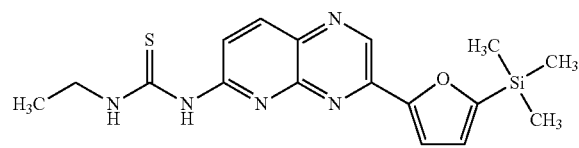 [SMILES: CCNC(=S)Nc1ccc2ncc(-c3ccc([Si](C)(C)C)o3)nc2n1]

Compound 416: 1-Ethyl-3-[3-(5-methyl-furan-2-yl)-pyrido[2,3-b]pyrazin-6-yl]-urea

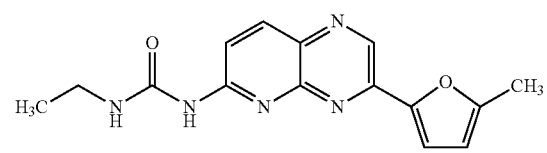 [SMILES: CCNC(=O)Nc1ccc2ncc(-c3ccc(C)o3)nc2n1]

Compound 417: 1-Ethyl-3-[3-(5-methyl-furan-2-yl)-pyrido[2,3-b]pyrazin-6-yl]-thiourea

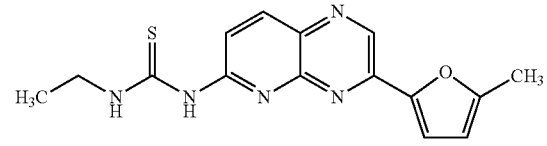

Compound 418: 1-Ethyl-3-(3-thiazol-5-yl-pyrido[2,3-b]pyrazin-6-yl)-urea

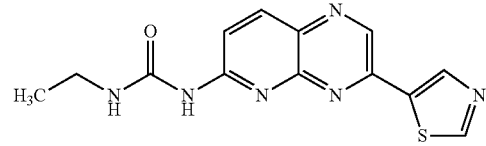 [SMILES: CCNC(=O)Nc1ccc2ncc(-c3cncs3)nc2n1]

Compound 419: 1-Ethyl-3-(3-thiazol-5-yl-pyrido[2,3-b]pyrazin-6-yl)-thiourea

Compound 420: 1-Ethyl-3-[3-(2-methyl-thiazol-4-yl)-pyrido[2,3-b]pyrazin-6-yl]-urea

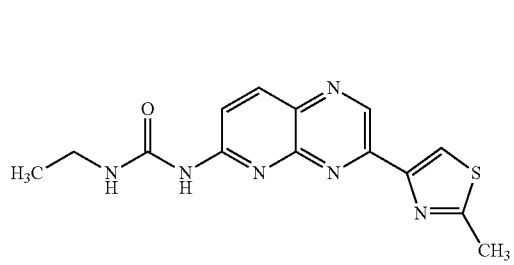 [SMILES: CCNC(=O)Nc1ccc2ncc(-c3csc(C)n3)nc2n1]

Compound 421: 1-Ethyl-3-[3-(2-methyl-thiazol-4-yl)-pyrido[2,3-b]pyrazin-6-yl]-thiourea

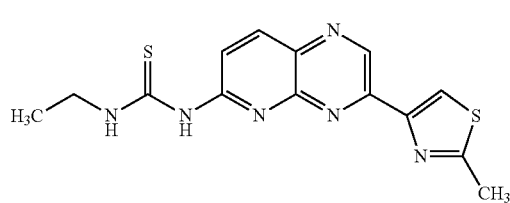

Compound 422: 1-Ethyl-3-[3-(1-isopropyl-1H-pyrazol-3-yl)-pyrido[2,3-b]pyrazin-6-yl]-urea

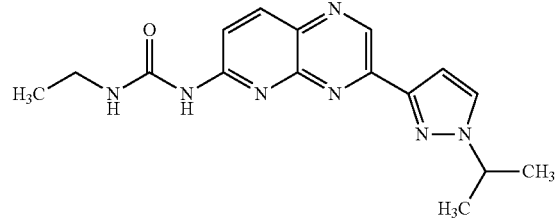 [SMILES: CCNC(=O)Nc1ccc2ncc(-c3ccn(C(C)C)n3)nc2n1]

Compound 423: 1-Ethyl-3-[3-(1-isopropyl-1H-pyrazol-3-yl)-pyrido[2,3-b]pyrazin-6-yl]-thiourea

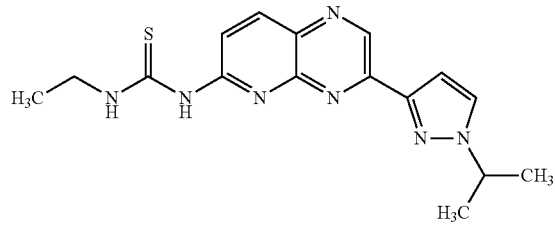 [SMILES: CCNC(=S)Nc1ccc2ncc(-c3ccn(C(C)C)n3)nc2n1]

Compound 424: 1-Ethyl-3-[3-(5-hydroxymethyl-thiophen-3-yl)-pyrido[2,3-b]pyrazin-6-yl]-urea

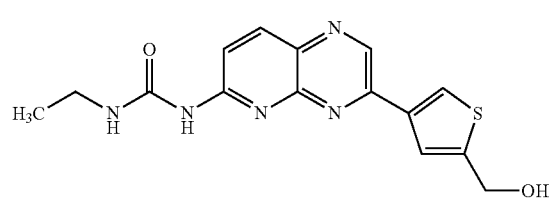 [SMILES: CCNC(=O)Nc1ccc2ncc(-c3csc(CO)c3)nc2n1]

Compound 425: 1-Ethyl-3-[3-(5-hydroxymethyl-thiophen-3-yl)-pyrido[2,3-b]pyrazin-6-yl]-thiourea

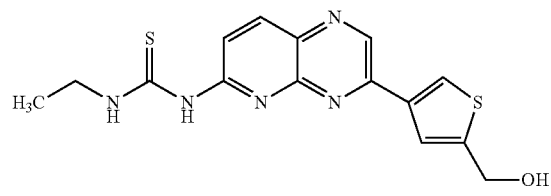 [SMILES: CCNC(=S)Nc1ccc2ncc(-c3csc(CO)c3)nc2n1]

Compound 426: 4-[6-(3-Ethyl-ureido)-pyrido[2,3-b]pyrazin-3-yl]-thiophene-2-carboxylic acid ethyl ester

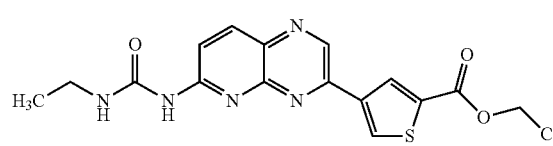

Compound 427: 4-[6-(3-Ethyl-thioureido)-pyrido[2,3-b]pyrazin-3-yl]-thiophene-2-carboxylic acid ethyl ester

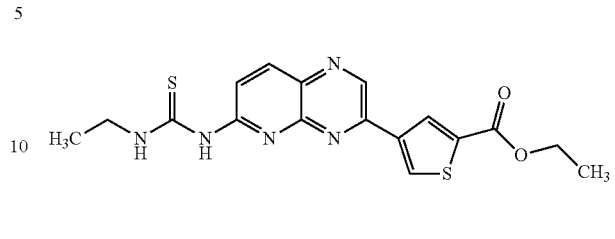

Compound 428: 4-[6-(3-Ethyl-ureido)-pyrido[2,3-b]pyrazin-3-yl]-thiophene-2-carboxylic acid

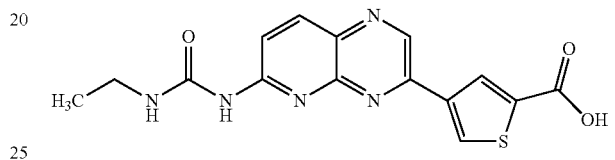

Compound 429: 4-[6-(3-Ethyl-thioureido)-pyrido[2,3-b]pyrazin-3-yl]-thiophene-2-carboxylic acid

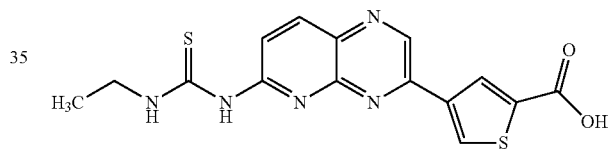

Compound 430: 1-Ethyl-3-[3-(4-methyl-thiazol-2-yl)-pyrido[2,3-b]pyrazin-6-yl]-urea

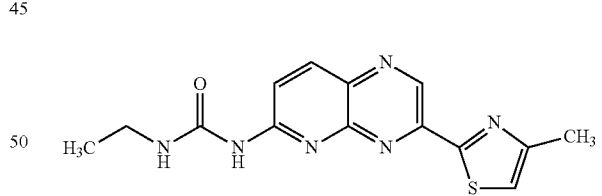

Compound 431: 1-Ethyl-3-[3-(4-methyl-thiazol-2-yl)-pyrido[2,3-b]pyrazin-6-yl]-thiourea

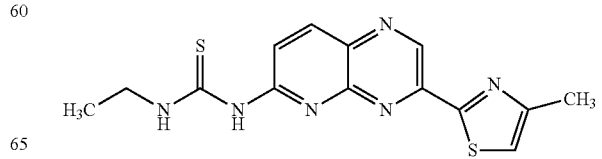

Compound 432: 1-Ethyl-3-(3-furan-3-yl-pyrido[2,3-b]pyrazin-6-yl)-urea

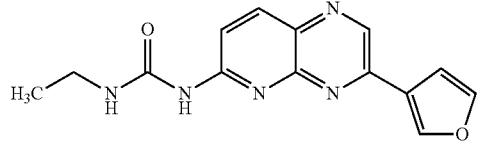 [SMILES: CCNC(=O)Nc1ccc2ncc(-c3ccoc3)nc2n1]

Compound 433: 1-Ethyl-3-(3-furan-3-yl-pyrido[2,3-b]pyrazin-6-yl)-thiourea

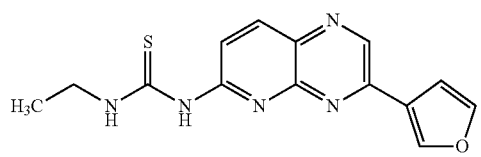

Compound 434: 1-Ethyl-3-[3-(1-methyl-1H-imidazol-4-yl)-pyrido[2,3-b]pyrazin-6-yl]-urea

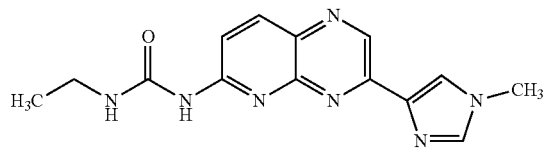 [SMILES: CCNC(=O)Nc1ccc2ncc(-c3cn(C)cn3)nc2n1]

Compound 435: 1-Ethyl-3-[3-(1-methyl-1H-imidazol-4-yl)-pyrido[2,3-b]pyrazin-6-yl]-thiourea

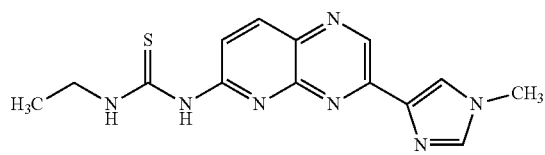 [SMILES: CCNC(=S)Nc1ccc2ncc(-c3cn(C)cn3)nc2n1]

Compound 436: 1-Ethyl-3-[3-(1-methyl-1H-[1,2,3]triazol-4-yl)-pyrido[2,3-b]pyrazin-6-yl]-urea

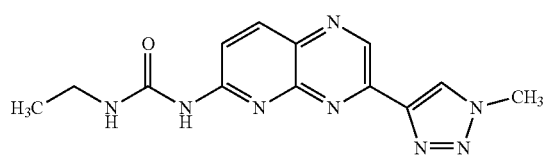 [SMILES: CCNC(=O)Nc1ccc2ncc(-c3cn(C)nn3)nc2n1]

Compound 437: 1-Ethyl-3-[3-(1-methyl-1H-[1,2,3]triazol-4-yl)-pyrido[2,3-b]pyrazin-6-yl]-thiourea

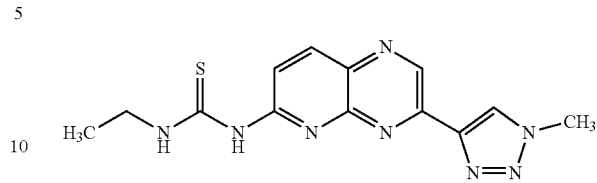

Compound 438: 1-Ethyl-3-(3-isoxazol-4-yl-pyrido[2,3-b]pyrazin-6-yl)-urea

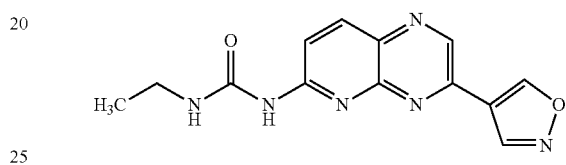

Compound 439: 1-Ethyl-3-(3-isoxazol-4-yl-pyrido[2,3-b]pyrazin-6-yl)-thiourea

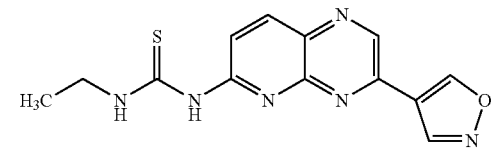 [SMILES: CCNC(=S)Nc1ccc2ncc(-c3cnoc3)nc2n1]

Compound 440: 1-Ethyl-3-[3-(1H-imidazol-2-yl)-pyrido[2,3-b]pyrazin-6-yl]-urea

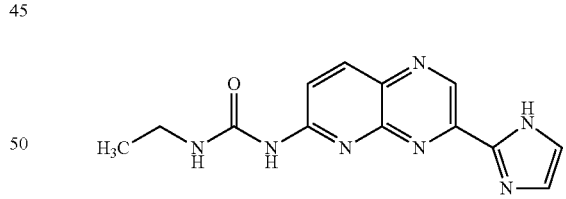

Compound 441: 1-Ethyl-3-[3-(1H-imidazol-2-yl)-pyrido[2,3-b]pyrazin-6-yl]-thiourea

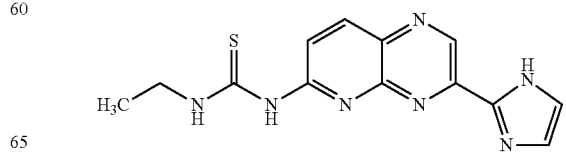

Compound 442: 1-[3-(6-Chloro-pyridin-2-yl)-pyrido[2,3-b]pyrazin-6-yl]-3-ethyl-urea

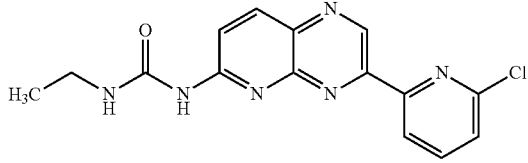 [SMILES: CCNC(=O)Nc1ccc2ncc(-c3cccc(Cl)n3)nc2n1]

Compound 443: 1-[3-(6-Chloro-pyridin-2-yl)-pyrido[2,3-b]pyrazin-6-yl]-3-ethyl-thiourea

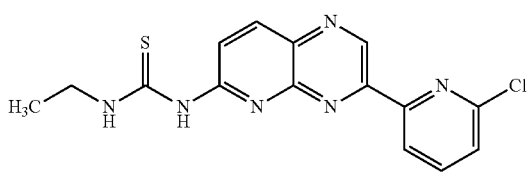 [SMILES: CCNC(=S)Nc1ccc2ncc(-c3cccc(Cl)n3)nc2n1]

Compound 444: 1-[3-(5-Methyl-thiophen-2-yl)-pyrido[2,3-b]pyrazin-6-yl]-3-pentyl-urea

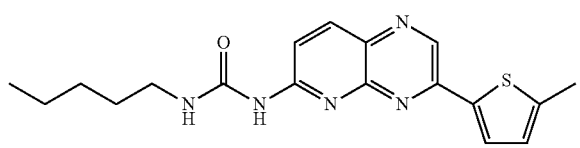 [SMILES: CCCCCNC(=O)Nc1ccc2ncc(-c3ccc(C)s3)nc2n1]

Compound 445: 1-[3-(5-Methyl-thiophen-2-yl)-pyrido[2,3-b]pyrazin-6-yl]-3-pentyl-thiourea

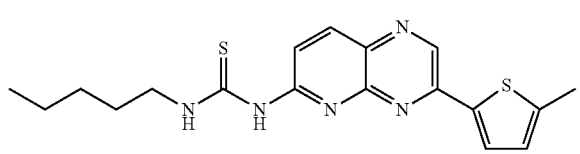 [SMILES: CCCCCNC(=S)Nc1ccc2ncc(-c3ccc(C)s3)nc2n1]

Compound 446: 1-[3-(4-Methyl-thiophen-2-yl)-pyrido[2,3-b]pyrazin-6-yl]-3-pentyl-urea

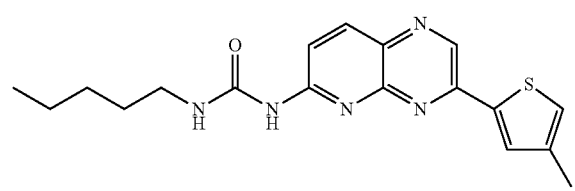 [SMILES: CCCCCNC(=O)Nc1ccc2ncc(-c3cc(C)cs3)nc2n1]

Compound 447: 1-[3-(4-Methyl-thiophen-2-yl)-pyrido[2,3-b]pyrazin-6-yl]-3-pentyl-thiourea

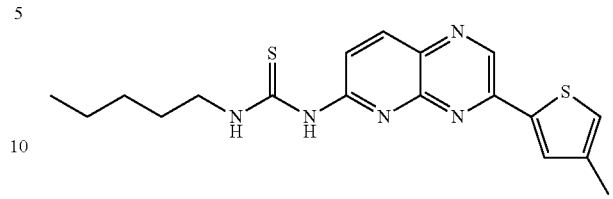

Compound 448: {5-[6-(3-Pentyl-ureido)-pyrido[2,3-b]pyrazin-3-yl]-thiophen-2-ylmethyl}-carbamic acid tert-butyl ester

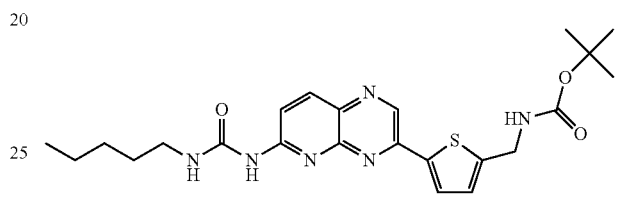

Compound 449: {5-[6-(3-Pentyl-thioureido)-pyrido[2,3-b]pyrazin-3-yl]-thiophen-2-ylmethyl}-carbamic acid tert-butyl ester

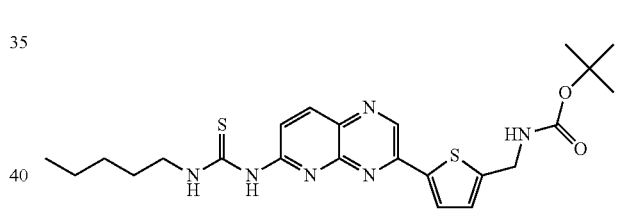

Compound 450: 1-[3-(5-Hydroxymethyl-thiophen-2-yl)-pyrido[2,3-b]pyrazin-6-yl]-3-pentyl-urea

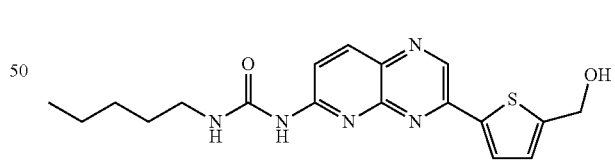

Compound 451: 1-[3-(5-Hydroxymethyl-thiophen-2-yl)-pyrido[2,3-b]pyrazin-6-yl]-3-pentyl-thiourea

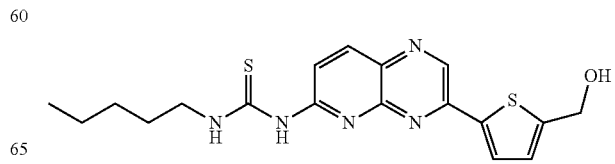

Compound 452: 5-[6-(3-Pentyl-ureido)-pyrido[2,3-b]pyrazin-3-yl]-thiophene-2-carboxylic acid

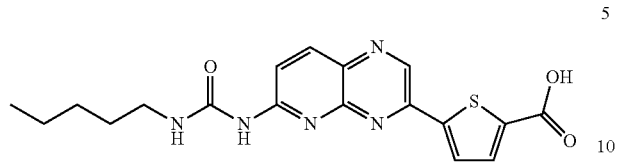

Compound 453: 5-[6-(3-Pentyl-thioureido)-pyrido[2,3-b]pyrazin-3-yl]-thiophene-2-carboxylic acid

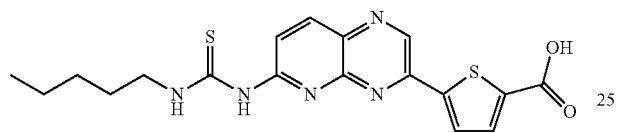

Compound 454: 4-[6-(3-Pentyl-ureido)-pyrido[2,3-b]pyrazin-3-yl]-pyrazole-1-carboxylic acid tert-butyl ester

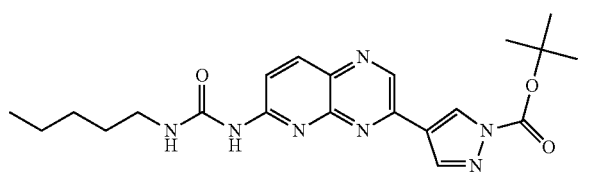 [SMILES: CCCCCNC(=O)Nc1ccc2ncc(-c3cnn(C(=O)OC(C)(C)C)c3)nc2n1]

Compound 455: 4-[6-(3-Pentyl-thioureido)-pyrido[2,3-b]pyrazin-3-yl]-pyrazole-1-carboxylic acid tert-butyl ester

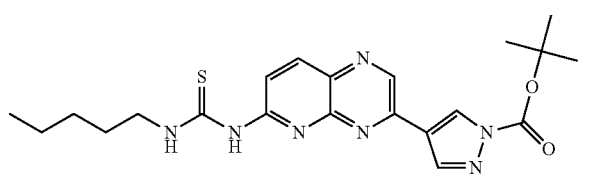 [SMILES: CCCCCNC(=S)Nc1ccc2ncc(-c3cnn(C(=O)OC(C)(C)C)c3)nc2n1]

Compound 456: {4-[6-(3-Pentyl-ureido)-pyrido[2,3-b]pyrazin-3-yl]-pyrazol-1-yl}-acetic acid ethyl ester Compound 457: {4-[6-(3-Pentyl-thioureido)-pyrido[2,3-b]pyrazin-3-yl]-pyrazol-1-yl}-acetic acid ethyl ester

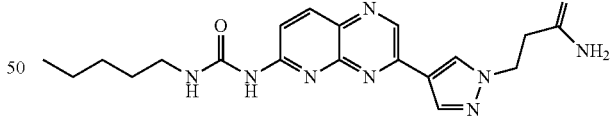

Compound 458: 3-{4-[6-(3-Pentyl-ureido)-pyrido[2,3-b]pyrazin-3-yl]-pyrazol-1-yl}-propionamide Compound 459: 3-{4-[6-(3-Pentyl-thioureido)-pyrido[2,3-b]pyrazin-3-yl]-pyrazol-1-yl}-propionamide

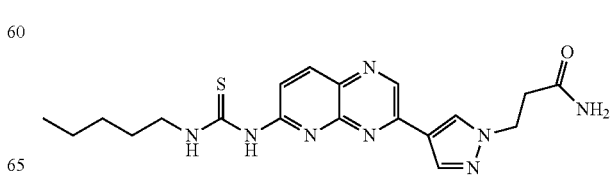

Compound 460: (2-{4-[6-(3-Pentyl-ureido)-pyrido[2,3-b]pyrazin-3-yl]-pyrazol-1-yl}-ethyl)-carbamic acid tert-butyl ester Compound 463: 2-Methyl-5-[6-(3-pentyl-thioureido)-pyrido[2,3-b]pyrazin-3-yl]-furan-3-carboxylic acid methyl ester

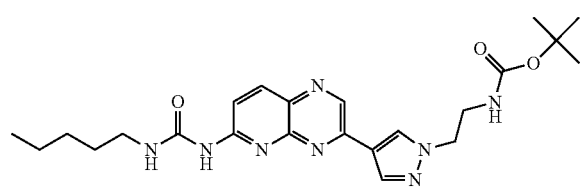 [SMILES: CCCCCNC(=O)Nc1ccc2ncc(-c3cnn(CCNC(=O)OC(C)(C)C)c3)nc2n1]

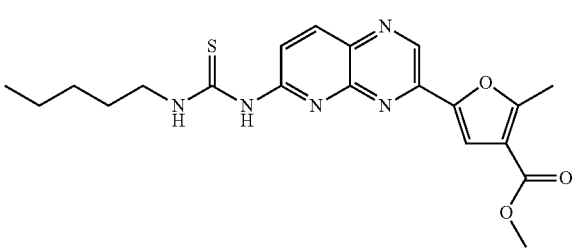 [SMILES: CCCCCNC(=S)Nc1ccc2ncc(-c3cc(C(=O)OC)c(C)o3)nc2n1]

Compound 461: (2-{4-[6-(3-Pentyl-thioureido)-pyrido[2,3-b]pyrazin-3-yl]-pyrazol-1-yl}-ethyl)-carbamic acid tert-butyl ester Compound 464: 1-[3-(5-Isopropyl-furan-2-yl)-pyrido[2,3-b]pyrazin-6-yl]-3-pentyl-urea

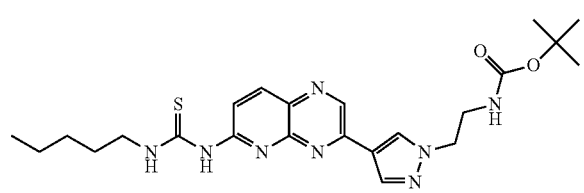

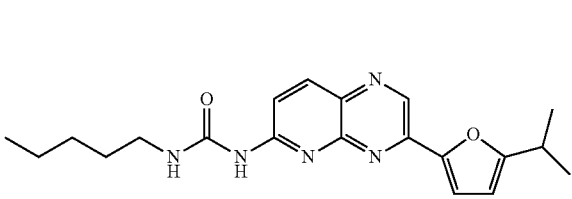 [SMILES: CCCCCNC(=O)Nc1ccc2ncc(-c3ccc(C(C)C)o3)nc2n1]

Compound 462: 2-Methyl-5-[6-(3-pentyl-ureido)-pyrido[2,3-b]pyrazin-3-yl]-furan-3-carboxylic acid methyl ester Compound 465: 1-[3-(5-Isopropyl-furan-2-yl)-pyrido[2,3-b]pyrazin-6-yl]-3-pentyl-thiourea

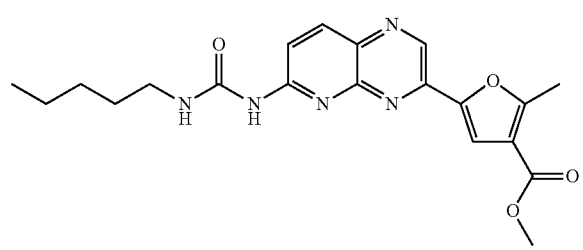

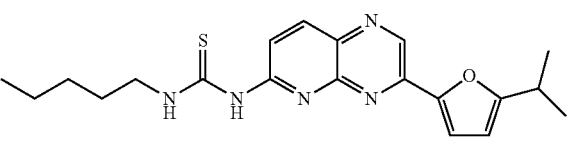 [SMILES: CCCCCNC(=S)Nc1ccc2ncc(-c3ccc(C(C)C)o3)nc2n1]

Compound 466: 1-[3-(5-Ethoxymethoxymethyl-furan-2-yl)-pyrido[2,3-b]pyrazin-6-yl]-3-pentyl-urea

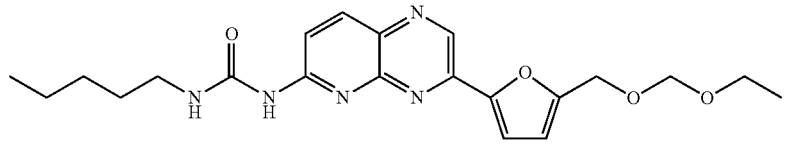 [SMILES: CCCCCNC(=O)Nc1ccc2ncc(-c3ccc(COCOCC)o3)nc2n1]

Compound 467: 1-[3-(5-Ethoxymethoxymethyl-furan-2-yl)-pyrido[2,3-b]pyrazin-6-yl]-3-pentyl-thiourea

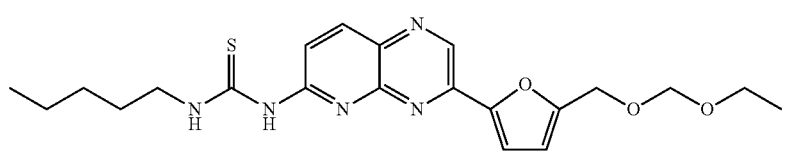

Compound 468: 1-Pentyl-3-[3-(5-trimethylsilanyl-furan-2-yl)-pyrido[2,3-b]pyrazin-6-yl]-urea

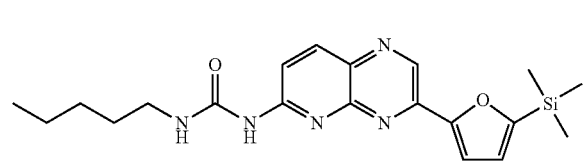 [SMILES: CCCCCNC(=O)Nc1ccc2ncc(-c3ccc([Si](C)(C)C)o3)nc2n1]

Compound 469: 1-Pentyl-3-[3-(5-trimethylsilanyl-furan-2-yl)-pyrido[2,3-b]pyrazin-6-yl]-thiourea

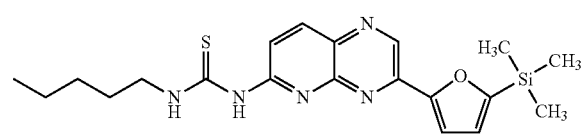 [SMILES: CCCCCNC(=S)Nc1ccc2ncc(-c3ccc([Si](C)(C)C)o3)nc2n1]

Compound 470: 1-Pentyl l-3-[3-(5-methyl-furan-2-yl)-pyrido[2,3-b]pyrazin-6-yl]-urea

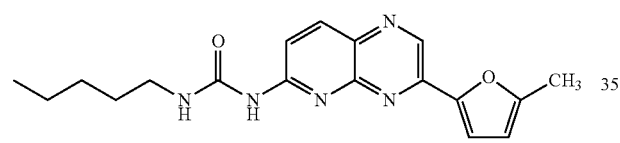

Compound 471: 1-Pentyl-3-[3-(5-methyl-furan-2-yl)-pyrido[2,3-b]pyrazin-6-yl]-thiourea

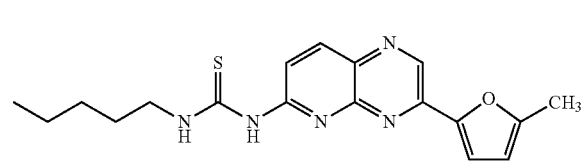 [SMILES: CCCCCNC(=O)Nc1ccc2ncc(-c3ccc(C)o3)nc2n1]

Compound 472: 1-Pentyl-3-(3-thiazol-5-yl-pyrido[2,3-b]pyrazin-6-yl)-urea

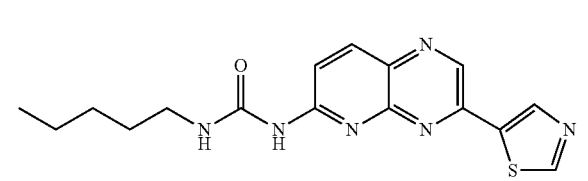 [SMILES: CCCCCNC(=O)Nc1ccc2ncc(-c3cncs3)nc2n1]

Compound 473: 1-Pentyl l-3-(3-thiazol-5-yl-pyrido[2,3-b]pyrazin-6-yl)-thiourea

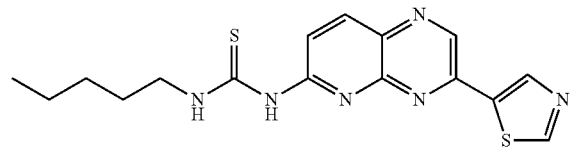 [SMILES: CCCCCNC(=S)Nc1ccc2ncc(-c3cncs3)nc2n1]

Compound 474: 1-Pentyl l-3-[3-(2-methyl-thiazol-4-yl)-pyrido[2,3-b]pyrazin-6-yl]-urea

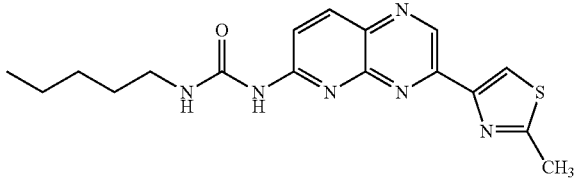 [SMILES: CCCCCNC(=O)Nc1ccc2ncc(-c3csc(C)n3)nc2n1]

Compound 475: 1-Pentyl-3-[3-(2-methyl-thiazol-4-yl)-pyrido[2,3-b]pyrazin-6-yl]-thiourea

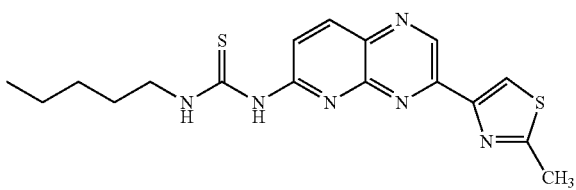 [SMILES: CCCCCNC(=S)Nc1ccc2ncc(-c3csc(C)n3)nc2n1]

Compound 476: 1-Pentyl-3-[3-(1-isopropyl-1H-pyrazol-3-yl)-pyrido[2,3-b]pyrazin-6-yl]-urea

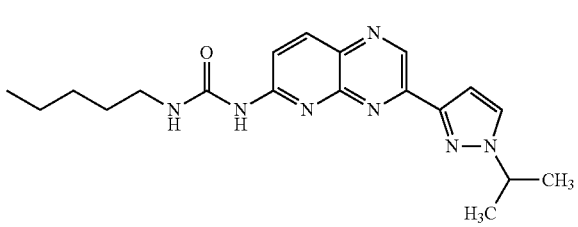

Compound 477: 1-Pentyl-3-[3-(1-isopropyl-1H-pyrazol-3-yl)-pyrido[2,3-b]pyrazin-6-yl]-thiourea

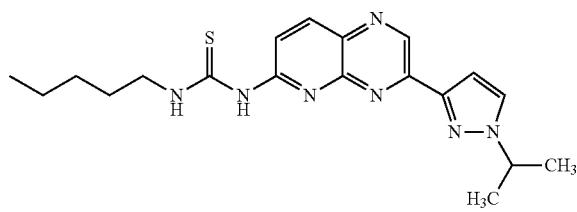 [SMILES: CCCCCNC(=O)Nc1ccc2ncc(-c3ccn(C(C)C)n3)nc2n1]

Compound 478: 1-Pentyl-3-[3-(5-hydroxymethyl-thiophen-3-yl)-pyrido[2,3-b]pyrazin-6-yl]-urea

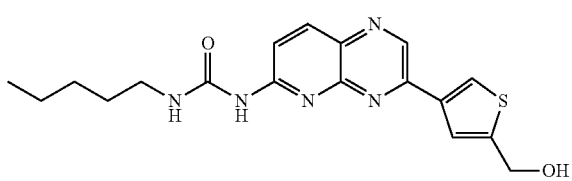 [SMILES: CCCCCNC(=O)Nc1ccc2ncc(-c3csc(CO)c3)nc2n1]

Compound 479: 1-Pentyl-3-[3-(5-hydroxymethyl-thiophen-3-yl)-pyrido[2,3-b]pyrazin-6-yl]-thiourea

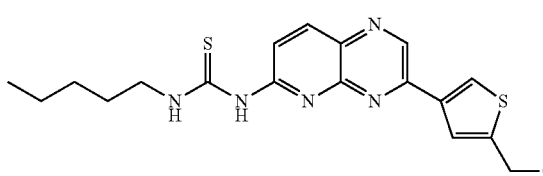

Compound 480: 4-[6-(3-Pentyl-ureido)-pyrido[2,3-b]pyrazin-3-yl]-thiophene-2-carboxylic acid ethyl ester

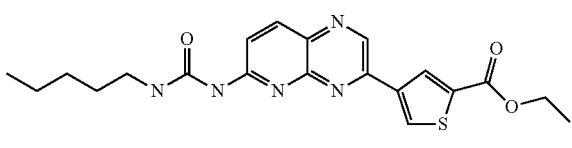 [SMILES: CCCCCNC(=O)Nc1ccc2ncc(-c3csc(C(=O)OCC)c3)nc2n1]

Compound 481: 4-[6-(3-Pentyl-thioureido)-pyrido[2,3-b]pyrazin-3-yl]-thiophene-2-carboxylic acid ethyl ester

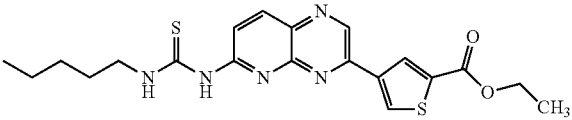 [SMILES: CCCCCNC(=S)Nc1ccc2ncc(-c3csc(C(=O)OCC)c3)nc2n1]

Compound 482: 4-[6-(3-Pentyl-ureido)-pyrido[2,3-b]pyrazin-3-yl]-thiophene-2-carboxylic acid

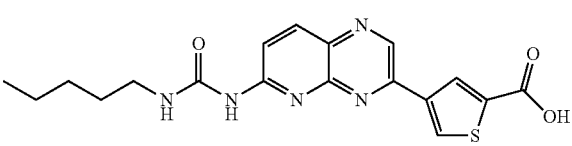 [SMILES: CCCCCNC(=O)Nc1ccc2ncc(-c3csc(C(=O)O)c3)nc2n1]

Compound 483: 4-[6-(3-Pentyl 1-thioureido)-pyrido[2,3-b]pyrazin-3-yl]-thiophene-2-carboxylic acid

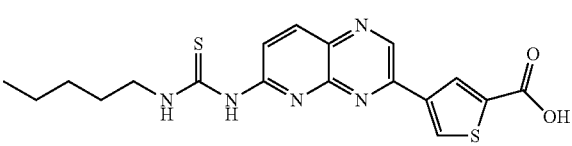 [SMILES: CCCCCNC(=S)Nc1ccc2ncc(-c3csc(C(=O)O)c3)nc2n1]

Compound 484: 1-Pentyl-3-[3-(4-methyl-thiazol-2-yl)-pyrido[2,3-b]pyrazin-6-yl]-urea

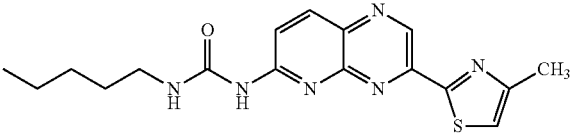 [SMILES: CCCCCNC(=O)Nc1ccc2ncc(-c3nc(C)cs3)nc2n1]

Compound 485: 1-Pentyl-3-[3-(4-methyl-thiazol-2-yl)-pyrido[2,3-b]pyrazin-6-yl]-thiourea

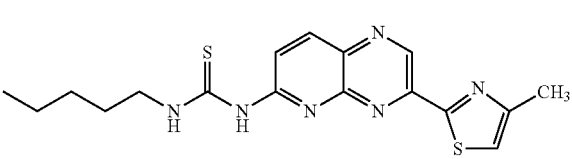 [SMILES: CCCCCNC(=S)Nc1ccc2ncc(-c3nc(C)cs3)nc2n1]

Compound 486: 1-Pentyl-3-(3-furan-3-yl-pyrido[2,3-b]pyrazin-6-yl)-urea

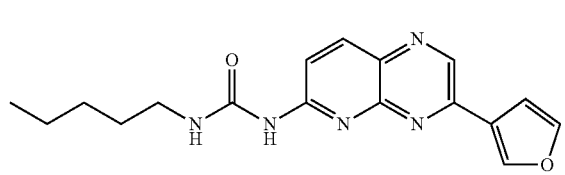 [SMILES: CCCCCNC(=O)Nc1ccc2ncc(-c3ccoc3)nc2n1]

Compound 487: 1-Pentyl-3-(3-furan-3-yl-pyrido[2,3-b]pyrazin-6-yl)-thiourea

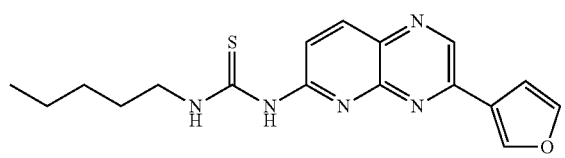 [SMILES: CCCCCNC(=S)Nc1ccc2ncc(-c3ccoc3)nc2n1]

Compound 488: 1-Pentyl-3-[3-(1-methyl-1H-imidazol-4-yl)-pyrido[2,3-b]pyrazin-6-yl]-urea

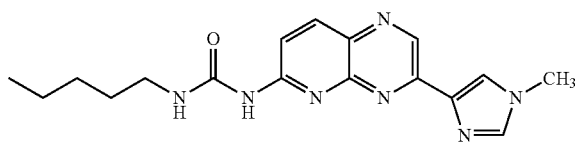 [SMILES: CCCCCNC(=O)Nc1ccc2ncc(-c3cn(C)cn3)nc2n1]

Compound 489: 1-Pentyl-3-[3-(1-methyl-1H-imidazol-4-yl)-pyrido[2,3-b]pyrazin-6-yl]-thiourea

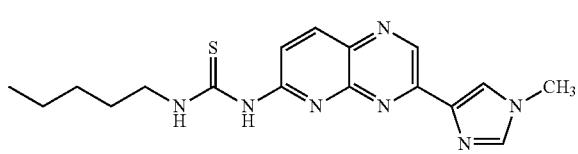 [SMILES: CCCCCNC(=S)Nc1ccc2ncc(-c3cn(C)cn3)nc2n1]

Compound 490: 1-Pentyl-3-[3-(1-methyl-1H-[1,2,3]triazol-4-yl)-pyrido[2,3-b]pyrazin-6-yl]-urea

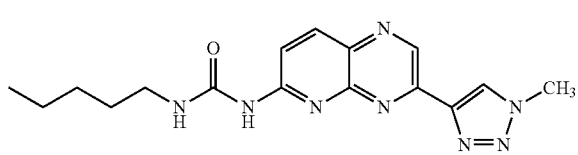 [SMILES: CCCCCNC(=O)Nc1ccc2ncc(-c3cn(C)nn3)nc2n1]

Compound 491: 1-Pentyl-3-[3-(1-methyl-1H-[1,2,3]triazol-4-yl)-pyrido[2,3-b]pyrazin-6-yl]-thiourea

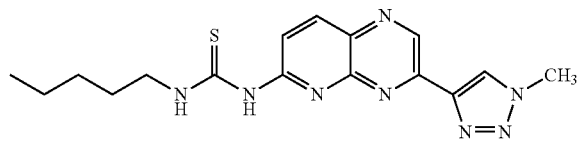 [SMILES: CCCCCNC(=S)Nc1ccc2ncc(-c3cn(C)nn3)nc2n1]

Compound 492: 1-Pentyl-3-(3-isoxazol-4-yl-pyrido[2,3-b]pyrazin-6-yl)-urea

Compound 493: 1-Pentyl-3-(3-isoxazol-4-yl-pyrido[2,3-b]pyrazin-6-yl)-thiourea

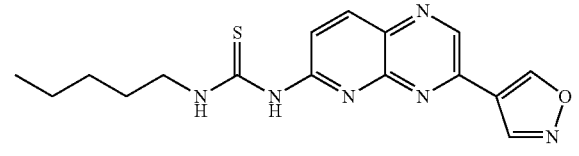 [SMILES: CCCCCNC(=S)Nc1ccc2ncc(-c3cnoc3)nc2n1]

Compound 494: 1-Pentyl-3-[3-(1H-imidazol-2-yl)-pyrido[2,3-b]pyrazin-6-yl]-urea

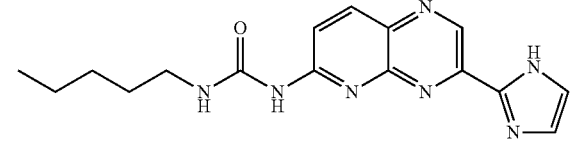 [SMILES: CCCCCNC(=O)Nc1ccc2ncc(-c3ncc[nH]3)nc2n1]

Compound 495: 1-Pentyl-3-[3-(1H-imidazol-2-yl)-pyrido[2,3-b]pyrazin-6-yl]-thiourea

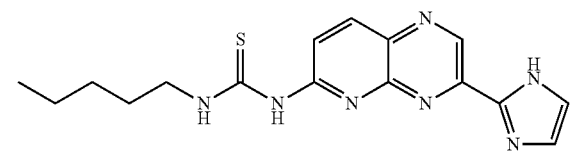 [SMILES: CCCCCNC(=S)Nc1ccc2ncc(-c3ncc[nH]3)nc2n1]

Compound 496: 1-[3-(6-Chloro-pyridin-2-yl)-pyrido[2,3-b]pyrazin-6-yl]-3-pentyl-urea

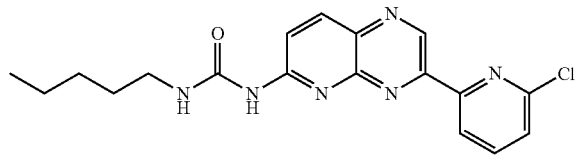 [SMILES: CCCCCNC(=O)Nc1ccc2ncc(-c3cccc(Cl)n3)nc2n1]

Compound 497: 1-[3-(6-Chloro-pyridin-2-yl)-pyrido[2,3-b]pyrazin-6-yl]-3-pentyl-thiourea

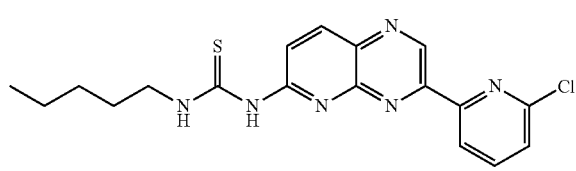

Compound 498: 1-Cyclopropylmethyl-3-[3-(5-methyl-thiophen-2-yl)-pyrido[2,3-b]pyrazin-6-yl]-urea

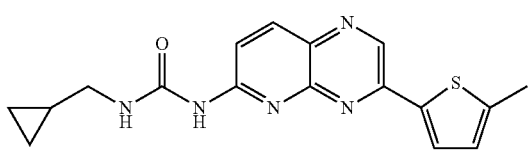 [SMILES: Cc1ccc(-c2cnc3ccc(NC(=O)NCC4CC4)nc3n2)s1]

Compound 499: 1-Cyclopropylmethyl-3-[3-(5-methyl-thiophen-2-yl)-pyrido[2,3-b]pyrazin-6-yl]thiourea

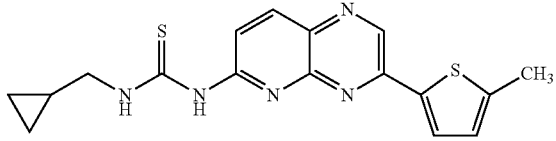

Compound 500: 1-Cyclopropylmethyl-3-[3-(4-methyl-thiophen-2-yl)-pyrido[2,3-b]pyrazin-6-yl]-urea

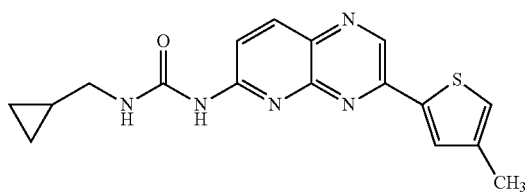 [SMILES: Cc1csc(-c2cnc3ccc(NC(=S)NCC4CC4)nc3n2)c1]

Compound 501: 1-Cyclopropylmethyl-3-[3-(4-methyl-thiophen-2-yl)-pyrido[2,3-b]pyrazin-6-yl]-thiourea

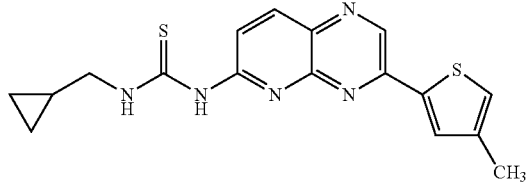

Compound 502: {5-[6-(3-Cyclopropylmethyl-ureido)-pyrido[2,3-b]pyrazin-3-yl]-thiophen-2-ylmethyl}-carbamic acid tert-butyl ester

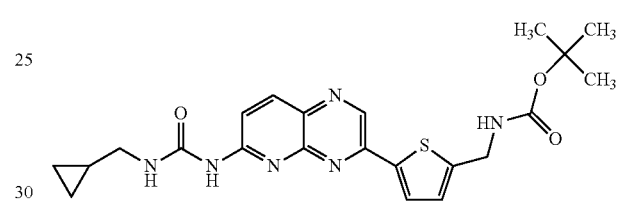

Compound 503: {5-[6-(3-Cyclopropylmethyl-thioureido)-pyrido[2,3-b]pyrazin-3-yl]-thiophen-2-ylmethyl}-carbamic acid tert-butyl ester

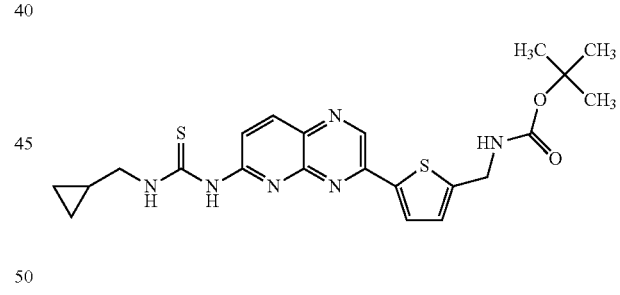

Compound 504: 1-Cyclopropylmethyl-3-[3-(5-hydroxymethyl-thiophen-2-yl)-pyrido[2,3-b]pyrazin-6-yl]-urea

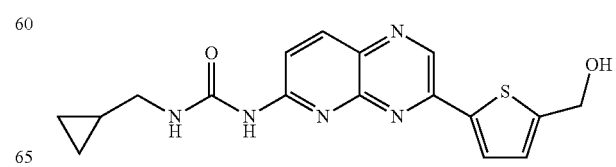

Compound 505: 1-Cyclopropylmethyl-3-[3-(5-hydroxymethyl-thiophen-2-yl)-pyrido[2,3-b]pyrazin-6-yl]-thiourea

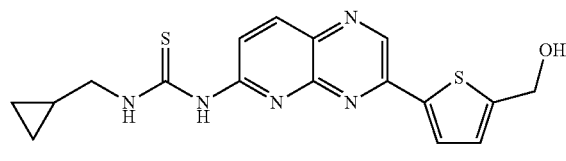 [SMILES: OCc1ccc(-c2cnc3ccc(NC(=S)NCC4CC4)nc3n2)s1]

Compound 506: 5-[6-(3-Cyclopropylmethyl-ureido)-pyrido[2,3-b]pyrazin-3-yl]-thiophene-2-carboxylic acid

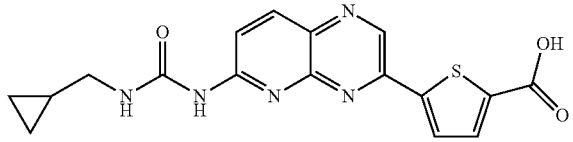 [SMILES: O=C(NCC1CC1)Nc1ccc2ncc(-c3ccc(C(=O)O)s3)nc2n1]

Compound 507: 5-[6-(3-Cyclopropylmethyl-thioureido)-pyrido[2,3-b]pyrazin-3-yl]-thiophene-2-carboxylicacid

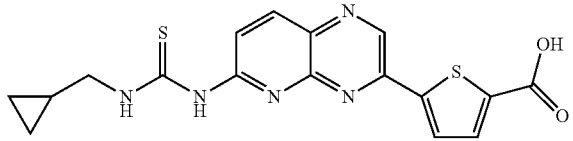 [SMILES: O=C(O)c1ccc(-c2cnc3ccc(NC(=S)NCC4CC4)nc3n2)s1]

Compound 508: 4-[6-(3-Cyclopropylmethyl-ureido)-pyrido[2,3-b]pyrazin-3-yl]-pyrazole-1-carboxylic acid tert-butyl ester

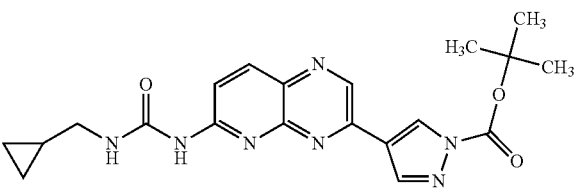 [SMILES: CC(C)(C)OC(=O)n1cc(-c2cnc3ccc(NC(=O)NCC4CC4)nc3n2)cn1]

Compound 509: 4-[6-(3-Cyclopropylmethyl-thioureido)-pyrido[2,3-b]pyrazin-3-yl]-pyrazole-1-carboxylic acid tert-butylester

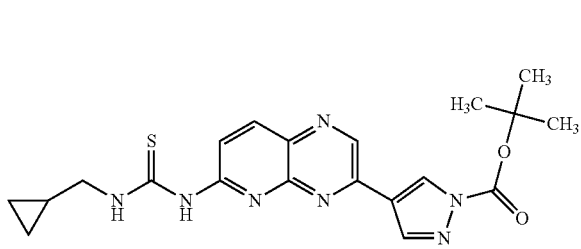 [SMILES: CC(C)(C)OC(=O)n1cc(-c2cnc3ccc(NC(=S)NCC4CC4)nc3n2)cn1]

Compound 510: {4-[6-(3-Cyclopropylmethyl-ureido)-pyrido[2,3-b]pyrazin-3-yl]-pyrazol-1-yl}-acetic acid ethyl ester

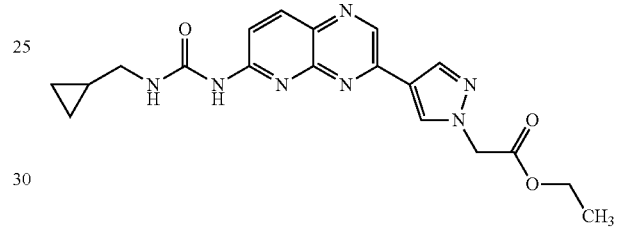

Compound 511: {4-[6-(3-Cyclopropylmethyl-thioureido)-pyrido[2,3-b]pyrazin-3-yl]-pyrazol-1-yl}-acetic acid ethyl ester

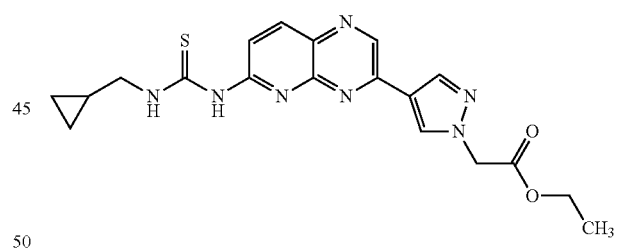

Compound 512: 3-{4-[6-(3-Cyclopropylmethyl-ureido)-pyrido[2,3-b]pyrazin-3-yl]-pyrazol-1-yl}-propionamide

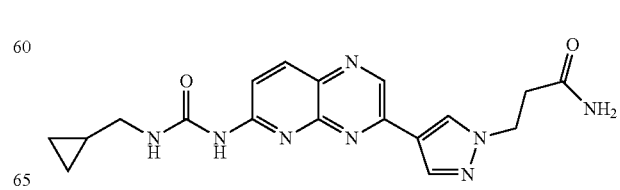

Compound 513: 3-{4-[6-(3-Cyclopropylmethyl-thio-ureido)-pyrido[2,3-b]pyrazin-3-yl]-pyrazol-1-yl}-propionamide

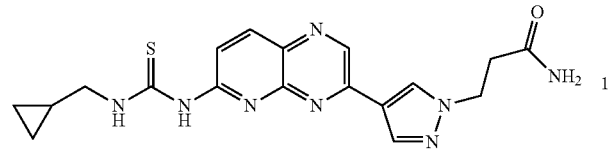

Compound 514: (2-{4-[6-(3-Cyclopropylmethyl-ureido)-pyrido[2,3-b]pyrazin-3-yl]-pyrazol-1-yl}-ethyl)-carbamic acid tert-butyl ester

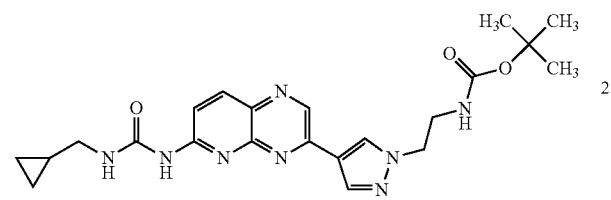

Compound 515: (2-{4-[6-(3-Cyclopropylmethyl-thioureido)-pyrido[2,3-b]pyrazin-3-yl]-pyrazol-1-yl}-ethyl)-carbamic acid tert-butyl ester

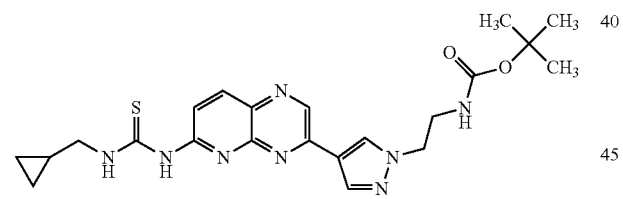

Compound 516: 5-[6-(3-Cyclopropylmethyl-ureido)-pyrido[2,3-b]pyrazin-3-yl]-2-methyl-furan-3-carboxylic acid methyl ester

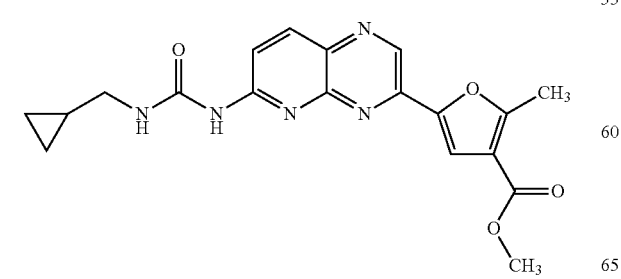

Compound 517: 5-[6-(3-Cyclopropylmethyl-thioureido)-pyrido[2,3-b]pyrazin-3-yl]-2-methyl-furan-3-carboxylic acid methyl ester

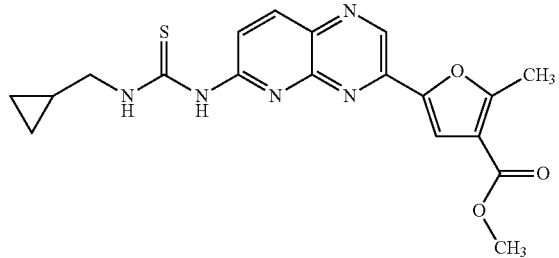 [SMILES: COC(=O)c1cc(-c2cnc3ccc(NC(=S)NCC4CC4)nc3n2)oc1C]

Compound 518: 1-Cyclopropylmethyl-3-[3-(5-iso-propyl-furan-2-yl)-pyrido[2,3-b]pyrazin-6-yl]-urea

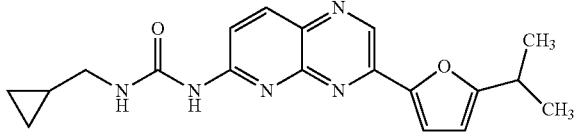 [SMILES: CC(C)c1ccc(-c2cnc3ccc(NC(=O)NCC4CC4)nc3n2)o1]

Compound 519: 1-Cyclopropylmethyl-3-[3-(5-iso-propyl-furan-2-yl)-pyrido[2,3-b]pyrazin-6-yl]-thiourea

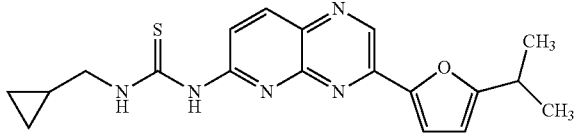 [SMILES: CC(C)c1ccc(-c2cnc3ccc(NC(=S)NCC4CC4)nc3n2)o1]

Compound 520: 1-[3-(5-Ethoxymethoxymethyl-furan-2-yl)-pyrido[2,3-b]pyrazin-6-yl]-3-cyclopropylmethyl-urea

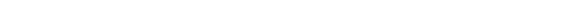

Compound 521: 1-[3-(5-Ethoxymethoxymethyl-furan-2-yl)-pyrido[2,3-b]pyrazin-6-yl]-3-cyclopropylmethyl-thiourea

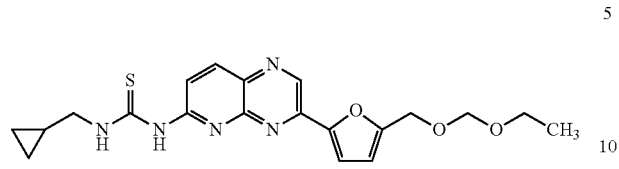

Compound 522: 1-Cyclopropylmethyl-3-[3-(5-trimethylsilanyl-furan-2-yl)-pyrido[2,3-b]pyrazin-6-yl]-urea

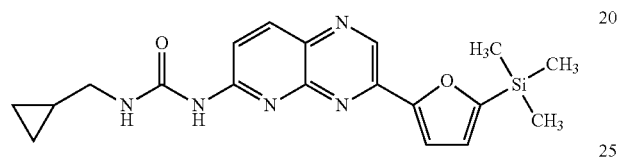

Compound 523: 1-Cyclopropylmethyl-3-[3-(5-trimethylsilanyl-furan-2-yl)-pyrido[2,3-b]pyrazin-6-yl]-thiourea

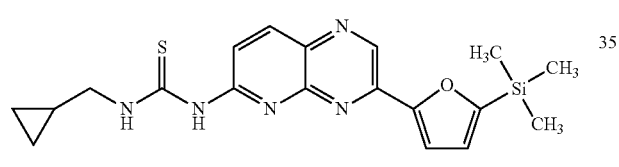

Compound 524: 1-Cyclopropylmethyl-3-[3-(5-methyl-furan-2-yl)-pyrido[2,3-b]pyrazin-6-yl]-urea

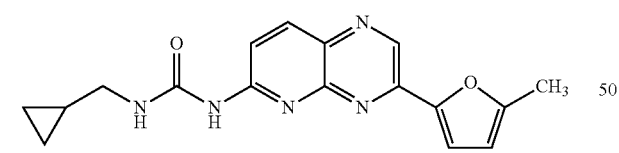

Compound 525: 1-Cyclopropylmethyl-3-[3-(5-methyl-furan-2-yl)-pyrido[2,3-b]pyrazin-6-yl]-thiourea

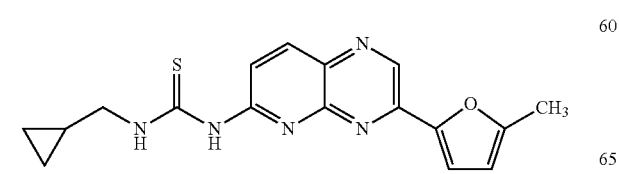

Compound 526: 1-Cyclopropylmethyl-3-(3-thiazol-5-yl-pyrido[2,3-b]pyrazin-6-yl)-urea

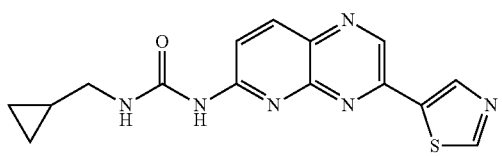

Compound 527: 1-Cyclopropylmethyl-3-(3-thiazol-5-yl-pyrido[2,3-b]pyrazin-6-yl)-thiourea

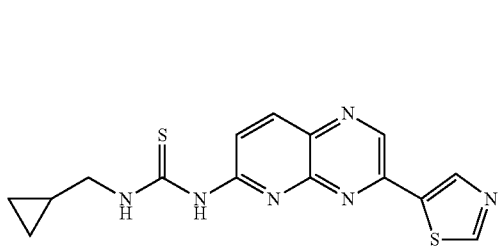 [SMILES: O=C(NCC1CC1)Nc1ccc2ncc(-c3cncs3)nc2n1]

Compound 528: 1-Cyclopropylmethyl-3-[3-(2-methyl-thiazol-4-yl)-pyrido[2,3-b]pyrazin-6-yl]-urea

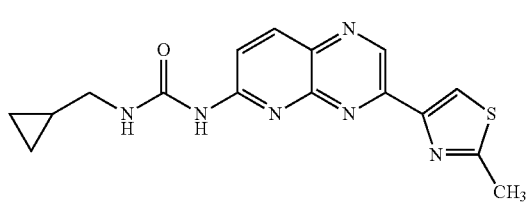

Compound 529: 1-Cyclopropylmethyl-3-[3-(2-methyl-thiazol-4-yl)-pyrido[2,3-b]pyrazin-6-yl]-thiourea

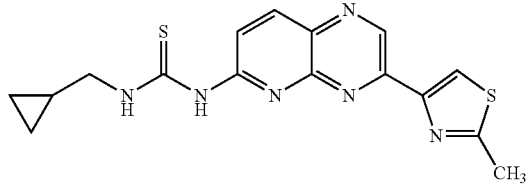 [SMILES: Cc1nc(-c2cnc3ccc(NC(=S)NCC4CC4)nc3n2)cs1]

Compound 530: 1-Cyclopropylmethyl-3-[3-(1-isopropyl-1H-pyrazol-3-yl)-pyrido[2,3-b]pyrazin-6-yl]-urea

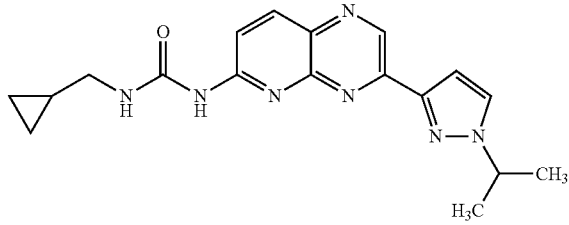 [SMILES: CC(C)n1ccc(-c2cnc3ccc(NC(=O)NCC4CC4)nc3n2)n1]

Compound 531: 1-Cyclopropylmethyl-3-[3-(1-isopropyl-1H-pyrazol-3-yl)-pyrido[2,3-b]pyrazin-6-yl]-thiourea

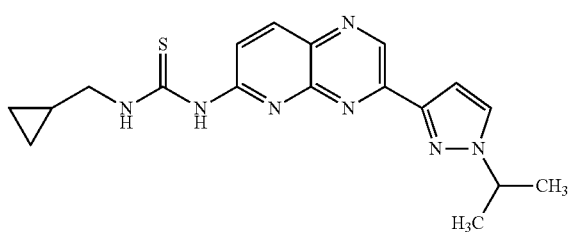

Compound 532: 1-Cyclopropylmethyl-3-[3-(5-hydroxymethyl-thiophen-3-yl)-pyrido[2,3-b]pyrazin-6-yl]-urea

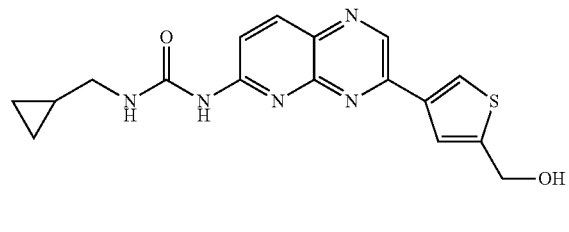 [SMILES: O=C(NCC1CC1)Nc1ccc2ncc(-c3csc(CO)c3)nc2n1]

Compound 533: 1-Cyclopropylmethyl-3-[3-(5-hydroxymethyl-thiophen-3-yl)-pyrido[2,3-b]pyrazin-6-yl]-thiourea

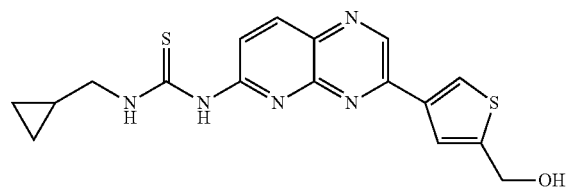 [SMILES: OCc1cc(-c2cnc3ccc(NC(=S)NCC4CC4)nc3n2)cs1]

Compound 534: 4-[6-(3-Cyclopropylmethyl-ureido)-pyrido[2,3-b]pyrazin-3-yl]-thiophene-2-carboxylic acid ethyl ester

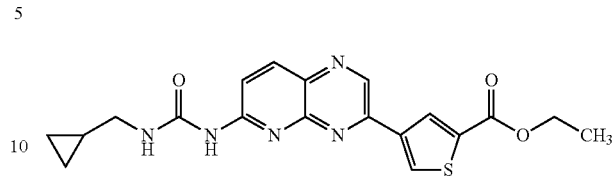

Compound 535: 4-[6-(3-Cyclopropylmethyl-thioureido)-pyrido[2,3-b]pyrazin-3-yl]-thiophene-2-carboxylic acid ethyl ester

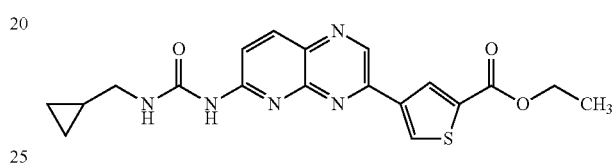

Compound 536: 4-[6-(3-Cyclopropylmethyl-ureido)-pyrido[2,3-b]pyrazin-3-yl]-thiophene-2-carboxylic acid

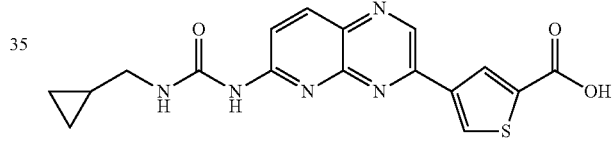

Compound 537: 4-[6-(3-Cyclopropylmethyl-thioureido)-pyrido[2,3-b]pyrazin-3-yl]-thiophene-2-carboxylic acid

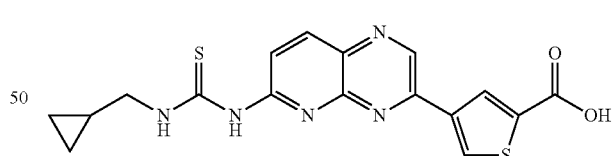

Compound 538: 1-Cyclopropylmethyl-3-[3-(4-methyl-thiazol-2-yl)-pyrido[2,3-b]pyrazin-6-yl]-urea

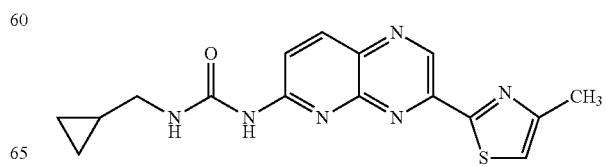

Compound 539: 1-Cyclopropylmethyl-3-[3-(4-methyl-thiazol-2-yl)-pyrido[2,3-b]pyrazin-6-yl]-thiourea

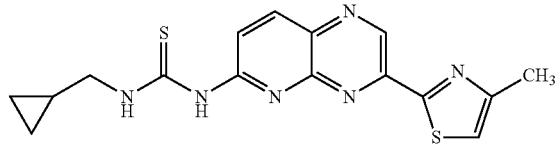 [SMILES: Cc1csc(-c2cnc3ccc(NC(=S)NCC4CC4)nc3n2)n1]

Compound 540: 1-Cyclopropylmethyl-3-(3-furan-3-yl-pyrido[2,3-b]pyrazin-6-yl)-urea

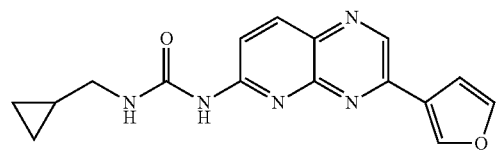 [SMILES: O=C(NCC1CC1)Nc1ccc2ncc(-c3ccoc3)nc2n1]

Compound 541: 1-Cyclopropylmethyl-3-(3-furan-3-yl-pyrido[2,3-b]pyrazin-6-yl)-thiourea

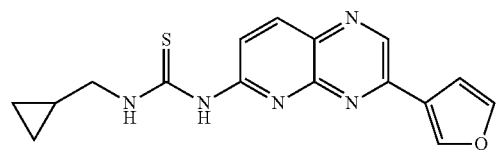 [SMILES: S=C(NCC1CC1)Nc1ccc2ncc(-c3ccoc3)nc2n1]

Compound 542: 1-Cyclopropylmethyl-3-[3-(1-methyl-1H-imidazol-4-yl)-pyrido[2,3-b]pyrazin-6-yl]-urea

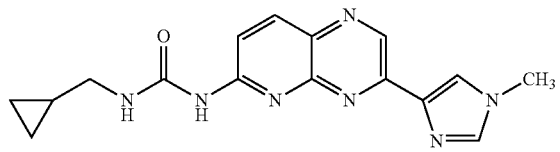 [SMILES: Cn1cnc(-c2cnc3ccc(NC(=O)NCC4CC4)nc3n2)c1]

Compound 543: 1-Cyclopropylmethyl-3-[3-(1-methyl-1H-imidazol-4-yl)-pyrido[2,3-b]pyrazin-6-yl]-thiourea

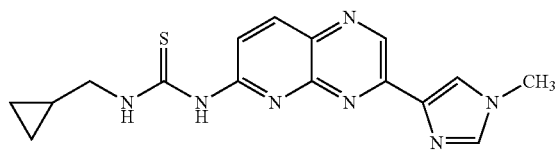 [SMILES: Cn1cnc(-c2cnc3ccc(NC(=S)NCC4CC4)nc3n2)c1]

Compound 544: 1-Cyclopropylmethyl-3-[3-(1-methyl-1H-[1,2,3]triazol-4-yl)-pyrido[2,3-b]pyrazin-6-yl]-urea

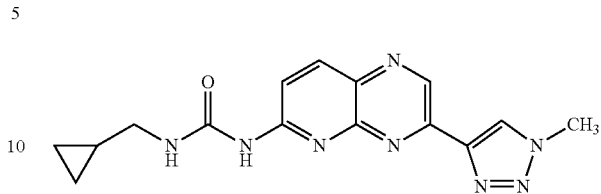

Compound 545: 1-Cyclopropylmethyl-3-[3-(1-methyl-1H-[1,2,3]triazol-4-yl)-pyrido[2,3-b]pyrazin-6-yl]-thiourea

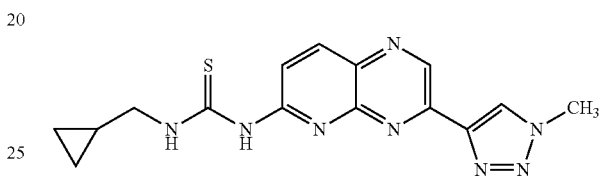

Compound 546: 1-Cyclopropylmethyl-3-(3-isoxazol-4-yl-pyrido[2,3-b]pyrazin-6-yl)-urea

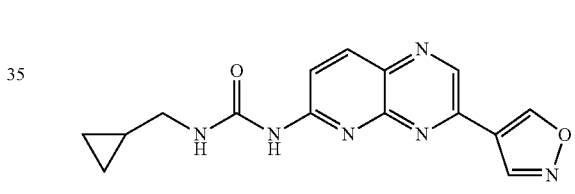

Compound 547: 1-Cyclopropylmethyl-3-(3-isoxazol-4-yl-pyrido[2,3-b]pyrazin-6-yl)-thiourea

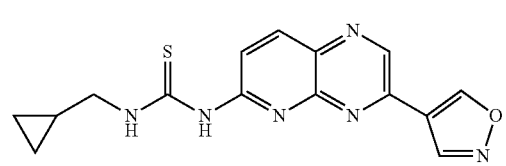 [SMILES: O=C(NCC1CC1)Nc1ccc2ncc(-c3cnoc3)nc2n1]

Compound 548: 1-Cyclopropylmethyl-3-[3-(1H-imidazol-2-yl)-pyrido[2,3-b]pyrazin-6-yl]-urea

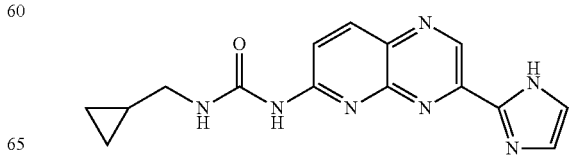

Compound 549: 1-Cyclopropylmethyl-3-[3-(1H-imidazol-2-yl)-pyrido[2,3-b]pyrazin-6-yl]-thiourea

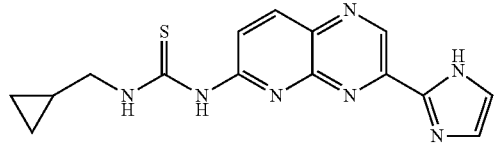 [SMILES: S=C(NCC1CC1)Nc1ccc2ncc(-c3ncc[nH]3)nc2n1]

Compound 550: 1-[3-(6-Chloro-pyridin-2-yl)-pyrido[2,3-b]pyrazin-6-yl]-3-cyclopropylmethyl-urea

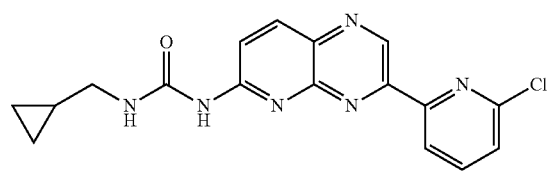 [SMILES: S=C(NCC1CC1)Nc1ccc2ncc(-c3cccc(Cl)n3)nc2n1]

Compound 551: 1-[3-(6-Chloro-pyridin-2-yl)-pyrido[2,3-b]pyrazin-6-yl]-3-cyclopropylmethyl-thiourea

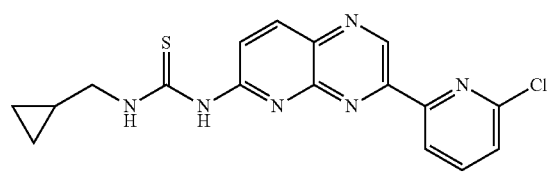

Compound 552: 1-Allyl-3-{3-[4-(2-methoxy-ethoxy)phenyl]-pyrido[2,3-b]pyrazin-6-yl}-thiourea

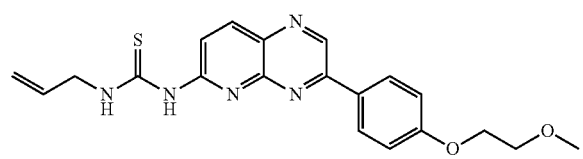 [SMILES: C=CCNC(=S)Nc1ccc2ncc(-c3ccc(OCCOC)cc3)nc2n1]

Compound 553: 1-Allyl-3-{3-[4-(2-dimethylamino-ethoxy)-phenyl]-pyrido[2,3-b]pyrazin-6-yl}-thiourea

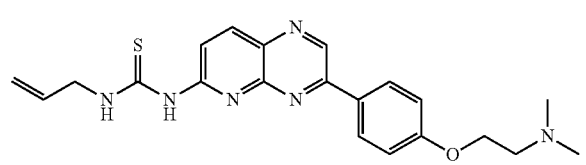 [SMILES: C=CCNC(=S)Nc1ccc2ncc(-c3ccc(OCCN(C)C)cc3)nc2n1]

Compound 554: 1-Allyl-3-{3-[4-(2-morpholin-4-yl-ethoxy)-phenyl]-pyrido[2,3-b]pyrazin-6-yl}-thiourea

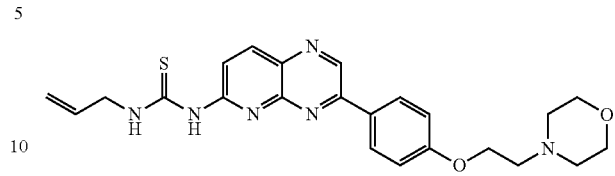

Compound 555: Ethyl-carbamic acid 4-[6-(3-allyl-thioureido)-pyrido[2,3-b]pyrazin-3-yl]-phenyl ester

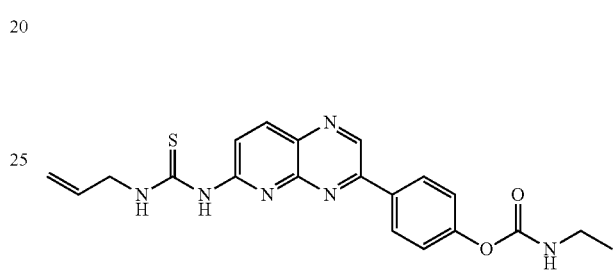

Compound 556: Methanesulfonic acid 4-[6-(3-allyl-thioureido)-pyrido[2,3-b]pyrazin-3-yl]-phenyl ester

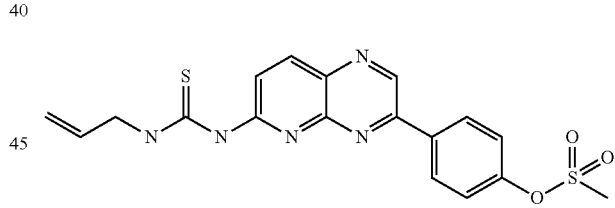

Compound 557: 1-Allyl-3-{3-[4-((2S,3R,4S,5S,6R)-3,4,5-trihydroxy-6-hydroxymethyl-tetrahydro-pyran-2-yloxy)-phenyl]-pyrido[2,3-b]pyrazin-6-yl}-thiourea

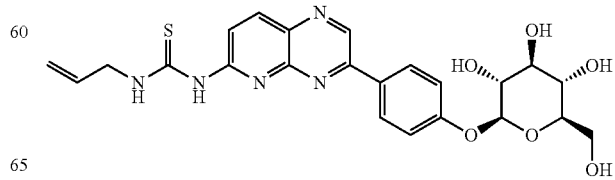

Compound 558: 1-Allyl-3-{3-[1-(3-phenyl-propyl)-1H-pyrazol-4-yl]-pyrido[2,3-b]pyrazin-6-yl}-thiourea

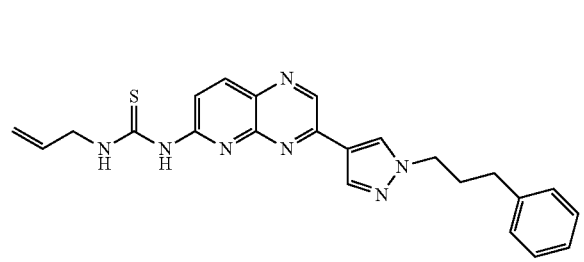 [SMILES: C=CCNC(=S)Nc1ccc2ncc(-c3cnn(CCCc4ccccc4)c3)nc2n1]

Compound 559: 1-Allyl-3-{3-[1-(3-methanesulfonyl-benzyl)-1H-pyrazol-4-yl]-pyrido[2,3-b]pyrazin-6-yl}-thiourea

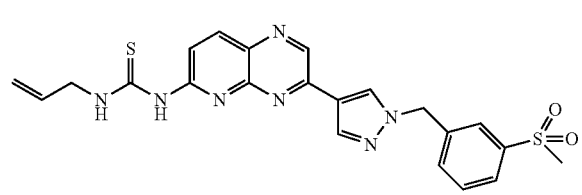 [SMILES: C=CCNC(=S)Nc1ccc2ncc(-c3cnn(Cc4cccc(S(C)(=O)=O)c4)c3)nc2n1]

Compound 560: 1-Allyl-3-{3-[1-(3-hydroxy-benzyl)-1H-pyrazol-4-yl]-pyrido[2,3-b]pyrazin-6-yl}-thiourea

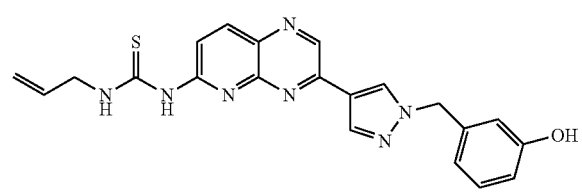 [SMILES: C=CCNC(=S)Nc1ccc2ncc(-c3cnn(Cc4cccc(O)c4)c3)nc2n1]

Compound 561: 1-Allyl-3-[3-(1-propyl-1H-pyrazol-4-yl)-pyrido[2,3-b]pyrazin-6-yl]-thiourea

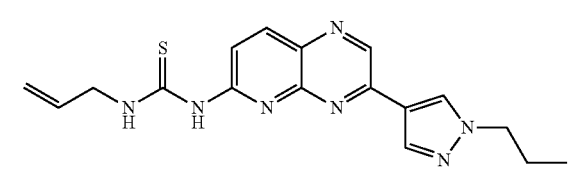 [SMILES: C=CCNC(=S)Nc1ccc2ncc(-c3cnn(CCC)c3)nc2n1]

Compound 562: 1-Allyl-3-[3-(1H-pyrazol-4-yl)-pyrido[2,3-b]pyrazin-6-yl]-thiourea

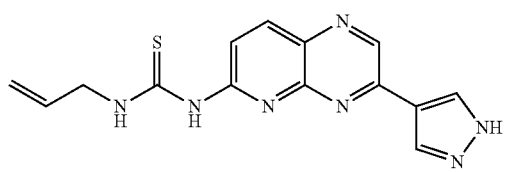 [SMILES: C=CCNC(=S)Nc1ccc2ncc(-c3cn[nH]c3)nc2n1]

Compound 563: 1-Allyl-3-[3-(1-benzyl-1H-pyrazol-4-yl)-pyrido[2,3-b]pyrazin-6-yl]-thiourea

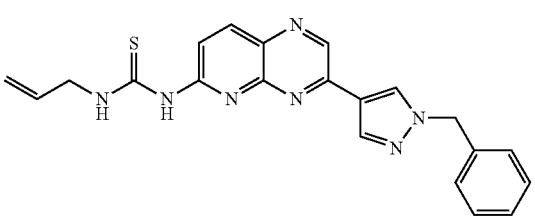 [SMILES: C=CCNC(=S)Nc1ccc2ncc(-c3cnn(Cc4ccccc4)c3)nc2n1]

Compound 564: 1-Allyl-3-{3-[1-(4-methoxy-benzyl)-1H-pyrazol-4-yl]-pyrido[2,3-b]pyrazin-6-yl}-thiourea

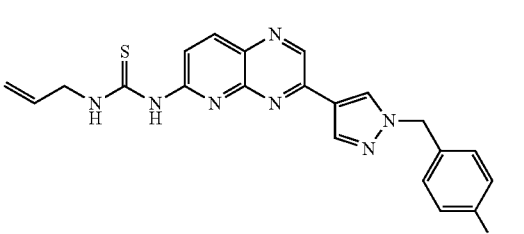

Compound 565: 1-Allyl-3-{3-[1-(3,4-dimethoxy-benzyl)-1H-pyrazol-4-yl]-pyrido[2,3-b]pyrazin-6-yl}thiourea

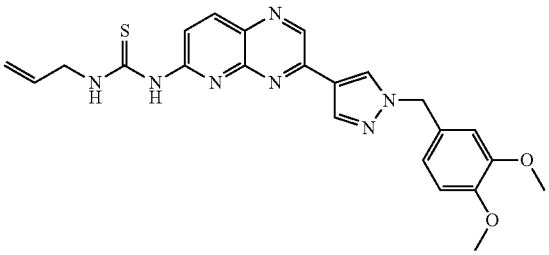 [SMILES: C=CCNC(=S)Nc1ccc2ncc(-c3cnn(Cc4ccc(OC)c(OC)c4)c3)nc2n1]

Compound 566: 1-Allyl-3-[3-(1-benzo[1,3]dioxol-5-ylmethyl-1H-pyrazol-4-yl)-pyrido[2,3-b]pyrazin 6yl]-thiourea

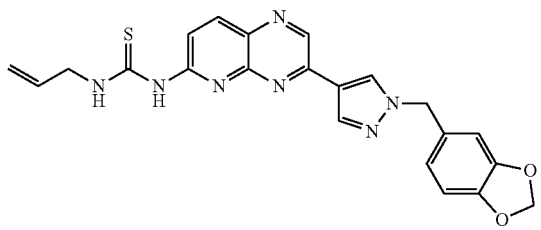 [SMILES: C=CCNC(=S)Nc1ccc2ncc(-c3cnn(Cc4ccc5c(c4)OCO5)c3)nc2n1]

Compound 567: 1-Allyl-3-{3-[1-(4-fluoro-3-methoxy-benzyl)-1H-pyrazol-4-yl]-pyrido[2,3-b]pyrazin-6-yl}-thiourea

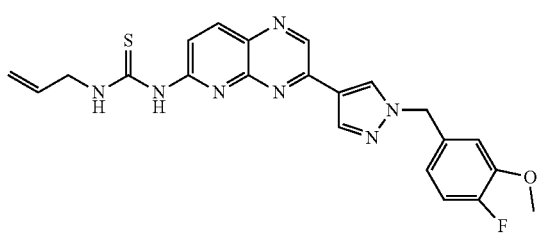 [SMILES: C=CCNC(=S)Nc1ccc2ncc(-c3cnn(Cc4ccc(F)c(OC)c4)c3)nc2n1]

Compound 568: 1-Allyl-3-{3-[1-(3-difluoromethoxy-benzyl)-1H-pyrazol-4-yl]-pyrido[2,3-b]pyrazin-6-yl}-thiourea

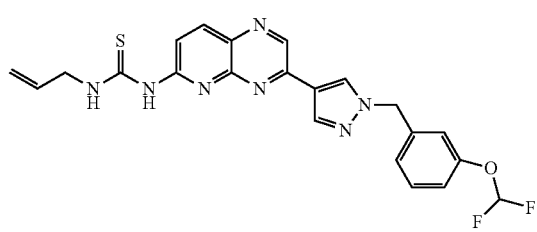 [SMILES: C=CCNC(=S)Nc1ccc2ncc(-c3cnn(Cc4cccc(OC(F)F)c4)c3)nc2n1]

Compound 569: 1-Allyl-3-[3-(1-{2-[2-(2-methoxyethoxy)-ethoxy]-ethyl}-1H-pyrazol-4-yl)-pyrido[2,3-b]pyrazin-6-yl]-thiourea

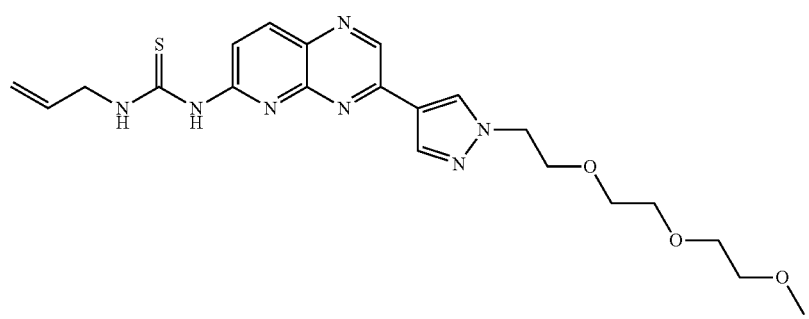 [SMILES: C=CCNC(=S)Nc1ccc2ncc(-c3cnn(CCOCCOCCOC)c3)nc2n1]

Compound 570: 1-Allyl-3-[3-(3,4-dimethoxy-phenyl)-pyrido[2,3-b]pyrazin-6-yl]-thiourea

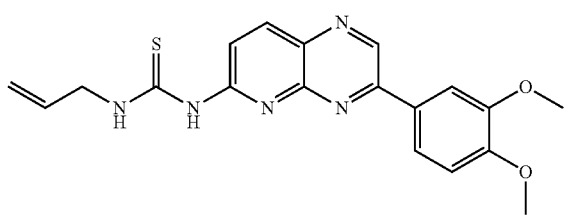 [SMILES: C=CCNC(=S)Nc1ccc2ncc(-c3ccc(OC)c(OC)c3)nc2n1]

Compound 571: 1-Allyl-3-[3-(3-hydroxy-4-methoxy-phenyl)-pyrido[2,3-b]pyrazin-6-yl]-thiourea

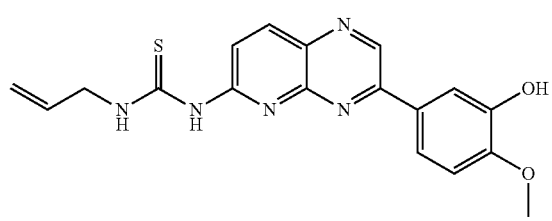 [SMILES: C=CCNC(=S)Nc1ccc2ncc(-c3ccc(OC)c(O)c3)nc2n1]

Compound 572: 1-Allyl-3-[3-(3,5-dichloro-4-hydroxy-phenyl)-pyrido[2,3-b]pyrazin-6-yl]-thiourea

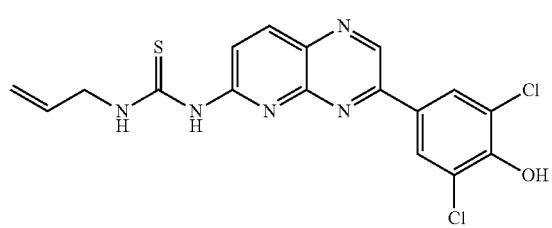 [SMILES: C=CCNC(=S)Nc1ccc2ncc(-c3cc(Cl)c(O)c(Cl)c3)nc2n1]

Compound 573: 1-Allyl-3-[3-(4-amino-phenyl)-pyrido[2,3-b]pyrazin-6-yl]-thiourea

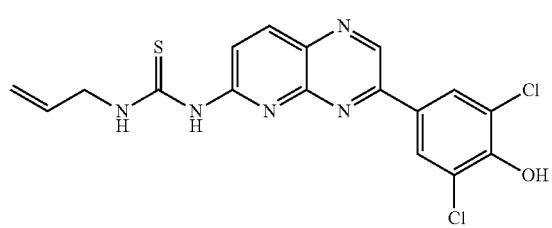 [SMILES: C=CCNC(=S)Nc1ccc2ncc(-c3cc(Cl)c(O)c(Cl)c3)nc2n1]

Compound 574: 1-Allyl-3-[3-(3-chloro-4-hydroxy-phenyl)-pyrido[2,3-b]pyrazin-6-yl]-thiourea

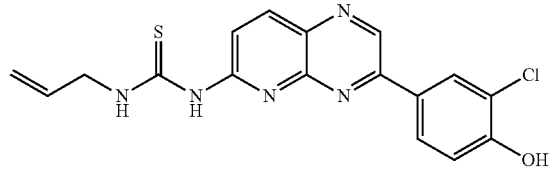 [SMILES: C=CCNC(=S)Nc1ccc2ncc(-c3ccc(O)c(Cl)c3)nc2n1]

Compound 575: 1-Allyl-3-[3-(3-chloro-4-hydroxy-5-methoxy-phenyl)-pyrido[2,3-b]pyrazin-6-yl]-thiourea

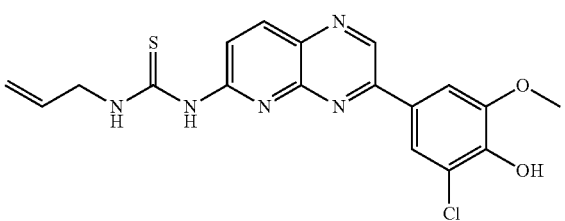 [SMILES: C=CCNC(=S)Nc1ccc2ncc(-c3cc(Cl)c(O)c(OC)c3)nc2n1]

Compound 576: 1-Allyl-3-[3-(2,3-dihydro-benzofuran-5-yl)-pyrido[2,3-b]pyrazin-6-yl]-thiourea

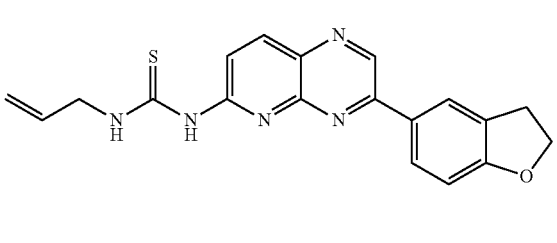 [SMILES: C=CCNC(=S)Nc1ccc2ncc(-c3ccc4c(c3)CCO4)nc2n1]

Compound 577: Phosphoric acid mono-{4-[6-(3-allyl-thioureido)-pyrido[2,3-b]pyrazin-3-yl]-phenyl}ester

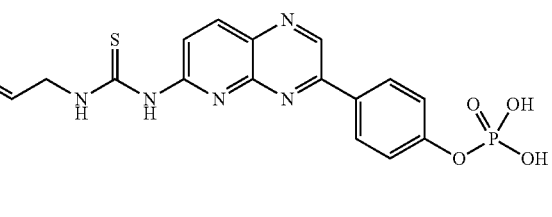

Compound 578: 2,2-Dimethyl-propionic acid 4-[6-(3-allyl-thioureido)-pyrido[2,3-b]pyrazin-3-yl]-phenyl ester

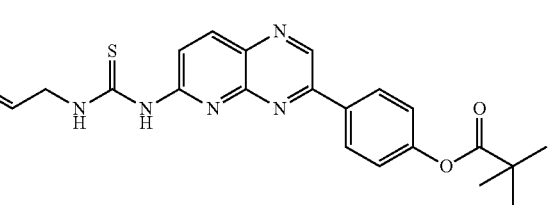

Compound 579: 1-Allyl-3-[3-(4-{2-[2-(2-hydroxy-ethoxy)-ethoxy]-ethoxy}-phenyl)-pyrido[2,3-b]pyrazin-6-yl]-thiourea

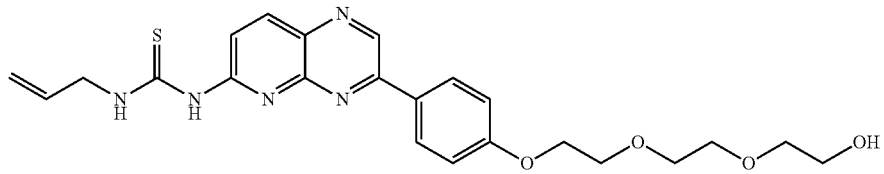 [SMILES: C=CCNC(=S)Nc1ccc2ncc(-c3ccc(OCCOCCOCCO)cc3)nc2n1]

Compound 580: 1-Allyl-3-{3-[1-(3-methoxy-benzyl)-1H-pyrazol-4-yl]-pyrido[2,3-b]pyrazin-6-yl}-thiourea

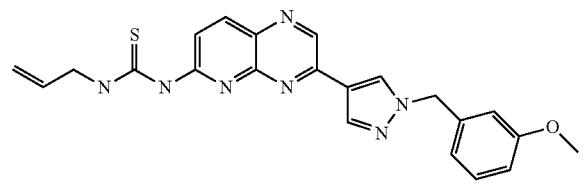 [SMILES: C=CCNC(=S)Nc1ccc2ncc(-c3cnn(Cc4cccc(OC)c4)c3)nc2n1]

Compound 581: 4-[6-(3-Cyclopentyl-thioureido)-pyrido[2,3-b]pyrazin-3-yl]-pyrazole-1-carboxylic acid tert-butyl ester

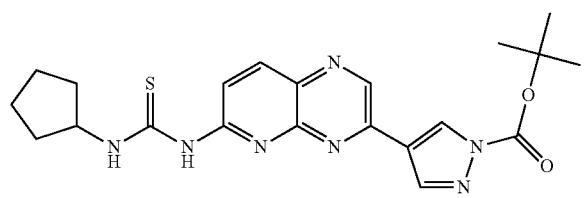

Compound 582: (2-{4-[6-(3-Cyclopentyl-ureido)-pyrido[2,3-b]pyrazin-3-yl]-pyrazol-1-yl}-ethyl)-carbamic acid tert-butyl ester

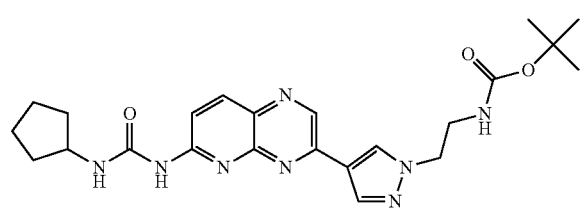 [SMILES: CC(C)(C)OC(=O)NCCn1cc(-c2cnc3ccc(NC(=O)NC4CCCC4)nc3n2)cn1]

which can be used for the production of a medicament for the treatment or prevention of physiological and/or pathophysiological states in mammals mediated by signal transduction pathways selected from the group consisting of: the PI3K-Akt signal transduction pathway and the ras-Raf-Mek-Erk signal transduction pathway.

In order to avoid ambiguities: when chemical structure and chemical name of the explicit compounds shown above erroneously do not match one another, the chemical structure shall unambiguously define the particular explicit compound.

The afore-mentioned generic compounds having the general formula (I) and preferred embodiments as well as the explicitly specified pyridopyrazine compounds 1 to 89, 190-193, 210-582 are hereinafter designated jointly as "compounds according to the invention".

The expressions and terms specified to explain the compounds according to the invention having the general formula (I), the preferred embodiments and compounds 1 to 89, 190-193, 210-582 basically have the following meanings unless specified otherwise in the description and the claims:

In the context of this invention, the expression "alkyl" encompasses acyclic saturated or unsaturated hydrocarbon radicals which may be branched or straight-chain and have 1 to 8 carbon atoms, i.e. $C_{1-8}$-alkanyls, $C_{2-8}$-alkenyls and $C_{2-8}$-alkynyls. Alkenyls have at least one C—C double bond and alkynyls at least one C—C triple bond. Alkynyls may additionally also have at least one C—C double bond. Preferred alkyl radicals are methyl, ethyl, n-propyl, 2-propyl, n-butyl, sec-butyl, tert-butyl, n-pentyl, iso-pentyl, neo-pentyl, n-hexyl, 2-hexyl, n-heptyl, n-octyl, n-nonyl, n-decyl, n-undecyl, n-dodecyl, ethylenyl (vinyl), ethynyl, propenyl (—CH$_2$CH=CH$_2$; —CH=CH—CH$_3$, —C(=CH$_2$)—CH$_3$), propynyl (—CH$_2$—C≡CH, —C≡C—CH$_3$), butenyl, butynyl, pentenyl, pentynyl, hexenyl, hexynyl, heptenyl, heptynyl, octenyl, octadienyl and octynyl.

For the purposes of this invention, the expression "cycloalkyl" means cyclic nonaromatic hydrocarbons having 1 to 3 rings with 3 to 20, preferably 3 to 12 carbon atoms, which may be saturated or unsaturated, more preferably ($C_3$-$C_8$)cycloalkyl. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Preferred cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

The expression "heterocyclyl" represents a 3- to 14-membered, preferably 3-, 4-, 5-, 6-, 7- or 8-membered, cyclic organic radical which contains at least 1 heteroatom, optionally 2, 3, 4 or 5 heteroatoms, especially nitrogen, oxygen and/or sulphur, the heteroatoms being the same or different and the cyclic radical being saturated or unsaturated but not aromatic. The heterocyclyl radical may also be part of a bi- or polycyclic system, where, for example, the heterocyclyl radical is fused to an aryl, heteroaryl or cycloalkyl radical as defined herein by any possible and desired ring member(s). The bonding to the compounds of the general formula (I) can be effected via any possible ring member of the heterocyclyl radical. Preferred heterocyclyl radicals are tetrahydrofuryl, pyrrolidinyl, imidazolidinyl, thiazolidinyl, tetrahydropyranyl, piperidinyl, piperazinyl, morpholinyl, thiapyrrolidinyl, oxapiperazinyl, oxapiperidinyl and oxadiazolyl.

In the context of this invention, the expression "aryl" means aromatic hydrocarbons having 3 to 14 carbon atoms, preferably 5 to 14 carbon atoms, more preferably 6 to 14 carbon atoms. The aryl radical may also be part of a bi- or polycyclic system, where, for example, the aryl radical is fused to a heterocyclyl, heteroaryl or cycloalkyl radical as defined herein by any possible and desired ring member(s), for example to tetrahydrofuran, tetrahydrothiophene, pyrrolidine, imidazolidine, thiazolidine, tetrahydropyran, dihydropyran, piperidine, furan, thiophene, imidazole, thiazole, oxazole, isoxazole. The bonding to the compounds of the general formula (I) can be effected via any possible ring member of the aryl radical. Preferred aryl radicals are phenyl, biphenyl, naphthyl and anthracenyl, but likewise indanyl, indenyl or 1,2,3,4-tetrahydronaphthyl.

The expression "heteroaryl" represents a 5-, 6- or 7-membered cyclic aromatic radical which contains at least 1 heteroatom, if appropriate also 2, 3, 4 or 5 heteroatoms, especially nitrogen, oxygen and/or sulphur, the heteroatoms being the same or different. The number of nitrogen atoms is preferably 0 to 3, that of oxygen and sulphur atoms preferably 0 or 1. The heteroaryl radical may also be part of a bi- or polycyclic system, where, for example, the heteroaryl radical is fused to a heterocyclyl, aryl or cycloalkyl radical as defined herein by any possible and desired ring member(s). The bonding to the compounds of the general formula (I) can be effected via any possible ring member of the heteroaryl radical. Preferred heteroaryl radicals are pyrrolyl, furyl, thienyl, thiazolyl, isothiazolyl, oxazolyl, oxadiazolyl, isoxazolyl, pyrazolyl, imidazolyl, triazole, tetrazole, pyridinyl, pyrimidinyl, pyridazinyl, pyrazinyl, triazinyl, phthalazinyl, indolyl, indazolyl, indolizinyl, benzimidazolyl, quinolinyl, isoquinolinyl, quinoxalinyl, quinazolinyl, pteridinyl, carbazolyl, phenazinyl, phenoxazinyl, phenothiazinyl, and acridinyl.

For the purposes of the present invention, the expressions "alkyl-cycloalkyl", "cycloalkylalkyl", "alkyl-heterocyclyl", "heterocyclylalkyl", "alkyl-aryl", "arylalkyl", "alkyl-heteroaryl" and "heteroarylalkyl" mean that alkyl, cycloalkyl, heterocycl, aryl and heteroaryl are each as defined above, and the cycloalkyl, heterocyclyl, aryl and heteroaryl radical is bonded to the compounds of the general formula (I) via an alkyl radical, preferably $C_1$-$C_8$-alkyl radical, more preferably $C_1$-$C_5$-alkyl radical.

In connection with "alkyl", "cycloalkyl", "heterocyclyl", "aryl", "heteroaryl", alkyl-cycloalkyl", "alkyl-heterocyclyl", "alkyl-aryl" and "alkyl-heteroaryl" the term substituted is understood in the sense of this invention unless defined explicitly above in the description and the claims as the substitution of one or more hydrogen groups by F, Cl, Br, I, CN, $CF_3$, $NH_2$, NH-alkyl, NH-aryl, N(alkyl)$_2$, $NO_2$, SH, S-alkyl, $SO_2$-alkyl, OH, $OCHF_2$, O—CH2-OAlkyl, O—CH2-OMe, O-Alkyl, $OCF_3$, OMe, OEt, O—CH2-CH2-NMe2, O—$CH_2$—$CH_2$—OMe; O—CH2-CH2-OH, O—$CH_2$—$CH_2$—O—$CH_2$—$CH_2$—OH, O—$CH_2$—$CH_2$—O—$CH_2$—$CH_2$—OMe; O-Alkyl-aryl, O-aryl, —O—CH—O—; OC(O)-Alkyl, $OSO_3H$, OP(O)(OH)$_2$, NC(O)O-Alkyl, CHO, $CO_2H$, C(O)O-Alkyl, C(O)NH2, $SO_3H$, alkyl, Alkyl-OH, heterocyclyl, or 4-methyl-piperazin-1-ylmethyl. The substituents can be the same or different and the substitutions can take place in any arbitrary and possible position of the alkyl, cycloalkyl, heterocyclyl, aryl and heteroaryl group.

In the context of this invention, the expression "halogen" encompasses the halogen atoms fluorine, chlorine, bromine and iodine.

Multiply substituted groups are to be understood as those which are multiply, e.g. doubly, triply, substituted either at different or at the same atoms, for example, triply substituted at the same C atoms as in the case of $CF_3$, —$CH_2CF_3$ or at different positions as in the case of —CH(OH)—CH=CH—$CHCl_2$. The multiple substitution can take place with the same or different substituents.

Insofar as the compounds according to the invention have at least one centre of asymmetry, they can be present in the form of their racemates, in the form of the pure enantiomers and/or diastereomers or in the form of mixtures of these enantiomers and/or diastereomers. The mixtures can be present in any arbitrary mixture ratio of the stereoisomers.

Thus, for example, the compounds according to the invention which have one or a plurality of centres of chirality and which occur as their racemates can be separated into their optical isomers, that is enantiomers or diastereomers, by methods known per se. The separation can be performed by column separation at chiral phases or by recrystallisation from an optically active solvent or by using an optically active acid or base or by derivatisation with an optically active reagent, such as for example, an optically active alcohol and subsequent separation of the residue.

The inventive compounds may be present in the form of their double bond isomers as "pure" E or Z isomers, or in the form of mixtures of these double bond isomers.

As far as possible, the compounds according to the invention can be present in the form of tautomers.

If they possess a sufficiently basic group, such as for example, a primary, secondary or tertiary amine, the compounds according to the invention can be converted into their physiologically compatible salts using inorganic and organic acids. The pharmaceutically acceptable salts of the compounds according to the invention are preferably formed with hydrochloric acid, bromic acid, sulphuric acid, phosphoric acid, methane sulfonic acid, p-toluene sulfonic acid, carbonic acid, formic acid, acetic acid, trifluoroacetic acid, sulfoacetic acid, oxalic acid, malonic acid, maleic acid, succinic acid, tartaric acid, racemic acid, malic acid, embonic acid, mandelic acid, fumaric acid, lactic acid, citric acid, glutamic acid or asparaginic acid. The salts formed include, among others, hydrochloride, hydrobromide, sulfate, hydrogen sulfate, phosphate, methane sulfonate, tosylate, carbonate, hydrogen carbonate, formiate, acetate, triflate, sulfoacetate, oxalate, malonate, maleate, succinate, tartrate, malate, embonate, mandelate, fumarate, lactate, citrate, glutaminate and aspartate. The stoichiometry of the salts of the compounds according to the invention which are formed can be integer or non-integer multiples of one.

If they contain a sufficiently acidic group, such as the carboxy group or phenolic group, for example, the compounds according to the invention can be converted into their physiologically compatible salts using inorganic and organic bases. Possible inorganic bases are, for example, sodium hydroxide, potassium hydroxide, calcium hydroxide, possible organic bases are ethanol amine, diethanol amine, triethanol amine, cyclohexylamine, dibenzylethylene diamine and lysine. The stoichiometry of the salts of the compounds according to the invention which are formed can be integer or non-integer multiples of one.

Likewise preferred are solvates and in particular hydrates of the compounds according to the invention, which can be obtained, for example, by crystallisation from a solvent or from aqueous solution. In this context, one, two, three or an arbitrary number of solvate or water molecules can combine with the compounds according to the invention to form solvates and hydrates.

It is known that chemical substances form solids which are present in various states of order, which are designated as polymorphous forms or modifications. The various modifications of a polymorphous substance can differ strongly in respect of their physical properties. The compounds according to the invention can be present in various polymorphous forms, in which case certain modifications can be metastable.

The compounds according to the invention can likewise be present in the form of any prodrugs such as, for example, esters, carbonates, carbamates, ureas, amides or phosphates, wherein the actually biologically active form is only released by catabolism.

It is further known that chemical substances are converted to metabolites in the body which optionally can likewise induce the desired biological effect, possibly even in a more distinct form.

Corresponding prodrugs and metabolites of the compounds according to the invention should also be considered as pertaining to the invention.

It was now surprisingly and advantageously determined that the compounds according to the invention can act simultaneously or have a modulating or inhibiting effect on one or more signal transduction pathways or enzymes. In this context, it has been found that the compounds according to the invention can act or have a modulating or inhibiting effect with high selectivity.

Such a simultaneous, for example, dual modulation or inhibition of one or more signal transduction pathways, e.g. the ras-Raf-Mek-Erk signal pathway and the PI3K-Akt signal pathway is advantageously compared with merely single modulation or inhibition of a signal transduction pathway since synergistic therapeutic effects can be brought about, such as for example, intensified apoptosis and faster and more efficient tumour regression.

The surprising advantageous effects of the compounds according to the invention allow multiple therapy approaches to be pursued in physiological and/or pathophysiological states or clinical pictures which are sensitive for the treatment or modulation of, or are mediated by, one or more signal transduction pathways.

It was further surprisingly and advantageously determined that the compounds according to the invention can also act with dual selectivity or have a modulating or inhibiting effect on the PI3K-Akt signal transduction pathway and ras-Raf-Mek-Erk signal transduction pathway or enzymes thereof and that the multiple mechanisms of action and therapy approaches described above can also be used with this signal pathway or enzymes comprising a pharmacologically active quantity of at least one compound selected from the group consisting of: "compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 190, 191, 192, 193, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581 and/or compound 582" and optionally pharmaceutically compatible excipients and/or adjuvants are covered by the present invention.

The term "modulation" is understood according to the invention as follows: "activation, partial activation, inhibition, partial inhibition". In this case, it is within the specialist knowledge of the average person skilled in the art to measure and determine such activation, partial activation, inhibition, partial inhibition by means of the usual methods of measurement and determination. Thus, a partial activation can be measured and determined in relation to a complete activation; likewise, a partial inhibition in relation to a complete inhibition.

The terms "inhibiting, inhibition and/or retardation" are understood as follows according to the invention: "partial or complete inhibiting, inhibition and/or retardation". In this case, it is within the specialist knowledge of the average person skilled in the art to measure and determine such inhibiting, inhibition, and/or retardation by means of the usual methods of measurement and determination. Thus, a partial inhibiting, inhibition and/or retardation, for example, can be measured and determined in relation to a complete inhibiting, inhibition and/or retardation.

The terms "modulation" and "inhibiting, inhibition and/or retardation" in connection with "enzymes" and/or "kinases" within the scope of this invention relate both to the inactive form (enzymatically inactive) and/or active form (enzymatically active) of the respective enzyme and/or kinase. This means within the scope of this invention that the compound according to the invention can have a modulating effect on the inactive form, active form or both forms of the enzyme and/or kinase.

In a further aspect, the inventive object was surprisingly achieved by preparing the compounds according to the invention which can be used to produce a medicament for the treatment or prevention of physiological and/or pathophysiological states in mammals, wherein the treatment or prevention is effected by modulation of the signal transduction pathway or pathways selected from the group consisting of: the "ras-Raf-Mek-Erk signal transduction pathway and the PI3K-Akt signal transduction pathway. In a further aspect, the inventive object was surprisingly achieved by preparing the compounds according to the invention which can be used to produce a medicament for the treatment or prevention of physiological and/or pathophysiological states in mammals, mediated by the PI3K-Akt signal transduction pathway.

In a further aspect, the inventive object was surprisingly achieved by preparing the compounds according to the invention which can be used to produce a medicament for the treatment or prevention of physiological and/or pathophysiological states in mammals, wherein the treatment or prevention is effected by modulation of the PI3K-Akt signal transduction pathway and the ras-Raf-Mek-Erk signal transduction pathway.

In a further preferred embodiment, the compounds according to the invention are prepared for the uses described above, wherein the modulation of the PI3K-Akt signal transduction pathway is effected by modulation of one or more enzymes selected from the group consisting of: "lipid kinase" and preferably selected from the group consisting of: "PI3K, PI3Kalpha, PI3Kbeta, PI3Kgamma, PI3Kdelta, PI3K-C2alpha, PI3K-C2beta, PI3K-Vps34p".

In a preferred embodiment, the compounds according to the invention are prepared for the uses described above, wherein the modulation of the ras-Raf-Mek-Erk signal transduction pathway is effected by modulation of one or more enzymes selected from the group consisting of: "tyrosine kinase, serine/threonine kinase, receptor tyrosine kinase, cytoplasmic tyrosine kinase, cytoplasmic serine/threonine kinase" and preferably selected from the group consisting of: "Erk, Erk1, Erk2".

In a further aspect, the inventive object was surprisingly achieved by preparing the compounds according to the invention according to the aspects, preferred embodiments and uses described above which can be used to produce a medicament for the treatment or prevention of physiological and/or pathophysiological states in mammals, wherein the treatment or prevention is effected by modulation of one or more enzymes.

In a further preferred embodiment, the compounds according to the invention are prepared for the uses described above, wherein in the treatment or prevention effected by modulation of two or more enzymes, at least one enzyme is selected from the group consisting of: "Erk, Erk1, Erk2" and at least one enzyme is selected from the group consisting of: "PI3K, PI3Kalpha, PI3Kbeta, PI3 Kgamma, PI3Kdelta, PI3K-C2alpha, PI3K-C2beta, PI3K-Vps34p".

In a further preferred embodiment, the compounds according to the invention are prepared for the uses described above, wherein the modulation is an inhibition.

The compounds according to the invention can be administered within the scope of this invention to all known mammals, in particular, humans, for the treatment and/or prevention.

In another preferred embodiment, the compounds according to the invention are prepared for the uses described above, wherein the mammal is selected from the group consisting of: "human, domesticated animal, cattle, pet, beef cattle, cow, sheep, pig, goat, horse, pony, donkey, hinny, mule, hare, rabbit, cat, dog, guinea pig, hamster, rat, mouse" and is preferably a human.

The compounds according to the invention can be used within the scope of this invention for the treatment and/or prevention of all known physiological and/or pathophysiological states.

In a preferred embodiment, the compounds according to the invention are prepared for the uses described above, wherein the physiological and/or pathophysiological states are selected from the group consisting of: "malignant tumours, benign tumours, inflammatory diseases, inflammations, pain, rheumatic diseases, arthritic diseases, HIV infections, neurological or neurodegenerative diseases, rheumatism, arthritis, AIDS, ARC (AIDS related complex), Kaposi's sarcoma, tumours originating from the brain and/or nervous system and/or meninges, dementia, Alzheimer's disease, hyperproliferative diseases, psoriasis, endometriosis, scarring, benign prostatahyperplasia (BPH), diseases of the immune system, autoimmune diseases, immunodeficiency diseases, colon tumour, gastric tumour, intestinal tumour, pulmonary tumour, pancreatic tumour, ovarian tumour, prostatic tumour, leukaemia, melanoma, hepatic tumour, renal tumour, head tumour, throat tumour, glioma, breast tumour, uterine cancer, endometrial cancer, cervico-uterine carcinoma, brain tumour, adeno-acanthoma, cancer of the bladder, gastric tumour, colorectal tumour, oesophageal cancer, gynocological tumour, ovarian tumour, cancer of the thyroid, lymphoma, chronic leukaemia, acute leukaemia, restenosis, diabetes, diabetic nephropathy, fibrotic diseases, cystic fibrosis, malignant nephrosclerosis, thrombotic microangiopathy syndrome, organ transplant rejection, glomerulopathy, metabolilc diseases, solid/fixed tumours, rheumatic arthritis, diabetic retinopathy, asthma, allergies, allergic diseases, chronic obstructive pulmonary diseases, inflammatory bowel disease, fibrosis, atheriosclerosis, heart diseases, cardiovascular diseases, diseases of the myocardium, vascular diseases, angiogenetic diseases, kidney diseases, rhinitis, Grave's disease, focal ischaemia, cardiac failure, ischaemia, cardiac hypertrophia, renal failure, cardiac myocytic malfunction, high blood pressure, vasoconstriction, stroke, anaphylactic shock, platelet agglutination, skeletomuscular atrophy, obesity, overweight, glucosis homeostasis, congestive cardiac insufficiency, angina, heart attack, cardiac infarction, hyperglycaemia, hypoglycaemia, hypertension".

In a further aspect of the present invention, the inventive object was surprisingly achieved by preparing the compounds according to the aspects, preferred embodiments and uses described above, for use for the production of a medicament for the treatment or prevention of physiological and/or pathophysiological states in mammals, wherein the medicament comprises at least one further pharmacologically active substance.

In a further aspect of the present invention, the inventive object was surprisingly achieved by preparing the compounds according to the aspects, preferred embodiments and uses described above, for use for the production of a medicament for the treatment or prevention of physiological and/or pathophysiological states in mammals, wherein the medicament is administered with at least one further pharmacologically active substance before and/or during and/or after treatment.

In a further aspect of the present invention, the inventive object was surprisingly achieved by preparing the compounds according to the aspects, preferred embodiments and uses described above, for use for the production of a medicament for the treatment or prevention of physiological and/or pathophysiological states in mammals, wherein the medicament is administered before and/or during and/or after treatment with radiation therapy and/or surgery.

The compounds according to the invention can be administered within the scope of this invention with all known pharmacologically active substances in a combination therapy as described.

In a preferred embodiment, the compounds according to the invention are prepared for the uses described above, wherein the further pharmacologically active substance is selected from the group consisting of: "DNA topoisomerase I and/or II inhibitors, DNA intercalators, alkylating agents, microtubuli destabilisors, hormone and/or growth factor receptor agonists and/or antagonists, antibodies against growth factors and their receptors, kinase inhibitors, alkylphospholipids, antimetabolites".

In a preferred embodiment, the compounds according to the invention are prepared for the uses described above, wherein the further pharmacologically active substance is selected from the group consisting of: "asparaginase, bleomycin, carboplatin, carmustin, chlorambucil, cisplatin, colaspase, cyclophosphamide, cytarabine, dacarbazine, dactinomycin, daunorubicin, doxorubicin(adriamycin), epirubicin, etoposide, 5-fluorouracil, hexamethylmelamine, hydroxurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifene, streptozocin, tamoxifen, thioguanine, topotecan, vinblastine, vincristine, vindesine, aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinylestradiol, 5-fluorodeoxyuridin, 5-fluorodeoxyuridin monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, oxaliplatin, pentostatin, N-phosphonoacetyl-L-aspartate (PALA), plicamycin, semustine, teniposide, testosterone propionate, thiotepa, trimethylmelamine, uridine, vinorelbin, epothilone, gemcitabine, Taxotere, BCNU, CCNU, DTIC, 5-fluorouracil, Herceptin, Avastin, Erbitux, Sorafenib, Gleevec, Iressa, Tarceva, rapamycin, perifosine, miltefosine, edelfosine, actinomycin D".

Oral administration can take place, for example, in solid form as tablet, capsule, gel capsule, dragee, granule or powder but also in the form of a potable solution. For oral administration, the new compounds according to the invention, as defined hereinbefore, can be combined with known physiologically compatible adjuvants and excipients usually used, such as gum Arabic, talc, starch, sugar such as, for example, mannite, methyl cellulose, lactose, gelatine, surfactants, magnesium stearate, cyclodextrin, aqueous or non-aqueous excipients, diluents, dispersants, emulsifiers, lubricants, preservatives and flavourings (e.g. ether oils). The compounds according to the invention can also be dispersed in a microparticle, e.g. nanoparticle composition.

Non-oral administration can be effected, for example, by intravenous, subcutaneous or intramuscular injection of sterile aqueous or oily solutions, suspensions or emulsions, by means of implants or by ointments, creams or suppositories. Optionally, administration can be effected as a retard form. Implants can contain inert materials, e.g. biologically degradable polymers or synthetic silicones such as, for example, silicone rubber. Intravaginal administration can be effected by means of vaginal rings, for example. Intrauterine administration can take place, for example, by means of diaphragms or other suitable intrauterine devices. In addition, transdermal administration can be provided, in particular by means of a formulation suitable for this purpose and/or suitable means such as plasters, for example.

As has already been explained, the new compounds according to the invention can also be combined with further pharmaceutically active substances. Within the framework of a combination therapy, the individual active constituents cam be administered simultaneously or separately and either by the same pathway (e.g. oral) or by separate pathways (e.g. oral and as injection). They can be present or administered in the same or different quantities in a unit dose. A certain dosage regime can be applied insofar as this seems appropriate. In this way, a plurality of the new compounds according to the invention can be combined with one another.

The dosage can vary according to the type of indication, the severity of the disease, the type of administration, the age, sex, body weight and sensitivity of the subject to be treated over a wide range. It is within the capabilities of a person skilled in the art to determine a "pharmacologically effective quantity" of the combined pharmaceutical composition. The administration can be made in a single dose or a plurality of separate doses.

A suitable unit dose is 0.001 mg to 100 mg of the active substance, i.e. at least one compound according to the invention and optionally a further pharmaceutically active substance, per kg body weight of a patient.

In a further aspect of the present invention, accordingly pharmaceutical compositions comprising a pharmacologically active quantity of at least one compound selected from the group consisting of: "compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 190, 191, 192, 193, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581 and/or compound 582" and optionally pharmaceutically compatible excipients and/or adjuvants are covered by the present invention.

Preferred and particularly preferred pharmaceutical compositions are those which comprise at least one of the aforesaid preferred compounds according to the invention. Pharmaceutical compositions according to the present invention can also contain, in addition to at least one compound according to the invention, as defined previously, at least one further pharmaceutically active substance, as has been described in detail hereinbefore.

The pharmaceutical compositions according to the invention contain at least one of the new compounds according to the invention, as defined hereinbefore, in a pharmacologically active quantity, preferably in a unit dose, e.g. the aforesaid unit dose and preferably in an administration form which allows oral administration.

With regard to pharmaceutical compositions comprising compounds according to the invention and with regard to the use of the compounds according to the invention as medicaments, reference is made to the statements made in connection with the use of the new compounds according to the invention themselves with regard to the possibilities for usage and administration.

In a further aspect of the present invention, the inventive object was surprisingly solved by preparing a kit comprising a pharmacologically active quantity of at least one preferred compound according to the invention as presented above and a pharmacologically active quantity of at least one further pharmacologically active substance as defined hereinbefore.

The naming of the compounds according to the invention having the general formula (I) together with preferred exemplary embodiments and in particular "compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 190, 191, 192, 193, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581 and/or compound 582" was made using AutoNom 2000—Software (ISIS™/Draw 2.5; MDL).

General Synthetic Regulations for the Compounds According to the Invention

The procedures for manufacturing substituted pyrido[2,3-b]pyrazine according to the invention are explained below.

The compounds according to the invention can be obtained according to the corresponding procedures known to the person skilled in the art. In addition, refer to patent specifications WO 2004/104002, WO 2004/104003, WO2007/054556 and WO 2008/138878 or to the corresponding methods known in the literature to manufacture the compounds in accordance with the invention. In order to manufacture the initial compounds, intermediate compounds and the pyridopyrazine according to the invention, refer amongst other things, to the primary literature below, the content of which is herewith to become an integral part of the disclosure of the present filing application:

1) Houben-Weyl, Methods of Organic Chemistry, Volume 4/1a, pp. 343-350
2) Houben-Weyl, Methods of Organic Chemistry, 4th edition, Volume E 7b (Part 2), p. 579; Degussa G B 1184848 (1970); p. Seko, et al. EP 735025 (1996)
3) D. Catarzi, et al.; *J. Med. Chem.* 1996, 1330-1336; J. K. Seydel, et al.; *J. Med. Chem.* 1994, 3016-3022
4) Houben-Weyl, Methods of Organic Chemistry, Volume E 9c, pp. 231-235
5) Houben-Weyl/Science of Synthesis, Volume 16, p. 1269
6) C. L. Leese, H. N. Rydon *J. Chem. Soc.* 1955, 303-309; T. S. Osdene, G. M. Timmis *J. Chem. Soc.* 1955, 2033-2035
7) W. He, et al. *Bioorg. Med. Chem. Lett.* 2003, 13, 3097-3100
8) M. S. A. El-Gaby, et al. *Indian J. Chem. Sect. B* 2001, 40, 195-200; M. R. Myers, et al. *Bioorg. Med. Chem. Lett.* 2003, 13, 3091-3096; A. R. Renslo, et al. *J. Amer. Chem. Soc.* 1999, 121, 7459-7460; C. O. Okafor, et al. *J. Heterocyclic Chem.* 1983, 20, 199-203; C. R. Hopkins, et al. *Tet. Lett.* 2004, 45, 8631-8633
9) J. Yin, et al. *Org. Lett.* 2002, 4, 3481-3484; O. A. El-Sayed, et al. *Arch. Pharm.* 2002, 335, 403-410; C. Temple, et al. *J. Med. Chem.* 1992, 35, 988-993
10) A. M. Thompson, et al. *J. Med. Chem.* 2000, 43, 4200-4211; N. A. Dales, et al. *Org. Lett.* 2001, 2313-2316; G. Dannhardt, et al. *Arch. Pharm.* 2000, 267-274; G. S. Poindexter, et al. *Bioorg. Med. Chem.* 2004, 12, 507-521; J.-M. Receveur, et al. *Bioorg. Med. Chem. Lett.* 2004, 14, 5075-5080
11) G. Heinisch, et al. *Arch. Pharm.* 1997, 207-210; K. Matsuno, et al. *J. Med. Chem.* 2002, 45, 4513-4523; A. M. Papini, et al. *J. Med. Chem.* 2004, 47, 5224-5229
12) L. Mao, et al. *Synthesis* 2004, 15, 2535-2539; M. Darabantu, et al. *Tetrahedron* 2005, 61, 2897-2905; E. Ford, et al. *Tet. Lett.* 2000, 41, 3197-3198; T. Shiota, et al. *J. Org. Chem.* 1999, 64, 453-457
13) J. F. Miravet, et al. *Org. Lett.* 2005, 7, 4791-4794; A. L. Castelhano, et al. *Bioorg. Med. Chem. Lett.* 2005, 15, 1501-1504
14) J. W. Huffmann, et al. *Bioorg. Med. Chem.* 2006, 14, 247-262; T. Liu, et al. *Org. & Biomolecular Chem.* 2005, 3, 1525-1533

The invention will be explained in detail with reference to the following examples without being restricted to these examples.

EXAMPLES

Compound 1: 1-Ethyl-3-{3-[1-(3,4,5-trimethoxybenzyl)-1H-pyrazol-4-yl]-pyrido[2,3-b]pyrazin-6-yl}-urea

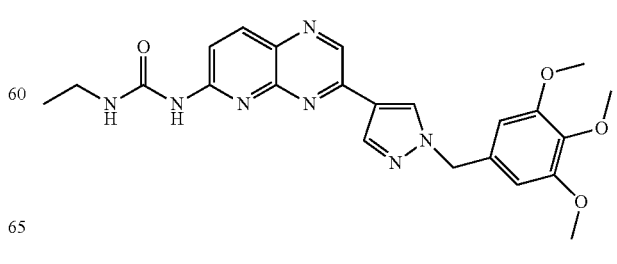

¹H-NMR (DMSO-d₆): δ=10.00 (s, 1H), 9.18 (s, 1H), 9.08 (bs, 1H), 8.30 (m, 3H), 7.75 (s, 1H), 8.35 (s, 1H), 8.27 (d, 1H), 7.57 (m, 1H), 6.71 (s, 2H), 5.35 (s, 2H), 3.76 (s, 6H), 3.64 (s, 3H), 3.22 (m, 2H), 1.19 (m, 3H), ppm
mp: 219° C.

Compound 2: 1-Ethyl-3-[3-(1-pyridin-2-ylmethyl-1H-pyrazol-4-yl)-pyrido[2,3-b]pyrazin-6-yl]-thiourea

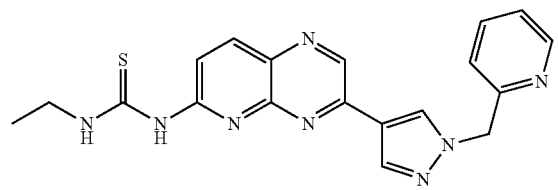 [SMILES: CCNC(=S)Nc1ccc2ncc(-c3cnn(Cc4ccccn4)c3)nc2n1]

¹H-NMR (DMSO-d₆): δ=12.24 (s, 1H), 11.14 (s, 1H), 9.25 (s, 1H), 8.82 (s, 1H), 8.55 (m, 1H), 8.38 (s, 1H), 8.36 (m, 1H), 7.81 (m, 1H), 7.53 (m, 2H), 7.34 (m, 1H), 7.22 (m, 1H), 5.57 (s, 2H), 3.37 (m, 2H), 1.33 (m, 3H), ppm Compound 3: 1-{3-[1-(3-Difluoromethoxy-benzyl)-1H-pyrazol-4-yl]-pyrido[2,3-b]pyrazin-6-yl}-3-ethyl-urea

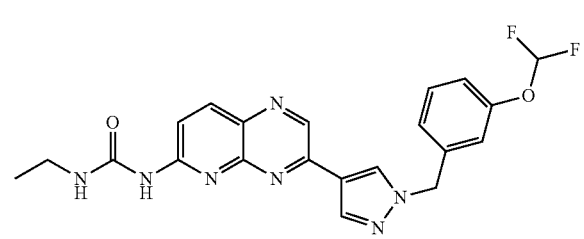 [SMILES: CCNC(=O)Nc1ccc2ncc(-c3cnn(Cc4cccc(OC(F)F)c4)c3)nc2n1]

¹H-NMR (DMSO-d₆): δ=10.01 (s, 1H), 9.18 (s, 1H), 9.09 (s, 1H), 8.80 (s, 1H), 8.37 (s, 1H), 8.28 (m, 1H), 7.57 (m, 1H), 7.44 (m, 1H), 7.16 (m, 4H), 5.48 (s, 2H), 3.33 (m, 2H), 1.19 (m, 3H), ppm
mp: 198° C.

Compound 4: 1-Ethyl-3-{3-[1-(3-hydroxy-benzyl)-1H-pyrazol-4-yl]-pyrido[2,3-b]pyrazin-6-yl}-urea

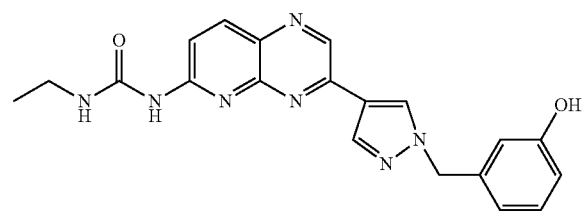 [SMILES: CCNC(=O)Nc1ccc2ncc(-c3cnn(Cc4cccc(O)c4)c3)nc2n1]

¹H-NMR (DMSO-d₆): δ=10.00 (s, 1H), 9.44 (s, 1H), 9.09 (s, 1H), 9.18 (s, 1H), 9.07 (s, 1H), 8.75 (s, 1H), 8.35 (s, 1H), 8.27 (m, 1H), 7.57 (m, 1H), 7.16 (m, 1H), 6.74 (m, 1H), 6.68 (m, 2H), 5.36 (s, 2H), 3.33 (m, 2H), 1.19 (m, 3H), ppm
mp: 242° C.

Compound 5: 1-[3-(1-Benzo[1,3]dioxol-5-ylmethyl-1H-pyrazol-4-yl)-pyrido[2,3-b]pyrazin-6-yl]-3-ethyl-thiourea

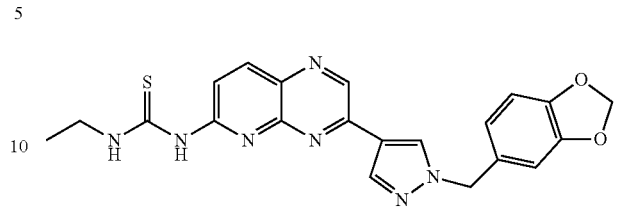

¹H-NMR (DMSO-d₆): δ=12.22 (m, 1H), 11.14 (s, 1H), 9.23 (s, 1H), 8.74 (s, 1H), 8.35 (m, 2H), 7.53 (d, 1H), 6.90 (m, 3H), 6.00 (s, 2H), 5.34 (s, 2H), 3.73 (m, 2H), 1.33 (m, 3H), ppm
mp: 244° C.

Compound 6: 1-Ethyl-3-{3-[1-(4-trifluoromethoxy-benzyl)-1H-pyrazol-4-yl]-pyrido[2,3-b]pyrazin-6-yl}-urea

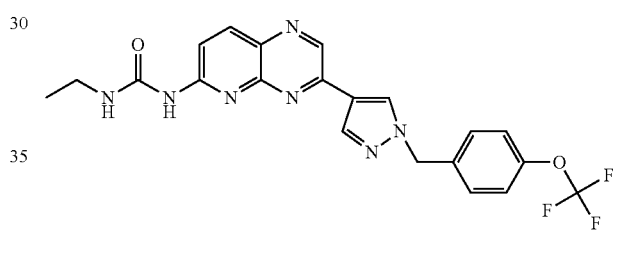

¹H-NMR (DMSO-d₆): δ=10.01 (s, 1H), 9.18 (s, 1H), 9.08 (s, 1H), 8.80 (s, 1H), 8.37 (d, 1H), 7.57 (d, 1H), 7.25 (d, 2H), 7.38 (d, 2H), 5.50 (s, 2H), 3.32 (m, 2H), 1.19 (m, 3H), ppm
mp: 231° C.

Compound 7: 1-{3-[1-(3,4-Dimethoxy-benzyl)-1H-pyrazol-4-yl]-pyrido[2,3-b]pyrazin-6-yl}-3-(2-methoxy-ethyl)-thiourea

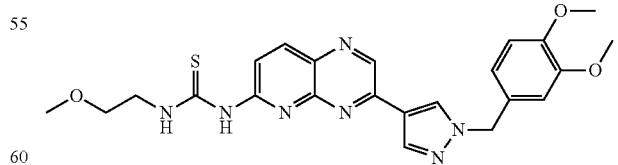

¹H-NMR (DMSO-d₆): δ=12.35 (m, 1H), 11.19 (s, 1H), 9.22 (s, 1H), 8.61 (s, 1H), 8.35 (d, 1H), 8.31 (s, 1H), 7.54 (d, 1H), 7.03 (s, 1H), 6.95 (m, 1H), 6.90 (m, 1H), 5.36 (s, 2H), 3.84 (m, 2H), 3.75 (m, 8H), 3.65 (m, 2H), 3.40 (s, 3H) ppm
mp: 198° C.

Compound 8: 1-{3-[1-(3-Chloro-4-fluoro-benzyl)-1H-pyrazol-4-yl]-pyrido[2,3-b]pyrazin-6-yl}-3-ethyl-urea

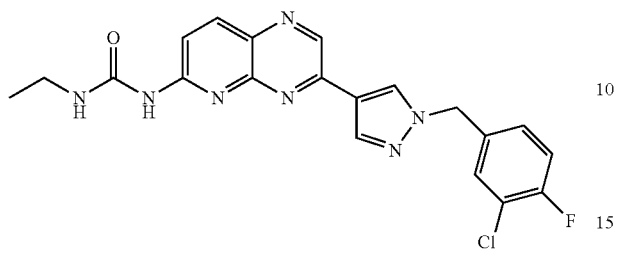

¹H-NMR (DMSO-d₆): δ=10.01 (s, 1H), 9.17 (s, 1H), 9.09 (s, 1H), 8.79 (s, 1H), 8.37 (s, 1H), 8.27 (d, 1H), 7.58 (m, 2H), 7.43 (m, 1H), 7.37 (m, 1H), 5.46 (s, 2H), 3.33 (m, 2H), 1.19 (m, 3H) ppm mp: 214-219° C.

Compound 9: 1-Ethyl-3-{3-[1-(3-phenyl-propyl)-1H-pyrazol-4-yl]-pyrido[2,3-b]pyrazin-6-yl}-urea

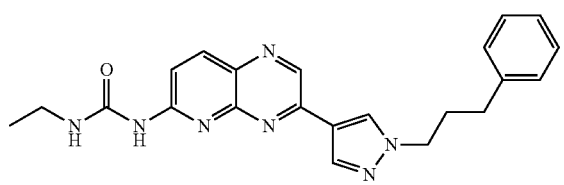 [SMILES: CCNC(=O)Nc1ccc2ncc(-c3cnn(CCCc4ccccc4)c3)nc2n1]

¹H-NMR (DMSO-d₆): δ=10.00 (s, 1H), 9.17 (s, 1H), 9.08 (s, 1H), 8.69 (s, 1H), 8.33 (s, 1H), 8.27 (d, 1H), 7.58 (m, 1H), 7.30 (m, 2H), 7.23 (m, 2H), 7.19 (m, 1H), 4.24 (m, 2H), 3.32 (m, 2H), 2.61 (m, 2H) 2.18 (m, 2H9, 1.19 (m, 3H) ppm mp: 251° C.

Compound 10: 1-{3-[1-(4-Cyano-benzyl)-1H-pyrazol-4-yl]-pyrido[2,3-b]pyrazin-6-yl}-3-ethyl-urea

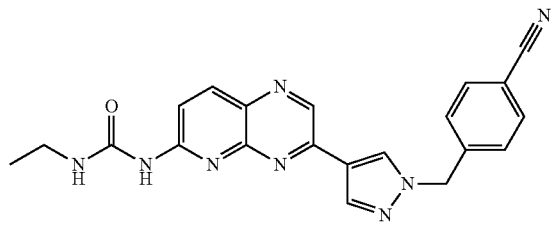 [SMILES: CCNC(=O)Nc1ccc2ncc(-c3cnn(Cc4ccc(C#N)cc4)c3)nc2n1]

¹H-NMR (DMSO-d₆): δ=10.01 (s, 1H), 9.18 (s, 1H), 9.09 (s, 1H), 8.82 (s, 1H), 8.39 (s, 1H), 7.85 (d, 2H), 7.59 (d, 1H), 7.46 (d, 2H), 5.58 (s, 2H), 3.29 (m, 2H), 1.19 (m, 3H) ppm mp: 208-215° C.

Compound 11: 1-{3-[1-(4-Difluoromethoxy-benzyl)-1H-pyrazol-4-yl]-pyrido[2,3-b]pyrazin-6-yl}-3-ethyl-urea

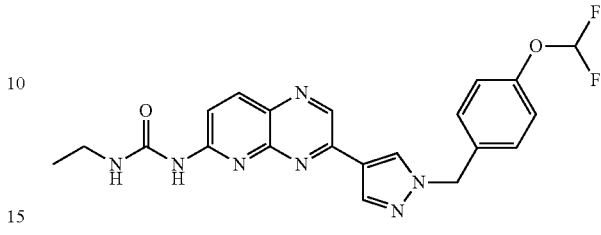

¹H-NMR (DMSO-d₆): δ=10.00 (s, 1H), 9.17 (s, 1H), 9.08 (s, 1H), 8.78 (s, 1H), 8.35 (s, 1H), 8.27 (d, 2H), 7.57 (d, 1H), 7.40 (d, 2H), 7.19 (m, 3H), 5.45 (s, 2H), 3.32 (m, 2H), 1.19 (m, 3H) ppm mp: 239° C.

Compound 12: 1-{3-[1-(3,5-Dimethyl-benzyl)-1H-pyrazol-4-yl]-pyrido[2,3-b]pyrazin-6-yl}-3-ethyl-thiourea

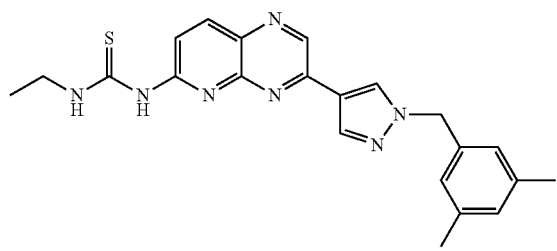 [SMILES: CCNC(=S)Nc1ccc2ncc(-c3cnn(Cc4cc(C)cc(C)c4)c3)nc2n1]

¹H-NMR (DMSO-d₆): δ=12.23 (m, 1H), 11.14 (s, 1H), 9.24 (s, 1H), 8.74 (s, 1H), 8.36 (m, 2H), 7.53 (m, 1H), 6.95 (m, 3H), 5.36 (s, 1H), 3.37 (m, 2H), 2.25 (s, 6H), 1.33 (m, 3H) ppm Compound 13: 1-Ethyl-3-{3-[1-(3-methyl-benzyl)-1H-pyrazol-4-yl]-pyrido[2,3-b]pyrazin-6-yl}-urea

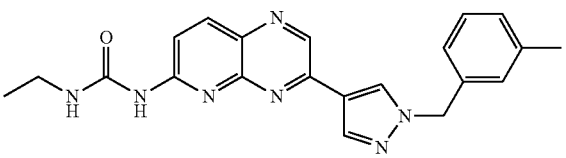

¹H-NMR (DMSO-d₆): δ=10.00 (s, 1H), 9.17 (s, 1H), 9.08 (s, 1H), 8.75 (s, 1H), 8.34 (m, 2H), 8.28 (m, 1H), 7.57 (m, 1H), 7.26 (m, 1H), 7.14 (m, 3H), 5.41 (s, 2H), 3.33 (m, 2H), 2.29 (s, 3H), 1.19 (m, 3H) ppm mp: 208-210° C.

Compound 14: 1-Ethyl-3-[3-(1-pyridin-4-ylmethyl-1H-pyrazol-4-yl)-pyrido[2,3-b]pyrazin-6-yl]-urea

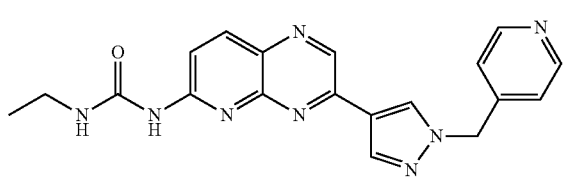 [SMILES: CCNC(=O)Nc1ccc2ncc(-c3cnn(Cc4ccncc4)c3)nc2n1]

¹H-NMR (DMSO-d₆): δ=10.02 (s, 1H), 9.19 (s, 1H), 9.08 (s, 1H), 8.83 (s, 1H), 8.55 (m, 2H), 8.41 (s, 1H), 8.28 (m, 1H), 7.58 (m, 1H), 7.22 (m, 2H), 5.54 (s, 2H), 3.32 (m, 2H), 1.19 (m, 3H) ppm Compound 15: 1-Ethyl-3-{3-[1-(4-methyl-benzyl)-1H-pyrazol-4-yl]-pyrido[2,3-b]pyrazin-6-yl}-urea

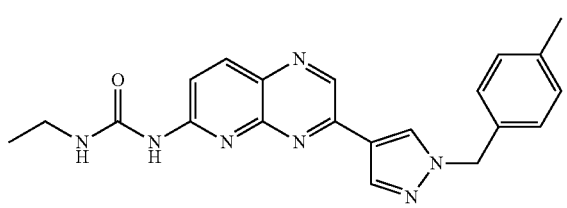

¹H-NMR (DMSO-d₆): δ=10.00 (s, 1H), 9.16 (s, 1H), 9.07 (s, 1H), 8.74 (s, 1H), 8.33 (s, 1H), 8.26 (d, 1H), 7.57 (m, 1H), 7.23 (d, 2H), 7.19 (d, 2H), 5.39 (s, 2H), 3.33 (m, 2H), 2.28 (s, 3H), 1.19 (m, 3H) ppm mp: 217-220° C.

Compound 16: 1-Ethyl-3-{3-[1-(4-phenyl-butyl)-1H-pyrazol-4-yl]-pyrido[2,3-b]pyrazin-6-yl}-urea

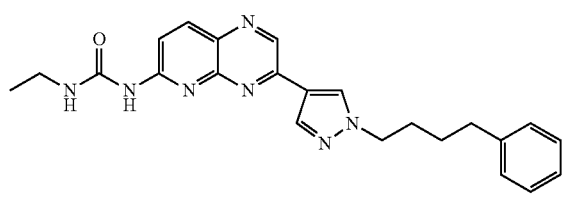 [SMILES: CCNC(=O)Nc1ccc2ncc(-c3cnn(CCCCc4ccccc4)c3)nc2n1]

¹H-NMR (DMSO-d₆): δ=10.00 (s, 1H), 9.15 (s, 1H), 9.08 (s, 1H), 8.66 (s, 1H), 8.30 (s, 1H), 8.26 (d, 1H), 7.56 (m, 1H), 7.26 (m, 2H), 7.18 (m, 3H), 4.24 (m, 2H), 3.32 (m, 2H), 2.26 (m, 3H), 1.87 (m, 2H), 1.57 (m, 2H), 1.19 (m, 3H) ppm mp: 182° C.

Compound 17: 1-Ethyl-3-{3-[1-(4-hydroxy-benzyl)-1H-pyrazol-4-yl]-pyrido[2,3-b]pyrazin-6-yl}-urea

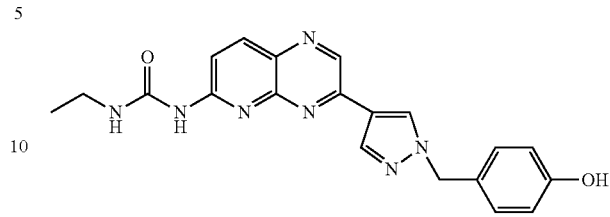

¹H-NMR (DMSO-d₆): δ=9.99 (s, 1H), 9.45 (s, 1H), 9.16 (s, 1H), 9.07 (s, 1H), 8.30 (s, 1H), 8.69 (s, 1H), 8.26 (m, 1H), 7.57 (m, 1H), 7.19 (d, 3H), 6.75 (d, 2H), 5.30 (s, 2H), 3.33 (m, 2H), 1.19 (m, 3H) ppm Compound 18: 1-{3-[1-(4-Chloro-benzyl)-1H-pyrazol-4-yl]-pyrido[2,3-b]pyrazin-6-yl}-3-ethyl-urea

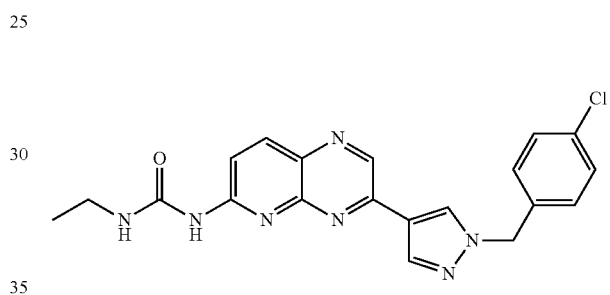

¹H-NMR (DMSO-d₆): δ=10.01 (s, 1H), 9.17 (s, 1H), 9.09 (bs, 1H), 8.78 (s, 1H), 8.36 (s, 1H), 8.27 (d, 1H), 7.57 (d, 1H), 7.44 (d, 2H), 7.25 (d, 2H), 5.46 (s, 2H), 3.31 (m, 2H), 1.19 (m, 3H) ppm mp: 240-244° C.

Compound 19: 1-{3-[1-(2,5-Dimethoxy-benzyl)-1H-pyrazol-4-yl]-pyrido[2,3-b]pyrazin-6-yl}-3-ethyl-thiourea

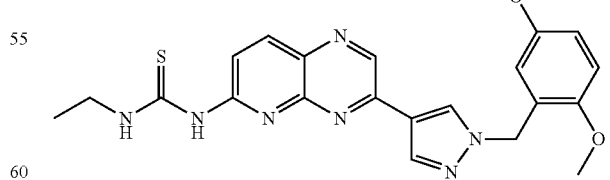

¹H-NMR (DMSO-d₆): δ=12.25 (m, 1H), 11.14 (s, 1H), 9.24 (s, 1H), 8.65 (s, 1H), 8.35 (m, 2H), 7.52 (d, 1H), 6.99 (d, 1H), 6.89 (m, 1H), 6.64 (m, 1H), 5.37 (s, 2H), 3.80 (s, 3H), 3.72 (m, 2H), 3.66 (s, 3H), 1.33 (m, 3H) ppm mp: 225° C.

Compound 20: 1-Ethyl-3-{3-[1-(4-methyl-benzyl)-1H-pyrazol-4-yl]-pyrido[2,3-b]pyrazin-6-yl}-thiourea

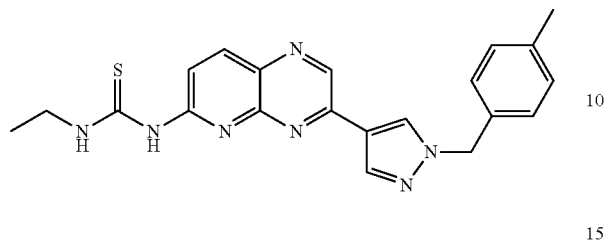

¹H-NMR (DMSO-d₆): δ=12.23 (m, 1H), 11.14 (s, 1H), 9.22 (s, 1H), 8.75 (s, 1H), 8.35 (m, 2H), 7.52 (d, 1H), 7.23 (d, 2H), 7.17 (d, 2H), 5.40 (s, 2H), 3.73 (m, 2H), 2.28 (s, 3H), 1.33 (m, 3H) ppm mp: 241° C.

Compound 21: 1-{3-[1-(3-Benzyloxy-benzyl)-1H-pyrazol-4-yl]-pyrido[2,3-b]pyrazin-6-yl}-3-ethyl-thiourea

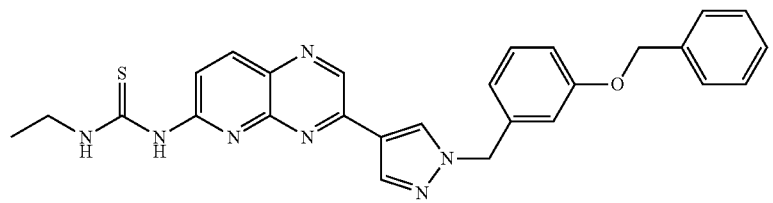 [SMILES: CCNC(=S)Nc1ccc2ncc(-c3cnn(Cc4cccc(OCc5ccccc5)c4)c3)nc2n1]

¹H-NMR (DMSO-d₆): δ=12.23 (m, 1H), 11.14 (s, 1H), 9.23 (s, 1H), 8.77 (s, 1H), 8.36 (m, 2H), 7.53 (m, 1H), 7.42 (m, 2H), 7.36 (m, 2H), 7.29 (m, 2H), 9.97 (m, 2H), 6.89 (m, 1H), 5.42 (s, 2H), 5.08 (s, 2H), 3.73 (m, 2H), 1.32 (m, 3H) ppm mp: 203-205

Compound 22: 1-{3-[1-(4-Bromo-3-methyl-benzyl)-1H-pyrazol-4-yl]-pyrido[2,3-b]pyrazin-6-yl}-3-ethyl-urea

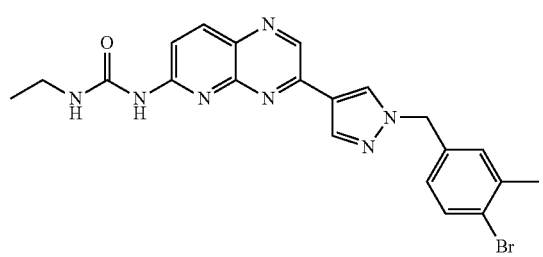 [SMILES: CCNC(=O)Nc1ccc2ncc(-c3cnn(Cc4ccc(Br)c(C)c4)c3)nc2n1]

¹H-NMR (DMSO-d₆): δ=10.01 (s, 1H), 9.17 (s, 1H), 9.08 (s, 1H), 8.77 (s, 1H), 8.35 (s, 1H), 8.27 (d, 1H). 7.57 (m, 2H), 7.34 (m, 1H), 7.09 (m, 1H), 5.40 (s, 2H), 3.33 (m, 2H), 2.34 (s, 3H), 1.19 (m, 3H) ppm mp: 250-252° C.

Compound 23: 1-Ethyl-3-{3-[1-(4-methoxy-benzyl)-1H-pyrazol-4-yl]-pyrido[2,3-b]pyrazin-6-yl}-thiourea

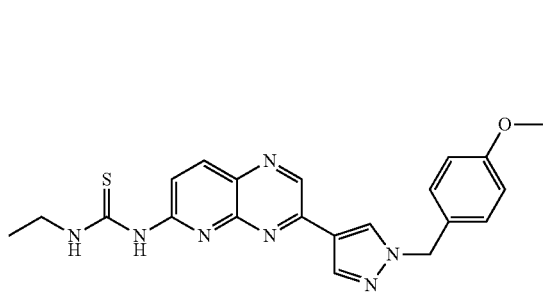 [SMILES: CCNC(=S)Nc1ccc2ncc(-c3cnn(Cc4ccc(OC)cc4)c3)nc2n1]

¹H-NMR (DMSO-d₆): δ=12.22 (m, 1H), 11.14 (s, 1H), 9.22 (s, 1H), 8.73 (s, 1H), 8.35 (m, 2H), 7.52 (d, 1H), 7.30 (d, 2H), 6.93 (d, 2H), 5.37 (s, 2H), 3.73 (m, 5H), 1.33 (m, 3H) ppm mp: 237° C.

Compound 24: 1-Ethyl-3-[3-(1-pyridin-3-ylmethyl-1H-pyrazol-4-yl)-pyrido[2,3-b]pyrazin-6-yl]-thiourea

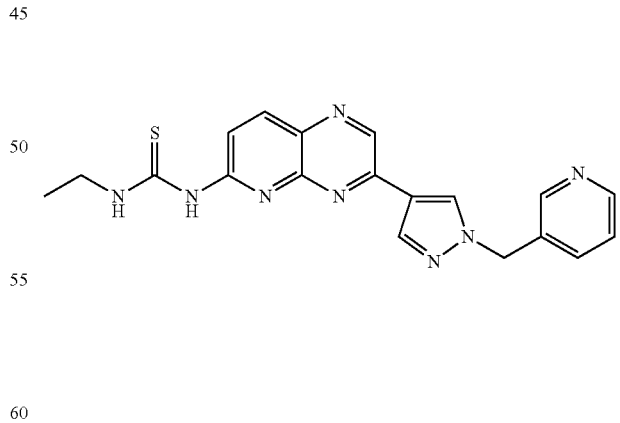

¹H-NMR (DMSO-d₆): δ=12.23 (m, 1H), 11.15 (s, 1H), 9.23 (s, 1H), 8.83 (s, 1H), 8.61 (m, 1H), 8.54 (m, 1H), 8.37 (m, 2H), 7.75 (m, 1H), 7.53 (m, 1H), 7.41 (m, 1H), 5.52 (s, 2H), 3.73 (m, 2H), 1.33 (m, 3H) ppm mp: 238° C.

Compound 25: 1-Ethyl-3-{3-[1-(3-fluoro-5-methyl-benzyl)-1H-pyrazol-4-yl]-pyrido[2,3-b]pyrazin-6-yl}-thiourea

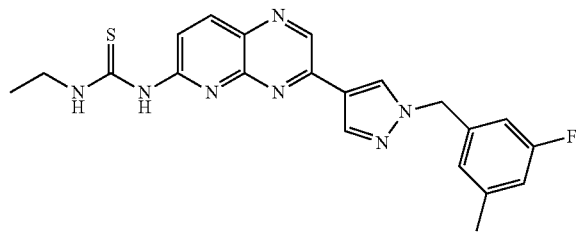 [SMILES: CCNC(=S)Nc1ccc2ncc(-c3cnn(Cc4cc(C)cc(F)c4)c3)nc2n1]

¹H-NMR (DMSO-d₆): δ=12.23 (m, 1H), 11.15 (s, 1H), 9.24 (s, 1H), 8.79 (s, 1H), 8.36 (m, 2H), 7.53 (m, 1H), 6.98 (m, 3H), 5.44 (s, 2H), 3.73 (m, 2H), 2.30 (s, 3H), 1.33 (m, 3H) ppm mp: 257-259° C.

Compound 26: 1-{3-[1-(2,3-Dimethoxy-benzyl)-1H-pyrazol-4-yl]-pyrido[2,3-b]pyrazin-6-yl}-3-ethyl-thiourea

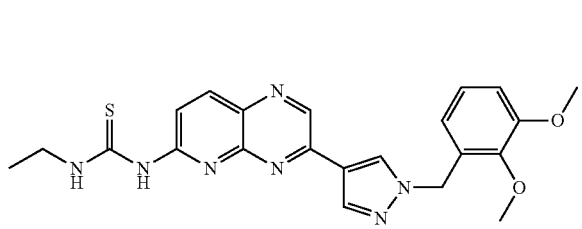 [SMILES: CCNC(=S)Nc1ccc2ncc(-c3cnn(Cc4cccc(OC)c4OC)c3)nc2n1]

¹H-NMR (DMSO-d₆): δ=12.23 (m, 1H), 11.14 (s, 1H), 9.24 (s, 1H), 8.71 (s, 1H), 8.35 (m, 2H), 7.53 (m, 1H), 7.04 (m, 2H), 6.74 (m, 1H), 5.43 (s, 2H), 3.82 (s, 3H), 3.75 (s, 3H), 3.72 (m, 2H), 1.33 (m, 3H) ppm mp: 218-222° C.

Compound 27: 1-{3-[1-(3-Difluoromethoxy-benzyl)-1H-pyrazol-4-yl]-pyrido[2,3-b]pyrazin-6-yl}-3-ethyl-thiourea

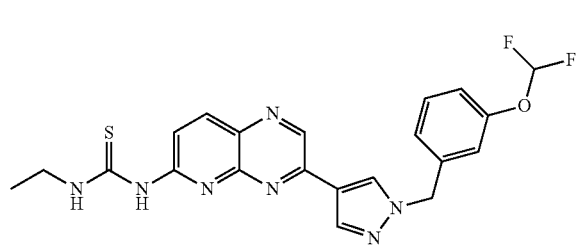

¹H-NMR (DMSO-d₆): δ=12.23 (t, 1H), 11.15 (s, 1H), 9.24 (s, 1H), 8.81 (s, 1H), 8.39 (s, 1H), 8.36 (d, 1H), 7.54 (d, 1H), 7.44 (t, 1H), 7.35 (s, 1H), 7.23 (s, 1H), 7.19 (m, 1H), 7.15 (m, 1H), 7.15 (m, 1H), 5.49 (s, 2H), 3.73 (m, 2H), 1.33 (t, 3H) ppm mp: 207° C.

Compound 28: 1-{3-[1-(3,4-Dimethoxy-benzyl)-1H-pyrazol-4-yl]-pyrido[2,3-b]pyrazin-6-yl}-3-ethyl-thiourea

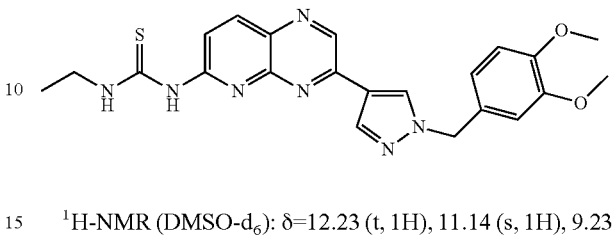

¹H-NMR (DMSO-d₆): δ=12.23 (t, 1H), 11.14 (s, 1H), 9.23 (s, 1H), 8.73 (s, 1H), 8.35 (t, 1H), 7.53 (d, 1H), 7.03 (m, 1H), 6.94 (m, 1H), 6.83 (m, 1H), 5.36 (s, 2H), 3.74 (m, 8H), 1.33 (t, 3H) ppm mp: 213° C.

Compound 29: 1-Ethyl-3-{3-[1-(2-fluoro-3-methoxy-benzyl)-1H-pyrazol-4-yl]-pyrido[2,3-b]pyrazin-6-yl}-thiourea

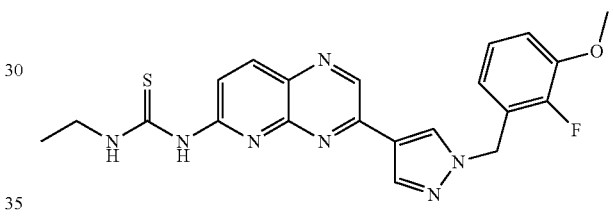

¹H-NMR (DMSO-d₆): δ=12.23 (m, 1H), 11.14 (s, 1H), 9.24 (s, 1H), 8.75 (s, 1H), 8.36 (m, 2H), 7.54 (d, 1H), 7.14 (m, 2H), 6.83 (m, 1H), 5.51 (s, 1H), 3.85 (s, 4H), 3.73 (m, 2H), 1.33 (t, 3H) ppm mp: 215-220° C.

Compound 30: 1-Ethyl-3-[3-(1-phenyl-1H-pyrazol-4-yl)-pyrido[2,3-b]pyrazin-6-yl]-urea

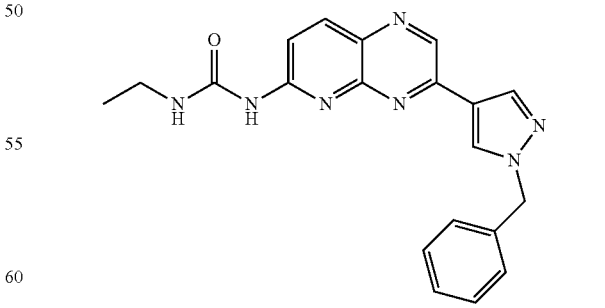

¹H-NMR (DMSO-d₆): δ=10.01 (s, 1H), 9.1 (m, 2H), 8.75 (s, 1H), 8.3 (m, 2H), 7.55 (d, 1H), 7.3 (m, 5H), 5.45 (s, 2H), 3.3 (s, 2H), 1.15 (t, 3H) ppm mp: 256-257° C.

Compound 31: 1-[3-(1-Benzyl-1H-pyrazol-4-yl)-pyrido[2,3-b]pyrazin-6-yl]-3-(2-methoxy-ethyl)-thiourea

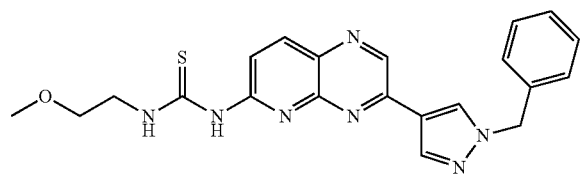

$^1$H-NMR (DMSO-d$_6$): δ=12.35 (m, 1H), 11.19 (s, 1H), 9.23 (s, 1H), 8.69 (s, 1H), 8.35 (m, 2H), 7.54 (d, 1H), 7.36 (m, 5H), 5.46 (m, 2H), 3.84 (m, 2H), 3.66 (m, 2H), 3.41 (s, 3H) ppm mp: 219° C.

Compound 32: 1-{3-[1-(3-Methoxy-benzyl)-1H-pyrazol-4-yl]-pyrido[2,3-b]pyrazin-6-yl}-3-(2-methoxy-ethyl)-thiourea

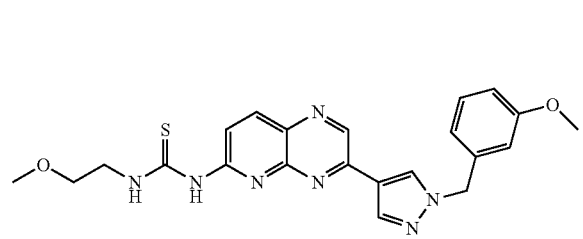

$^1$H-NMR (DMSO-d$_6$): δ=12.36 (s, 1H), 11.19 (s, 1H), 9.23 (s, 1H), 8.68 (s, 1H), 8.34 (m, 2H), 7.54 (d, 1H), 7.30 (t, 1H), 6.91 (m, 3H), 5.42 (s, 2H), 3.85 (m, 2H), 3.74 (m, 3H), 3.66 (m, 2H), 3.42 (m, 3H) ppm mp: 215° C.

Compound 33: 1-{3-[1-(3-Methoxy-benzyl)-1H-pyrazol-4-yl]-pyrido[2,3-b]pyrazin-6-yl}-3-methoxymethyl-thiourea

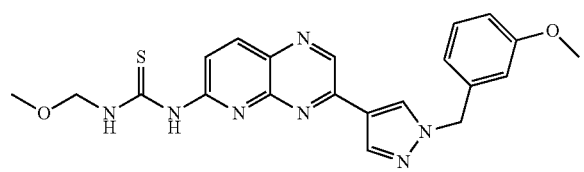

$^1$H-NMR (DMSO-d$_6$): δ=12.63 (m, 1H), 11.39 (s, 1H), 9.27 (s, 1H), 8.79 (s, 1H), 8.39 (m, 2H), 7.58 (d, 1H), 7.28 (m, 1H), 6.91 (m, 2H), 5.43 (s, 2H), 5.22 (m, 2H), 3.74 (m, 3H), 3.42 (m, 3H), 3.3 (s, 1H) ppm mp: 187° C.

Compound 34: 1-[3-(1-Benzyl-1H-pyrazol-4-yl)-pyrido[2,3-b]pyrazin-6-yl]-3-methoxymethyl-thiourea

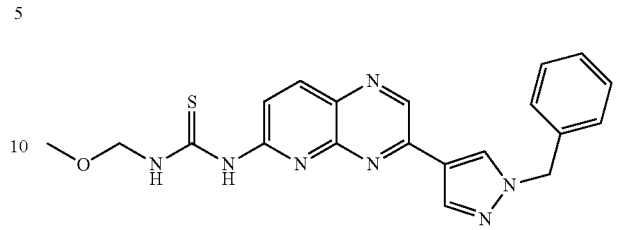

$^1$H-NMR (DMSO-d$_6$): δ=12.64 (m, 1H), 11.38 (s, 1H), 9.27 (s, 1H), 8.80 (s, 1H), 8.39 (m, 2H), 7.58 (d, 1H), 7.35 (m, 5H), 5.46 (s, 2H), 5.43 (m, 2H), 3.41 (s, 3H) ppm Compound 35: 1-{3-[1-(3,4-Dimethoxy-benzyl)-1H-pyrazol-4-yl]-pyrido[2,3-b]pyrazin-6-yl}-3-methoxymethyl-thiourea

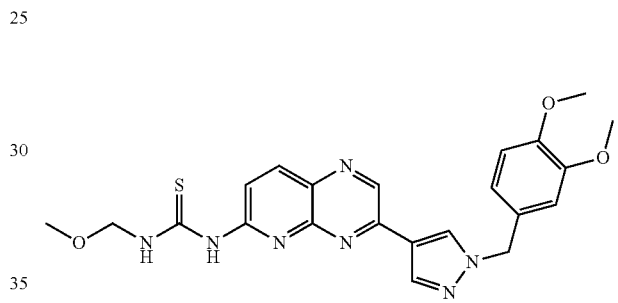

$^1$H-NMR (DMSO-d$_6$): δ=12.63 (m, 1H), 11.38 (s, 1H), 9.26 (s, 1H), 8.73 (s, 1H), 8.37 (m, 2H), 7.58 (d, 1H), 7.04 (s, 1H), 6.92 (m, 2H), 5.35 (s, 2H), 5.23 (d, 2H), 3.75 (m, 6H), 3.41 (m, 3H) ppm mp: 188° C.

Compound 36: 1-Ethyl-3-{3-[1-(3-hydroxy-benzyl)-1H-pyrazol-4-yl]-pyrido[2,3-b]pyrazin-6-yl}-thiourea

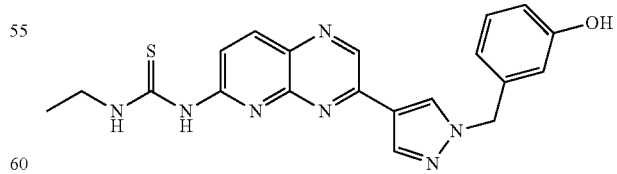

$^1$H-NMR (DMSO-d$_6$): δ=12.23 (m, 1H), 11.14 (s, 1H), 9.44 (s, 1H), 9.23 (s, 1H), 8.76 (s, 1H), 8.36 (m, 2H), 7.54 (d, 1H), 7.17 (t, 1H), 6.71 (m, 3H), 5.37 (s, 2H), 3.74 (m, 2H), 1.33 (m, 3H) ppm mp: 239° C.

Compound 37: 1-{3-[1-(3-Dimethylamino-benzyl)-1H-pyrazol-4-yl]-pyrido[2,3-b]pyrazin-6-yl}-3-ethyl-thiourea

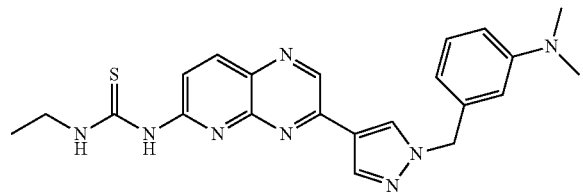 [SMILES: CCNC(=S)Nc1ccc2ncc(-c3cnn(Cc4cccc(N(C)C)c4)c3)nc2n1]

$^1$H-NMR (DMSO-$d_6$): δ=12.23 (m, 1H), 11.14 (s, 1H), 9.23 (s, 1H), 8.76 (s, 1H), 8.35 (m, 2H), 7.54 (d, 1H), 7.15 (t, 1H), 6.74 (s, 1H), 6.67 (d, 1H), 6.58 (d, 1H), 5.36 (s, 2H), 3.73 (m, 2H), 2.88 (s, 6H), 1.33 (t, 3H) ppm mp: 215° C.

Compound 38: 1-{3-[1-(3-Chloro-4-fluoro-benzyl)-1H-pyrazol-4-yl]-pyrido[2,3-b]pyrazin-6-yl}-3-ethyl-thiourea

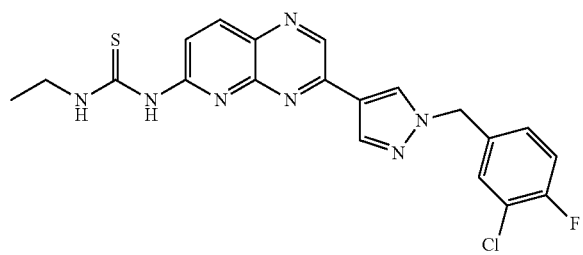

$^1$H-NMR (DMSO-$d_6$): δ=12.23 (m, 1H), 11.16 (s, 1H), 9.23 (s, 1H), 8.80 (s, 1H), 8.38 (m, 2H), 7.60 (m, 1H), 7.54 (d, 1H), 7.43 (m, 1H), 7.37 (m, 1H), 5.46 (s, 2H), 3.73 (m, 2H), 1.33 (t, 3H) ppm mp: 235-238° C.

Compound 39: 1-{3-[1-(3,5-Dimethoxy-benzyl)-1H-pyrazol-4-yl]-pyrido[2,3-b]pyrazin-6-yl}-3-ethyl-thiourea

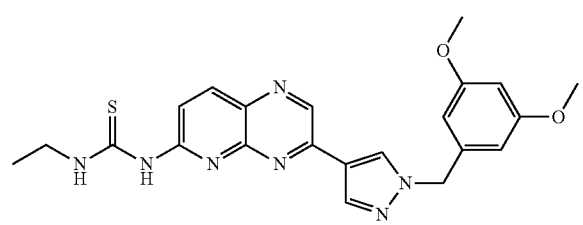 [SMILES: CCNC(=S)Nc1ccc2ncc(-c3cnn(Cc4cc(OC)cc(OC)c4)c3)nc2n1]

$^1$H-NMR (DMSO-$d_6$): δ=12.23 (m, 1H), 11.14 (s, 1H), 9.24 (s, 1H), 8.77 (s, 1H), 8.36 (m, 2H), 7.54 (d, 1H), 6.47 (m, 3H), 5.37 (s, 2H), 3.73 (m, 2H), 1.33 (t, 3H) ppm mp: 230° C.

Compound 40: 1-Ethyl-3-{3-[1-(3-methoxy-benzyl)-1H-pyrazol-4-yl]-pyrido[2,3-b]pyrazin-6-yl}-thiourea

$^1$H-NMR (DMSO-$d_6$): δ=12.23 (m, 1H), 11.14 (s, 1H), 9.24 (s, 1H), 8.77 (s, 1H), 8.36 (m, 2H), 7.54 (d, 1H), 7.29 (t, 1H), 6.90 (m, 3H), 5.43 (s, 2H), 3.73 (m, 5H), 1.33 (t, 3H) ppm mp: 217-220° C.

Compound 41: 1-Ethyl-3-{3-[1-(3-methyl-benzyl)-1H-pyrazol-4-yl]-pyrido[2,3-b]pyrazin-6-yl}-thiourea

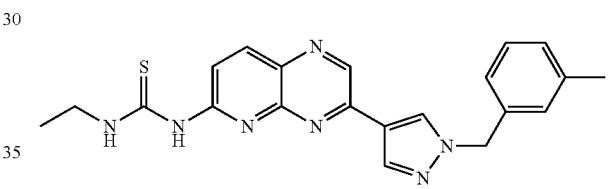

$^1$H-NMR (DMSO-$d_6$): δ=12.23 (m, 1H), 11.14 (s, 1H), 9.23 (s, 1H), 8.77 (s, 1H), 8.36 (m, 2H), 7.53 (d, 1H), 7.26 (t, 1H), 7.14 (m, 3H), 5.42 (s, 2H), 3.73 (m, 5H), 2.30 (s, 3H), 1.33 (t, 3H) ppm mp: 258-261° C.

Compound 42: 1-{3-[1-(3,4-Dimethoxy-benzyl)-1H-pyrazol-4-yl]-pyrido[2,3-b]pyrazin-6-yl}-3-ethyl-urea

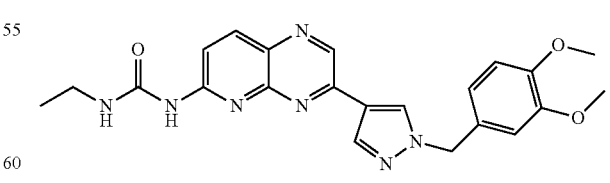

$^1$H-NMR (DMSO-$d_6$): δ=9.99 (s, 1H), 9.16 (s, 1H), 9.08 (s, 1H), 8.71 (s, 1H), 8.31 (s, 1H), 8.27 (d, 1H), 7.57 (d, 1H), 7.03 (m, 1H), 6.94 (m, 1H), 6.89 (m, 1H), 5.35 (s, 2H), 3.74 (m, 6H), 3.33 (m, 2H), 1.19 (t, 3H) ppm mp: 205° C.

Compound 43: 1-Ethyl-3-{3-[1-(2,3,4-trimethoxy-benzyl)-1H-pyrazol-4-yl]-pyrido[2,3-b]pyrazin-6-yl}-thiourea

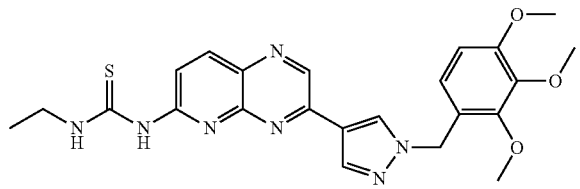 [SMILES: CCNC(=S)Nc1ccc2ncc(-c3cnn(Cc4ccc(OC)c(OC)c4OC)c3)nc2n1]

¹H-NMR (DMSO-d₆): δ=12.23 (m, 1H), 11.14 (s, 1H), 9.24 (s, 1H), 8.65 (s, 1H), 8.35 (m, 2H), 7.52 (d, 1H), 6.96 (d, 1H), 6.81 (d, 1H), 5.35 (s, 2H), 3.76 (m, 11H), 1.33 (t, 3H) ppm mp: 213° C.

Compound 44: 1-Ethyl-3-{3-[1-(3-phenyl-propyl)-1H-pyrazol-4-yl]-pyrido[2,3-b]pyrazin-6-yl}-thiourea

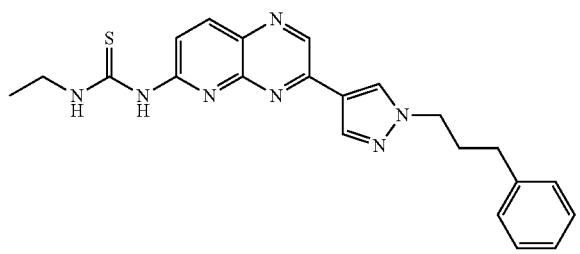 [SMILES: CCNC(=S)Nc1ccc2ncc(-c3cnn(CCCc4ccccc4)c3)nc2n1]

¹H-NMR (DMSO-d₆): δ=12.25 (m, 1H), 11.14 (s, 1H), 9.24 (s, 1H), 8.71 (s, 1H), 8.36 (m, 2H), 7.53 (d, 1H), 7.26 (m, 5H), 4.24 (t, 2H), 3.73 (m, 2H), 2.61 (t, 2H), 2.18 (m, 2H), 1.33 (t, 3H) ppm mp: 206-208° C.

Compound 45: 1-[3-(1-Benzyl-1H-pyrazol-4-yl)-pyrido[2,3-b]pyrazin-6-yl]-3-ethyl-thiourea

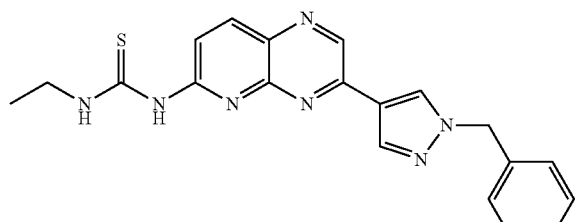

¹H-NMR (DMSO-d₆): δ=12.23 (m, 1H), 11.14 (s, 1H), 9.23 (s, 1H), 8.79 (s, 1H), 8.36 (m, 2H), 7.54 (d, 1H), 7.35 (m, 5H), 5.46 (s, 2H), 3.73 (m, 2H), 1.33 (t, 3H) ppm mp: 252° C.

Compound 46: 1-Ethyl-3-{3-[1-(3,4,5-trimethoxy-benzyl)-1H-pyrazol-4-yl]-pyrido[2,3-b]pyrazin-6-yl}-thiourea

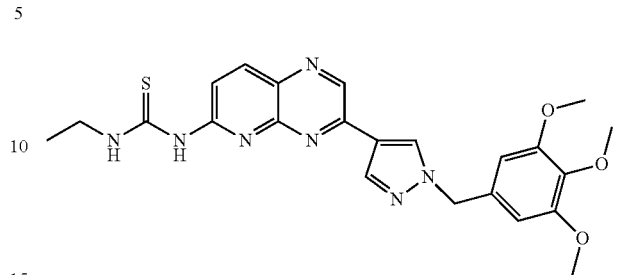

¹H-NMR (DMSO-d₆): δ=12.23 (m, 1H), 11.14 (s, 1H), 9.24 (s, 1H), 8.75 (s, 1H), 8.36 (m, 2H), 7.54 (d, 1H), 6.72 (s, 2H), 5.36 (s, 2H), 3.75 (m, 8H), 3.64 (m, 3H), 1.33 (t, 3H) ppm mp: 232° C.

Compound 47: 1-{3-[1-(3-Methoxy-benzyl)-1H-pyrazol-4-yl]-pyrido[2,3-b]pyrazin-6-yl}-3-(2,2,2-trifluoro-ethyl)-thiourea

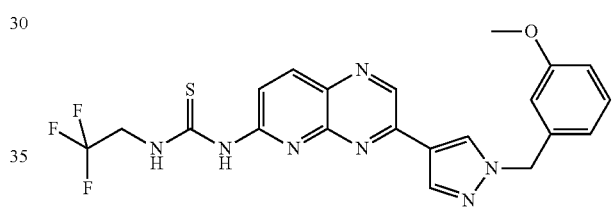

¹H-NMR (DMSO-d₆): δ=12.80 (t, 1H), 11.61 (s, 1H), 9.27 (s, 1H), 8.72 (s, 1H), 8.42 (d, 1H), 8.34 (s, 1H), 7.58 (d, 1H), 7.29 (t, 1H), 6.89 (m, 3H), 5.44 (m, 2H), 4.80 (m, 2H), 3.74 (m, 3H) ppm mp: 217° C.

Compound 48: 1-Ethyl-3-{3-[1-(2-fluoro-3-methyl-benzyl)-1H-pyrazol-4-yl]-pyrido[2,3-b]pyrazin-6-yl}-thiourea

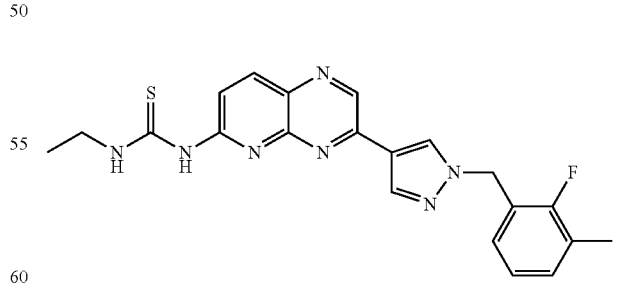

¹H-NMR (DMSO-d₆): δ=12.23 (t, 1H), 11.14 (s, 1H), 9.24 (s, 1H), 8.75 (s, 1H), 8.36 (m, 2H), 7.54 (d, 1H), 7.27 (t, 1H), 7.11 (m, 2H), 5.51 (s, 2H), 3.73 (m, 2H), 2.25 (s, 3H), 1.33 (t, 3H) ppm mp: 242-245° C.

Compound 49: 1-{3-[1-(3-Ethoxy-benzyl)-1H-pyrazol-4-yl]-pyrido[2,3-b]pyrazin-6-yl}-3-ethyl-thiourea

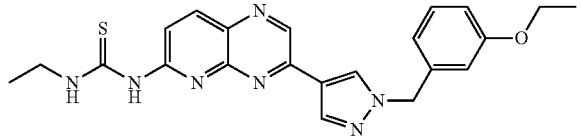 [SMILES: CCNC(=S)Nc1ccc2ncc(-c3cnn(Cc4cccc(OCC)c4)c3)nc2n1]

¹H-NMR (DMSO-d₆): δ=12.23 (t, 1H), 11.14 (s, 1H), 9.24 (s, 1H), 8.78 (s, 1H), 8.36 (m, 2H), 7.54 (d, 1H), 7.27 (t, 1H), 6.87 (m, 3H), 5.42 (s, 2H), 4.01 (m, 2H), 3.73 (m, 2H), 1.33 (m, 6H) ppm mp: 222° C.

Compound 50: 1-{3-[1-(4-Chloro-benzyl)-1H-pyrazol-4-yl]-pyrido[2,3-b]pyrazin-6-yl}-3-ethyl-thiourea

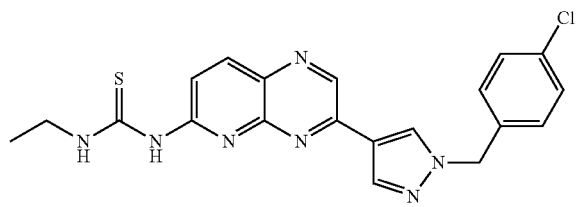 [SMILES: CCNC(=S)Nc1ccc2ncc(-c3cnn(Cc4ccc(Cl)cc4)c3)nc2n1]

¹H-NMR (DMSO-d₆): δ=12.23 (t, 1H), 11.15 (s, 1H), 9.23 (s, 1H), 8.79 (s, 1H), 8.38 (s, 1H), 8.36 (d, 1H), 7.54 (d, 1H), 7.44 (m, 2H), 7.35 (m, 2H), 5.47 (s, 2H), 3.73 (m, 2H), 1.33 (t, 3H) ppm mp: 249° C.

Compound 51: 1-{3-[1-(3-Methyl-benzyl)-1H-pyrazol-4-yl]-pyrido[2,3-b]pyrazin-6-yl}-3-(2,2,2-trifluoro-ethyl)-thiourea

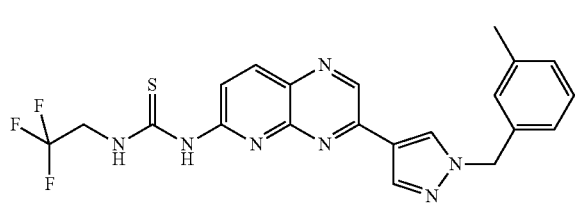 [SMILES: Cc1cccc(Cn2cc(-c3cnc4ccc(NC(=S)NCC(F)(F)F)nc4n3)cn2)c1]

¹H-NMR (DMSO-d₆): δ=12.8 (t, 1H), 11.61 (s, 1H), 9.27 (s, 1H), 8.70 (s, 1H), 8.42 (d, 1H), 8.33 (s, 1H), 7.58 (d, 1H), 7.26 (t, 1H), 7.13 (m, 3H), 5.43 (s, 2H), 4.80 (m, 2H), 2.30 (s, 3H) ppm mp: 249° C.

Compound 52: 1-Ethyl-3-{3-[1-(2-methyl-benzyl)-1H-pyrazol-4-yl]-pyrido[2,3-b]pyrazin-6-yl}-thiourea

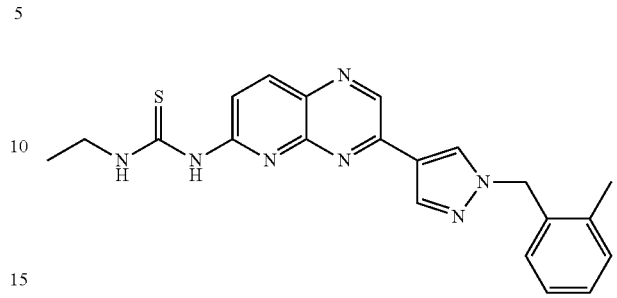

¹H-NMR (DMSO-d₆): δ=12.22 (m, 1H), 11.14 (s, 1H), 9.24 (s, 1H), 8.69 (s, 1H), 8.38 (s, 1H), 8.35 (d, 1H), 7.53 (d, 1H), 7.23 (m, 2H), 7.18 (m, 1H), 7.06 (d, 1H), 5.47 (s, 2H), 3.72 (m, 2H), 2.36 (s, 3H), 1.32 (t, 3H) ppm mp: 252-255° C.

Compound 53: 1-Ethyl-3-[3-(1-phenethyl-1H-pyrazol-4-yl)-pyrido[2,3-b]pyrazin-6-yl]-thiourea

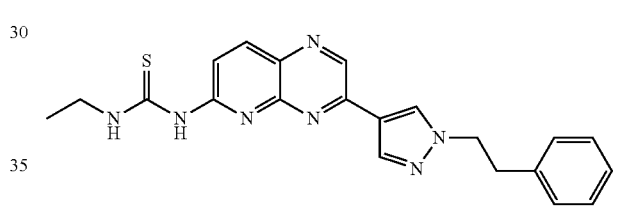

¹H-NMR (DMSO-d₆): δ=12.23 (m, 1H), 11.14 (s, 1H), 9.19 (s, 1H), 8.57 (s, 1H), 8.35 (m, 2H), 7.53 (d, 1H), 7.28 (t, 2H), 7.21 (m, 3H), 4.47 (t, 2H), 3.73 (m, 2H), 3.19 (t, 2H), 1.33 (t, 3H) ppm mp: 231-233° C.

Compound 54: 1-Ethyl-3-{3-[1-(4-hydroxy-3-methoxy-benzyl)-1H-pyrazol-4-yl]-pyrido[2,3-b]pyrazin-6-yl}-urea

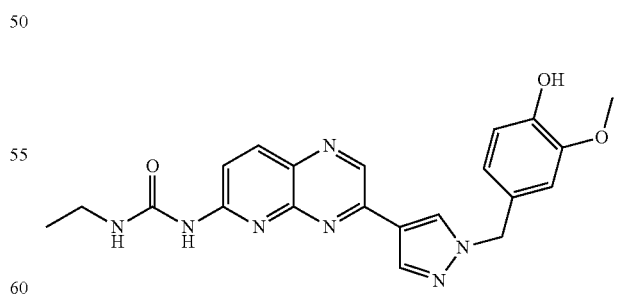

1H-NMR (DMSO-d6) δ=9.99 (s, 1H), 9.16 (s, 1H), 9.07 (s, 1H), 9.02 (s, 1H), 8.69, (s, 1H), 8.32 (s, 1H), 8.26 (m, 1H), 7.57 (m, 1H), 7.00 (s, 1H), 6.76 (m, 2H), 5.30 (s, 2H), 3.76 (s, 3H), 3.32 (m, 2H), 1.19 (m, 3H) ppm m.p.: 237° C.

Compound 55: 1-Ethyl-3-{3-[1-(4-hydroxy-3-methoxy-benzyl)-1H-pyrazol-4-yl]-pyrido[2,3-b]pyrazin-6-yl}-thiourea

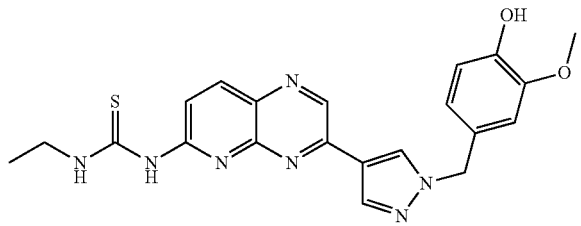 [SMILES: CCNC(=S)Nc1ccc2ncc(-c3cnn(Cc4ccc(O)c(OC)c4)c3)nc2n1]

1H-NMR (DMSO-d6) δ=12.23 (m, 1H), 11.14 (s, 1H), 9.22 (s, 1H), 9.02 (s, 1H), 8.70, (s, 1H), 8.34 (m, 2H), 7.53 (m, 1H), 7.00 (s, 1H), 6.76 (m, 2H), 5.31 (s, 2H), 3.75 (m, 5H), 1.33 (m, 3H) ppm m.p.: 242° C.

Compound 56: 1-Ethyl-3-{3-[1-(3-hydroxy-4-methoxy-benzyl)-1H-pyrazol-4-yl]-pyrido[2,3-b]pyrazin-6-yl}-urea

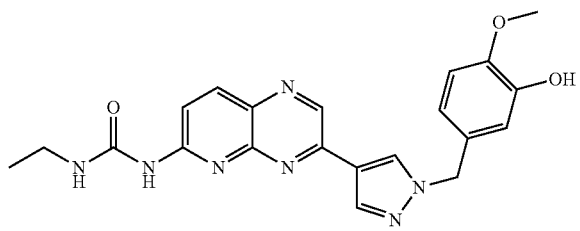 [SMILES: CCNC(=O)Nc1ccc2ncc(-c3cnn(Cc4ccc(OC)c(O)c4)c3)nc2n1]

1H-NMR (DMSO-d6) δ=10.00 (s, 1H), 9.16 (s, 1H), 9.07 (s, 1H), 9.02 (s, 1H), 8.70, (s, 1H), 8.33 (s, 1H), 8.27 (m, 1H), 7.57 (m, 1H), 6.89 (m, 1H), 6.77 (m, 2H), 5.28 (s, 2H), 3.74 (s, 3H), 3.33 (m, 2H), 1.19 (m, 3H) ppm m.p.: 250° C.

Compound 57: 1-Ethyl-3-{3-[1-(3-hydroxy-4-methoxy-benzyl)-1H-pyrazol-4-yl]-pyrido[2,3-b]pyrazin-6-yl}-thiourea

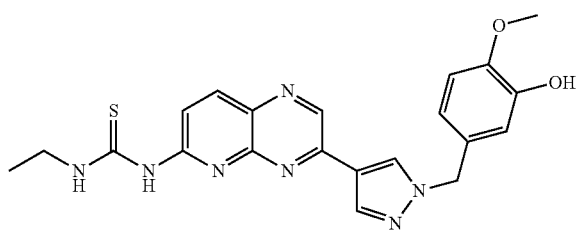

1H-NMR (DMSO-d6) δ=12.23 (m, 1H), 11.14 (s, 1H), 9.23 (s, 1H), 9.02 (s, 1H), 8.71, (s, 1H), 8.35 (m, 2H), 7.53 (m, 1H), 6.89 (m, 1H), 6.77 (m, 2H), 7.12 (m, 1H), 5.29 (m, 2H), 3.73 (m, 5H), 1.33 (m, 3H) ppm m.p.: 230° C.

Compound 64: 1-Ethyl-3-{3-[1-(3-methanesulfonyl-benzyl)-1H-pyrazol-4-yl]-pyrido[2,3-b]pyrazin-6-yl}-urea

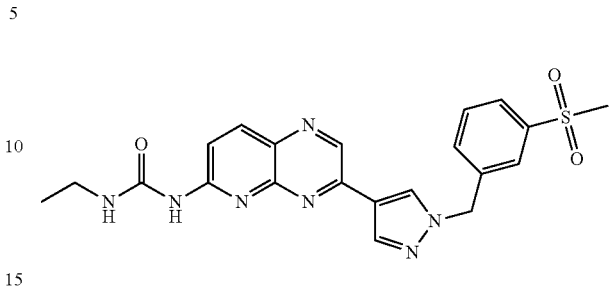

1H-NMR (DMSO-d6) δ=10.01 (s, 1H), 9.18 (s, 1H), 9.09 (s, 1H), 8.84 (s, 1H), 8.39, (s, 1H), 8.28 (m, 1H), 7.91 (m, 2H), 7.59 (m, 1H), 5.60 (s, 2H), 3.22 (s, 3H), 1.19 (m, 3H) ppm m.p.: 218° C.

Compound 65: 1-Ethyl-3-{3-[1-(3-methanesulfonyl-benzyl)-1H-pyrazol-4-yl]-pyrido[2,3-b]pyrazin-6-yl}-thiourea

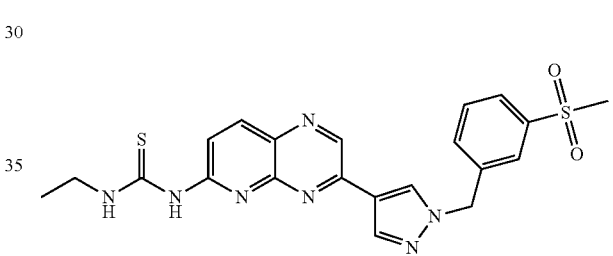

1H-NMR (DMSO-d6) δ=12.23 (s, 1H), 11.15 (s, 1H), 9.25 (s, 1H), 8.85 (s, 1H), 8.42, (s, 1H), 8.36 (m, 1H), 7.91 (m, 2H), 7.67 (m, 2H), 6.54 (m, 1H), 5.61 (s, 2H), 3.73 (m, 2H), 3.22 (s, 3H), 1.33 (m, 3H) ppm Compound 66: 1-Ethyl-3-(3-{1-[3-(2-methoxy-ethoxy)-benzyl]-1H-pyrazol-4-yl}-pyrido[2,3-b]pyrazin-6-yl)-urea

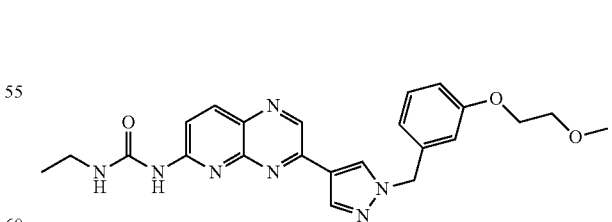

1H-NMR (DMSO-d6) δ=10.00 (s, 1H), 9.17 (s, 1H), 9.08 (s, 1H), 8.77 (s, 1H), 8.35 (s, 1H), 8.28 (m, 1H), 7.57 (m, 1H), 7.28 (m, 1H), 6.89 (m, 3H), 5.41 (s, 2H), 4.07 (m, 2H), 3.64 (m, 2H), 3.32 (m, 2H), 3.29 (s, 3H), 1.19 (m, 3H) ppm m.p.: 201° C.

Compound 210: 1-Ethyl-3-{3-[1-(4-hydroxy-benzyl)-1H-pyrazol-4-yl]-pyrido[2,3-b]pyrazin-6-yl}-thiourea

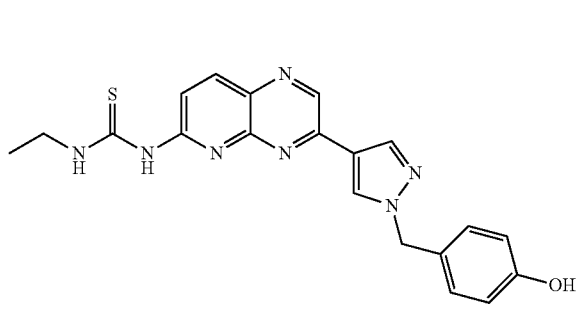 [SMILES: CCNC(=S)Nc1ccc2ncc(-c3cnn(Cc4ccc(O)cc4)c3)nc2n1]

1H-NMR (DMSO-d6) δ=12.22 (s, 1H), 11.13 (s, 1H), 9.45 (s, 1H), 9.22 (s, 1H), 8.70 (s, 1H), 8.34 (m, 2H), 7.53 (m, 1H), 7.20 (d, 2H), 6.75 (d, 1H), 5.30 (s, 2H), 3.73 (m, 2H), 1.34 (m, 3H) ppm m.p.: 257° C.

Compound 211: 1-Ethyl-3-(3-{1-[4-methoxy-3-(2-methoxy-ethoxy)-benzyl]-1H-pyrazol-4-yl}-pyrido[2,3-b]pyrazin-6-yl)-urea

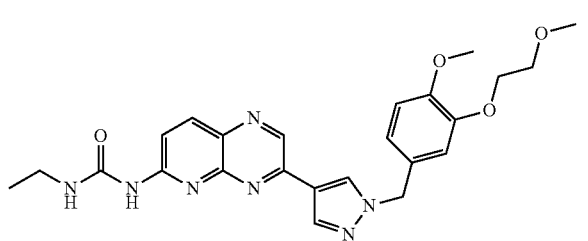 [SMILES: CCNC(=O)Nc1ccc2ncc(-c3cnn(Cc4ccc(OC)c(OCCOC)c4)c3)nc2n1]

1H-NMR (DMSO-d6) δ=10.01 (s, 1H), 9.16 (s, 1H), 9.09 (s, 1H), 8.71 (s, 1H), 8.33 (s, 1H), 8.27 (m, 1H), 7.56 (m, 1H), 7.04 (s, 1H), 6.95 (m, 1H), 6.90 (m, 1H), 5.33 (s, 2H), 4.05 (m, 2H), 3.74 (s, 3H), 3.64 (m, 2H), 3.29 (s, 3H), 1.19 (m, 3H) ppm Compound 212: 4-[6-(3-Ethyl-ureido)-pyrido[2,3-b]pyrazin-3-yl]-thiophene-2-carboxylic acid

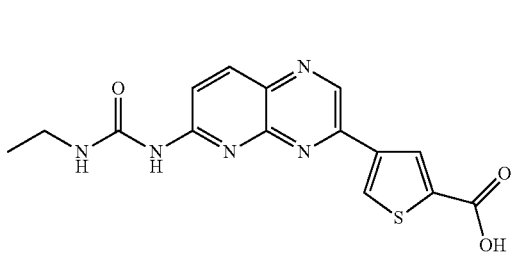

1H-NMR (DMSO-d6) δ=13.41 (s, 1H), 10.09 (s, 1H), 9.43 (s, 1H), 9.04 (s, 1H), 8.89 (s, 1H), 8.54 (s, 1H), 8.35 (d, 1H), 7.69 (d, 1H), 3.36 (s, 2H), 1.20 (m, 3H) ppm mp: 250° C. (dec.)

Compound 213: 1-Ethyl-3-[3-(5-methyl-furan-2-yl)-pyrido[2,3-b]pyrazin-6-yl]-urea

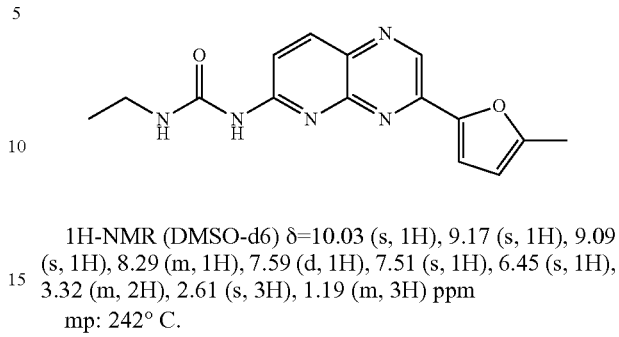

1H-NMR (DMSO-d6) δ=10.03 (s, 1H), 9.17 (s, 1H), 9.09 (s, 1H), 8.29 (m, 1H), 7.59 (d, 1H), 7.51 (s, 1H), 6.45 (s, 1H), 3.32 (m, 2H), 2.61 (s, 3H), 1.19 (m, 3H) ppm mp: 242° C.

Compound 396: 1-Ethyl-3-[3-(5-hydroxymethyl-thiophen-2-yl)-pyrido[2,3-b]pyrazin-6-yl]-urea

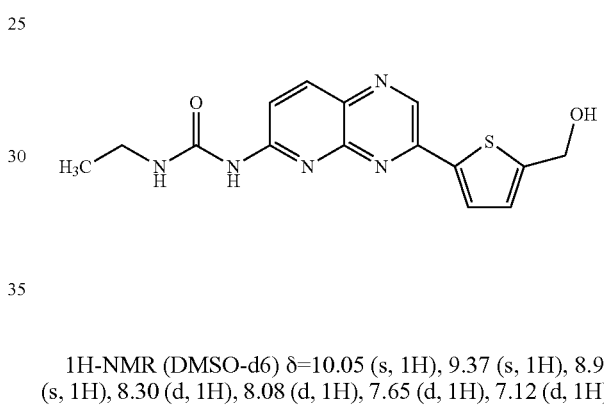

1H-NMR (DMSO-d6) δ=10.05 (s, 1H), 9.37 (s, 1H), 8.94 (s, 1H), 8.30 (d, 1H), 8.08 (d, 1H), 7.65 (d, 1H), 7.12 (d, 1H), 5.67 (m, 1H), 4.72 (d, 2H), 3.23 (s, 2H), 1.20 (m, 3H) ppm mp: 222° C.

Compound 404: 3-{4-[6-(3-Ethyl-ureido)-pyrido[2,3-b]pyrazin-3-yl]-pyrazol-1-yl}-propionamide

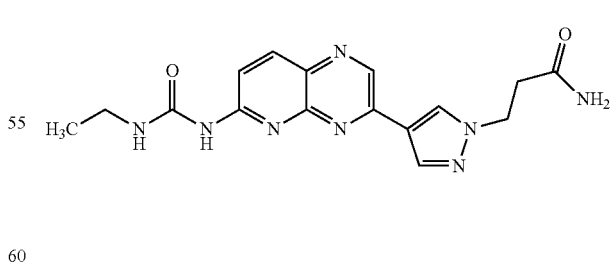

1H-NMR (DMSO-d6) δ=10.00 (s, 1H), 9.17 (s, 1H), 9.08 (s, 1H), 8.60 (s, 1H), 8.32 (s, 1H), 8.27 (d, 1H), 7.59 (d, 1H), 7.43 (s, 1H), 6.91 (s, 1H), 4.41 (m, 2H), 3.33 (m, 2H), 2.72 (m, 2H), 1.20 (m, 3H), ppm mp: 247° C.

Compound 406: (2-{4-[6-(3-Ethyl-ureido)-pyrido[2,3-b]pyrazin-3-yl]-pyrazol-1-yl}ethyl)-carbamic acid tert-butyl ester

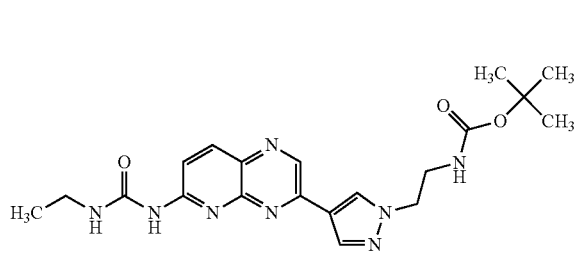 [SMILES: CCNC(=O)Nc1ccc2ncc(-c3cnn(CCNC(=O)OC(C)(C)C)c3)nc2n1]

1H-NMR (DMSO-d6) δ=10.00 (s, 1H), 9.17 (s, 1H), 8.59 (s, 1H), 8.30 (m, 1H), 8.27 (s, 1H), 7.57 (d, 1H), 6.98 (s, 1H), 4.25 (m, 2H), 3.40 (m, 2H), 1.35 (s, 10H), 1.25 (s, 2H), 1.20 (m, 4H) ppm mp: 235° C.

Compound 416: D-1194221-Ethyl-3-[3-(5-methyl-furan-2-yl)-pyrido[2,3-b]pyrazin-6-yl]-urea

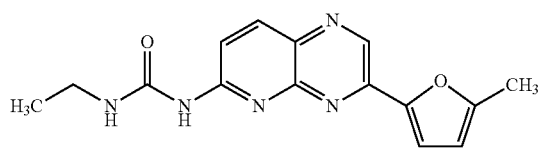 [SMILES: CCNC(=O)Nc1ccc2ncc(-c3ccc(C)o3)nc2n1]

1H-NMR (DMSO-d6) δ=10.03 (s, 1H), 9.17 (s, 1H), 9.09 (s, 1H), 8.29 (m, 1H), 7.59 (d, 1H), 7.51 (s, 1H), 6.45 (s, 1H), 3.32 (m, 2H), 2.61 (s, 3H), 1.19 (m, 3H) ppm mp: 242° C.

Compound 428: 4-[6-(3-Ethyl-ureido)-pyrido[2,3-b]pyrazin-3-yl]-thiophene-2-carboxylic acid

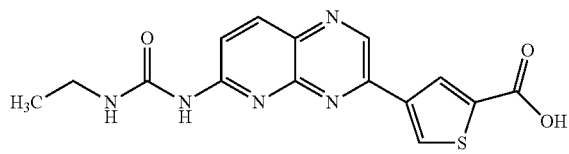 [SMILES: CCNC(=O)Nc1ccc2ncc(-c3csc(C(=O)O)c3)nc2n1]

1H-NMR (DMSO-d6) δ=10.09 (s, 1H), 9.43 (s, 1H), 9.04 (s, 1H), 8.89 (s, 1H), 8.54 (s, 1H), 8.35 (d, 1H), 7.69 (d, 1H), 3.36 (s, 2H), 1.20 (m, 3H) ppm mp: 250° C. (dec.)

Compound 432: 1-Ethyl-3-(3-furan-3-yl-pyrido[2,3-b]pyrazin-6-yl)-urea

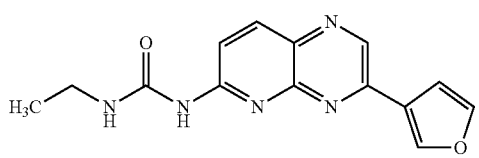 [SMILES: CCNC(=O)Nc1ccc2ncc(-c3ccoc3)nc2n1]

1H-NMR (DMSO-d6) δ=10.05 (s, 1H), 9.23 (s, 1H), 9.00 (s, 1H), 8.75 (s, 1H), 8.32 (d, 1H), 7.82 (s, 1H), 7.66 (d, 1H), 7.26 (s, 1H), 3.33 (s, 2H), 1.20 (m, 3H) ppm mp: 240° C.

Evidence of the Kinase Inhibition of Compounds According to the Invention

Cell-Free Kinase Assays (Using ALPHA Technology)

The inhibitory effect of the compounds according to the invention was tested on various serine/threonine, tyrosine and lipid kinases in enzymatic assays. Recombinant human kinases such as, for example, Erk2, PI3Kalpha and others were used in this case, partly as full-length kinases, partly as shortened fragments, but at least consisting of the functional kinase domains. The commercial kinase proteins (Proqinase, Upstate) were used as recombinant fusion proteins with GST (glutathion-S-transferase) or His-Tag. Depending on the type of substrate, the various kinase reactions were quantified by means of suitable ALPHA™ beads (Perkin-Elmer).

Testing

The substance testing is described in detail hereinafter for the Erk assay. Selected test results of the Erk2 and PI3Kalpha assays are given below. To determine the $IC_{50}$ value, the potential inhibitor substances were investigated in 10 semi-logarithmically graded concentrations of 3.16 nM-100 μM.

a) MAPK-ALPHAs (e.g. Erk2): the test substance, 0.625 ng Erk2 (#14-173, Upstate), 10 μM ATP and 15 nM biotinylated MBP (myelin basic protein) substrate were incubated on a 384-well Optiplate (Perkin-Elmer) in a volume of 15 μl for 1 h in 25 mM Tris, 10 mM $MgCl_2$, 0.1% Tween-20, 100 μM $NaVO_4$, 2 mM DTT at pH 7.5. The kinase reaction was then stopped by adding 10 μl of the ALPHA bead mixes (10 μg/ml, #6760617/Perkin-Elmer) pre-incubated with anti-phospho MBP antibody (320 μM, #05-429/Upstate) in 25 mM Tris, 200 mM NaCl, 100 mM EDTA and 0.3% BSA and left to stand overnight.

b) PI3K-ALPHAs (e.g. PI3Kalpha): the test substance, 1 ng PI3Kalpha (#14-602, Upstate), 100 μM ATP and 20 μM $PIP_2$ substrate (#64910, Cayman Chemicals) were incubated on a 384-well Optiplate (Perkin-Elmer) for 1 h in 50 mM Hepes, 50 mM NaCl, 5 mM $MgCl_2$, 0.05% Chaps, 5 mM DTT at pH 7.4. The kinase reaction was then stopped by adding ALPHA bead mixes (10 μg/ml, #6760603/Perkin-Elmer) pre-incubated with 1 nM GST:Grp1 fusion protein (Upstate) and 15 nM biotinylated PIP3 (#10009531, Cayman Chemicals) in 50 mM Hepes, 50 mM NaCl, 50 mM EDTA and 0.1% BSA and left to stand overnight.

The fluorescence was detected the following morning in a Envision plate reader (Perkin-Elmer).

Evaluation

The %-inhibition values per substance concentration were calculated by means of the following formula from the raw data determined in the Envision plate reader:

$$\% \text{ Kinase inhibition}_{(Sample)} =$$
$$100 - \left(100 \times \frac{Mean_{(Sample)} - Mean_{(0\% \ Control)}}{Mean_{(100\% \ Control)} - Mean_{(0\% \ Control)}}\right)$$

Eight determinations were made for each control and two for the substance samples. The 0% control either contains no ATP or no substrate, the 100% control (fully active kinase) contains no test substance. The $IC_{50}$ values were determined using GraphPadPrism.

The inventive compounds exhibited effective inhibition of Erk and/PI3K $IC_{50}$ values up to 1 nM (see Table 1).

TABLE 1

Erk2 and PI3Kalpha kinase assay test results ($IC_{50}$ [μM]) at 10 μM or 100 μM* ATP)

| Compound | Erk2 | PI3Kalpha* |
|---|---|---|
| 27 | 0.75 | 0.059 |
| 28 | 0.112 | 0.082 |
| 29 | 0.492 | 0.112 |
| 40 | 0.336 | 0.168 |
| 41 | 0.400 | 0.184 |
| 42 | 0.043 | 0.274 |
| 45 | 0.272 | 0.249 |
| 55 | 0.523 | 0.391 |
| 65 | 0.225 | 0.180 |
| 210 | 0.225 | 0.208 |

Cellular Assay: Testing for Anti-Proliferative Effect (XTT Assay)

The principle of this test is based on the intracellular reduction of the tetrazolium dye XTT (sodium 3'-[1-(phenylaminocarbonyl)-3,4-tetrazolium]-bis(4-methoxy-6-nitro)benzene sulfonic acid, Sigma) to a formazan dye by mitochondrial dehydrogenases. The dye is only formed by metabolically active cells and its photometrically measurable intensity is a quantitative indicator for the presence of living cells. The reduction of dye formation by incubation of the cells with substances serves as a parameter for the anti-proliferative effect.

Testing

The tumour cell lines (ATCC) were injected into 96-well microtitre plates in a defined cell number (1250 cells/well for Hct116) and then incubated overnight in an incubator at 37° C., 5% $CO_2$ and 95% air humidity. The test substances were prepared as stock solutions (10 mM) in DMSO. To determine the $EC_{50}$ values the potential inhibitor substances were added to the cells in half-logarithmically graded dilutions, resulting in final concentrations of 1.58 nM-50 μM. The cell plates were then incubated for ~48 h in an incubator at 37° C., 5% $CO_2$ and 95% air humidity.

For the detection reaction the substrate XTT was mixed with PMS (N-Methyl dibenzopyrazine methylsulfate, Sigma) and added to the cells so that a final concentration of 325 μg XTT/ml and 2.5 μg PMS/ml was obtained. It was then incubated for 3 h at 37° C., 95% air humidity. The formazan salt formed by the cellular dehydrogenases could then be quantified by adsorption at 490 nm.

Evaluation

The % inhibition value was evaluated by means of the following formula from the values for the optical densities measured in each case at 490 nm:

$$\% \text{ Inhibition of cell proliferation}_{(Sample)} =$$
$$100 - \left(100 \times \frac{Mean_{(Sample)} - Mean_{(0\% \ Control)}}{Mean_{(100\% \ Control)} - Mean_{(0\% \ Control)}}\right)$$

Eight determinations were made for each control and two for the substance samples. The 0% control contains no cells, the 100% control (proliferation control) contains no test substance. The $EC_{50}$ values were determined using GraphPad-Prism.

The compounds according to the invention showed partly effective inhibition of the cell proliferation with $EC_{50}$ values of to <1 μM (see Table 2).

TABLE 2

XTT assay test results ($EC_{50}$ [μM])

| Compound | Hct116 |
|---|---|
| 27 | 1.53 |
| 28 | 1.65 |
| 29 | 2.56 |
| 40 | 2.57 |
| 41 | 3.01 |
| 42 | 1.98 |
| 45 | 1.95 |
| 65 | 2.11 |
| 210 | 1.70 |

The invention claimed is:
1. A Pyridopyrazine selected from the group consisting of
1-Ethyl-3-[3-(1-pyridin-2-ylmethyl-1H-pyrazol-4-yl)-pyrido[2,3-b]pyrazin-6-yl]-thiourea
1-Ethyl-3-[3-(1-pyridin-3-ylmethyl-1H-pyrazol-4-yl)-pyrido[2,3-b]pyrazin-6-yl]-thiourea
1-{3-[1-(3,4-Dimethoxy-benzyl)-1H-pyrazol-4-yl]-pyrido[2,3-b]pyrazin-6-yl}-3-ethyl-thiourea
1-Ethyl-3-{3-[1-(2-fluoro-3-methoxy-benzyl)-1H-pyrazol-4-yl]-pyrido[2,3-b]pyrazin-6-yl}-thiourea
1-{3-[1-(3-Methoxy-benzyl)-1H-pyrazol-4-yl]-pyrido[2,3-b]pyrazin-6-yl}-3-methoxymethyl-thiourea
1-{3-[1-(3,4-Dimethoxy-benzyl)-1H-pyrazol-4-yl]-pyrido[2,3-b]pyrazin-6-yl}-3-methoxymethyl-thiourea
1-Ethyl-3-{3-[1-(3-hydroxy-benzyl)-1H-pyrazol-4-yl]-pyrido[2,3-b]pyrazin-6-yl}-thiourea
1-Ethyl-3-{3-[1-(3-methoxy-benzyl)-1H-pyrazol-4-yl]-pyrido[2,3-b]pyrazin-6-yl}-thiourea
1-Ethyl-3-{3-[1-(3-methyl-benzyl)-1H-pyrazol-4-yl]-pyrido[2,3-b]pyrazin-6-yl}-thiourea
1-{3-[1-(3,4-Dimethoxy-benzyl)-1H-pyrazol-4-yl]-pyrido[2,3-b]pyrazin-6-yl}-3-ethyl-urea
1-Ethyl-3-{3-[1-(2,3,4-trimethoxy-benzyl)-1H-pyrazol-4-yl]-pyrido[2,3-b]pyrazin-6-yl}-thiourea
1-[3-(1-Benzyl-1H-pyrazol-4-yl)-pyrido[2,3-b]pyrazin-6-yl]-3-ethyl-thiourea
1-Ethyl-3-{3-[1-(4-hydroxy-3-methoxy-benzyl)-1H-pyrazol-4-yl]-pyrido[2,3-b]pyrazin-6-yl}-thiourea
1-Ethyl-3-{3-[1-(3-methanesulfonyl-benzyl)-1H-pyrazol-4-yl]-pyrido[2,3-b]pyrazin-6-yl}-thiourea
1-Ethyl-3-(3-{1-[2-(2-methoxy-ethoxy)-ethyl]-1H-pyrazol-4-yl}-pyrido[2,3-b]pyrazin-6-yl)-thiourea
1-Ethyl-3-[3-(1-{2-[2-(2-methoxy-ethoxy)-ethoxy]-ethyl}-1H-pyrazol-4-yl)-pyrido[2,3-b]pyrazin-6-yl]-thiourea
1-Ethyl-3-{3-[1-(4-hydroxy-benzyl)-1H-pyrazol-4-yl]-pyrido[2,3-b]pyrazin-6-yl}-thiourea

1-Ethyl-3-(3-{1-[4-methoxy-3-(2-methoxy-ethoxy)-benzyl]-1H-pyrazol-4-yl}-pyrido[2,3-b]pyrazin-6-yl)-urea
1-Ethyl-3-[3-(5-methyl-furan-2-yl)-pyrido[2,3-b]pyrazin-6-yl]-thiourea
3-{4-[6-(3-Ethyl-thioureido)-pyrido[2,3-b]pyrazin-3-yl]-pyrazol-1-yl}-propionamide
Sodium; 4-{4-[6-(3-ethyl-thioureido)-pyrido[2,3-b]pyrazin-3-yl]-pyrazol-1-ylmethyl}-phenolate
1-Ethyl-3-(3-{1-[4-(2-methoxy-ethoxy)-benzyl]-1H-pyrazol-4-yl}-pyrido[2,3-b]pyrazin-6-yl)-thiourea
1-Ethyl-3-(3-{1-[4-(2-morpholin-4-yl-ethoxy)-benzyl]-1H-pyrazol-4-yl}-pyrido[2,3-b]pyrazin-6-yl)-thiourea
1-Ethyl-3-{3-[1-(4-methanesulfonyl-benzyl)-1H-pyrazol-4-yl]-pyrido[2,3-b]pyrazin-6-yl}-thiourea
3-{4-[6-(3-Allyl-thioureido)-pyrido[2,3-b]pyrazin-3-yl]-pyrazol-1-yl}-propionamide
1-Cyclopentyl-3-[3-(5-hydroxymethyl-thiophen-2-yl)-pyrido[2,3-b]pyrazin-6-yl]-urea
5-[6-(3-Cyclopentyl-ureido)-pyrido[2,3-b]pyrazin-3-yl]-thiophene-2-carboxylic acid
3-{4-[6-(3-Cyclopentyl-thioureido)-pyrido[2,3-b]pyrazin-3-yl]-pyrazol-1-yl}-propionamide
1-Cyclopentyl-3-[3-(5-hydroxymethyl-thiophen-2-yl)-pyrido[2,3-b]pyrazin-6-yl]-urea
1-Cyclopentyl-3-(3-furan-3-yl-pyrido[2,3-b]pyrazin-6-yl)-urea
1-Ethyl-3-[3-(5-hydroxymethyl-thiophen-2-yl)-pyrido[2,3-b]pyrazin-6-yl]-thiourea
1-Allyl-3-{3-[1-(3-methanesulfonyl-benzyl)-1H-pyrazol-4-yl]-pyrido[2,3-b]pyrazin-6-yl}-thiourea
   or a physiologically acceptable salt, a racemate, a pure enantiomer, a diastereomer, a mixture of enantiomers, a mixture of diastereomers, and a tautomer thereof.

2. A pharmaceutical composition which comprises a pharmacologically active amount of at the least one compound according to claim 1, and a pharmaceutically acceptable carrier.

3. The pharmaceutical composition according to claim 2, wherein the at least one compound is present in a unit dose of 0.001 mg to 100 mg per kg body weight of a patient.

4. The pyridopyrazin according to claim 1, which is selected from the group consisting of 1-{3-[1-(3,4-Dimethoxy-benzyl)-1H-pyrazol-4-yl]-pyrido[2,3-b]pyrazin-6-yl}-3-ethyl-thiourea
1-Ethyl-3-{3-[1-(3-methoxy-benzyl)-1H-pyrazol-4-yl]-pyrido[2,3-b]pyrazin-6-yl}-thiourea
1-Ethyl-3-{3-[1-(3-methanesulfonyl-benzyl)-1H-pyrazol-4-yl]-pyrido[2,3-b]pyrazin-6-yl}-thiourea; and
1-Ethyl-3-{3-[1-(4-hydroxy-benzyl)-1H-pyrazol-4-yl]-pyrido[2,3-b]pyrazin-6-yl}-thiourea
   or a physiologically acceptable salt, a racemate, a pure enantiomer, a diastereomer, a mixture of enantiomers, a mixture of diastereomers, and a tautomer thereof.

5. A pharmaceutical composition which comprises a pharmaceutical active amount of at the least one compound according to claim 4, and a pharmaceutical acceptable carrier.

6. The pharmaceutical composition according to claim 5, which comprises a pharmaceutical active amount of 1-{3-[1-(3,4-Dimethoxy-benzyl)-1H-pyrazol-4-yl]-pyrido[2,3-b]pyrazin-6-yl}-3-ethyl-thiourea or a physiologically acceptable salt, a racemate, a pure enantiomer, a diastereomer, a mixture of enantiomers, a mixture of diastereomers, and a tautomer thereof.

7. The pharmaceutical composition according to claim 5, which comprises a pharmaceutical active amount of 1-Ethyl-3-{3-[1-(3-methoxy-benzyl)-1H-pyrazol-4-yl]-pyrido[2,3-b]pyrazin-6-yl}-thiourea or a physiologically acceptable salt, a racemate, a pure enantiomer, a diastereomer, a mixture of enantiomers, a mixture of diastereomers, and a tautomer thereof.

8. The pharmaceutical composition according to claim 5, which comprises a pharmaceutical active amount of 1-Ethyl-3-{3-[1-(3-methanesulfonyl-benzyl)-1H-pyrazol-4-yl]-pyrido[2,3-b]pyrazin-6-yl}-thiourea or a physiologically acceptable salt, a racemate, a pure enantiomer, a diastereomer, a mixture of enantiomers, a mixture of diastereomers, and a tautomer thereof.

9. The pharmaceutical composition according to claim 5, which comprises a pharmaceutical active amount of 1-Ethyl-3-{3-[1-(4-hydroxy-benzyl)-1H-pyrazol-4-yl]-pyrido[2,3-b]pyrazin-6-yl}-thiourea or a physiologically acceptable salt, a racemate, a pure enantiomer, a diastereomer, a mixture of enantiomers, a mixture of diastereomers, and a tautomer thereof.

* * * * *